US008962917B2

(12) United States Patent
Damude et al.

(10) Patent No.: US 8,962,917 B2
(45) Date of Patent: *Feb. 24, 2015

(54) DELTA-5 DESATURASE AND ITS USE IN MAKING POLYUNSATURATED FATTY ACIDS

(75) Inventors: Howard Glenn Damude, Hockessin, DE (US); Quinn Qun Zhu, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1949 days.

This patent is subject to a terminal disclaimer.

(21) Appl. No.: 11/749,889

(22) Filed: May 17, 2007

(65) Prior Publication Data

US 2007/0277266 A1 Nov. 29, 2007

Related U.S. Application Data

(60) Provisional application No. 60/801,172, filed on May 17, 2006.

(51) Int. Cl.
| | |
|---|---|
| A01H 5/00 | (2006.01) |
| C12N 15/82 | (2006.01) |
| C12N 1/20 | (2006.01) |
| C12N 5/10 | (2006.01) |
| C12P 7/64 | (2006.01) |
| C12N 9/02 | (2006.01) |

(52) U.S. Cl.
CPC .............. *C12P 7/6427* (2013.01); *C12N 9/0083* (2013.01); *C12P 7/6472* (2013.01)
USPC .......... 800/281; 800/298; 435/252.3; 435/419

(58) Field of Classification Search
None
See application file for complete search history.

(56) References Cited

U.S. PATENT DOCUMENTS

| | | | |
|---|---|---|---|
| 5,968,809 A | 10/1999 | Knutzon et al. | |
| 5,972,664 A | 10/1999 | Knutzon et al. | |
| 6,051,754 A | 4/2000 | Knutzon et al. | |
| 6,075,183 A | 6/2000 | Knutzon et al. | |
| 6,136,574 A | 10/2000 | Knutzon et al. | |
| 6,403,349 B1 | 6/2002 | Mukerji et al. | |
| 6,410,288 B1 | 6/2002 | Knutzon et al. | |
| 6,677,145 B2 | 1/2004 | Mukerji et al. | |
| 6,825,017 B1 | 11/2004 | Browse et al. | |
| 7,125,672 B2 | 10/2006 | Picataggio et al. | |
| 7,129,089 B2 | 10/2006 | Kinney et al. | |
| 7,189,559 B2 | 3/2007 | Damude et al. | |
| 7,192,762 B2 | 3/2007 | Macool et al. | |
| 7,198,937 B2 | 4/2007 | Xue et al. | |
| 7,202,356 B2 | 4/2007 | Pollak et al. | |
| 7,678,560 B2 * | 3/2010 | Damude et al. | 435/254.11 |
| 2003/0196217 A1 | 10/2003 | Mukerji et al. | |
| 2004/0053379 A1 | 3/2004 | Lerchl et al. | |
| 2005/0136519 A1 | 6/2005 | Picataggio et al. | |
| 2005/0273885 A1 | 12/2005 | Singh et al. | |

FOREIGN PATENT DOCUMENTS

| | | |
|---|---|---|
| CA | 2533613 | 2/2005 |
| WO | WO 98/46763 A1 | 10/1998 |
| WO | WO 98/46764 A1 | 10/1998 |
| WO | WO 00/12720 A2 | 3/2000 |
| WO | WO 00/34439 A1 | 6/2000 |
| WO | WO 00/40705 A2 | 7/2000 |
| WO | WO 02/00904 A2 | 1/2002 |
| WO | WO 02/08401 A2 | 1/2002 |
| WO | WO 02057465 | 7/2002 |
| WO | WO 02/077213 | 10/2002 |
| WO | WO 02/081668 A2 | 10/2002 |
| WO | WO 02/090493 A2 | 11/2002 |
| WO | WO 2004/057001 A2 | 7/2004 |
| WO | WO 2004/101753 A2 | 11/2004 |
| WO | WO 2004/101757 A2 | 11/2004 |
| WO | WO 2004/076617 | 12/2004 |
| WO | WO 2005012316 | 2/2005 |
| WO | WO 2005/047479 A2 | 5/2005 |
| WO | WO 2005/103253 A1 | 11/2005 |
| WO | WO 2006/012325 A1 | 2/2006 |
| WO | WO 2006/012326 A1 | 2/2006 |
| WO | WO 2006/052870 A2 | 5/2006 |
| WO | WO 2006/052871 A2 | 5/2006 |
| WO | WO 2006/055322 A2 | 5/2006 |
| WO | WO 2004/071467 A2 | 8/2006 |

OTHER PUBLICATIONS

Fourgoux-Nicol et al, Plant Mol Biol:40 857-872, 1999.*
Pereira et al., Identification of Two Novel Microalgal Enzymes in the Conversion of the 3-Fatty Acid, Eicosapentaenoic Acid, Docosahexaenoic Acid, Biochem. J., 2004, vol. 384:357-366.
Sayanova et al., The Alternative Pathway C20 8-Desaturase From the Non-Photosynthetic Organism *Acanthamoeba castellanii* Is an Atypical Cytochrome B5-Fusion Desaturase, FEBS Lett., 2006, vol. 580:1946-1952.
National Center for Biotechnology Information General Identifier No. 4003522, Accession No. AF078796, Dec. 11, 1998, Michaelson,L.V. et al., Functional Identification of a Fatty Acid Delta5 Desaturase Gene From *Caenorhabditis elegans*.
U.S. Appl. No. 11/190,750, filed Jul. 27, 2005, Stephen K. Picataggio et al.
U.S. Appl. No. 11/198,975, filed Aug. 8, 2005, Quinn Qun Zhu et al.
U.S. Appl. No. 11/225,354, filed Sep. 13, 2005, Zhixiong Xue et al.
U.S. Appl. No. 11/253,882, filed Oct. 19, 2005, Daniel Joseph Macool et al.
U.S. Appl. No. 11/264,784, filed Nov. 1, 2005, Howard Glenn Damude et al.
U.S. Appl. No. 11/264,737, filed Nov. 1, 2005, Howard Glenn Damude et al.
U.S. Appl. No. 11/265,761, filed Nov. 2, 2005, Howard Glenn Damude et al.
U.S. Appl. No. 11/737,772, filed Apr. 20, 2007, Howard Glenn Damude et al.

(Continued)

*Primary Examiner* — Elizabeth McElwain

(57) ABSTRACT

Isolated nucleic acid fragments and recombinant constructs comprising such fragments encoding delta-5 desaturase along with a method of making long chain polyunsaturated fatty acids (PUFAs) using this delta-5 desaturase in plants and oleaginous yeast are disclosed.

22 Claims, 14 Drawing Sheets

(56) References Cited

OTHER PUBLICATIONS

U.S. Appl. No. 11/787,772, filed Apr. 18, 2007, Zhixiong Xue et al.
U.S. Appl. No. 11/740,298, filed Apr. 26, 2007, Narendra S. Yadav et al.
U.S. Appl. No. 60/801,172, filed May 17, 2006, Howard Glenn Damude et al.
U.S. Appl. No. 60/801,119, filed May 17, 2006, Howard Glenn Damude.
U.S. Appl. No. 60/853,563, filed Oct. 23, 2006, Howard Glenn Damude.
U.S. Appl. No. 60/855,177, filed Oct. 30, 2006, Zhixiong Xue et al.
U.S. Appl. No. 11/601,563, filed Nov. 16, 2006, Howard Glenn Damude et al.
U.S. Appl. No. 11/601,564, filed Nov. 16, 2006, Howard Glenn Damude et al.
U.S. Appl. No. 11/635,258, filed Dec. 7, 2006, Howard Glenn Damude et al.
U.S. Appl. No. 11/613,420, filed Dec. 20, 2006, John E. Seip et al.
U.S. Appl. No. 60/909,790, filed Apr. 3, 2007, Howard Glenn Damude.
U.S. Appl. No. 60/911,925, filed Apr. 16, 2007, Howard Glenn Damude et al.
Amine Abbadi et al., Biosynthesis of Very-Long-Chain Polyunsaturated Fatty Acids in Transgenic Oilseeds: Constraints on Their Accumulation, The Plant Cell, vol. 16, pp. 2734-2748, Oct. 2004.
McCaskill D. et al., Lecithin as a Food Ingredient—Properties and Functions, Food Tech Europe, vol. 3, No. 3, pp. 146 and 148, Oct. 1996.
F. Domergue et al., Method for producing polyunsaturated fatty acids, novel bioysnthesis genes and novel plant expression constructs, Database EPO Proteins (online) Sequence 31 from patent WO02057465, retrieved from EBI accession No. EPOP: AX481641, Aug. 16, 2002, XP-002474581.
T. Zank et al., Method for the production of multiply-unsaturated fatty acids in transgenic organisms, Database EPO Proteins (online) Sequence 6 from Patent WO2005012316, retrieved from EBI accession No. EPOP: CS020052, Feb. 23, 2005, XP002474582.
F. Domergue et al., Cloning and functional characterization of *Phaeodactylum tricornutum* from-end desaturases involved in eicosapentaenoic acid biosynthesis, Database UniProt (online, retrieved from EBI accession No. UNIPROT: Q8RXB1, Jun. 1, 2002, XP002474583.
James G. Wallis et al., The Delta-8 Desaturase of *Euglena gracilis* : An Alternate Pathway for Synthesis of 20-Carbon Polyunsaturated Fatty Acids, archives of Biochemistry and Biophysics, vol. 365, No. 2, pp. 307-316, May 15, 1999.
Astrid Meyer et al., Biosynthesis of Docosahexaenoic Acid in *Euglena gracilis*: Biochemical and Molecular Evidence for the Involvement of Delta4-Fatty Acyl Group Desaturase, Biochemistry 42, pp. 9779-9788, Mar. 19, 2003.
F. Domergue et al., Cloning and functional characterization of *Phaeodactylum tricornutum* from-end desaturases involved in eicosapentaenoic acid biosynthesis, Eur. J. Biochem, vol. 269, No. 16, pp. 4105-4113, Aug. 2002.
National Center for Biotechnology Information General Identifier No. 3859487, Nov. 11, 1998, D.S. Knutzon et al., Identification of Delta-5 Desaturase From *Mortierella alpina* by Heterologous Expression in Bakers Yeast and Canola, AF067654.
National Center for Biotechnology Information General Identifier No. 4150955, Apr. 17, 2003, T. Saito et al., A Second Functional Delta5 Fatty Acid Desaturase in the Cellular Slime Mould *Dictyostelium discoideum*, AB022097.
National Center for Biotechnology Information General Identifier No. 16033740, Mar. 24, 2005, H. Hong et al., Isolation and Characterization of a Delta5 FA Desaturase From *Pythium irregulare* by Heterologous Expression in *Saccharomyces cerevisiae* and Oilseed Crops, AAL13311.
National Center for Biotechnology Information General Identifier No. 23894018, Apr. 15, 2005, E. Hornung et al., Specific Formation of Archidonic Acid by a Front-End Delta5-Desaturase From *Phytophthora megasperma*, CAD53323.
National Center for Biotechnology Information General Identifier No. 19879687, Aug. 23, 2002, F. Domergue et al., Cloning and Functional Characterization of *Phaeodactylum tricornutum* Front-End Desaturases Involved in Eicosapentaenoic Acid Biosynthesis, AAL92562.
National Center for Biotechnology Information General Identifier No. 66812304, Aug. 17, 2006, L. Eichinger et al., The Genome of the Social Amoeba *Dictyostelium discoideum*, XP_640331.
National Center for Biotechnology Information General Identifier No. 60172920, Jul. 16, 2005, T. Tonon et al., Fatty Acid Desaturaes From the Microalga *Thalassiosira pseudonana*, AAX14502.
National Center for Biotechnology Information General Identifier No. 60499699, Nov. 1, 2005, H. Lu et al., Identification and Characterization of a Novel 6-Fatty Acid Desaturase Gene From *Rhizopus nigricans*, NCBI AAX22052.
National Center for Biotechnology Information General Identifier No. 83027409, Dec. 7, 2005, Y.B. Zhang et al., Identification and Characterization of a Novel 6-Fatty Acid Desaturases Gene From *Rhizopus stolonifer*, ABB96724.
National Center for Biotechnology Information General Identifier No. 17226122, Mar. 8, 2006, B. Qi et al., Identification of a cDNA Encoding a Novel C18-Delta (9) Polyunsaturated Fatty Acid, AF390174.
National Center for Biotechnology Information General Identifier No. 34221934, Jul. 28, 2004, E. Sakuradani et al., Gene Cloning and Functional Analysis of a Second Delta 6-Fatty Acid Desaturase From an Arachidonic Acid-Producing *Mortierella* Fungus, BAC82361.
U.S. Appl. No. 60/910,831, filed Apr. 10, 2007, Howard Glenn Damude et al.
U.S. Appl. No. 60/915,733, filed May 3, 2007, Howard Glenn Damude et al.
U.S. Appl. No. 60/795,810, filed Apr. 28, 2006, Howard Glenn Damude et al.
U.S. Appl. No. 60/801,119, filed May 17, 2006, Howard Glenn Damude et al.
U.S. Appl. No. 10/840,579, filed May 6, 2004, Stephen K. Picataggio et al.
U.S. Appl. No. 10/840,325, filed May 6, 2004, Narendra S. Yadav et al.
U.S. Appl. No. 10/869,630, filed Jun. 16, 2004, Stephen K. Picataggio et al.
U.S. Appl. No. 10/882,760, filed Jul. 1, 2004, Narendra S. Yadav et al.
U.S. Appl. No. 10/985,254, filed Nov. 10, 2004, Narendra S. Yadav et al.
U.S. Appl. No. 10/985,691, filed Nov. 10, 2004, Narendra S. Yadav et al.
U.S. Appl. No. 11/024,544, filed Dec. 29, 2004, Narendra S. Yadav et al.
U.S. Appl. No. 11/166,993, filed Jun. 24, 2005, Howard Glenn Damude et al.
U.S. Appl. No. 11/183,664, filed Jul. 18, 2005, Stephen K. Picataggio et al.
U.S. Appl. No. 11/185,301, filed Jul. 20, 2005, Zhixiong Xue et al.
J. Dyerberg et al., Fatty Acid Composition of the Plasma Lipids in Greenland Eskimos, Amer. J. Clin. Nutr., 1975, vol. 28:958-866.
J. Dyerberg et al., Eicosapentaenoic Acid and Prevention of Thrombosis and Atherosclerosis?, Lancet., 1978, vol. 2:117-119.
Schacky et al., 3 Fatty Acids From Eskimos to Clinical Cardiology—What Took US So Long?, World Rev. Nutr. Diet, 2001, vol. 88:90-99.
Shimokawa, Beneficial Effects of Eicosapentaenoic Acid on Endothelial Vasodilator Functions in Animals and Humans, World Rev. Nutr. Diet, 2001, vol. 88:100-108.
National Center for Biotechnology Information General Identifier No. 6842049, Jun. 21, 2000, H.P. Cho et al., Cloning, Expression, and Fatty Acid Deregulation of the Human Delta-5 Desaturase, AF199596.
National Center for Biotechnology Information General Identifier No. 7861969, May 17, 2000, A.E. Leonard et al., cDNA Cloning and Characterization of Human Delta-5 Desaturase Involved in the Biosynthesis of Archidonic Acid, AF226273.

(56) References Cited

OTHER PUBLICATIONS

National Center for Biotechnology Information General Identifier No. 11386008, Aug. 13, 2001, R. Zolfaghari et al., Fatty Acid Delta (5)-Desaturase mRNA Is Regulated by Dietary Vitamin A and Exogenous Retinoic Acid in Liver of Adult Rate, AF320509.

National Center for Biotechnology Information General Identifier No. 16151828, Oct. 16, 2001, T. Matsuzaka et al., Dual Gene Regulation of Mouse Delta-5 and -6 Desaturases by SREBP-1 and PPAR Alpha, AB072976.

National Center for Biotechnology Information General Identifier No. 20069122, Apr. 8, 2002, X. Qiu et al., Identification of a Delta 4 Fatty Acid Desaturase From *Thraustochytrium* sp. Involved in the Biosynthesis of Docosahexanoic Acid by Heterologous Expression in *Saccharomyces cerevisiae* and *Brassica Juncea*, AF489588.

National Center for Biotechnology Information General Identifier No. 23894017, Apr. 15, 2005, E. Hornung et al., Specific Formation of Arachidonic Acid by a Front-End Delta5-Desaturase From *Phytophthora megasperma*, AJ510244.

National Center for Biotechnology Information General Identifier No. 16033739, Mar. 24, 2005, H. Hong et al., Isolation and Characterization of a Delta5 FA Desaturase From *Pythium irregulare* by Heterologous Expression in *Saccharomyces cerevisiae* and Oilseed Crops, AF419297.

Okuley, John et al., "*Arabidopsis* FAD2 Gene Encodes the Enzyme That is Essential for Polyunsaturated Lipid Synthesis," *The Plant Cell*, 1994, vol. 6, pp. 147-158.

Dyerberg, J., et al., "Fatty acid composition of the plasma lipids in Greenland Eskimos," *The American Journal of Clinical Nutrition*, 1975, vol. 28, pp. 958-966.

Dyerberg, J., et al., "Eicosapentaenoic Acid and Prevention of Thrombosis and Atherosclerosis?," *The Lancet*, 1978, vol. 2, pp. 117-119.

Genbank Accession No. ADR49327, "cytochrome oxidase subunit 1 [*Hymenoptera* sp. BOLD: AAE4683]," 2010.

Genbank Accession No. AF199596, "*Homo sapiens* delta-5 desaturase mRNA, complete cds," 2000.

Genbank Accession No. AF226273, "*Homo sapiens* delta-5 fatty acid desaturase (FADSD5) mRNA, complete cds," 2000.

Genbank Accession No. AF320509, "*Rattus norvegicus* liver delta-5 desaturase mRNA, complete cds," 2001.

Genbank Accession No. AF489588, "*Thraustochytrium* sp. ATCC21685 delta-5 fatty acid desaturase mRNA, complete cds," 2002.

International Search Report for PCT/US2007/011776, (2008).

Shimokawa, Hiroaki, "Beneficial Effects of Eicosapentaenoic Acid on Endothelial Vasodilator Functions in Animals and Humans," *World Rev Nutr Diet*, 2001, vol. 88, pp. 100-108.

Von Schacky, C., et al., "From Eskimos to Clinical Cardiology—What Took Us so Long?" *World Rev Nutr Diet*, 2001, vol. 88, pp. 90-99.

\* cited by examiner

| Fatty Acid | Clone | Gene | Fatty acid composition (wt.%) | | | | | | | | | | | | | | |
|---|---|---|---|---|---|---|---|---|---|---|---|---|---|---|---|---|---|
| | | | 16:0 | 16:1 | 18:0 | 18:1 | LA | GLA | ALA | STA | EDA | SCI | DGLA | ARA | ETrA | JUP | ETA | EPA |
| None | pY98 | MaD5 | 9.5 | 9.5 | 0.7 | 37.4 | 42.8 | 0.0 | 0.0 | 0.0 | 0.0 | 0.0 | 0.0 | 0.0 | 0.0 | 0.0 | 0.0 | 0.0 |
| | pDMW367 | EgD5 | 9.8 | 10.0 | 0.3 | 24.1 | 55.7 | 0.0 | 0.0 | 0.0 | 0.0 | 0.0 | 0.0 | 0.0 | 0.0 | 0.0 | 0.0 | 0.0 |
| EDA | pY98 | MaD5 | 9.8 | 8.2 | 0.8 | 39.7 | 34.1 | 0.0 | 0.0 | 0.0 | 7.1 | 0.2 | 0.0 | 0.0 | 0.0 | 0.0 | 0.0 | 0.0 |
| | pDMW367 | EgD5 | 9.6 | 7.7 | 0.9 | 33.6 | 39.4 | 0.0 | 0.0 | 0.0 | 8.1 | 0.8 | 0.0 | 0.0 | 0.0 | 0.0 | 0.0 | 0.0 |
| DGLA | pY98 | MaD5 | 12.0 | 6.8 | 1.4 | 38.8 | 19.3 | 0.6 | 0.0 | 0.0 | 0.0 | 0.0 | 18.2 | 3.0 | 0.0 | 0.0 | 0.0 | 0.0 |
| | pDMW367 | EgD5 | 12.4 | 6.9 | 0.9 | 32.8 | 22.9 | 1.1 | 0.0 | 0.0 | 0.0 | 0.0 | 13.7 | 9.3 | 0.0 | 0.0 | 0.0 | 0.0 |
| ETrA | pY98 | MaD5 | 8.9 | 7.2 | 1.0 | 41.2 | 17.2 | 0.0 | 12.1 | 0.0 | 0.0 | 0.0 | 0.0 | 0.0 | 11.7 | 0.6 | 0.0 | 0.0 |
| | pDMW367 | EgD5 | 8.8 | 7.2 | 0.6 | 35.8 | 18.4 | 0.0 | 16.2 | 0.0 | 0.0 | 0.0 | 0.0 | 0.0 | 12.3 | 0.7 | 0.0 | 0.0 |
| ETA | pY98 | MaD5 | 11.9 | 6.5 | 0.8 | 38.5 | 12.2 | 0.0 | 0.0 | 0.4 | 0.0 | 0.0 | 0.0 | 0.0 | 0.0 | 0.0 | 26.1 | 3.6 |
| | pDMW367 | EgD5 | 10.4 | 7.1 | 0.6 | 30.2 | 16.2 | 0.0 | 0.0 | 0.9 | 0.0 | 0.0 | 0.0 | 0.0 | 0.0 | 0.0 | 23.6 | 11.0 |

B

| Fatty Acid | Clone | Gene | % delta-5 desat | Ratio Desat Eg/Ma | Ratio Prod/By-Prod | Ratio Prod/By-Prod Eg/Ma | Ratio n-6/n-3 |
|---|---|---|---|---|---|---|---|
| None | pY98 | MaD5 | | | | | |
| | pDMW367 | EgD5 | | | | | |
| EDA | pY98 | MaD5 | 3.4 | 2.7 | | | 0.68 |
| | pDMW367 | EgD5 | 8.9 | | | | 1.76 |
| DGLA | pY98 | MaD5 | 14.0 | 2.9 | 4.17 | 1.08 | 1.17 |
| | pDMW367 | EgD5 | 40.3 | | 4.52 | | 1.27 |
| ETrA | pY98 | MaD5 | 4.9 | 1.0 | | | |
| | pDMW367 | EgD5 | 5.1 | | | | |
| ETA | pY98 | MaD5 | 12.0 | 2.6 | 2.44 | 2.56 | |
| | pDMW367 | EgD5 | 31.8 | | 6.25 | | |

FIG. 12A

Average Fatty acid composition (wt. %)

| Event | 16:0 | 18:0 | 18:1 | LA | ALA | EDA | SCI | DGLA | ARA | ERA | JUP | ETA | EPA | Other | Correct % delta-5 desat | Wrong % delta-5 desat |
|---|---|---|---|---|---|---|---|---|---|---|---|---|---|---|---|---|
| 2010-5-4-1 | 13.4 | 2.7 | 8.1 | 25.9 | 13.8 | 4.9 | 5.1 | 0.0 | 0.8 | 1.7 | 8.9 | 0.0 | 9.0 | 5.7 | 100.0 | 67.7 |
| 2010-5-12-1 | 17.2 | 5.0 | 14.3 | 28.4 | 12.5 | 5.7 | 0.8 | 0.3 | 0.0 | 2.1 | 4.8 | 0.4 | 6.0 | 2.6 | 89.3 | 41.5 |
| 2010-13-2-1 | 14.6 | 4.5 | 17.6 | 25.0 | 6.6 | 9.9 | 1.7 | 1.1 | 0.5 | 1.7 | 3.8 | 0.5 | 8.8 | 3.7 | 85.2 | 32.0 |
| 2010-9-10-1 | 17.2 | 4.3 | 14.7 | 22.1 | 7.1 | 7.1 | 0.7 | 0.8 | 0.1 | 3.4 | 5.9 | 1.7 | 10.5 | 4.4 | 80.6 | 38.8 |
| 2010-13-3-1 | 15.9 | 4.5 | 15.0 | 28.5 | 9.2 | 7.6 | 0.1 | 2.1 | 0.5 | 1.3 | 2.2 | 0.6 | 9.5 | 3.0 | 78.1 | 20.8 |
| 2010-6-2-1 | 17.9 | 3.4 | 10.1 | 18.8 | 9.4 | 8.1 | 0.8 | 0.3 | 0.1 | 6.6 | 15.1 | 1.3 | 4.9 | 3.3 | 76.4 | 52.0 |
| 2010-6-1-1 | 16.9 | 3.2 | 9.8 | 22.5 | 7.6 | 19.2 | 2.1 | 3.5 | 6.5 | 2.7 | 0.8 | 0.5 | 2.6 | 2.0 | 69.5 | 11.8 |
| 2010-12-8-1 | 16.0 | 3.9 | 14.9 | 17.2 | 5.2 | 18.2 | 0.3 | 1.9 | 0.0 | 7.0 | 2.2 | 1.9 | 8.4 | 2.9 | 68.8 | 9.2 |
| 2010-9-13-1 | 16.6 | 3.6 | 8.6 | 26.3 | 13.1 | 7.4 | 0.8 | 7.2 | 7.6 | 1.6 | 0.2 | 1.0 | 4.2 | 1.7 | 59.0 | 10.2 |
| 2010-12-4-1 | 15.7 | 4.2 | 27.6 | 17.2 | 4.7 | 6.7 | 0.0 | 3.5 | 0.0 | 1.6 | 0.0 | 6.8 | 7.2 | 4.9 | 41.2 | 0.0 |

FIG. 12B

Average Fatty acid composition (wt. %)

| Event | 16:0 | 18:0 | 18:1 | LA | ALA | EDA | SCI | DGLA | ARA | ERA | JUP | ETA | EPA | Other | Correct % delta-5 desat | Wrong % delta-5 desat |
|---|---|---|---|---|---|---|---|---|---|---|---|---|---|---|---|---|
| 2036-5-1-1 | 14.1 | 3.8 | 18.8 | 26.6 | 8.3 | 9.8 | 1.4 | 0.0 | 0.3 | 2.4 | 3.4 | 0.1 | 8.2 | 2.7 | 98.6 | 28.2 |
| 2041-5-4-1 | 16.7 | 4.4 | 17.1 | 32.5 | 11.1 | 7.3 | 0.3 | 0.0 | 0.1 | 2.1 | 1.4 | 0.1 | 5.4 | 1.5 | 97.8 | 15.2 |
| 2036-6-1-1 | 14.2 | 3.3 | 19.3 | 32.1 | 11.5 | 6.0 | 0.3 | 0.1 | 0.2 | 1.7 | 2.3 | 0.1 | 6.7 | 2.4 | 97.0 | 25.3 |
| 2036-5-3-1 | 12.7 | 2.7 | 17.2 | 29.4 | 7.4 | 10.2 | 0.4 | 0.2 | 0.3 | 2.0 | 1.7 | 0.3 | 12.8 | 2.6 | 96.3 | 14.9 |
| 2041-6-1-1 | 16.4 | 4.2 | 13.2 | 24.9 | 8.4 | 13.8 | 4.8 | 0.4 | 6.2 | 2.0 | 1.1 | 0.0 | 2.3 | 2.3 | 95.0 | 27.2 |
| 2036-3-2-1 | 12.9 | 2.7 | 14.5 | 28.8 | 5.4 | 13.8 | 0.9 | 0.3 | 0.5 | 2.9 | 3.7 | 0.4 | 9.4 | 3.9 | 93.4 | 21.4 |
| 2041-1-3-1 | 15.0 | 4.5 | 23.7 | 21.5 | 9.1 | 8.3 | 1.0 | 0.7 | 7.4 | 1.5 | 0.6 | 0.3 | 3.8 | 2.6 | 92.3 | 13.8 |
| 2036-7-2-1 | 18.0 | 4.5 | 16.5 | 25.3 | 13.2 | 5.4 | 0.4 | 0.9 | 8.9 | 1.0 | 0.2 | 0.4 | 3.1 | 2.2 | 90.1 | 9.1 |
| 2036-6-5-1 | 13.3 | 3.0 | 18.5 | 25.3 | 6.9 | 10.1 | 0.6 | 0.9 | 3.1 | 1.2 | 0.4 | 0.9 | 12.4 | 3.3 | 89.6 | 8.1 |
| 2036-6-7-1 | 12.8 | 3.4 | 14.9 | 30.2 | 6.0 | 13.3 | 0.7 | 2.7 | 8.8 | 1.1 | 0.2 | 0.7 | 2.4 | 2.9 | 76.5 | 5.5 |

SEQUENCE LISTING

```
<160> NUMBER OF SEQ ID NOS: 94

<210> SEQ ID NO 1
<211> LENGTH: 1350
<212> TYPE: DNA
<213> ORGANISM: Euglena gracilis
<220> FEATURE:
<221> NAME/KEY: misc_feature
<222> LOCATION: (1)..(1350)
<223> OTHER INFORMATION: delta-5 desaturase

<400> SEQUENCE: 1
atggctctca gtcttaccac agaacagctg ttagaacgcc ctgatttggt tgcgattgat      60
ggcatcctct acgaccttga agggcttgcc aaagttcatc caggaggaga tttgattctc     120
gcttctggtg cctctgatgc ctcccctctc ttttattcaa tgcatccata cgtcaaaccg     180
gagaattcca aattgcttca acagttcgtc cgagggaagc atgaccgcac ctcgaaggac     240
attgtctaca cgtatgattc tccttcgca caagacgtta agcggacaat gcgcgaggtg      300
atgaaaggga ggaactggta cgcaacccct ggcttctggc tgcgcaccgt tgggatcatc     360
gccgtgacgg ccttttgcga gtggcactgg gctaccacgg ggatggtgct gtggggcctg     420
ttgactggat tcatgcacat gcagatcggc ttatccatcc agcatgatgc gtcccacggg     480
gccatcagca agaagccttg ggtcaacgcc ctcttcgcct acggcattga cgtcatcgga     540
tcgtcccggt ggatttggct gcagtcgcac atcatgcggc accacaccta caccaaccag     600
cacggcctcg acctggatgc ggagtcggca gagccgttcc tggtgttcca caactacccc     660
gccgcaaaca ccgcccgaaa gtggttccac cgcttccaag cttggtacat gtaccttgtg     720
ctgggggcat acgggtatc gctggtgtac aacccgctct acattttccg gatgcagcac     780
aatgacacca tcccagagtc tgtcacggcc atgcgggaga tggctttct gcggcgctac    840 cgcacacttg cattcgtgat gcgagctttc ttcatcttcc ggaccgcatt cttgccctgg    900
tacctcactg ggacctcatt gctgatcacc attcctctgg tgcccactgc aactggtgcc    960
ttcttgacgt tcttcttcat tttgtcccac aattttgatg gctccgaacg gatccccgac  1020
```

```
aagaactgca aggttaagag ctctgagaag gacgttgagg ctgaccaaat tgactggtat   1080
cgggcgcagg tggagacgtc ctccacatac ggtggcccca tcgccatgtt cttcactggc   1140
ggtctcaatt ccagatcga gcaccacctc tttccccgga tgtcgtcttg cactacccc    1200 ttcgtccagc aggcggtccg ggagtgttgc gaacgccatg gagtgcgata tgttttctac   1260
cctaccatcg tcggcaacat catctccacc ctgaagtaca tgcataaggt gggtgtcgtc   1320
cactgcgtga aggacgcaca ggattcctga                                   1350
```

<210> SEQ ID NO 2
<211> LENGTH: 449
<212> TYPE: PRT
<213> ORGANISM: Euglena gracilis

<400> SEQUENCE: 2

```
Met Ala Leu Ser Leu Thr Thr Glu Gln Leu Leu Glu Arg Pro Asp Leu
1               5                   10                  15

Val Ala Ile Asp Gly Ile Leu Tyr Asp Leu Glu Gly Leu Ala Lys Val
            20                  25                  30

His Pro Gly Gly Asp Leu Ile Leu Ala Ser Gly Ala Ser Asp Ala Ser
        35                  40                  45

Pro Leu Phe Tyr Ser Met His Pro Tyr Val Lys Pro Glu Asn Ser Lys
    50                  55                  60

Leu Leu Gln Gln Phe Val Arg Gly Lys His Asp Arg Thr Ser Lys Asp
65                  70                  75                  80

Ile Val Tyr Thr Tyr Asp Ser Pro Phe Ala Gln Asp Val Lys Arg Thr
                85                  90                  95

Met Arg Glu Val Met Lys Gly Arg Asn Trp Tyr Ala Thr Pro Gly Phe
            100                 105                 110

Trp Leu Arg Thr Val Gly Ile Ile Ala Val Thr Ala Phe Cys Glu Trp
        115                 120                 125

His Trp Ala Thr Thr Gly Met Val Leu Trp Gly Leu Leu Thr Gly Phe
    130                 135                 140

Met His Met Gln Ile Gly Leu Ser Ile Gln His Asp Ala Ser His Gly
145                 150                 155                 160

Ala Ile Ser Lys Lys Pro Trp Val Asn Ala Leu Phe Ala Tyr Gly Ile
                165                 170                 175

Asp Val Ile Gly Ser Ser Arg Trp Ile Trp Leu Gln Ser His Ile Met
            180                 185                 190

Arg His His Thr Tyr Thr Asn Gln His Gly Leu Asp Leu Asp Ala Glu
        195                 200                 205

Ser Ala Glu Pro Phe Leu Val Phe His Asn Tyr Pro Ala Ala Asn Thr
    210                 215                 220

Ala Arg Lys Trp Phe His Arg Phe Gln Ala Trp Tyr Met Tyr Leu Val
225                 230                 235                 240

Leu Gly Ala Tyr Gly Val Ser Leu Val Tyr Asn Pro Leu Tyr Ile Phe
                245                 250                 255

Arg Met Gln His Asn Asp Thr Ile Pro Glu Ser Val Thr Ala Met Arg
            260                 265                 270

Glu Asn Gly Phe Leu Arg Arg Tyr Arg Thr Leu Ala Phe Val Met Arg
        275                 280                 285

Ala Phe Phe Ile Phe Arg Thr Ala Phe Leu Pro Trp Tyr Leu Thr Gly
    290                 295                 300

Thr Ser Leu Leu Ile Thr Ile Pro Leu Val Pro Thr Ala Thr Gly Ala
```

```
                305                 310                 315                 320
      Phe Leu Thr Phe Phe Phe Ile Leu Ser His Asn Phe Asp Gly Ser Glu
                       325                 330                 335

Arg Ile Pro Asp Lys Asn Cys Lys Val Lys Ser Ser Glu Lys Asp Val
                       340                 345                 350

Glu Ala Asp Gln Ile Asp Trp Tyr Arg Ala Gln Val Glu Thr Ser Ser
                       355                 360                 365

Thr Tyr Gly Gly Pro Ile Ala Met Phe Phe Thr Gly Gly Leu Asn Phe
              370                 375                 380

Gln Ile Glu His His Leu Phe Pro Arg Met Ser Ser Trp His Tyr Pro
      385                 390                 395                 400

Phe Val Gln Gln Ala Val Arg Glu Cys Cys Glu Arg His Gly Val Arg
                       405                 410                 415

Tyr Val Phe Tyr Pro Thr Ile Val Gly Asn Ile Ile Ser Thr Leu Lys
                       420                 425                 430

Tyr Met His Lys Val Gly Val Val His Cys Val Lys Asp Ala Gln Asp
              435                 440                 445

Ser
```

<210> SEQ ID NO 3
<211> LENGTH: 1350
<212> TYPE: DNA
<213> ORGANISM: Euglena gracilis
<220> FEATURE:
<221> NAME/KEY: misc_feature
<223> OTHER INFORMATION: synthetic delta-5 desaturase (codon-optimized)
      for Yarrowia lipolytica

<400> SEQUENCE: 3

```
atggctctct cccttactac cgagcagctg ctcgagcgac ccgacctggt tgccatcgac      60
ggcattctct acgatctgga aggtcttgcc aaggtccatc ccggaggcga cttgatcctc     120
gcttctggtg cctccgatgc ttctcctctg ttctactcca tgcacccctt cgtcaagccc     180
gagaactcga agctgcttca acagttcgtg cgaggcaagc acgaccgaac ctccaaggac     240
attgtctaca cctacgactc tccctttgca caggacgtca agcgaactat gcgagaggtc     300
atgaaaggtc ggaactggta tgccacacct ggattctggc tgcgaaccgt tggcatcatt     360
gctgtcaccg cctttgcga gtggcactgg gctactaccg gaatggtgct gtggggtctc     420
ttgactggat tcatgcacat gcagatcggc ctgtccattc agcacgatgc tctctcatggt     480
gccatcagca aaaagccctg gtcaacgct ctctttgcct acggcatcga cgtcattgga     540
tcgtccagat ggatctggct gcagtctcac atcatgcgac atcacaccta caccaatcag     600
catggtctcg acctggatgc cgagtccgca gaaccattcc ttgtgttcca caactaccct     660
gctgccaaca ctgctcgaaa gtggtttcac cgattccagg cctggtacat gtacctcgtg     720
cttgagcct acggcgtttc gctggtgtac aaccctctct acatcttccg aatgcagcac     780
aacgacacca ttcccgagtc tgtcacagcc atgcgagaga cggctttct gcgacggtac     840
cgaacccttg cattcgttat gcgagctttc ttcatctttc gaaccgcctt cttgccctgg     900
tatctcactg aacctccct gctcatcacc attcctctgg tgcccactgc taccggtgcc     960
ttcctcacct tcttttcat cttgtctcac aacttcgatg gctcggagcg aatccccgac    1020
aagaactgca aggtcaagag ctccgagaag gacgttgaag ccgatcagat cgactggtac    1080
agagctcagg tggagacctc ttccacctac ggtggaccca ttgccatgtt ctttactggc    1140
ggtctcaact tccagatcga gcatcacctc tttcctcgaa tgtcgtcttg gcactatccc    1200
```

```
ttcgtgcagc aagctgtccg agagtgttgc gaacgacacg gagttcggta cgtcttctac    1260
cctaccattg tgggcaacat catttccacc ctcaagtaca tgcacaaagt cggtgtggtt    1320
cactgtgtca aggacgctca ggattcctaa                                    1350
```

<210> SEQ ID NO 4
<211> LENGTH: 590
<212> TYPE: DNA
<213> ORGANISM: Euglena gracilis

<400> SEQUENCE: 4

```
ggccaccaca tctacaccaa ccagcacggc ctcgacctgg atgcggagtc ggcagagccg     60
ttcctggtgt tccacaacta ccccgccgca acaccgccc gaaagtggtt ccaccgcttc    120
caagcttggt acatgtacct tgtgctgggg catacgggg tatcgctggt gtacaacccg    180
ctctacattt tccggatgca gcacaatgac accatcccag agtctgtcac ggccatgcgg    240
gaaaatggct ttctgcggcg ctaccgcaca cttgcattcg tgatgcgagc tttcttcatc    300
ttccggaccg cattcttgcc ctggtacctc actgggacct cattgctgat caccattcct    360
ctggtgccca ccgcaactgg tgccttcttg acgttcttct tcattttgtc ccacaatttt    420
gatggctccg aacggatccc cgacaagaac tgcaaggtta agagctctga aaggacgtt    480 gaggctgacc aaattgactg gtatcgggcg caggtggaga cgtcctccac atacggtggc    540
cccatcgcca tgttcttcac tggcggtctc aactaccaaa tcgtccacca              590
```

<210> SEQ ID NO 5
<211> LENGTH: 196
<212> TYPE: PRT
<213> ORGANISM: Euglena gracilis

<400> SEQUENCE: 5

```
Gly His His Ile Tyr Thr Asn Gln His Gly Leu Asp Leu Asp Ala Glu
1               5                   10                  15

Ser Ala Glu Pro Phe Leu Val Phe His Asn Tyr Pro Ala Ala Asn Thr
            20                  25                  30

Ala Arg Lys Trp Phe His Arg Phe Gln Ala Trp Tyr Met Tyr Leu Val
        35                  40                  45

Leu Gly Ala Tyr Gly Val Ser Leu Val Tyr Asn Pro Leu Tyr Ile Phe
    50                  55                  60

Arg Met Gln His Asn Asp Thr Ile Pro Glu Ser Val Thr Ala Met Arg
65                  70                  75                  80

Glu Asn Gly Phe Leu Arg Arg Tyr Arg Thr Leu Ala Phe Val Met Arg
                85                  90                  95

Ala Phe Phe Ile Phe Arg Thr Ala Phe Leu Pro Trp Tyr Leu Thr Gly
            100                 105                 110

Thr Ser Leu Leu Ile Thr Ile Pro Leu Val Pro Thr Ala Thr Gly Ala
        115                 120                 125

Phe Leu Thr Phe Phe Phe Ile Leu Ser His Asn Phe Asp Gly Ser Glu
    130                 135                 140

Arg Ile Pro Asp Lys Asn Cys Lys Val Lys Ser Ser Glu Lys Asp Val
145                 150                 155                 160

Glu Ala Asp Gln Ile Asp Trp Tyr Arg Ala Gln Val Glu Thr Ser Ser
                165                 170                 175

Thr Tyr Gly Gly Pro Ile Ala Met Phe Phe Thr Gly Gly Leu Asn Tyr
            180                 185                 190
```

Gln Ile Val His
    195

<210> SEQ ID NO 6
<211> LENGTH: 797
<212> TYPE: DNA
<213> ORGANISM: Euglena gracilis

<400> SEQUENCE: 6

| | | | | | |
|---|---|---|---|---|---|
| cacagaacag | ctgttagaac | gccctgattt | ggttgcgatt | gatggcatcc | tctacgacct | 60 |
| tgaagggctt | gccaaagttc | atccaggagg | agatttgatt | ctcgcttctg | gtgcctctga | 120 |
| tgcctcccct | ctcttttatt | caatgcatcc | atacgtcaaa | ccggagaatt | ccaaattgct | 180 |
| tcaacagttc | gtccgaggga | agcatgaccg | cacctcgaag | gacattgtct | acacgtatga | 240 |
| ttctcccttc | gcacaagacg | ttaagcggac | aatgcgcgag | gtgatgaaag | ggaggaactg | 300 |
| gtacgcaacc | cctggcttct | ggctgcgcac | cgttgggatc | atcgccgtga | cggccttttg | 360 |
| cgagtggcac | tgggctacca | cggggatggt | gctgtggggc | ctgttgactg | gattcatgca | 420 |
| catgcagatc | ggcttatcca | tccagcatga | tgcgtcccac | ggggccatca | gcaaggagcc | 480 |
| ttgggtcaac | gccctcttcg | cctacggcat | tgacgtcatc | ggatcgtccc | ggtggatttg | 540 |
| gctgcagtca | cacatcatgc | ggcaccacac | ctacaccaac | cagcacggcc | tcgacctgga | 600 |
| tgcggagtcg | gcagagccgt | tcctggtgtt | ccacagctac | cccgccgcaa | acaccgcccg | 660 |
| aaagtggttc | caccgcttcc | aagcttggta | catgtacctt | gcgctggggg | catacggggt | 720 |
| atcgctggtg | tacaacccgc | tctacatttt | ccggatgcag | cacaatgaca | ccatcccaga | 780 |
| gtctgtcacg | gccatgc | | | | | 797 |

<210> SEQ ID NO 7
<211> LENGTH: 559
<212> TYPE: DNA
<213> ORGANISM: Euglena gracilis

<400> SEQUENCE: 7

| | | | | | |
|---|---|---|---|---|---|
| cacagaacag | ctgttagaac | gccctgattt | ggttgcgatt | gatggcatcc | tctacgacct | 60 |
| tgaagggctt | gccaaagttc | atccaggagg | agatttgatt | ctcgcttctg | gtgcctctga | 120 |
| tgcctcccct | ctcttttatt | caatgcatcc | atacgtcaaa | ccggagaatt | ccaaattgct | 180 |
| tcaacagttc | gtccgaggga | agcatgaccg | cacctcgaag | gacattgtct | acacgtatga | 240 |
| ttctcccttc | gcacaagacg | ttaagcggac | aatgcgcgag | gtgatgaaag | ggaggaactg | 300 |
| gtacgcaacc | cctggcttct | ggctgcgcac | cgttgggatc | atcgccgtga | cggccttttg | 360 |
| cgagtggcac | tgggctacca | cggggatggt | gctgtggggc | ctgttgactg | gattcatgca | 420 |
| catgcagatc | ggcttatcca | tccagcatga | tgcgtcccac | ggggccatca | gcaaggagcc | 480 |
| ttgggtcaac | gccctcttcg | cctacggcat | tgacgtcatc | ggatcgtccc | ggtggatttg | 540 |
| gctgcagtca | cacatcatg | | | | | 559 |

<210> SEQ ID NO 8
<211> LENGTH: 273
<212> TYPE: DNA
<213> ORGANISM: Euglena gracilis

<400> SEQUENCE: 8

| | | | | | |
|---|---|---|---|---|---|
| ggaatggctc | tcagtcttac | cacagaacag | ctgttagaac | gccctgattt | ggttgcgatt | 60 |
| gatggcatcc | tctacgacct | tgaagggctt | gccaaagttc | atccaggagg | agatttgatt | 120 |

```
ctcgcttctg gtgcctctga tgcctcccct ctctttattt caatgcatcc atacgtcaaa      180
ccggagaatt ccaaattgct tcaacagttc gtccgaggga agcatgaccg cacctcgaag      240
gacattgtct acacgtatga ttctcccttc gca                                   273

<210> SEQ ID NO 9
<211> LENGTH: 20
<212> TYPE: DNA
<213> ORGANISM: Euglena gracilis

<400> SEQUENCE: 9
ggaatggctc tcagtcttac                                                   20

<210> SEQ ID NO 10
<211> LENGTH: 728
<212> TYPE: DNA
<213> ORGANISM: Euglena gracilis

<400> SEQUENCE: 10
cctcactggg acctcattgc tgatcaccat tcctctggtg cccacygcaa ctggtgcctt       60
cttgacgttc ttcttcattt tgtcccacaa ttttgatggc tccgaacgga tccccgacaa      120
gaactgcaag gttaagagct ctgagaagga cgttgaggct gaccaaattg actggtatcg      180
ggcgcaggtg gagacgtcct ccacatacgt tggccccatc gccatgttct tcactggcgg      240
tctcaatttc cagatcgagc accacctctt tccccgatg tcgtcttggc actacccctt       300
cgtccagcag gcggtccggg agtgttgcga acgccatgga gtgcgatatg ttttctaccc      360
taccatcgtc ggcaacatca tctccaccct gaagtacatg cataaggtgg tgtcgtcca      420 ctgcgtgaag gacgcacagg attcctgagg ggcagggtga ccaagaacga tcatcgatgt      480
gttcttctgg ccctttggtg gggtactcgc cagattgctc cactgaaccg tatcctaact      540
ctgaccctct ccaaccctgt gttgagtgtt tgctttatgc tccaaagtgg cttcttatt       600 ggtgacccgt ggggcagcgg cacctgtgcc atgcagctga taacccaggc tgctactcta      660
agttggatgg ccaatcgtct ggcattgata tccctgctca gcgttgcatt ccaatggttt      720
gcttatcc                                                              728

<210> SEQ ID NO 11
<211> LENGTH: 464
<212> TYPE: DNA
<213> ORGANISM: Euglena gracilis

<400> SEQUENCE: 11
cctctttccc cggatgtcgt cttggcacta ccccttcgtc cagcaggcgg tccgggagtg       60
ttgcgaacgc catggagtgc gatatgtttt ctaccctacc atcgtcggca acatcatctc      120
caccctgaag tacatgcata aggtgggtgt cgtccactgc gtgaaggacg cacaggattc      180
ctgaggggca gggtgaccaa gaacgatcat cgatgtgttc ttctggccct ttggtggggt      240
actcgccaga ttgctccact gaaccgtatc ctaactctga ccctctccaa ccctgtgttg      300
agtgtttgct ttatgctcca aagtggcttc ttatttggtg acccgtgggg cagcggcacc      360
tgtgccatgc agctgataac ccaggctgct actctaagtt ggatggccaa tcgtctggca      420
ttgatatccc tgctcagcgt tgcattccaa tggtttgctt atcc                      464

<210> SEQ ID NO 12
<211> LENGTH: 456
<212> TYPE: PRT
<213> ORGANISM: Pythium irregulare (GenBank Accession No. AAL13311)
```

<220> FEATURE:
<221> NAME/KEY: MISC_FEATURE
<223> OTHER INFORMATION: delta-5 desaturase

<400> SEQUENCE: 12

```
Met Gly Thr Asp Gln Gly Lys Thr Phe Thr Trp Gln Glu Val Ala Lys
1               5                   10                  15

His Asn Thr Ala Lys Ser Ala Trp Val Ile Ile Arg Gly Glu Val Tyr
            20                  25                  30

Asp Val Thr Glu Trp Ala Asp Lys His Pro Gly Gly Ser Glu Leu Ile
        35                  40                  45

Val Leu His Ser Gly Arg Glu Cys Thr Asp Thr Phe Tyr Ser Tyr His
    50                  55                  60

Pro Phe Ser Asn Arg Ala Asp Lys Ile Leu Ala Lys Tyr Lys Ile Gly
65                  70                  75                  80

Lys Leu Val Gly Gly Tyr Glu Phe Pro Val Phe Lys Pro Asp Ser Gly
                85                  90                  95

Phe Tyr Lys Glu Cys Ser Glu Arg Val Ala Glu Tyr Phe Lys Thr Asn
            100                 105                 110

Asn Leu Asp Pro Lys Ala Ala Phe Ala Gly Leu Trp Arg Met Val Phe
        115                 120                 125

Val Phe Ala Val Ala Ala Leu Ala Tyr Met Gly Met Asn Glu Leu Ile
    130                 135                 140

Pro Gly Asn Val Tyr Ala Gln Tyr Ala Trp Gly Val Val Phe Gly Val
145                 150                 155                 160

Phe Gln Ala Leu Pro Leu Leu His Val Met His Asp Ser Ser His Ala
                165                 170                 175

Ala Cys Ser Ser Ser Pro Ala Met Trp Gln Ile Ile Gly Arg Gly Val
            180                 185                 190

Met Asp Trp Phe Ala Gly Ala Ser Met Val Ser Trp Leu Asn Gln His
        195                 200                 205

Val Val Gly His His Ile Tyr Thr Asn Val Ala Gly Ala Asp Pro Asp
    210                 215                 220

Leu Pro Val Asp Phe Glu Ser Asp Val Arg Arg Ile Val His Arg Gln
225                 230                 235                 240

Val Leu Leu Pro Ile Tyr Lys Phe Gln His Ile Tyr Leu Pro Pro Leu
                245                 250                 255

Tyr Gly Val Leu Gly Leu Lys Phe Arg Ile Gln Asp Val Phe Glu Thr
            260                 265                 270

Phe Val Ser Leu Thr Asn Gly Pro Val Arg Val Asn Pro His Pro Val
        275                 280                 285

Ser Asp Trp Val Gln Met Ile Phe Ala Lys Ala Phe Trp Thr Phe Tyr
    290                 295                 300

Arg Ile Tyr Ile Pro Leu Val Trp Leu Lys Ile Thr Pro Ser Thr Phe
305                 310                 315                 320

Trp Gly Val Phe Phe Leu Ala Glu Phe Thr Thr Gly Trp Tyr Leu Ala
                325                 330                 335

Phe Asn Phe Gln Val Ser His Val Ser Thr Glu Cys Glu Tyr Pro Cys
            340                 345                 350

Gly Asp Ala Pro Ser Ala Glu Val Gly Asp Glu Trp Ala Ile Ser Gln
        355                 360                 365

Val Lys Ser Ser Val Asp Tyr Ala His Gly Ser Pro Leu Ala Ala Phe
    370                 375                 380

Leu Cys Gly Ala Leu Asn Tyr Gln Val Thr His His Leu Tyr Pro Gly
```

```
                385                 390                 395                 400
Ile Ser Gln Tyr His Tyr Pro Ala Ile Ala Pro Ile Ile Asp Val
                    405                 410                 415

Cys Lys Lys Tyr Asn Ile Lys Tyr Thr Val Leu Pro Thr Phe Thr Glu
                    420                 425                 430

Ala Leu Leu Ala His Phe Lys His Leu Lys Asn Met Gly Glu Leu Gly
                    435                 440                 445

Lys Pro Val Glu Ile His Met Gly
                    450                 455

<210> SEQ ID NO 13
<211> LENGTH: 477
<212> TYPE: PRT
<213> ORGANISM: Phytophthora megasperma (GenBank Accession No. CAD53323)
<220> FEATURE:
<221> NAME/KEY: MISC_FEATURE
<223> OTHER INFORMATION: delta-5 desaturase

<400> SEQUENCE: 13

Met Ala Pro Ile Glu Thr Val Lys Asp Ala Asn Glu Gly Leu His Gln
1               5                   10                  15

Arg Lys Gly Ala Ala Ala Ser Lys Asp Thr Thr Thr Phe Thr Trp
            20                  25                  30

Gln Asp Val Ala Lys His Asn Thr Ala Lys Ser Ala Trp Val Thr Ile
            35                  40                  45

Arg Gly Val Val Tyr Asp Val Thr Glu Trp Ala Asp Arg His Pro Gly
        50                  55                  60

Gly Arg Glu Leu Val Leu Leu His Ser Gly Arg Glu Cys Thr Asp Thr
65                  70                  75                  80

Phe Asp Ser Tyr His Pro Phe Ser Asp Arg Ala Asp Lys Ile Leu Ala
                85                  90                  95

Lys Tyr Ala Ile Gly Lys Leu Val Gly Gly Ser Glu Phe Pro Thr Tyr
            100                 105                 110

Lys Pro Asp Thr Gly Phe Tyr Lys Glu Cys Cys Asp Arg Val Asn Gln
        115                 120                 125

Tyr Phe Lys Asp Asn Lys Leu Asp Pro Arg Ser Pro Tyr Ser Gly Leu
130                 135                 140

Trp Arg Met Ile Leu Val Ala Ile Val Gly Ala Val Ala Tyr Met Gly
145                 150                 155                 160

Met Asn Gln Leu Leu Pro Gly Asn Ile Tyr Ala His Tyr Ala Trp Gly
                165                 170                 175

Ala Leu Phe Gly Val Cys Gln Ala Leu Pro Leu Leu His Val Met His
            180                 185                 190

Asp Ala Ser His Ala Ala Ile Thr Ser Ser Pro Thr Gly Trp Arg Leu
        195                 200                 205

Ile Gly Arg Leu Ala Met Asp Trp Val Ala Gly Ala Asn Met Val Ser
    210                 215                 220

Trp Leu Asn Gln His Val Val Gly His His Ile Tyr Thr Asn Val Ala
225                 230                 235                 240

Gly Ala Asp Pro Asp Leu Pro Val Asp Phe Lys Ser Asp Val Arg Arg
                245                 250                 255

Ile Val Tyr Arg Gln Val Leu Leu Pro Ile Tyr Lys Tyr Gln His Leu
            260                 265                 270

Tyr Leu Pro Pro Leu Tyr Gly Val Leu Gly Leu Lys Phe Arg Val Gln
        275                 280                 285
```

```
Asp Val Phe Glu Thr Phe Val Thr Leu Thr Asn Gly Pro Leu Arg Val
    290                 295                 300

Asn Pro Leu Ser Val Gly Asp Trp Ala Glu Met Ile Leu Ser Lys Ala
305                 310                 315                 320

Phe Trp Val Phe Tyr Arg Ile Tyr Leu Pro Leu Ala Val Leu Gln Val
                325                 330                 335

Asp Pro Ala Arg Phe Trp Gly Val Phe Phe Leu Ala Glu Phe Ser Thr
            340                 345                 350

Gly Trp Tyr Leu Ala Phe Asn Phe Gln Val Ser His Val Ser Thr Ala
        355                 360                 365

Cys Glu Tyr Pro Gly Gly Asp Glu Glu Val Thr Ser Ile Asp Asp Glu
    370                 375                 380

Trp Ala Ile Ser Gln Val Lys Ser Ser Val Asp Tyr Gly His Gly Ser
385                 390                 395                 400

Phe Ile Thr Thr Phe Leu Thr Gly Ala Leu Asn Tyr Gln Val Thr His
                405                 410                 415

His Leu Phe Pro Gly Val Ser Gln Tyr His Tyr Pro Ala Ile Ala Pro
            420                 425                 430

Leu Ile Leu Asp Val Cys His Lys Tyr Lys Val Lys Tyr Asn Val Leu
        435                 440                 445

Pro Asp Phe Thr Ala Ala Met Ala Gly His Phe Asp His Leu Val Ile
    450                 455                 460

Met Gly Lys Met Gly Lys Arg Val Thr Ile His Met Gly
465                 470                 475

<210> SEQ ID NO 14
<211> LENGTH: 469
<212> TYPE: PRT
<213> ORGANISM: Phaeodactylum tricornutum (GenBank Accession No.
      AAL92562)
<220> FEATURE:
<221> NAME/KEY: MISC_FEATURE
<223> OTHER INFORMATION: delta-5 desaturase

<400> SEQUENCE: 14

Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
            20                  25                  30

Leu Ser Ser Leu Lys Gly Glu Glu Val Cys Ile Asp Gly Ile Ile Tyr
        35                  40                  45

Asp Leu Gln Ser Phe Asp His Pro Gly Gly Glu Thr Ile Lys Met Phe
    50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
    130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
```

```
                165                 170                 175
Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
            260                 265                 270

Leu Asp Leu Gln Gln Arg Gly Ala Leu Ser Val Gly Ile Arg Leu Asp
        275                 280                 285

Asn Ala Phe Ile His Ser Arg Arg Lys Tyr Ala Val Phe Trp Arg Ala
    290                 295                 300

Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
            340                 345                 350

Glu Ser Ala Asp Arg Asp Pro Thr Ala Pro Leu Lys Lys Thr Gly Glu
        355                 360                 365

Pro Val Asp Trp Phe Lys Thr Gln Val Glu Thr Ser Cys Thr Tyr Gly
    370                 375                 380

Gly Phe Leu Ser Gly Cys Phe Thr Gly Gly Leu Asn Phe Gln Val Glu
385                 390                 395                 400

His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
            420                 425                 430

Tyr Pro Trp Ile His Gln Asn Phe Leu Ser Thr Val Arg Tyr Met His
        435                 440                 445

Ala Ala Gly Thr Gly Ala Asn Trp Arg Gln Met Ala Arg Glu Asn Pro
    450                 455                 460

Leu Thr Gly Arg Ala
465

<210> SEQ ID NO 15
<211> LENGTH: 467
<212> TYPE: PRT
<213> ORGANISM: Dictyostelium discoideum (GenBank Accession No.
      XP_640331)
<220> FEATURE:
<221> NAME/KEY: MISC_FEATURE
<223> OTHER INFORMATION: delta-5 desaturase

<400> SEQUENCE: 15

Met Met Glu Thr Asn Asn Glu Asn Lys Glu Lys Leu Lys Leu Tyr Thr
1               5                   10                  15

Trp Asp Glu Val Ser Lys His Asn Gln Lys Asn Asp Leu Trp Ile Ile
            20                  25                  30

Val Asp Gly Lys Val Tyr Asn Ile Thr Lys Trp Val Pro Leu His Pro
        35                  40                  45
```

```
Gly Gly Glu Asp Ile Leu Leu Leu Ser Ala Gly Arg Asp Ala Thr Asn
    50                  55                  60

Leu Phe Glu Ser Tyr His Pro Met Thr Asp Lys His Tyr Ser Leu Ile
 65                  70                  75                  80

Lys Gln Tyr Glu Ile Gly Tyr Ile Ser Ser Tyr Glu His Pro Lys Tyr
                    85                  90                  95

Val Glu Lys Ser Glu Phe Tyr Ser Thr Leu Lys Gln Arg Val Arg Lys
                100                 105                 110

His Phe Gln Thr Ser Ser Gln Asp Pro Lys Val Ser Val Gly Val Phe
                115                 120                 125

Thr Arg Met Val Leu Ile Tyr Leu Phe Leu Phe Val Thr Tyr Tyr Leu
            130                 135                 140

Ser Gln Phe Ser Thr Asp Arg Phe Trp Leu Asn Cys Ile Phe Ala Val
145                 150                 155                 160

Leu Tyr Gly Val Ala Asn Ser Leu Phe Gly Leu His Thr Met His Asp
                165                 170                 175

Ala Cys His Thr Ala Ile Thr His Asn Pro Met Thr Trp Lys Ile Leu
            180                 185                 190

Gly Ala Thr Phe Asp Leu Phe Ala Gly Ala Ser Phe Tyr Ala Trp Cys
            195                 200                 205

His Gln His Val Ile Gly His His Leu Tyr Thr Asn Val Arg Asn Ala
210                 215                 220

Asp Pro Asp Leu Gly Gln Gly Glu Ile Asp Phe Arg Val Val Thr Pro
225                 230                 235                 240

Tyr Gln Ala Arg Ser Trp Tyr His Lys Tyr Gln His Ile Tyr Ala Pro
                245                 250                 255

Ile Leu Tyr Gly Val Tyr Ala Leu Lys Tyr Arg Ile Gln Asp His Glu
                260                 265                 270

Ile Phe Thr Lys Lys Ser Asn Gly Ala Ile Arg Tyr Ser Pro Ile Ser
            275                 280                 285

Thr Ile Asp Thr Ala Ile Phe Ile Leu Gly Lys Leu Val Phe Ile Ile
        290                 295                 300

Ser Arg Phe Ile Leu Pro Leu Ile Tyr Asn His Ser Phe Ser His Leu
305                 310                 315                 320

Ile Cys Phe Phe Leu Ile Ser Glu Leu Val Leu Gly Trp Tyr Leu Ala
                325                 330                 335

Ile Ser Phe Gln Val Ser His Val Val Glu Asp Leu Gln Phe Met Ala
            340                 345                 350

Thr Pro Glu Ile Phe Asp Gly Ala Asp His Pro Leu Pro Thr Thr Phe
        355                 360                 365

Asn Gln Asp Trp Ala Ile Leu Gln Val Lys Thr Thr Gln Asp Tyr Ala
370                 375                 380

Gln Asp Ser Val Leu Ser Thr Phe Phe Ser Gly Gly Leu Asn Leu Gln
385                 390                 395                 400

Val Ile His His Cys Phe Pro Thr Ile Ala Gln Asp Tyr Tyr Pro Gln
                405                 410                 415

Ile Val Pro Ile Leu Lys Glu Val Cys Lys Glu Tyr Asn Val Thr Tyr
                420                 425                 430

His Tyr Lys Pro Thr Phe Thr Glu Ala Ile Lys Ser His Ile Asn Tyr
            435                 440                 445

Leu Tyr Lys Met Gly Asn Asp Pro Asp Tyr Val Arg Lys Pro Val Asn
        450                 455                 460
```

-continued

Lys Asn Asp
465

<210> SEQ ID NO 16
<211> LENGTH: 421
<212> TYPE: PRT
<213> ORGANISM: Euglena gracilis
<220> FEATURE:
<221> NAME/KEY: MISC_FEATURE
<223> OTHER INFORMATION: delta-8 desaturase
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO2006012325
<311> PATENT FILING DATE: 2005-06-24
<312> PUBLICATION DATE: 2006-02-02
<313> RELEVANT RESIDUES: (1)..(421)
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO2006012326
<311> PATENT FILING DATE: 2005-06-24
<312> PUBLICATION DATE: 2006-02-02
<313> RELEVANT RESIDUES: (1)..(421)

<400> SEQUENCE: 16

Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
                20                  25                  30

Ile Glu Asn Tyr Gln Gly Arg Asp Ala Thr Asp Ala Phe Met Val Met
                35                  40                  45

His Ser Gln Glu Ala Phe Asp Lys Leu Lys Arg Met Pro Lys Ile Asn
50                  55                  60

Pro Ser Ser Glu Leu Pro Pro Gln Ala Ala Val Asn Glu Ala Gln Glu
65                  70                  75                  80

Asp Phe Arg Lys Leu Arg Glu Glu Leu Ile Ala Thr Gly Met Phe Asp
                85                  90                  95

Ala Ser Pro Leu Trp Tyr Ser Tyr Lys Ile Ser Thr Thr Leu Gly Leu
                100                 105                 110

Gly Val Leu Gly Tyr Phe Leu Met Val Gln Tyr Gln Met Tyr Phe Ile
                115                 120                 125

Gly Ala Val Leu Leu Gly Met His Tyr Gln Gln Met Gly Trp Leu Ser
        130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
                180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
                260                 265                 270

```
His Trp Thr Leu Lys Thr Leu Phe His Leu Phe Met Pro Ser Ile
            275                 280                 285
Leu Thr Ser Leu Leu Val Phe Val Ser Glu Leu Val Gly Gly Phe
    290                 295                 300
Gly Ile Ala Ile Val Val Phe Met Asn His Tyr Pro Leu Glu Lys Ile
305                 310                 315                 320
Gly Asp Ser Val Trp Asp Gly His Gly Phe Ser Val Gly Gln Ile His
                325                 330                 335
Glu Thr Met Asn Ile Arg Arg Gly Ile Ile Thr Asp Trp Phe Phe Gly
            340                 345                 350
Gly Leu Asn Tyr Gln Ile Glu His His Leu Trp Pro Thr Leu Pro Arg
        355                 360                 365
His Asn Leu Thr Ala Val Ser Tyr Gln Val Glu Gln Leu Cys Gln Lys
    370                 375                 380
His Asn Leu Pro Tyr Arg Asn Pro Leu Pro His Glu Gly Leu Val Ile
385                 390                 395                 400
Leu Leu Arg Tyr Leu Ala Val Phe Ala Arg Met Ala Glu Lys Gln Pro
                405                 410                 415
Ala Gly Lys Ala Leu
            420

<210> SEQ ID NO 17
<211> LENGTH: 1269
<212> TYPE: DNA
<213> ORGANISM: Pavlova lutheri
<220> FEATURE:
<221> NAME/KEY: misc_feature
<223> OTHER INFORMATION: delta-8 desaturase

<400> SEQUENCE: 17
atgggcaagg gtggagacgg cggcgcgcag gcggtgagcg ggaccgacgc gtctctcgct      60
gaggtgagct ccgtcgatag caagagcgtg cacgtcgtgc tctacggcaa gcgcgtggat     120
gtcacaaagt tccagaaggc acacccgggc gggagcaagg tgttccgcat cttccaggag     180
cgcgacgcga cggagcagtt cgagtcttac cactcgccca aggccatcaa gatgatggag     240
ggcatgctca agaagtcgga ggatgcgccc gcttccgtgc ccctgccctc gcggtccacc     300
atgggcacgg agttcaagga gatgattgag cgccacaaga gggctggtct ctacgaccct     360
tgcccgttgg acgagctgtt caagctcacc atcgtccttg cgcccatctt cgtgggcgcc     420
tatctcgtgc ggagcggcgt ctcgccgctc gcgggcgcgc tctccatggg ctttggcttc     480
tacctcgacg gctggcttgc tcacgactac ctgcatcacg cagtcttcaa gggctcggtc     540
aacacgctcg tcaaggcgaa caacgccatg ggatacgccc tcggcttcct ccagggctac     600
gacgtggcct ggtggcgcgc gcgccataac acgcaccacg tgtgcaccaa cgaggatggt     660
tcggacccgg acatcaagac ggcgcccctg ctcatctacg tgcgagagaa cccgtccatt     720
gccaagcggc tcaacttctt ccagcgctgg cagcagtact actatgtgcc gaccatggcc     780
atcctcgacc tctactggcg cctggagtcc atcgcgtacg tggctgtgcg cctgcctaag     840
atgtggatgc aggccgccgc tcttgccgct cactacgcgc tcctgtgctg ggtcttcgca     900
gcgcatctca acctcatccc ctctcatgatg gttgcacgcg gcttcgcgac gggcatcgtt     960
gtctttgcaa cccactatgg tgaggacatc ctcgaccgcg agcacgtcga gggcatgacg    1020
ctcgtcgagc agaccgccaa gacctcccgt aacatcacgg gcggctggct agtgaacgtg    1080
ctcacgggct tcatctcccct gcagaccgag catcacctct ccccatgat gcccaccggc    1140
```

```
aacctaatga ctatccagcc cgaggtacgc gacttcttca agaagcatgg cctcgagtac    1200
cgcgagggca acctcttcca gtgcgtgcac cagaacatca aggctctcgc cttcgagcac    1260
ctcctccac                                                            1269
```

<210> SEQ ID NO 18
<211> LENGTH: 423
<212> TYPE: PRT
<213> ORGANISM: Pavlova lutheri

<400> SEQUENCE: 18

```
Met Gly Lys Gly Gly Asp Gly Gly Ala Gln Ala Val Ser Gly Thr Asp
1               5                   10                  15

Ala Ser Leu Ala Glu Val Ser Ser Val Asp Ser Lys Ser Val His Val
            20                  25                  30

Val Leu Tyr Gly Lys Arg Val Asp Val Thr Lys Phe Gln Lys Ala His
        35                  40                  45

Pro Gly Gly Ser Lys Val Phe Arg Ile Phe Gln Glu Arg Asp Ala Thr
    50                  55                  60

Glu Gln Phe Glu Ser Tyr His Ser Pro Lys Ala Ile Lys Met Met Glu
65              70                  75                  80

Gly Met Leu Lys Lys Ser Glu Asp Ala Pro Ala Ser Val Pro Leu Pro
            85                  90                  95

Ser Arg Ser Thr Met Gly Thr Glu Phe Lys Glu Met Ile Glu Arg His
            100                 105                 110

Lys Arg Ala Gly Leu Tyr Asp Pro Cys Pro Leu Asp Glu Leu Phe Lys
        115                 120                 125

Leu Thr Ile Val Leu Ala Pro Ile Phe Val Gly Ala Tyr Leu Val Arg
130             135                 140

Ser Gly Val Ser Pro Leu Ala Gly Ala Leu Ser Met Gly Phe Gly Phe
145             150                 155                 160

Tyr Leu Asp Gly Trp Leu Ala His Asp Tyr Leu His His Ala Val Phe
            165                 170                 175

Lys Gly Ser Val Asn Thr Leu Val Lys Ala Asn Asn Ala Met Gly Tyr
        180                 185                 190

Ala Leu Gly Phe Leu Gln Gly Tyr Asp Val Ala Trp Trp Arg Ala Arg
    195                 200                 205

His Asn Thr His His Val Cys Thr Asn Glu Asp Gly Ser Asp Pro Asp
    210                 215                 220

Ile Lys Thr Ala Pro Leu Leu Ile Tyr Val Arg Glu Asn Pro Ser Ile
225             230                 235                 240

Ala Lys Arg Leu Asn Phe Phe Gln Arg Trp Gln Gln Tyr Tyr Tyr Val
            245                 250                 255

Pro Thr Met Ala Ile Leu Asp Leu Tyr Trp Arg Leu Glu Ser Ile Ala
            260                 265                 270

Tyr Val Ala Val Arg Leu Pro Lys Met Trp Met Gln Ala Ala Ala Leu
        275                 280                 285

Ala Ala His Tyr Ala Leu Leu Cys Trp Val Phe Ala Ala His Leu Asn
    290                 295                 300

Leu Ile Pro Leu Met Met Val Ala Arg Gly Phe Ala Thr Gly Ile Val
305             310                 315                 320

Val Phe Ala Thr His Tyr Gly Glu Asp Ile Leu Asp Arg Glu His Val
            325                 330                 335

Glu Gly Met Thr Leu Val Glu Gln Thr Ala Lys Thr Ser Arg Asn Ile
        340                 345                 350
```

```
Thr Gly Gly Trp Leu Val Asn Val Leu Thr Gly Phe Ile Ser Leu Gln
        355                 360                 365

Thr Glu His His Leu Phe Pro Met Met Pro Thr Gly Asn Leu Met Thr
    370                 375                 380

Ile Gln Pro Glu Val Arg Asp Phe Phe Lys Lys His Gly Leu Glu Tyr
385                 390                 395                 400

Arg Glu Gly Asn Leu Phe Gln Cys Val His Gln Asn Ile Lys Ala Leu
                405                 410                 415

Ala Phe Glu His Leu Leu His
            420

<210> SEQ ID NO 19
<211> LENGTH: 7
<212> TYPE: PRT
<213> ORGANISM: Artificial Sequence
<220> FEATURE:
<223> OTHER INFORMATION: Conserved region #1 within delta-5 and delta-8
      desaturases
<220> FEATURE:
<221> NAME/KEY: MISC_FEATURE
<222> LOCATION: (4)..(4)
<223> OTHER INFORMATION: X = Ile or Val

<400> SEQUENCE: 19

Gly His His Xaa Tyr Thr Asn
1               5

<210> SEQ ID NO 20
<211> LENGTH: 7
<212> TYPE: PRT
<213> ORGANISM: Artificial Sequence
<220> FEATURE:
<223> OTHER INFORMATION: Conserved region #2 within delta-5 and delta-8
      desaturases
<220> FEATURE:
<221> NAME/KEY: MISC_FEATURE
<222> LOCATION: (2)..(2)
<223> OTHER INFORMATION: X = Y or F
<220> FEATURE:
<221> NAME/KEY: MISC_FEATURE
<222> LOCATION: (4)..(4)
<223> OTHER INFORMATION: X = Val or Ile

<400> SEQUENCE: 20

Asn Xaa Gln Xaa Glu His His
1               5

<210> SEQ ID NO 21
<211> LENGTH: 476
<212> TYPE: PRT
<213> ORGANISM: Thalassiosira pseudonana (GenBank Accession No.
      AAX14502)
<220> FEATURE:
<221> NAME/KEY: MISC_FEATURE
<223> OTHER INFORMATION: delta-8 desaturase

<400> SEQUENCE: 21

Met Pro Pro Asn Ala Asp Ile Ser Arg Ile Arg Asn Arg Ile Pro Thr
1               5                   10                  15

Lys Thr Gly Thr Val Ala Ser Ala Asp Asn Asn Asp Pro Ala Thr Gln
            20                  25                  30

Ser Val Arg Thr Leu Lys Ser Leu Lys Gly Asn Glu Val Val Ile Asn
        35                  40                  45

Gly Thr Ile Tyr Asp Ile Ala Asp Phe Val His Pro Gly Gly Glu Val
    50                  55                  60
```

```
Val Lys Phe Phe Gly Gly Asn Asp Val Thr Ile Gln Tyr Asn Met Ile
 65                  70                  75                  80

His Pro Tyr His Thr Gly Lys His Leu Glu Lys Met Lys Ala Val Gly
                 85                  90                  95

Lys Val Val Asp Trp Gln Ser Asp Tyr Lys Phe Asp Thr Pro Phe Glu
            100                 105                 110

Arg Glu Ile Lys Ser Glu Val Phe Lys Ile Val Arg Arg Gly Arg Glu
        115                 120                 125

Phe Gly Thr Thr Gly Tyr Phe Leu Arg Ala Phe Phe Tyr Ile Ala Leu
    130                 135                 140

Phe Phe Thr Met Gln Tyr Thr Phe Ala Thr Cys Thr Thr Phe Thr Thr
145                 150                 155                 160

Tyr Asp His Trp Tyr Gln Ser Gly Val Phe Ile Ala Ile Val Phe Gly
                165                 170                 175

Ile Ser Gln Ala Phe Ile Gly Leu Asn Val Gln His Asp Ala Asn His
            180                 185                 190

Gly Ala Ala Ser Lys Arg Pro Trp Val Asn Asp Leu Leu Gly Phe Gly
        195                 200                 205

Thr Asp Leu Ile Gly Ser Asn Lys Trp Asn Trp Met Ala Gln His Trp
    210                 215                 220

Thr His His Ala Tyr Thr Asn His Ser Glu Lys Asp Pro Asp Ser Phe
225                 230                 235                 240

Ser Ser Glu Pro Met Phe Ala Phe Asn Asp Tyr Pro Ile Gly His Pro
                245                 250                 255

Lys Arg Lys Trp Trp His Arg Phe Gln Gly Gly Tyr Phe Leu Phe Met
            260                 265                 270

Leu Gly Leu Tyr Trp Leu Pro Thr Val Phe Asn Pro Gln Phe Ile Asp
        275                 280                 285

Leu Arg Gln Arg Gly Ala Gln Tyr Val Gly Ile Gln Met Glu Asn Asp
    290                 295                 300

Phe Ile Val Lys Arg Arg Lys Tyr Ala Val Ala Leu Arg Met Met Tyr
305                 310                 315                 320

Ile Tyr Leu Asn Ile Val Ser Pro Phe Met Asn Asn Gly Leu Ser Trp
                325                 330                 335

Ser Thr Phe Gly Ile Ile Met Leu Met Gly Ile Ser Glu Ser Leu Thr
            340                 345                 350

Leu Ser Val Leu Phe Ser Leu Ser His Asn Phe Ile Asn Ser Asp Arg
        355                 360                 365

Asp Pro Thr Ala Asp Phe Lys Lys Thr Gly Glu Gln Val Cys Trp Phe
    370                 375                 380

Lys Ser Gln Val Glu Thr Ser Ser Thr Tyr Gly Gly Phe Ile Ser Gly
385                 390                 395                 400

Cys Leu Thr Gly Gly Leu Asn Phe Gln Val Glu His His Leu Phe Pro
                405                 410                 415

Arg Met Ser Ser Ala Trp Tyr Pro Tyr Ile Ala Pro Thr Val Arg Glu
            420                 425                 430

Val Cys Lys Lys His Gly Met Ser Tyr Ala Tyr Tyr Pro Trp Ile Gly
        435                 440                 445

Gln Asn Leu Val Ser Thr Phe Lys Tyr Met His Arg Ala Gly Ser Gly
    450                 455                 460

Ala Asn Trp Glu Leu Lys Pro Leu Ser Gly Ser Ala
465                 470                 475
```

<210> SEQ ID NO 22
<211> LENGTH: 8165
<212> TYPE: DNA
<213> ORGANISM: Artificial Sequence
<220> FEATURE:
<223> OTHER INFORMATION: Plasmid pZUF17

<400> SEQUENCE: 22

```
gtacgagccg gaagcataaa gtgtaaagcc tggggtgcct aatgagtgag ctaactcaca      60
ttaattgcgt tgcgctcact gcccgctttc cagtcgggaa acctgtcgtg ccagctgcat     120
taatgaatcg gccaacgcgc ggggagaggc ggtttgcgta ttgggcgctc ttccgcttcc     180
tcgctcactg actcgctgcg ctcggtcgtt cggctgcggc gagcggtatc agctcactca     240
aaggcggtaa tacggttatc cacagaatca ggggataacg caggaaagaa catgtgagca     300
aaaggccagc aaaaggccag gaaccgtaaa aaggccgcgt tgctggcgtt tttccatagg     360
ctccgccccc ctgacgagca tcacaaaaat cgacgctcaa gtcagaggtg gcgaaacccg     420
acaggactat aaagatacca ggcgtttccc cctggaagct ccctcgtgcg ctctcctgtt     480
ccgaccctgc cgcttaccgg atacctgtcc gcctttctcc cttcgggaag cgtggcgctt     540
tctcatagct cacgctgtag gtatctcagt tcggtgtagg tcgttcgctc caagctgggc     600
tgtgtgcacg aaccccccgt tcagcccgac cgctgcgcct tatccggtaa ctatcgtctt     660
gagtccaacc cggtaagaca cgacttatcg ccactggcag cagccactgg taacaggatt     720
agcagagcga ggtatgtagg cggtgctaca gagttcttga agtggtggcc taactacggc     780
tacactagaa ggacagtatt tggtatctgc gctctgctga gccagttac  cttcggaaaa     840
agagttggta gctcttgatc cggcaaacaa accaccgctg gtagcggtgg ttttttttgtt     900
tgcaagcagc agattacgcg cagaaaaaaa ggatctcaag aagatccttt gatcttttct     960
acggggtctg acgctcagtg gaacgaaaac tcacgttaag ggattttggt catgagatta    1020
tcaaaaagga tcttcaccta gatccttttta aattaaaaat gaagttttaa atcaatctaa    1080
agtatatatg agtaaacttg gtctgacagt taccaatgct taatcagtga ggcacctatc    1140
tcagcgatct gtctatttcg ttcatccata gttgcctgac tccccgtcgt gtagataact    1200
acgatacggg agggcttacc atctggcccc agtgctgcaa tgataccgcg agacccacgc    1260
tcaccggctc cagatttatc agcaataaac cagccagccg aagggccga  gcgcagaagt    1320
ggtcctgcaa ctttatccgc ctccatccag tctattaatt gttgccggga agctagagta    1380
agtagttcgc cagttaatag tttgcgcaac gttgttgcca ttgctacagg catcgtggtg    1440
tcacgctcgt cgtttggtat ggcttcattc agctccggtt cccaacgatc aaggcgagtt    1500
acatgatccc ccatgttgtg caaaaaagcg gttagctcct tcggtcctcc gatcgttgtc    1560
agaagtaagt tggccgcagt gttatcactc atggttatgg cagcactgca taattctctt    1620
actgtcatgc catccgtaag atgcttttct gtgactggtg agtactcaac caagtcattc    1680
tgagaatagt gtatgcggcg accgagttgc tcttgcccgg cgtcaatacg ggataatacc    1740
gcgccacata gcagaacttt aaaagtgctc atcattggaa aacgttcttc ggggcgaaaa    1800
ctctcaagga tcttaccgct gttgagatcc agttcgatgt aacccactcg tgcacccaac    1860
tgatcttcag catcttttac tttcaccagc gtttctgggt gagcaaaaac aggaaggcaa    1920
aatgccgcaa aaaagggaat aagggcgaca cggaaatgtt gaatactcat actcttcctt    1980
tttcaatatt attgaagcat ttatcagggt tattgtctca tgagcggata catatttgaa    2040
tgtatttaga aaaataaaca aataggggtt ccgcgcacat ttccccgaaa agtgccacct    2100
```

```
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tcccttagg gttccgattt    2280 agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tattttttatt 3120 acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aattttttgc ttaaattcaa tcccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgtttttt ttgtttttt ttttctaat     4020 gattcattac cgctatgtat acctacttgt acttgtagta agccgggtta ttggcgttca   4080
attaatcata gacttatgaa tctgcacggt gtgcgctgcg agttacttt agcttatgca    4140 tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
```

```
cagttaaatt acatatccat agtctaacct ctaacagtta atcttctggt aagcctccca    4500
gccagccttc tggtatcgct tggcctcctc aataggatct cggttctggc cgtacagacc    4560
tcggccgaca attatgatat ccgttccggt agacatgaca tcctcaacag ttcggtactg    4620
ctgtccgaga gcgtctccct tgtcgtcaag acccaccccg ggggtcagaa taagccagtc    4680
ctcagagtcg cccttaggtc ggttctgggc aatgaagcca accacaaact cggggtcgga    4740
tcgggcaagc tcaatggtct gcttggagta ctcgccagtg ccagagagc ccttgcaaga     4800
cagctcggcc agcatgagca gacctctggc cagcttctcg ttgggagagg ggactaggaa    4860
ctccttgtac tgggagttct cgtagtcaga gacgtcctcc ttcttctgtt cagagacagt    4920
ttcctcggca ccagctcgca ggccagcaat gattccggtt ccgggtacac cgtgggcgtt    4980
ggtgatatcg gaccactcgg cgattcggtg acaccggtac tggtgcttga cagtgttgcc    5040
aatatctgcg aactttctgt cctcgaacag gaagaaaccg tgcttaagag caagttcctt    5100
gaggggggagc acagtgccgg cgtaggtgaa gtcgtcaatg atgtcgatat gggttttgat    5160
catgcacaca taaggtccga ccttatcggc aagctcaatg agctccttgg tggtggtaac    5220
atccagagaa gcacacaggt tggttttctt ggctgccacg agcttgagca ctcgagcggc    5280
aaaggcggac ttgtggacgt tagctcgagc ttcgtaggag ggcattttgg tggtgaagag    5340
gagactgaaa taaatttagt ctgcagaact ttttatcgga accttatctg gggcagtgaa    5400
gtatatgtta tggtaatagt tacgagttag ttgaacttat agatagactg gactatacgg    5460
ctatcggtcc aaattagaaa gaacgtcaat ggctctctgg gcgtcgcctt tgccgacaaa    5520
aatgtgatca tgatgaaagc cagcaatgac gttgcagctg atattgttgt cggccaaccg    5580
cgccgaaaac gcagctgtca gacccacagc ctccaacgaa gaatgtatcg tcaaagtgat    5640
ccaagcacac tcatagttgg agtcgtactc caaaggcggc aatgacgagt cagacagata    5700
ctcgtcgact caggcgacga cggaattcct gcagcccatc tgcagaattc aggagagacc    5760
ggggttggcgg cgtatttgtg tcccaaaaaa cagccccaat tgccccggag aagacggcca    5820
ggccgcctag atgacaaatt caacaactca cagctgactt tctgccattg ccactagggg    5880
ggggccttttt tatatggcca agccaagctc tccacgtcgg ttgggctgca cccaacaata    5940
aatgggtagg gttgcaccaa caagggatg ggatgggggg tagaagatac gaggataacg      6000
gggctcaatg gcacaaataa gaacgaatac tgccattaag actcgtgatc cagcgactga    6060
caccattgca tcatctaagg gcctcaaaac tacctcggaa ctgctgcgct gatctggaca    6120
ccacagaggt tccgagcact ttaggttgca ccaaatgtcc caccaggtgc aggcagaaaa    6180
cgctggaaca gcgtgtacag tttgtcttaa caaaaagtga gggcgctgag gtcgagcagg    6240
gtggtgtgac ttgttatagc ctttagagct gcgaaagcgc gtatggattt ggctcatcag    6300
gccagattga gggtctgtgg acacatgtca tgttagtgta cttcaatcgc ccctggata    6360
tagccccgac aataggccgt ggcctcattt ttttgcctc cgcacatttc cattgctcgg     6420
tacccacacc ttgcttctcc tgcacttgcc aaccttaata ctggtttaca ttgaccaaca    6480
tcttacaagc ggggggcttg tctagggtat atataaacag tggctctccc aatcggttgc    6540
cagtctcttt tttcctttct ttccccacag attcgaaatc taaactacac atcacacaat    6600
gcctgttact gacgtcctta agcgaaagtc cggtgtcatc gtcggcgacg atgtccgagc    6660
cgtgagtatc cacgcaaaga tcagtgtcga cgacgcgt tttgtgtaat gacacaatcc      6720
gaaagtcgct agcaacacac actctctaca caaactaacc cagctctcca tggctgagga    6780
taagaccaag gtcgagttcc ctaccctgac tgagctgaag cactctatcc ctaacgcttg    6840
```

```
ctttgagtcc aacctcggac tctcgctcta ctacactgcc cgagcgatct tcaacgcatc    6900
tgcctctgct gctctgctct acgctgcccg atctactccc ttcattgccg ataacgttct    6960
gctccacgct ctggtttgcg ccacctacat ctacgtgcag ggtgtcatct tctgggtttt    7020
ctttaccgtc ggtcacgact gtggtcactc tgccttctcc cgataccact ccgtcaactt    7080
catcattggc tgcatcatgc actctgccat tctgactccc ttcgagtcct ggcgagtgac    7140
ccaccgacac catcacaaga acactggcaa cattgataag gacgagatct tctaccctca    7200
tcggtccgtc aaggacctcc aggacgtgcg acaatgggtc tacaccctcg aggtgcttg     7260
gtttgtctac ctgaaggtcg atatgctccc tcgaaccatg tcccactttg acccctggga    7320
ccctctcctg cttcgacgag cctccgctgt catcgtgtcc ctcggagtct gggctgcctt    7380
cttcgctgcc tacgcctacc tcacatactc gctcggcttt gccgtcatgg gcctctacta    7440
ctatgctcct ctctttgtct ttgcttcgtt cctcgtcatt actaccttct tgcatcacaa    7500
cgacgaagct actccctggt acggtgactc ggagtggacc tacgtcaagg gcaacctgag    7560
ctccgtcgac cgatcgtacg gagctttcgt ggacaacctg tctcaccaca ttggcaccca    7620
ccaggtccat cacttgttcc ctatcattcc ccactacaag ctcaacgaag ccaccaagca    7680
ctttgctgcc gcttaccctc acctcgtgag acgtaacgac gagcccatca ttactgcctt    7740
cttcaagacc gctcacctct ttgtcaacta cggagctgtg cccgagactg ctcagatttt    7800
caccctcaaa gagtctgccg ctgcagccaa ggccaagagc gactaagcgg ccgcaagtgt    7860
ggatggggaa gtgagtgccc ggttctgtgt gcacaattgg caatccaaga tggatggatt    7920
caacacaggg atatagcgag ctacgtggtg gtgcgaggat atagcaacgg atatttatgt    7980
ttgacacttg agaatgtacg atacaagcac tgtccaagta caatactaaa catactgtac    8040
atactcatac tcgtacccgg gcaacggttt cacttgagtg cagtggctag tgctcttact    8100
cgtacagtgt gcaatactgc gtatcatagt ctttgatgta tatcgtattc attcatgtta    8160
gttgc                                                                8165
```

<210> SEQ ID NO 23
<211> LENGTH: 8438
<212> TYPE: DNA
<213> ORGANISM: Artificial Sequence
<220> FEATURE:
<223> OTHER INFORMATION: Plasmid pDMW367

<400> SEQUENCE: 23

```
catggctctc agtcttacca cagaacagct gttagaacgc cctgatttgg ttgcgattga      60
tggcatcctc tacgaccttg aagggcttgc caaagttcat ccaggaggag atttgattct     120
cgcttctggt gcctctgatg cctcccctct cttttattca atgcatccat acgtcaaacc     180
ggagaattcc aaattgcttc aacagttcgt ccgagggaag catgaccgca cctcgaagga     240
cattgtctac acgtatgatt ctcccttcgc acaagacgtt aagcggacaa tgcgcgaggt     300
gatgaaaggg aggaactggt acgcaacccc tggcttctgg ctgcgcaccg ttgggatcat     360
cgccgtgacg gcctttttgcg agtggcactg ggctaccacg gggatggtgc tgtggggcct     420
gttgactgga ttcatgcaca tgcagatcgg cttatccatc cagcatgatg cgtcccacgg     480
ggccatcagc aagaagcctt gggtcaacgc cctcttcgcc tacggcattg acgtcatcgg     540
atcgtcccgg tggatttggc tgcagtcgca catcatgcgg caccacacct acaccaacca     600
gcacggcctc gacctggatg cggagtcggc agagccgttc ctggtgttcc acaactaccc     660
```

-continued

| | |
|---|---|
| cgccgcaaac accgcccgaa agtggttcca ccgcttccaa gcttggtaca tgtaccttgt | 720 |
| gctgggggca tacggggtat cgctggtgta caacccgctc tacatttcc ggatgcagca | 780 |
| caatgacacc atcccagagt ctgtcacggc catgcgggaa aatggctttc tgcggcgcta | 840 |
| ccgcacactt gcattcgtga tgcgagcttt cttcatcttc cggaccgcat tcttgccctg | 900 |
| gtacctcact gggacctcat tgctgatcac cattcctctg gtgcccaccg caactggtgc | 960 |
| cttcttgacg ttcttcttca ttttgtccca caattttgat ggctccgaac ggatccccga | 1020 |
| caagaactgc aaggttaaga gatctgagaa ggacgttgag gctgaccaaa ttgactggta | 1080 |
| tcggcgcag gtggagacgt cctccacata cggtggcccc atcgccatgt tcttcactgg | 1140 |
| cggtctcaat ttccagatcg agcaccacct ctttccccgg atgtcgtctt ggcactaccc | 1200 |
| cttcgtccag caggcggtcc gggagtgttg cgaacgccat ggagtgcgat atgttttcta | 1260 |
| ccctaccatc gtcggcaaca tcatctccac cctgaagtac atgcataagg tgggtgtcgt | 1320 |
| ccactgcgtg aaggacgcac aggattccta agcggccgca agtgtggatg gggaagtgag | 1380 |
| tgcccggttc tgtgtgcaca attggcaatc caagatggat ggattcaaca cagggatata | 1440 |
| gcgagctacg tggtggtgcg aggatatagc aacggatatt tatgtttgac acttgagaat | 1500 |
| gtacgataca agcactgtcc aagtacaata ctaaacatac tgtacatact catactcgta | 1560 |
| cccgggcaac ggtttcactt gagtgcagtg gctagtgctc ttactcgtac agtgtgcaat | 1620 |
| actgcgtatc atagtctttg atgtatatcg tattcattca tgttagttgc gtacgagccg | 1680 |
| gaagcataaa gtgtaaagcc tggggtgcct aatgagtgag ctaactcaca ttaattgcgt | 1740 |
| tgcgctcact gcccgctttc cagtcgggaa acctgtcgtg ccagctgcat taatgaatcg | 1800 |
| gccaacgcgc ggggagaggc ggtttgcgta ttgggcgctc ttccgcttcc tcgctcactg | 1860 |
| actcgctgcg ctcggtcgtt cggctgcggc gagcggtatc agctcactca aaggcggtaa | 1920 |
| tacggttatc cacagaatca ggggataacg caggaaagaa catgtgagca aaaggccagc | 1980 |
| aaaaggccag gaaccgtaaa aaggccgcgt tgctggcgtt tttccatagg ctccgccccc | 2040 |
| ctgacgagca tcacaaaaat cgacgctcaa gtcagaggtg gcgaaacccg acaggactat | 2100 |
| aaagatacca ggcgtttccc cctggaagct ccctcgtgcg ctctcctgtt ccgaccctgc | 2160 |
| cgcttaccgg atacctgtcc gcctttctcc cttcgggaag cgtggcgctt tctcatagct | 2220 |
| cacgctgtag gtatctcagt tcggtgtagg tcgttcgctc caagctgggc tgtgtgcacg | 2280 |
| aaccccccgt tcagcccgac cgctgcgcct tatccggtaa ctatcgtctt gagtccaacc | 2340 |
| cggtaagaca cgacttatcg ccactggcag cagccactgg taacaggatt agcagagcga | 2400 |
| ggtatgtagg cggtgctaca gagttcttga agtggtggcc taactacggc tacactagaa | 2460 |
| ggacagtatt tggtatctgc gctctgctga agccagttac cttcggaaaa agagttggta | 2520 |
| gctcttgatc cggcaaacaa accaccgctg gtagcggtgg ttttttgtt tgcaagcagc | 2580 |
| agattacgcg cagaaaaaaa ggatctcaag aagatccttt gatcttttct acggggtctg | 2640 |
| acgctcagtg gaacgaaaac tcacgttaag ggattttggt catgagatta tcaaaaagga | 2700 |
| tcttcaccta gatccttta aattaaaaat gaagttttaa atcaatctaa agtatatatg | 2760 |
| agtaaacttg gtctgacagt taccaatgct taatcagtga gcacctatc tcagcgatct | 2820 |
| gtctatttcg ttcatccata gttgcctgac tccccgtcgt gtagataact acgatacggg | 2880 |
| agggcttacc atctggcccc agtgctgcaa tgataccgcg agacccacgc tcaccggctc | 2940 |
| cagatttatc agcaataaac cagccagccg gaagggccga gcgcagaagt ggtcctgcaa | 3000 |
| ctttatccgc ctccatccag tctattaatt gttgccggga agctagagta agtagttcgc | 3060 |

```
cagttaatag tttgcgcaac gttgttgcca ttgctacagg catcgtggtg tcacgctcgt   3120
cgtttggtat ggcttcattc agctccggtt cccaacgatc aaggcgagtt acatgatccc   3180
ccatgttgtg caaaaaagcg gttagctcct tcggtcctcc gatcgttgtc agaagtaagt   3240
tggccgcagt gttatcactc atggttatgg cagcactgca taattctctt actgtcatgc   3300
catccgtaag atgctttct gtgactggtg agtactcaac caagtcattc tgagaatagt   3360
gtatgcggcg accgagttgc tcttgcccgg cgtcaatacg ggataatacc gcgccacata   3420
gcagaacttt aaaagtgctc atcattggaa aacgttcttc ggggcgaaaa ctctcaagga   3480
tcttaccgct gttgagatcc agttcgatgt aacccactcg tgcacccaac tgatcttcag   3540
catcttttac tttcaccagc gtttctgggt gagcaaaaac aggaaggcaa atgccgcaa   3600
aaagggaat aagggcgaca cggaaatgtt gaatactcat actcttcctt tttcaatatt   3660
attgaagcat ttatcagggt tattgtctca tgagcggata catatttgaa tgtatttaga   3720
aaataaaca aatagggtt ccgcgcacat ttccccgaaa agtgccacct gacgcgccct   3780
gtagcggcgc attaagcgcg gcgggtgtgg tggttacgcg cagcgtgacc gctacacttg   3840
ccagcgccct agcgcccgct cctttcgctt tcttcccttc ctttctcgcc acgttcgccg   3900
gctttccccg tcaagctcta aatcgggggc tcccttagg gttccgattt agtgctttac   3960
ggcacctcga ccccaaaaaa cttgattagg gtgatggttc acgtagtggg ccatcgccct   4020
gatagacggt ttttcgccct tgacgttgg agtccacgtt ctttaatagt ggactcttgt   4080
tccaaactgg aacaacactc aaccctatct cggtctattc ttttgattta aagggattt   4140
tgccgatttc ggcctattgg ttaaaaaatg agctgattta acaaaaattt aacgcgaatt   4200
ttaacaaaat attaacgctt acaatttcca ttcgccattc aggctgcgca actgttggga   4260
agggcgatcg gtgcgggcct cttcgctatt acgccagctg gcgaaagggg gatgtgctgc   4320
aaggcgatta agttgggtaa cgccagggtt ttcccagtca cgacgttgta aaacgacggc   4380
cagtgaattg taatacgact cactataggg cgaattgggt accgggcccc ccctcgaggt   4440
cgatggtgtc gataagcttg atatcgaatt catgtcacac aaaccgatct tcgcctcaag   4500
gaaacctaat tctacatccg agagactgcc gagatccagt ctacactgat taattttcgg   4560
gccaataatt taaaaaaatc gtgttatata atattatatg tattatatat atacatcatg   4620
atgatactga cagtcatgtc ccattgctaa atagacagac tccatctgcc gcctccaact   4680
gatgttctca atatttaagg ggtcatctcg cattgtttaa taataaacag actccatcta   4740
ccgcctccaa atgatgttct caaaatatat tgtatgaact tatttttatt acttagtatt   4800
attagacaac ttacttgctt tatgaaaaac acttcctatt taggaaacaa tttataatgg   4860
cagttcgttc atttaacaat ttatgtagaa taaatgttat aaatgcgtat gggaaatctt   4920
aaatatggat agcataaatg atatctgcat tgcctaattc gaaatcaaca gcaacgaaaa   4980
aaatcccttg tacaacataa atagtcatcg agaaatatca actatcaaag aacagctatt   5040
cacacgttac tattgagatt attattggac gagaatcaca cactcaactg tctttctctc   5100
ttctagaaat acaggtacaa gtatgtacta ttctcattgt tcatacttct agtcatttca   5160
tcccacatat tccttggatt tctctccaat gaatgacatt ctatcttgca aattcaacaa   5220
ttataataag atataccaaa gtagcggtat agtggcaatc aaaaagcttc tctggtgtgc   5280
ttctcgtatt tatttttatt ctaatgatcc attaaaggta tatatttatt tcttgttata   5340
taatccttt gttattaca tgggctggat acataaaggt attttgattt aatttttgc   5400
```

```
ttaaattcaa tcccccctcg ttcagtgtca actgtaatgg taggaaatta ccatactttt   5460
gaagaagcaa aaaaaatgaa agaaaaaaaa aatcgtattt ccaggttaga cgttccgcag   5520
aatctagaat gcggtatgcg gtacattgtt cttcgaacgt aaaagttgcg ctccctgaga   5580
tattgtacat ttttgctttt acaagtacaa gtacatcgta caactatgta ctactgttga   5640
tgcatccaca acagtttgtt ttgttttttt ttgttttttt tttttctaat gattcattac   5700
cgctatgtat acctacttgt acttgtagta agccgggtta ttggcgttca attaatcata   5760
gacttatgaa tctgcacggt gtgcgctgcg agttactttt agcttatgca tgctacttgg   5820
gtgtaatatt gggatctgtt cggaaatcaa cggatgctca atcgatttcg acagtaatta   5880
attaagtcat acacaagtca gctttcttcg agcctcatat aagtataagt agttcaacgt   5940
attagcactg tacccagcat ctccgtatcg agaaacacaa caacatgccc cattggacag   6000
atcatgcgga tacacaggtt gtgcagtatc atacatactc gatcagacag gtcgtctgac   6060
catcatacaa gctgaacaag cgctccatac ttgcacgctc tctatataca cagttaaatt   6120
acatatccat agtctaacct ctaacagtta atcttctggt aagcctccca gccagccttc   6180
tggtatcgct tggcctcctc aataggatct cggttctggc cgtacagacc tcggccgaca   6240
attatgatat ccgttccggt agacatgaca tcctcaacag ttcggtactg ctgtccgaga   6300
gcgtctccct tgtcgtcaag acccaccccg ggggtcagaa taagccagtc ctcagagtcg   6360
cccttaggtc ggttctgggc aatgaagcca accacaaact cggggtcgga tcgggcaagc   6420
tcaatggtct gcttggagta ctcgccagtg ccagagagc ccttgcaaga cagctcggcc    6480
agcatgagca gacctctggc cagcttctcg ttgggagagg ggactaggaa ctccttgtac   6540
tgggagttct cgtagtcaga gacgtcctcc ttcttctgtt cagagacagt ttcctcggca   6600
ccagctcgca ggccagcaat gattccggtt ccgggtacac cgtgggcgtt ggtgatatcg   6660
gaccactcgg cgattcggtg acaccggtac tggtgcttga cagtgttgcc aatatctgcg   6720
aactttctgt cctcgaacag gaagaaaccg tgcttaagag caagttcctt gaggggagc    6780
acagtgccgg cgtaggtgaa gtcgtcaatg atgtcgatat gggttttgat catgcacaca   6840
taaggtccga ccttatcggc aagctcaatg agctccttgg tggtggtaac atccagagaa   6900
gcacacaggt tggttttctt ggctgccacg agcttgagca ctcgagcggc aaaggcggac   6960
ttgtggacgt tagctcgagc ttcgtaggag ggcattttgg tggtgaagag gagactgaaa   7020
taaatttagt ctgcagaact ttttatcgga accttatctg gggcagtgaa gtatatgtta   7080
tggtaatagt tacgagttag ttgaacttat agatagactg gactatacgg ctatcggtcc   7140
aaattagaaa gaacgtcaat ggctctctgg gcgtcgcctt tgccgacaaa aatgtgatca   7200
tgatgaaagc cagcaatgac gttgcagctg atattgttgt cggccaaccg cgccgaaaac   7260
gcagctgtca gacccacagc ctccaacgaa gaatgtatcg tcaaagtgat ccaagcacac   7320
tcatagttgg agtcgtactc caaaggcggc aatgacgagt cagacagata tcgtcgact    7380
caggcgacga cggaattcct gcagcccatc tgcagaattc aggagagacc gggttggcgg   7440
cgtatttgtg tcccaaaaaa cagccccaat tgccccggag aagacggcca ggccgcctag   7500
atgacaaatt caacaactca cagctgactt tctgccattg ccactagggg ggggccttt    7560
tatatggcca agccaagctc tccacgtcgg ttgggctgca cccaacaata aatgggtagg   7620
gttgcaccaa caaagggatg ggatgggggg tagaagatac gaggataacg gggctcaatg   7680
gcacaaataa gaacgaatac tgccattaag actcgtgatc cagcgactga caccattgca   7740
tcatctaagg gcctcaaaac tacctcggaa ctgctgcgct gatctggaca ccacagaggt   7800
```

```
tccgagcact ttaggttgca ccaaatgtcc caccaggtgc aggcagaaaa cgctggaaca    7860
gcgtgtacag tttgtcttaa caaaaagtga gggcgctgag gtcgagcagg gtggtgtgac    7920
ttgttatagc ctttagagct gcgaaagcgc gtatggattt ggctcatcag gccagattga    7980
gggtctgtgg acacatgtca tgttagtgta cttcaatcgc cccctggata tagccccgac    8040
aataggccgt ggcctcattt ttttgccttc cgcacatttc cattgctcgg tacccacacc    8100
ttgcttctcc tgcacttgcc aaccttaata ctggtttaca ttgaccaaca tcttacaagc    8160 gggggggcttg tctagggtat atataaacag tggctctccc aatcggttgc cagtctcttt    8220
tttcctttct ttccccacag attcgaaatc taaactacac atcacacaat gcctgttact    8280
gacgtcctta agcgaaagtc cggtgtcatc gtcggcgacg atgtccgagc cgtgagtatc    8340
cacgacaaga tcagtgtcga gacgacgcgt tttgtgtaat gacacaatcc gaaagtcgct    8400
agcaacacac actctctaca caaactaacc cagctctc                            8438
```

<210> SEQ ID NO 24
<211> LENGTH: 12649
<212> TYPE: DNA
<213> ORGANISM: Artificial Sequence
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 24

```
taaccctcac taagggaac aaaagctgga gctccaccgc ggacacaata tctggtcaaa      60
tttcagtttc gttacataaa tcgttatgtc aaaggagtgt gggaggttaa gagaattatc    120
accggcaaac tatctgttaa ttgctaggta cctctagacg tccacccggg tcgcttggcg    180
gccgaagagg ccggaatctc gggccgcggt ggcggccgct tagttggtct tggacttctt    240
gggcttcttc aggtaggact ggacaaagaa gttgccgaac agagcgagca gggtgatcat    300
gtacacgccg agcagctgga ccagagcctg agggtagtcg caggggaaga ggtagtcgta    360
cagggactgc accagcatag ccatgaactg ggtcatctgc agagtggtga tgtagggctt    420
gatgggcttg acgaagccga agccctgaga ggaaaagaag tagtaggcgt acatgacggt    480
gtggacgaag gagttgagga tgacggagaa gtaggcgtcg ccaccaggag cgtacttggc    540
aatagcccac cagatggcga agatggtggc atggtggtac acgtgcagga aggagacctg    600
gttgaacttc ttgcacagga tcatgatagc ggtgtccagg aactcgtagg ccttggagac    660
gtagaacacg tagacgattc gggacatgcc ctgagcgtgg gactcgttgc ccttctccat    720
gtcgttgccg aagaccttgt agccacccag gatagcctgt cggatggtct cgacgcacat    780
gtagagggac agtccgaaga ggaacaggtt gtggagcagc ttgatggtct tcagctcgaa    840
gggcttctcc atctgcttca tgatgggaat gccgaagagc agcatggcca tgtagccgac    900
ctcgaaggcg agcatggtgg agacgtccat catgggcaga ccgtcggtca gagcgtaggg    960
cttagctccg tccatccact ggtcgacacc ggtctcgact cgtccgacca cgtcgtccca   1020
gacagaggag ttggccatgg tgaatgattc ttatactcag aaggaaatgc ttaacgattt   1080
cgggtgtgag ttgacaagga gagagagaaa agaagaggaa aggtaattcg gggacggtgg   1140
```

```
tcttttatac ccttggctaa agtcccaacc acaaagcaaa aaaattttca gtagtctatt      1200
ttgcgtccgg catgggttac ccggatggcc agacaaagaa actagtacaa agtctgaaca      1260
agcgtagatt ccagactgca gtaccctacg cccttaacgg caagtgtggg aaccggggga      1320
ggtttgatat gtggggtgaa gggggctctc gccggggttg ggcccgctac tgggtcaatt      1380
tggggtcaat tggggcaatt gggctgtttt tttgggacac aaatacgccg ccaacccggt      1440
ctctcctgaa ttctgcatcg atcgaggaag aggacaagcg gctgcttctt aagtttgtga      1500
catcagtatc caaggcacca ttgcaaggat tcaaggcttt gaacccgtca tttgccattc      1560
gtaacgctgg tagacaggtt gatcggttcc ctacggcctc cacctgtgtc aatcttctca      1620
agctgcctga ctatcaggac attgatcaac ttcggaagaa acttttgtat gccattcgat      1680
cacatgctgg tttcgatttg tcttagagga acgcatatac agtaatcata gagaataaac      1740
gatattcatt tattaaagta gatagttgag gtagaagttg taaagagtga taaatagcgg      1800
ccgcgcctac ttaagcaacg gcttgataa cagcgggggg ggtgcccacg ttgttgcggt       1860
tgcggaagaa cagaacaccc ttaccagcac cctcggcacc agcgctgggc tcaacccact      1920
ggcacatacg cgcactgcgg tacatggcgc ggatgaagcc acgaggacca tcctggacat      1980
cagcccggta gtgcttgccc atgatgggct taatggcctc ggtggcctcg tccgcgttgt      2040
agaaggggat gctgctgacg tagtggtgga ggacatgagt ctcgatgatg ccgtggagaa      2100
ggtggcggcc gatgaagccc atctcacggt caatggtagc agcggcacca cggacgaagt      2160
tccactcgtc gttggtgtag tggggaaggg tagggtcggt gtgctggagg aaggtgatgg      2220
caacgagcca gtggttaacc cagaggtagg gaacaaagta ccagatggcc atgttgtaga      2280
aaccgaactt ctgaacgagg aagtacagag cagtggccat cagaccgata ccaatatcgc      2340
tgaggacgat gagcttagcg tcactgttct cgtacagagg gctgcgggga tcgaagtggt      2400
taacaccacc gccgaggccg ttatgcttgc ccttgccgcg accctcacgc tggcgctcgt      2460
ggtagttgtg gccggtaaca ttggtgatga ggtagttggg ccagccnacg annnnctcag      2520
taagatgagc gagctcgtgg gtcatctttc cgagacgagt agcctgctgc tcgcgggttc      2580
ggggaacgaa gaccatgtca cgctccatgt tgccagtggc cttgtggtgc tttcggtggg      2640
agatttgcca gctgaagtag gggacaagga gggaagagtg aagaacccag ccagtaatgt      2700
cgttgatgat gcgagaatcg gagaaagcac cgtgaccgca ctcatgggca ataacccaga      2760
gaccagtacc gaaaagaccc tgaagaacgg tgtacacggc ccacagacca gcgcgggcgg      2820
gggtggaggg gatatattcg ggggtcacaa agttgtacca gatgctgaaa gtggtagtca      2880
ggaggacaat gtcgcggagg atataaccgt atcccttgag agcggagcgc ttgaagcagt      2940
gcttagggat ggcattgtag atgtccttga tggtaaagtc gggaacctcg aactggttgc      3000
cgtaggtgtc gagcatgaca ccatactcgg acttgggctt ggcgatatca acctcggaca      3060
tggacgagag cgatgtggaa gaggccgagt ggcggggaga gtctgaagga gagacggcgg      3120
cagactcaga atccgtcaca gtagttgagg tgacggtgcg tctaagcgca gggttctgct      3180
tgggcagagc cgaagtggac gccatggaga gctgggttag tttgtgtaga gagtgtgtgt      3240
tgctagcgac tttcggattg tgtcattaca caaaacgcgt cgtctcgaca ctgatcttgt      3300
cgtggatact cacggctcgg acatcgtcgc cgacgatgac accggacttt cgcttaagga      3360
cgtcagtaac aggcattgtg tgatgtgtag tttagatttc gaatctgtgg ggaaagaaag      3420
gaaaaaagag actggcaacc gattgggaga gccactgttt atatataccc tagacaagcc      3480
ccccgcttgt aagatgttgg tcaatgtaaa ccagtattaa ggttggcaag tgcaggagaa      3540
```

```
gcaaggtgtg ggtaccgagc aatggaaatg tgcggaaggc aaaaaaatga ggccacggcc    3600
tattgtcggg gctatatcca gggggcgatt gaagtacact aacatgacat gtgtccacag    3660
accctcaatc tggcctgatg agccaaatcc atacgcgctt tcgcagctct aaaggctata    3720
acaagtcaca ccaccctgct cgacctcagc gccctcactt tttgttaaga caaactgtac    3780
acgctgttcc agcgttttct gcctgcacct ggtgggacat ttggtgcaac ctaaagtgct    3840
cggaacctct gtggtgtcca gatcagcgca gcagttccga ggtagttttg aggcccttag    3900
atgatgcaat ggtgtcagtc gctggatcac gagtcttaat ggcagtattc gttcttattt    3960
gtgccattga gccccgttat cctcgtatct tctacccccc atcccatccc tttgttggtg    4020
caaccctacc catttattgt tgggtgcagc ccaaccgacg tggagagctt ggcttggcca    4080
tataaaaagg ccccccccta gtggcaatgg cagaaagtca gctgtgagtt gttgaatttg    4140
tcatctaggc ggcctggccg tcttctccgg ggcaattgtt cctctatagt actgcgtaca    4200
ctgtttaaac agtgtacgca gatctgcgac gacggaattc ctgcagccca tctgcagaat    4260
tcaggagaga ccgggttggc ggcgtatttg tgtcccaaaa aacagcccca attgccccaa    4320
ttgaccccaa attgacccag tagcgggccc aaccccggcg agagcccct tcaccccaca    4380 tatcaaacct ccccggttc ccacacttgc cgttaagggc gtagggtact gcagtctgga    4440
atctacgctt gttcagactt tgtactagtt tctttgtctg gccatccggg taacccatgc    4500
cggacgcaaa atagactact gaaaattttt ttgctttgtg gttgggactt tagccaaggg    4560
tataaaagac caccgtcccc gaattacctt tcctcttctt ttctctctct ccttgtcaac    4620
tcacacccga aatcgttaag catttccttc tgagtataag aatcattcac catggctgcc    4680
gctccctctg tgcgaaacctt tacccgagcc gaggttctga acgctgaggc tctgaacgag    4740
ggcaagaagg acgctgaggc tcccttcctg atgatcatcg acaacaaggt gtacgacgtc    4800
cgagagttcg tccctgacca tcctggaggc tccgtgattc tcacccacgt tggcaaggac    4860
ggcaccgacg tctttgacac cttccatccc gaggctgctt gggagactct cgccaacttc    4920
tacgttggag acattgacga gtccgaccga gacatcaaga acgatgactt tgccgctgag    4980
gtccgaaagc tgcgaaccct gttccagtct ctcggctact acgactcctc taaggcctac    5040
tacgccttca aggtctcctt caacctctgc atctggggac tgtccaccgt cattgtggcc    5100
aagtggggtc agacctccac cctcgccaac gtgctctctg ctgccctgct cggcctgttc    5160
tggcagcagt gcggatggct ggctcacgac tttctgcacc accaggtctt ccaggaccga    5220 ttctgggggtg atctcttcgg agccttcctg ggaggtgtct gccagggctt ctcctcttcc    5280
tggtggaagg acaagcacaa cactcaccat gccgctccca acgtgcatgg cgaggatcct    5340
gacattgaca cccaccctct cctgacctgg tccgagcacg ctctggagat gttctccgac    5400
gtccccgatg aggagctgac ccgaatgtgg tctcgattca tggtcctgaa ccagacctgg    5460
ttctacttcc ccattctctc cttcgctcga ctgtcttggt gcctccagtc cattctcttt    5520
gtgctgccca acggtcaggc tcacaagccc tccggagctc gagtgcccat ctccctggtc    5580
gagcagctgt ccctcgccat gcactggacc tggtacctcg ctaccatgtt cctgttcatc    5640
aaggatcctg tcaacatgct cgtgtacttc ctggtgtctc aggctgtgtg cggaaacctg    5700
ctcgccatcg tgttctcccct caaccacaac ggtatgcctg tgatctccaa ggaggaggct    5760
gtcgacatga atttctttac caagcagatc atcactggtc gagatgtcca tcctggactg    5820
ttcgccaact ggttcaccgg tggcctgaac taccagatcg agcatcacct gttcccttcc    5880
```

```
atgcctcgac acaacttctc caagatccag cctgccgtcg agaccctgtg caagaagtac    5940
aacgtccgat accacaccac tggtatgatc gagggaactg ccgaggtctt ctcccgactg    6000
aacgaggtct ccaaggccac ctccaagatg ggcaaggctc agtaagcggc cgcatgagaa    6060
gataaatata taaatacatt gagatattaa atgcgctaga ttagagagcc tcatactgct    6120
cggagagaag ccaagacgag tactcaaagg ggattacacc atccatatcc acagacacaa    6180
gctggggaaa ggttctatat acactttccg gaataccgta gtttccgatg ttatcaatgg    6240
gggcagccag gatttcaggc acttcggtgt ctcggggtga atggcgttc ttggcctcca     6300 tcaagtcgta ccatgtcttc atttgcctgt caaagtaaaa cagaagcaga tgaagaatga    6360
acttgaagtg aaggaattta aattgccccg gagaagacgg ccaggccgcc tagatgacaa    6420
attcaacaac tcacagctga ctttctgcca ttgccactag ggggggggcct ttttatatgg    6480 ccaagccaag ctctccacgt cggttgggct gcacccaaca ataaatgggt agggttgcac    6540
caacaagggg atgggatggg gggtagaaga tacgaggata acgggctca atggcacaaa     6600 taagaacgaa tactgccatt aagactcgtg atccagcgac tgacaccatt gcatcatcta    6660
agggcctcaa aactacctcg gaactgctgc gctgatctgg acaccacaga ggttccgagc    6720
actttaggtt gcaccaaatg tcccaccagg tgcaggcaga aaacgctgga acagcgtgta    6780
cagtttgtct taacaaaaag tgagggcgct gaggtcgagc agggtggtgt gacttgttat    6840
agcctttaga gctgcgaaag cgcgtatgga tttggctcat caggccagat tgagggtctg    6900
tggacacatg tcatgttagt gtacttcaat cgcccctgg atatagcccc gacaataggc     6960
cgtggcctca ttttttttgcc ttccgcacat ttccattgct cggtacccac accttgcttc    7020
tcctgcactt gccaacctta atactggttt acattgacca acatcttaca agcgggggc     7080 ttgtctaggg tatatataaa cagtggctct cccaatcggt tgccagtctc ttttttcctt    7140
tctttcccca cagattcgaa atctaaacta cacatcacac aatgcctgtt actgacgtcc    7200
ttaagcgaaa gtccggtgtc atcgtcggcg acgatgtccg agccgtgagt atccacgaca    7260
agatcagtgt cgagacgacg cgttttgtgt aatgacacaa tccgaaagtc gctagcaaca    7320
cacactctct acacaaacta acccagctct ccatggagtc cattgctccc ttcctgccct    7380
ccaagatgcc tcaggacctg ttcatggacc tcgccagcgc tatcggtgtc cgagctgctc    7440
cctacgtcga tccctggag gctgccctgg ttgcccaggc cgagaagtac attcccacca    7500
ttgtccatca cactcgaggc ttcctggttg ccgtggagtc tcccctggct cgagagctgc    7560
ctctgatgaa ccccttccac gtgctcctga tcgtgctcgc ctacctggtc accgtgtttg    7620
tgggtatgca gatcatgaag aactttgaac gattcgaggt caagaccttc tccctcctgc    7680
acaacttctg tctggtctcc atctccgcct acatgtgcgg tggcatcctg tacgaggctt    7740
atcaggccaa ctatggactg tttgagaacg ctgccgatca caccttcaag ggtctcccta    7800
tggctaagat gatctggctc ttctacttct ccaagatcat ggagtttgtc gacaccatga    7860
tcatggtcct caagaagaac aaccgacaga tttcctttct gcacgtgtac caccactctt    7920
ccatcttcac catctggtgg ctggtcacct tcgttgctcc caacggtgaa gcctacttct    7980
ctgctgccct gaactccttc atccacgtca tcatgtacgg ctactacttt ctgtctgccc    8040
tgggcttcaa gcaggtgtcg ttcatcaagt tctacatcac tcgatcccag atgacccagt    8100
tctgcatgat gtctgtccag tcttcctggg acatgtacgc catgaaggtc cttggccgac    8160
ctggataccc cttcttcatc accgctctgc tctggttcta catgtggacc atgctcggtc    8220
tcttctacaa cttttaccga aagaacgcca agctcgccaa gcaggccaag gctgacgctg    8280
```

```
ccaaggagaa ggccagaaag ctccagtaag cggccgcaag tgtggatggg gaagtgagtg    8340
cccggttctg tgtgcacaat tggcaatcca agatggatgg attcaacaca gggatatagc    8400
gagctacgtg gtggtgcgag gatatagcaa cggatatttta tgtttgacac ttgagaatgt   8460
acgatacaag cactgtccaa gtacaatact aaacatactg tacatactca tactcgtacc    8520
cgggcaacgg tttcacttga gtgcagtggc tagtgctctt actcgtacag tgtgcaatac    8580
tgcgtatcat agtctttgat gtatatcgta ttcattcatg ttagttgcgt acgaagtcgt    8640
caatgatgtc gatatgggtt ttgatcatgc acacataagg tccgaccttta tcggcaagct   8700
caatgagctc cttggtggtg gtaacatcca gagaagcaca caggttggtt ttcttggctg    8760
ccacgagctt gagcactcga gcggcaaagg cggacttgtg gacgttagct cgagcttcgt    8820
aggagggcat tttggtggtg aagaggagac tgaaataaat ttagtctgca gaactttttta  8880
tcggaacctt atctggggca gtgaagtata tgttatggta atagttacga gttagttgaa    8940
cttatagata gactggacta tacgctatc ggtccaaatt agaaagaacg tcaatggctc     9000
tctgggcgtc gcctttgccg acaaaaatgt gatcatgatg aaagccagca atgacgttgc    9060
agctgatatt gttgtcggcc aaccgcgccg aaaacgcagc tgtcagaccc acagcctcca    9120
acgaagaatg tatcgtcaaa gtgatccaag cacactcata gttggagtcg tactccaaag    9180
gcggcaatga cgagtcagac agatactcgt cgacctttttc cttgggaacc accaccgtca   9240
gcccttctga ctcacgtatt gtagccaccg acacaggcaa cagtccgtgg atagcagaat    9300
atgtcttgtc ggtccatttc tcaccaactt taggcgtcaa gtgaatgttg cagaagaagt    9360
atgtgccttc attgagaatc ggtgttgctg atttcaataa agtcttgaga tcagtttggc    9420
gcgccagctg cattaatgaa tcggccaacg cgcggggaga ggcggtttgc gtattgggcg    9480
ctcttccgct tcctcgctca ctgactcgct gcgctcggtc gttcggctgc ggcgagcggt    9540
atcagctcac tcaaaggcgg taatacggtt atccacagaa tcaggggata acgcaggaaa    9600
gaacatgtga gcaaaaggcc agcaaaaggc caggaaccgt aaaaaggccg cgttgctggc    9660
gttttttccat aggctccgcc cccctgacga gcatcacaaa aatcgacgct caagtcagag   9720
gtggcgaaac ccgacaggac tataaagata ccaggcgttt ccccctggaa gctccctcgt    9780
gcgctctcct gttccgaccc tgccgcttac cggatacctg tccgcctttc tcccttcggg    9840
aagcgtggcg ctttctcata gctcacgctg taggtatctc agttcggtgt aggtcgttcg    9900
ctccaagctg ggctgtgtgc acgaaccccc cgttcagccc gaccgctgcg ccttatccgg    9960
taactatcgt cttgagtcca acccggtaag acacgactta tcgccactgg cagcagccac   10020
tggtaacagg attagcagag cgaggtatgt aggcggtgct acagagttct tgaagtggtg   10080
gcctaactac ggctacacta agaacagt atttggtatc tgcgctctgc tgaagccagt     10140
taccttcgga aaagagttg gtagctcttg atccggcaaa caaaccaccg ctggtagcgg    10200
tggtttttttt gtttgcaagc agcagattac gcgcagaaaa aaaggatctc aagaagatcc   10260
tttgatcttt tctacggggt ctgacgctca gtggaacgaa aactcacgtt aagggatttt   10320
ggtcatgaga ttatcaaaaa ggatcttcac ctagatcctt ttaaattaaa aatgaagttt   10380
taaatcaatc taaagtatat atgagtaaac ttggtctgac agttaccaat gcttaatcag   10440
tgaggcacct atctcagcga tctgtctatt tcgttcatcc atagttgcct gactccccgt   10500
cgtgtagata actacgatac gggagggctt accatctggc cccagtgctg caatgatacc   10560
gcgagaccca cgctcaccgg ctccagattt atcagcaata aaccagccag ccggaagggc   10620
```

-continued

```
cgagcgcaga agtggtcctg caactttatc cgcctccatc cagtctatta attgttgccg    10680
ggaagctaga gtaagtagtt cgccagttaa tagtttgcgc aacgttgttg ccattgctac    10740
aggcatcgtg gtgtcacgct cgtcgtttgg tatggcttca ttcagctccg gttcccaacg    10800
atcaaggcga gttacatgat ccccccatgtt gtgcaaaaaa gcggttagct ccttcggtcc    10860
tccgatcgtt gtcagaagta agttggccgc agtgttatca ctcatggtta tggcagcact    10920
gcataattct cttactgtca tgccatccgt aagatgcttt tctgtgactg gtgagtactc    10980
aaccaagtca ttctgagaat agtgtatgcg gcgaccgagt tgctcttgcc cggcgtcaat    11040
acgggataat accgcgccac atagcagaac tttaaaagtg ctcatcattg gaaaacgttc    11100
ttcggggcga aaactctcaa ggatcttacc gctgttgaga tccagttcga tgtaacccac    11160
tcgtgcaccc aactgatctt cagcatcttt tactttcacc agcgtttctg ggtgagcaaa    11220
aacaggaagg caaaatgccg caaaaagggg aataagggcg acacggaaat gttgaatact    11280
catactcttc cttttcaat attattgaag catttatcag ggttattgtc tcatgagcgg    11340
atacatattt gaatgtattt agaaaaataa acaaataggg gttccgcgca catttccccg    11400
aaaagtgcca cctgatgcgg tgtgaaatac cgcacagatg cgtaaggaga aaataccgca    11460
tcaggaaatt gtaagcgtta atattttgtt aaaattcgcg ttaaattttt gttaaatcag    11520
ctcatttttt aaccaatagg ccgaaatcgg caaaatccct tataaatcaa agaatagac    11580
cgagataggg ttgagtgttg ttccagtttg gaacaagagt ccactattaa agaacgtgga    11640
ctccaacgtc aaagggcgaa aaaccgtcta tcagggcgat ggcccactac gtgaaccatc    11700
accctaatca agttttttgg ggtcgaggtg ccgtaaagca ctaaatcgga accctaaagg    11760
gagcccccga tttagagctt gacggggaaa gccggcgaac gtggcgagaa aggaagggaa    11820
gaaagcgaaa ggagcgggcg ctagggcgct ggcaagtgta gcggtcacgc tgcgcgtaac    11880
caccacaccc gccgcgctta atgcgccgct acagggcgcg tccattcgcc attcaggctg    11940
cgcaactgtt gggaagggcg atcggtgcgg gcctcttcgc tattacgcca gctggcgaaa    12000
gggggatgtg ctgcaaggcg attaagttgg gtaacgccag ggttttccca gtcacgacgt    12060
tgtaaaacga cggccagtga attgtaatac gactcactat agggcgaatt gggcccgacg    12120
tcgcatgcag tggtggtatt gtgactgggg atgtagttga gaataagtca tacacaagtc    12180
agctttcttc gagcctcata taagtataag tagttcaacg tattagcact gtacccagca    12240
tctccgtatc gagaaacaca caacatgccc cattggacaa gatcatgcgg atacacaggt    12300
tgtgcagtat catacatact cgatcagaca ggtcgtctga ccatcataca agctgaacaa    12360
gcgctccata cttgcacgct ctctatatac acagttaaat tacatatcca tagtctaacc    12420
tctaacagtt aatcttctgg taagcctccc agccagcctt ctggtatcgc ttggcctcct    12480
caataggatc tcggttctgg ccgtacagac ctcggccgac aattatgata tccgttccgg    12540
tagacatgac atcctcaaca gttcggtact gctgtccgag agcgtctccc ttgtcgtcaa    12600
gacccacccc gggggtcaga ataagccagt cctcagagtc gcccttaat             12649
```

<210> SEQ ID NO 25
<211> LENGTH: 819
<212> TYPE: DNA
<213> ORGANISM: Thraustochytrium aureum
<220> FEATURE:
<221> NAME/KEY: misc_feature
<223> OTHER INFORMATION: synthetic elongase (codon-optimized) for
      Yarrowia lipolytica

<400> SEQUENCE: 25

```
atggccaact cctctgtctg ggacgacgtg gtcggacgag tcgagaccgg tgtcgaccag      60
tggatggacg gagctaagcc ctacgctctg accgacggtc tgcccatgat ggacgtctcc     120
accatgctcg ccttcgaggt cggctacatg gccatgctgc tcttcggcat tcccatcatg     180
aagcagatgg agaagccctt cgagctgaag accatcaagc tgctccacaa cctgttcctc     240
ttcggactgt ccctctacat gtgcgtcgag accatccgac aggctatcct gggtggctac     300
aaggtcttcg gcaacgacat ggagaagggc aacgagtccc acgctcaggg catgtcccga     360
atcgtctacg tgttctacgt ctccaaggcc tacgagttcc tggacaccgc tatcatgatc     420
ctgtgcaaga agttcaacca ggtctccttc ctgcacgtgt accaccatgc caccatcttc     480
gccatctggt gggctattgc caagtacgct cctggtggcg acgcctactt ctccgtcatc     540
ctcaactcct tcgtccacac cgtcatgtac gcctactact tcttttcctc tcagggcttc     600
ggcttcgtca agcccatcaa gccctacatc accactctgc agatgaccca gttcatggct     660
atggtggtgc agtccctgta cgactacctc ttcccctgcg actacctcca ggctctggtc     720
cagctgctcg gcgtgtacat gatcaccctg ctcgctctgt tcggcaactt ctttgtccag     780
tcctacctga agaagcccaa gaagtccaag accaactaa                            819
```

<210> SEQ ID NO 26
<211> LENGTH: 272
<212> TYPE: PRT
<213> ORGANISM: Thraustochytrium aureum

<400> SEQUENCE: 26

```
Met Ala Asn Ser Ser Val Trp Asp Asp Val Val Gly Arg Val Glu Thr
1               5                   10                  15

Gly Val Asp Gln Trp Met Asp Gly Ala Lys Pro Tyr Ala Leu Thr Asp
            20                  25                  30

Gly Leu Pro Met Met Asp Val Ser Thr Met Leu Ala Phe Glu Val Gly
        35                  40                  45

Tyr Met Ala Met Leu Leu Phe Gly Ile Pro Ile Met Lys Gln Met Glu
    50                  55                  60

Lys Pro Phe Glu Leu Lys Thr Ile Lys Leu Leu His Asn Leu Phe Leu
65                  70                  75                  80

Phe Gly Leu Ser Leu Tyr Met Cys Val Glu Thr Ile Arg Gln Ala Ile
                85                  90                  95

Leu Gly Gly Tyr Lys Val Phe Gly Asn Asp Met Glu Lys Gly Asn Glu
            100                 105                 110

Ser His Ala Gln Gly Met Ser Arg Ile Val Tyr Val Phe Tyr Val Ser
        115                 120                 125

Lys Ala Tyr Glu Phe Leu Asp Thr Ala Ile Met Ile Leu Cys Lys Lys
    130                 135                 140

Phe Asn Gln Val Ser Phe Leu His Val Tyr His His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
            180                 185                 190

Tyr Phe Phe Ser Ser Gln Gly Phe Gly Phe Val Lys Pro Ile Lys Pro
        195                 200                 205

Tyr Ile Thr Thr Leu Gln Met Thr Gln Phe Met Ala Met Leu Val Gln
    210                 215                 220
```

Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
            245                 250                 255

Phe Phe Val Gln Ser Tyr Leu Lys Lys Pro Lys Lys Ser Lys Thr Asn
        260                 265                 270

<210> SEQ ID NO 27
<211> LENGTH: 20
<212> TYPE: DNA
<213> ORGANISM: Artificial Sequence
<220> FEATURE:
<223> OTHER INFORMATION: Primer 5-1A

<400> SEQUENCE: 27
gghcaycayr tbtayacaaa                                          20

<210> SEQ ID NO 28
<211> LENGTH: 20
<212> TYPE: DNA
<213> ORGANISM: Artificial Sequence
<220> FEATURE:
<223> OTHER INFORMATION: Primer 5-1B

<400> SEQUENCE: 28
gghcaycayr tbtayaccaa                                          20

<210> SEQ ID NO 29
<211> LENGTH: 20
<212> TYPE: DNA
<213> ORGANISM: Artificial Sequence
<220> FEATURE:
<223> OTHER INFORMATION: Primer 5-1C

<400> SEQUENCE: 29
gghcaycayr tbtayacgaa                                          20

<210> SEQ ID NO 30
<211> LENGTH: 20
<212> TYPE: DNA
<213> ORGANISM: Artificial Sequence
<220> FEATURE:
<223> OTHER INFORMATION: Primer 5-1D

<400> SEQUENCE: 30
gghcaycayr tbtayactaa                                          20

<210> SEQ ID NO 31
<211> LENGTH: 20
<212> TYPE: DNA
<213> ORGANISM: Artificial Sequence
<220> FEATURE:
<223> OTHER INFORMATION: Primer 5-5AR

<400> SEQUENCE: 31
tgrtgvacaa yytgrwartt                                          20

<210> SEQ ID NO 32
<211> LENGTH: 20
<212> TYPE: DNA
<213> ORGANISM: Artificial Sequence
<220> FEATURE:
<223> OTHER INFORMATION: Primer 5-5BR

<400> SEQUENCE: 32
tgrtgvacta yytgrwartt                                                   20

<210> SEQ ID NO 33
<211> LENGTH: 20
<212> TYPE: DNA
<213> ORGANISM: Artificial Sequence
<220> FEATURE:
<223> OTHER INFORMATION: Primer 5-5CR

<400> SEQUENCE: 33
tgrtgvacca yytgrwartt                                                   20

<210> SEQ ID NO 34
<211> LENGTH: 20
<212> TYPE: DNA
<213> ORGANISM: Artificial Sequence
<220> FEATURE:
<223> OTHER INFORMATION: Primer 5-5DR

<400> SEQUENCE: 34
tgrtgvacga yytgrwartt                                                   20

<210> SEQ ID NO 35
<211> LENGTH: 27
<212> TYPE: DNA
<213> ORGANISM: Artificial Sequence
<220> FEATURE:
<223> OTHER INFORMATION: Primer ODMW480

<400> SEQUENCE: 35
ccgataccag tcaatttggt cagcctc                                           27

<210> SEQ ID NO 36
<211> LENGTH: 23
<212> TYPE: DNA
<213> ORGANISM: Artificial Sequence
<220> FEATURE:
<223> OTHER INFORMATION: CDSIII 5' primer

<400> SEQUENCE: 36
aagcagtggt atcaacgcag agt                                               23

<210> SEQ ID NO 37
<211> LENGTH: 28
<212> TYPE: DNA
<213> ORGANISM: Artificial Sequence
<220> FEATURE:
<223> OTHER INFORMATION: Primer ODMW479

<400> SEQUENCE: 37
cttaaccttg cagttcttgt cggggatc                                          28

<210> SEQ ID NO 38
<211> LENGTH: 22
<212> TYPE: DNA
<213> ORGANISM: Artificial Sequence
<220> FEATURE:
<223> OTHER INFORMATION: Primer DNR CDS 5'

<400> SEQUENCE: 38
caacgcagag tggccattac gg                                                22

<210> SEQ ID NO 39
<211> LENGTH: 27
<212> TYPE: DNA
<213> ORGANISM: Artificial Sequence -continued

```
<220> FEATURE:
<223> OTHER INFORMATION: Primer YL791

<400> SEQUENCE: 39
cacctcgcgc attgtccgct taacgtc                                          27

<210> SEQ ID NO 40
<211> LENGTH: 27
<212> TYPE: DNA
<213> ORGANISM: Artificial Sequence
<220> FEATURE:
<223> OTHER INFORMATION: Primer YL792

<400> SEQUENCE: 40
tgcgaaggga gaatcatacg tgtagac                                          27

<210> SEQ ID NO 41
<211> LENGTH: 26
<212> TYPE: DNA
<213> ORGANISM: Artificial Sequence
<220> FEATURE:
<223> OTHER INFORMATION: Primer ODMW469

<400> SEQUENCE: 41
cttcatcttc cggaccgcat tcttgc                                           26

<210> SEQ ID NO 42
<211> LENGTH: 20
<212> TYPE: DNA
<213> ORGANISM: Artificial Sequence
<220> FEATURE:
<223> OTHER INFORMATION: Primer AUAP

<400> SEQUENCE: 42
ggccacgcgt cgactagtac                                                  20

<210> SEQ ID NO 43
<211> LENGTH: 28
<212> TYPE: DNA
<213> ORGANISM: Artificial Sequence
<220> FEATURE:
<223> OTHER INFORMATION: Primer ODMW470

<400> SEQUENCE: 43
cctcactggg acctcattgc tgatcacc                                         28

<210> SEQ ID NO 44
<211> LENGTH: 32
<212> TYPE: DNA
<213> ORGANISM: Artificial Sequence
<220> FEATURE:
<223> OTHER INFORMATION: Primer YL794

<400> SEQUENCE: 44
tttccatggc tctcagtctt accacagaac ag                                    32

<210> SEQ ID NO 45
<211> LENGTH: 27
<212> TYPE: DNA
<213> ORGANISM: Artificial Sequence
<220> FEATURE:
<223> OTHER INFORMATION: Primer YL797

<400> SEQUENCE: 45
gtacatgtac caagcttgga agcggtg                                          27
```

<210> SEQ ID NO 46
<211> LENGTH: 27
<212> TYPE: DNA
<213> ORGANISM: Artificial Sequence
<220> FEATURE:
<223> OTHER INFORMATION: Primer YL796

<400> SEQUENCE: 46
caccgcttcc aagcttggta catgtac                                           27

<210> SEQ ID NO 47
<211> LENGTH: 39
<212> TYPE: DNA
<213> ORGANISM: Artificial Sequence
<220> FEATURE:
<223> OTHER INFORMATION: Primer YL795

<400> SEQUENCE: 47
tttgcggccg cttaggaatc ctgtgcgtcc ttcacgcag                              39

<210> SEQ ID NO 48
<211> LENGTH: 4070
<212> TYPE: DNA
<213> ORGANISM: Artificial Sequence
<220> FEATURE:
<223> OTHER INFORMATION: Plasmid pEgD5S

<400> SEQUENCE: 48

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctggc ttaactatgc ggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt acctcgcgaa | 420 |
| tgcatctaga tccatggctc tctcccttac taccgagcag ctgctcgagc gacccgacct | 480 |
| ggttgccatc gacggcattc tctacgatct ggaaggtctt gccaaggtcc atcccggagg | 540 |
| cgacttgatc ctcgcttctg gtgcctccga tgcttctcct ctgttctact ccatgcaccc | 600 |
| ttacgtcaag cccgagaact cgaagctgct tcaacagttc gtgcgaggca agcacgaccg | 660 |
| aacctccaag gacattgtct acacctacga ctctcccttt gcacaggacg tcaagcgaac | 720 |
| tatgcgagag gtcatgaaag gtcggaactg gtatgccaca cctggattct ggctgcgaac | 780 |
| cgttggcatc attgctgtca ccgccttttg cgagtggcac tgggctacta ccggaatggt | 840 |
| gctgtgggt ctcttgactg gattcatgca catgcagatc ggcctgtcca ttcagcacga | 900 |
| tgcctctcat ggtgccatca gcaaaaagcc ctgggtcaac gctctctttg cctacggcat | 960 |
| cgacgtcatt ggatcgtcca gatggatctg gctgcagtct cacatcatgc gacatcacac | 1020 |
| ctacaccaat cagcatggtc tcgacctgga tgccgagtcc gcagaaccat tccttgtgtt | 1080 |
| ccacaactac cctgctgcca acactgctcg aaagtggttt caccgattcc aggcctggta | 1140 |
| catgtacctc gtgcttggag cctacggcgt ttcgctggtg tacaaccctc tctacatctt | 1200 |
| ccgaatgcag cacaacgaca ccattcccga gtctgtcaca gccatgcgag agaacggctt | 1260 |
| tctgcgacgg taccgaaccc ttgcattcgt tatgcgagct ttcttcatct ttcgaaccgc | 1320 |
| cttcttgccc tggtatctca ctggaacctc cctgctcatc accattcctc tggtgcccac | 1380 |

```
tgctaccggt gccttcctca ccttcttttt catcttgtct cacaacttcg atggctcgga    1440
gcgaatcccc gacaagaact gcaaggtcaa gagctccgag aaggacgttg aagccgatca    1500
gatcgactgg tacagagctc aggtggagac ctcttccacc tacggtggac ccattgccat    1560
gttctttact ggcggtctca acttccagat cgagcatcac ctctttcctc gaatgtcgtc    1620
ttggcactat cccttcgtgc agcaagctgt ccgagagtgt tgcgaacgac acggagttcg    1680
gtacgtcttc taccctacca ttgtgggcaa catcatttcc accctcaagt acatgcacaa    1740
agtcggtgtg gttcactgtg tcaaggacgc tcaggattcc taagcggccg catcggatcc    1800
cgggcccgtc gactgcagag gcctgcatgc aagcttggcg taatcatggt catagctgtt    1860
tcctgtgtga aattgttatc cgctcacaat tccacacaac atacgagccg aagcataaa    1920
gtgtaaagcc tggggtgcct aatgagtgag ctaactcaca ttaattgcgt tgcgctcact    1980
gcccgctttc cagtcgggaa acctgtcgtg ccagctgcat taatgaatcg gccaacgcgc    2040
ggggagaggc ggtttgcgta ttgggcgctc ttccgcttcc tcgctcactg actcgctgcg    2100
ctcggtcgtt cggctgcggc gagcggtatc agctcactca aaggcggtaa tacggttatc    2160
cacagaatca ggggataacg caggaaagaa catgtgagca aaaggccagc aaaaggccag    2220
gaaccgtaaa aaggccgcgt tgctggcgtt tttccatagg ctccgccccc ctgacgagca    2280
tcacaaaaat cgacgctcaa gtcagaggtg cgaaacccg acaggactat aaagatacca    2340
ggcgtttccc cctggaagct ccctcgtgcg ctctcctgtt ccgaccctgc cgcttaccgg    2400
atacctgtcc gcctttctcc cttcgggaag cgtggcgctt tctcatagct cacgctgtag    2460
gtatctcagt tcggtgtagg tcgttcgctc caagctgggc tgtgtgcacg aaccccccgt    2520
tcagcccgac cgctgcgcct tatccggtaa ctatcgtctt gagtccaacc cggtaagaca    2580
cgacttatcg ccactggcag cagccactgg taacaggatt agcagagcga ggtatgtagg    2640
cggtgctaca gagttcttga agtggtggcc taactacggc tacactagaa gaacagtatt    2700
tggtatctgc gctctgctga agccagttac cttcggaaaa agagttggta gctcttgatc    2760
cggcaaacaa accaccgctg gtagcggtgg tttttttgtt tgcaagcagc agattacgcg    2820
cagaaaaaaa ggatctcaag aagatccttt gatcttttct acggggtctg acgctcagtg    2880
gaacgaaaac tcacgttaag ggattttggt catgagatta tcaaaaagga tcttaccta    2940
gatccttta aattaaaaat gaagttttaa atcaatctaa agtatatatg agtaaacttg    3000
gtctgacagt taccaatgct taatcagtga ggcacctatc tcagcgatct gtctatttcg    3060
ttcatccata gttgcctgac tccccgtcgt gtagataact acgatacggg agggcttacc    3120
atctggcccc agtgctgcaa tgataccgcg agacccacgc tcaccggctc cagatttatc    3180
agcaataaac cagccagccg gaagggccga gcgcagaagt ggtcctgcaa ctttatccgc    3240
ctccatccag tctattaatt gttgccggga agctagagta agtagttcgc cagttaatag    3300
tttgcgcaac gttgttgcca ttgctacagg catcgtggtg tcacgctcgt cgtttggtat    3360
ggcttcattc agctccggtt cccaacgatc aaggcgagtt acatgatccc ccatgttgtg    3420
caaaaaagcg gttagctcct tcggtcctcc gatcgttgtc agaagtaagt tggccgcagt    3480
gttatcactc atggttatgg cagcactgca taattctctt actgtcatgc catccgtaag    3540
atgcttttct gtgactggtg agtactcaac caagtcattc tgagaatagt gtatgcggcg    3600
accgagttgc tcttgcccgg cgtcaatacg ggataatacc gcgccacata gcagaacttt    3660
aaaagtgctc atcattggaa aacgttcttc ggggcgaaaa ctctcaagga tcttaccgct    3720
```

```
gttgagatcc agttcgatgt aacccactcg tgcacccaac tgatcttcag catctttttac    3780 tttcaccagc gtttctgggt gagcaaaaac aggaaggcaa aatgccgcaa aaagggaat    3840 aagggcgaca cggaaatgtt gaatactcat actcttcctt tttcaatatt attgaagcat    3900
ttatcagggt tattgtctca tgagcggata catatttgaa tgtatttaga aaataaaca    3960 aataggggtt ccgcgcacat ttccccgaaa agtgccacct gacgtctaag aaaccattat    4020
tatcatgaca ttaacctata aaataggcg tatcacgagg ccctttcgtc               4070
```

<210> SEQ ID NO 49
<211> LENGTH: 8438
<212> TYPE: DNA
<213> ORGANISM: Artificial Sequence
<220> FEATURE:
<223> OTHER INFORMATION: Plasmid pDMW369

<400> SEQUENCE: 49

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt tcacttgag tgcagtggct      240 agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta attgcgttgc gctcactgcc cgctttccag tcgggaaacc     420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
gaaagaacat gtgagcaaaa ggccagcaaa aggccaggaa ccgtaaaaag gccgcgttgc     660
tggcgttttt ccataggctc cgcccccctg acgagcatca aaaaatcga cgctcaagtc     720 agaggtggcg aaacccgaca ggactataaa gataccaggc gtttccccct ggaagctccc     780
tcgtgcgctc tcctgttccg accctgccgc ttaccggata cctgtccgcc tttctccctt     840
cgggaagcgt ggcgctttct catagctcac gctgtaggta tctcagttcg gtgtaggtcg     900
ttcgctccaa gctgggctgt gtgcacgaac cccccgttca gcccgaccgc tgcgccttat     960
ccggtaacta tcgtcttgag tccaacccgg taagacacga cttatcgcca ctggcagcag    1020
ccactggtaa caggattagc agagcgaggt atgtaggcgg tgctacagag ttcttgaagt    1080
ggtggcctaa ctacggctac actagaagga cagtatttgg tatctgcgct ctgctgaagc    1140
cagttacctt cggaaaaaga gttggtagct cttgatccgg caaacaaacc accgctggta    1200
gcggtggttt ttttgtttgc aagcagcaga ttacgcgcag aaaaaaagga tctcaagaag    1260
atcctttgat cttttctacg ggtctgacgc tcagtggaa cgaaaactca cgttaaggga    1320
ttttggtcat gagattatca aaaaggatct tcacctagat cctttttaaat taaaaatgaa    1380 gttttaaatc aatctaaagt atatatgagt aaacttggtc tgacagttac caatgcttaa    1440
tcagtgaggc acctatctca gcgatctgtc tatttcgttc atccatagtt gcctgactcc    1500
ccgtcgtgta gataactacg atacgggagg gcttaccatc tggccccagt gctgcaatga    1560
taccgcgaga cccacgctca ccggctccag atttatcagc aataaaccag ccagccggaa    1620
gggccgagcg cagaagtggt cctgcaactt tatccgcctc catccagtct attaattgtt    1680
gccgggaagc tagagtaagt agttcgccag ttaatagttt cgcaacgtt gttgccattg    1740
```

```
ctacaggcat cgtggtgtca cgctcgtcgt ttggtatggc ttcattcagc tccggttccc    1800
aacgatcaag gcgagttaca tgatccccca tgttgtgcaa aaaagcggtt agctccttcg    1860
gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga gaatagtgta tgcggcgacc gagttgctct tgcccggcgt    2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttcctttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgcctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca gctctaaat cggggggctcc    2580 ctttagggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt taatagtgga ctcttgttcc aaactggaac aacactcaac cctatctcgg    2760
tctattcttt tgatttataa gggattttgc cgatttcggc ctattggtta aaaaatgagc    2820
tgatttaaca aaaatttaac gcgaatttta acaaaatatt aacgcttaca atttccattc    2880
gccattcagg ctgcgcaact gttgggaagg gcgatcggtg cgggcctctt cgctattacg    2940
ccagctggcg aaagggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa aatatattgt    3420
atgaacttat ttttattact tagtattatt agacaacttac cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat tttttgctta aattcaatcc ccctcgttc agtgtcaact    4080
```

```
gtaatggtag gaaattacca tacttttgaa gaagcaaaaa aaatgaaaga aaaaaaaaat    4140
cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg ttttttttg    4320
tttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tactttagc ttatgcatgc tacttgggtg taatattggg atctgttcgg aaatcaacgg     4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc caccccgggg    4980
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccgcgct aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgactcag gcgacgacgg aattcctgca gcccatctgc    6060
agaattcagg agagaccggg ttggcggcgt atttgtgtcc caaaaacag ccccaattgc     6120
cccggagaag acggccaggc cgcctagatg acaaattcaa caactcacag ctgactttct    6180
gccattgcca ctaggggggg gccttttat atggccaagc caagctctcc acgtcggttg     6240
ggctgcaccc aacaataaat gggtagggtt gcaccaacaa agggatggga tgggggtag     6300
aagatacgag gataacgggg ctcaatggca caaataagaa cgaatactgc cattaagact    6360
cgtgatccag cgactgacac cattgcatca tctaagggcc tcaaaactac ctcggaactg    6420
ctgcgctgat ctggacacca cagaggttcc gagcacttta ggttgcacca aatgtcccac    6480
```

```
caggtgcagg cagaaaacgc tggaacagcg tgtacagttt gtcttaacaa aaagtgaggg    6540
cgctgaggtc gagcagggtg gtgtgacttg ttatagcctt tagagctgcg aaagcgcgta    6600
tggatttggc tcatcaggcc agattgaggg tctgtggaca catgtcatgt tagtgtactt    6660
caatcgcccc ctggatatag ccccgacaat aggccgtggc ctcattttt  tgccttccgc    6720 acatttccat tgctcggtac ccacaccttg cttctcctgc acttgccaac cttaatactg    6780
gtttacattg accaacatct tacaagcggg gggcttgtct agggtatata taaacagtgg    6840
ctctcccaat cggttgccag tctcttttt  cctttctttc cccacagatt cgaaatctaa    6900
actacacatc acacaatgcc tgttactgac gtccttaagc gaaagtccgg tgtcatcgtc    6960
ggcgacgatg tccgagccgt gagtatccac gacaagatca gtgtcgagac gacgcgtttt    7020
gtgtaatgac acaatccgaa agtcgctagc aacacacact ctctacacaa actaacccag    7080
ctctccatgg ctctctccct tactaccgag cagctgctcg agcgacccga cctggttgcc    7140
atcgacggca ttctctacga tctggaaggt cttgccaagg tccatcccgg aggcgacttg    7200
atcctcgctt ctggtgcctc cgatgcttct cctctgttct actccatgca cccttacgtc    7260
aagcccgaga actcgaagct gcttcaacag ttcgtgcgag gcaagcacga ccgaacctcc    7320
aaggacattg tctacaccta cgactctccc tttgcacagg acgtcaagcg aactatgcga    7380
gaggtcatga aggtcggaa  ctggtatgcc acacctggat tctggctgcg aaccgttggc    7440
atcattgctg tcaccgcctt tgcgagtgg  cactgggcta ctaccggaat ggtgctgtgg    7500
ggtctcttga ctggattcat gcacatgcag atcggcctgt ccattcagca cgatgcctct    7560
catggtgcca tcagcaaaaa gccctgggtc aacgctctct tgcctacgg  catcgacgtc    7620 attggatcgt ccagatggat ctggctgcag tctcacatca tgcgacatca cacctacacc    7680
aatcagcatg gtctcgacct ggatgccgag tccgcagaac cattccttgt gttccacaac    7740 tacccgtgctg ccaacactgc tcgaaagtgg tttcaccgat tccaggcctg gtacatgtac    7800
ctcgtgcttg gagcctacgg cgtttcgctg gtgtacaacc ctctctacat cttccgaatg    7860
cagcacaacg acaccattcc cgagtctgtc acagccatgc gagagaacgg ctttctgcga    7920
cggtaccgaa cccttgcatt cgttatgcga gctttcttca tctttcgaac cgccttcttg    7980
ccctggtatc tcactggaac ctccctgctc atcaccattc ctctggtgcc cactgctacc    8040
ggtgccttcc tcaccttctt tttcatcttg tctcacaact tcgatggctc ggagcgaatc    8100
cccgacaaga actgcaaggt caagagctcc gagaaggacg ttgaagccga tcagatcgac    8160
tggtacagag ctcaggtgga gacctcttcc acctacggtg gacccattgc catgttcttt    8220
actggcggtc tcaacttcca gatcgagcat cacctctttc ctcgaatgtc gtcttggcac    8280
tatcccttcg tgcagcaagc tgtccgagag tgttgcgaac gacacggagt tcggtacgtc    8340
ttctacccta ccattgtggg caacatcatt tccaccctca agtacatgca caaagtcggt    8400
gtggttcact gtgtcaagga cgctcaggat tcctaagc                           8438
```

<210> SEQ ID NO 50
<211> LENGTH: 19
<212> TYPE: DNA
<213> ORGANISM: Artificial Sequence
<220> FEATURE:
<223> OTHER INFORMATION: Primer T7

<400> SEQUENCE: 50
ggaaacagct atgaccatg                                                  19

```
<210> SEQ ID NO 51
<211> LENGTH: 459
<212> TYPE: PRT
<213> ORGANISM: Rhizopus stolonifer (GenBank Accession No. AAX22052)

<400> SEQUENCE: 51

Met Ser Thr Leu Asp Arg Gln Ser Ile Phe Thr Ile Lys Glu Leu Glu
1               5                   10                  15

Ser Ile Ser Gln Arg Ile His Asp Gly Asp Glu Glu Ala Met Lys Phe
            20                  25                  30

Ile Ile Ile Asp Lys Lys Val Tyr Asp Val Thr Glu Phe Ile Glu Asp
        35                  40                  45

His Pro Gly Gly Ala Gln Val Leu Leu Thr His Val Gly Lys Asp Ala
    50                  55                  60

Ser Asp Val Phe His Ala Met His Pro Glu Ser Ala Tyr Glu Val Leu
65                  70                  75                  80

Asn Asn Tyr Phe Val Gly Asp Val Gln Glu Thr Val Val Thr Glu Lys
                85                  90                  95

Ser Ser Ser Ala Gln Phe Ala Val Glu Met Arg Gln Leu Arg Asp Gln
            100                 105                 110

Leu Lys Lys Glu Gly Tyr Phe His Ser Ser Lys Leu Phe Tyr Ala Tyr
        115                 120                 125

Lys Val Leu Ser Thr Leu Ala Ile Cys Ile Ala Gly Leu Ser Leu Leu
    130                 135                 140

Tyr Ala Tyr Gly Arg Thr Ser Thr Leu Ala Val Val Ala Ser Ala Ile
145                 150                 155                 160

Thr Val Gly Ile Phe Trp Gln Gln Cys Gly Trp Leu Ala His Asp Phe
                165                 170                 175

Gly His His Gln Cys Phe Glu Asp Arg Thr Trp Asn Asp Val Leu Val
            180                 185                 190

Val Phe Leu Gly Asn Phe Cys Gln Gly Phe Ser Leu Ser Trp Trp Lys
        195                 200                 205

Asn Lys His Asn Thr His His Ala Ser Thr Asn Val His Gly Gln Asp
    210                 215                 220

Pro Asp Ile Asp Thr Ala Pro Val Leu Leu Trp Asp Glu Tyr Ala Ser
225                 230                 235                 240

Ala Ala Tyr Tyr Ala Ser Leu Asp Gln Glu Pro Thr Met Val Ser Arg
                245                 250                 255

Phe Leu Ala Glu Gln Val Leu Pro His Gln Thr Arg Tyr Phe Phe Phe
            260                 265                 270

Ile Leu Ala Phe Ala Arg Leu Ser Trp Ala Leu Gln Ser Leu Ser Tyr
        275                 280                 285

Ser Phe Lys Lys Glu Ser Ile Asn Lys Ser Arg Gln Leu Asn Leu Phe
    290                 295                 300

Glu Arg Val Cys Ile Val Gly His Trp Ala Leu Phe Ala Phe Cys Ile
305                 310                 315                 320

Tyr Ser Trp Cys Ser Asn Val Tyr His Met Val Leu Phe Leu Val
                325                 330                 335

Ser Gln Ala Thr Thr Gly Tyr Thr Leu Ala Leu Val Phe Ala Leu Asn
            340                 345                 350

His Asn Gly Met Pro Val Ile Thr Glu Glu Lys Ala Glu Ser Met Glu
        355                 360                 365

Phe Phe Glu Ile Gln Val Ile Thr Gly Arg Asp Val Thr Leu Ser Pro
    370                 375                 380
```

Leu Gly Asp Trp Phe Met Gly Gly Leu Asn Tyr Gln Ile Glu His His
385                 390                 395                 400

Val Phe Pro Asn Met Pro Arg His Asn Leu Pro Thr Val Lys Pro Met
            405                 410                 415

Val Lys Ser Leu Cys Gln Lys Tyr Asp Ile Asn Tyr His Asp Thr Gly
        420                 425                 430

Phe Leu Lys Gly Thr Leu Glu Val Leu Gln Thr Leu Asp Ile Thr Ser
    435                 440                 445

Lys Leu Ser Leu Gln Leu Ser Lys Lys Ser Phe
    450                 455

<210> SEQ ID NO 52
<211> LENGTH: 695
<212> TYPE: DNA
<213> ORGANISM: Pavlova lutheri

<400> SEQUENCE: 52

```
agggccaagg gtgccaacca ccttccacgt gagactacac accgtaggcc gatgggcaag      60
ggtggagacg gcggcgcgca ggcggtgagc gggaccgacg cgtctctcgc tgaggtgagc     120
tccgtcgata gcaagagcgt gcacgtcgtg ctctacggca agcgcgtgga tgtcacaaag     180
ttccagggct acgacgtggc ctggtggcgc gcgcgccata acacgcacca cgtgtgcacc     240
aacgaggatg gttcggaccc ggacatcaag acggcgcccc tgctcatcta cgtgcgagag     300
aacccgtcca ttgccaagcg gctcaacttc ttccagcgct ggcagcagta ctactatgtg     360
ccgaccatgg ccatcctcga cctctactgg cgcctggagt ccatcgcgta cgtggctgtg     420
cgcctgccta agatgtggat gcaggccgcc gctcttgccg ctcactacgc gctcctgtgc     480
tgggtcttcg cagcgcatct caacctcatc cctctcatga tggttgcacg cggcttcgcg     540
acgggcatcg ttgtctttgc aacccactat ggtgaggaca tcctcgaccg cgagcacgtc     600
gagggcatga cgctcgtcga gcagaccgcc aagacctccc gtaacatcac gggcggctgg     660
ctagtgaacg tgctcacggg cttcatctcc ctgca                                695
```

<210> SEQ ID NO 53
<211> LENGTH: 1106
<212> TYPE: DNA
<213> ORGANISM: Pavlova lutheri

<400> SEQUENCE: 53

```
agggccaagg gtgccaacca ccttccacgt gagactacac accgtaggcc gatgggcaag      60
ggtggagacg gcggcgcgca ggcggtgagc gggaccgacg cgtctctcgc tgaggtgagc     120
tccgtcgata gcaagagcgt gcacgtcgtg ctctacggca agcgcgtgga tgtcacaaag     180
ttccagggct acgacgtggc ctggtggcgc gcgcgccata acacgcacca cgtgtgcacc     240
aacgaggatg gttcggaccc ggacatcaag acggcgcccc tgctcatcta cgtgcgagag     300
aacccgtcca ttgccaagcg gctcaacttc ttccagcgct ggcagcagta ctactatgtg     360
ccgaccatgg ccatcctcga cctctactgg cgcctggagt ccatcgcgta cgtggctgtg     420
cgcctgccta agatgtggat gcaggccgcc gctcttgccg ctcactacgc gctcctgtgc     480
tgggtcttcg cagcgcatct caacctcatc cctctcatga tggttgcacg cggcttcgcg     540
acgggcatcg ttgtctttgc aacccactat ggtgaggaca tcctcgaccg cgagcacgtc     600
gagggcatga cgctcgtcga gcagaccgcc aagacctccc gtaacatcac gggcggctgg     660
ctagtgaacg tgctcacggg cttcatctcc ctgcagaccg agcatcacct cttccccatg     720
```

-continued

```
atgcccaccg gcaacctaat gactatccag cccgaggtac gcgacttctt caagaagcat        780
ggcctcgagt accgcgaggg caacctcttc cagtgcgtgc accagaacat caaggctctc        840
gccttcgagc acctcctcca ctgagcgtca ccactcaagc gtcctaagtg cacaggtact        900
gtcttctgac cgatggccgc gcggctccct cggctggcag tggggccaac gagtggcctc        960
gcgggatcgg gcacgatcgg gcctccatga aacttcagtg ttcagagaca agccgacaac       1020
ctccgcatcg tgagaaatct tttaaagcag tatgttccat cacgccgctt ttgcagtcaa       1080
taacattacc caaaaaaaaa aaaaaa                                             1106
```

<210> SEQ ID NO 54
<211> LENGTH: 287
<212> TYPE: PRT
<213> ORGANISM: Pavlova lutheri

<400> SEQUENCE: 54

```
Arg Ala Lys Gly Ala Asn His Leu Pro Arg Glu Thr Thr His Arg Arg
1               5                   10                  15

Pro Met Gly Lys Gly Gly Asp Gly Gly Ala Gln Ala Val Ser Gly Thr
            20                  25                  30

Asp Ala Ser Leu Ala Glu Val Ser Ser Val Asp Ser Lys Ser Val His
        35                  40                  45

Val Val Leu Tyr Gly Lys Arg Val Asp Val Thr Lys Phe Gln Gly Tyr
    50                  55                  60

Asp Val Ala Trp Trp Arg Ala Arg His Asn Thr His His Val Cys Thr
65                  70                  75                  80

Asn Glu Asp Gly Ser Asp Pro Asp Ile Lys Thr Ala Pro Leu Leu Ile
                85                  90                  95

Tyr Val Arg Glu Asn Pro Ser Ile Ala Lys Arg Leu Asn Phe Phe Gln
            100                 105                 110

Arg Trp Gln Gln Tyr Tyr Tyr Val Pro Thr Met Ala Ile Leu Asp Leu
        115                 120                 125

Tyr Trp Arg Leu Glu Ser Ile Ala Tyr Val Ala Val Arg Leu Pro Lys
    130                 135                 140

Met Trp Met Gln Ala Ala Ala Leu Ala Ala His Tyr Ala Leu Leu Cys
145                 150                 155                 160

Trp Val Phe Ala Ala His Leu Asn Leu Ile Pro Leu Met Met Val Ala
                165                 170                 175

Arg Gly Phe Ala Thr Gly Ile Val Val Phe Ala Thr His Tyr Gly Glu
            180                 185                 190

Asp Ile Leu Asp Arg Glu His Val Glu Gly Met Thr Leu Val Glu Gln
        195                 200                 205

Thr Ala Lys Thr Ser Arg Asn Ile Thr Gly Gly Trp Leu Val Asn Val
    210                 215                 220

Leu Thr Gly Phe Ile Ser Leu Gln Thr Glu His His Leu Phe Pro Met
225                 230                 235                 240

Met Pro Thr Gly Asn Leu Met Thr Ile Gln Pro Glu Val Arg Asp Phe
                245                 250                 255

Phe Lys Lys His Gly Leu Glu Tyr Arg Glu Gly Asn Leu Phe Gln Cys
            260                 265                 270

Val His Gln Asn Ile Lys Ala Leu Ala Phe Glu His Leu Leu His
        275                 280                 285
```

<210> SEQ ID NO 55

```
<211> LENGTH: 20
<212> TYPE: DNA
<213> ORGANISM: Artificial Sequence
<220> FEATURE:
<223> OTHER INFORMATION: Primer SeqE

<400> SEQUENCE: 55
cgacacactc caatctttcc                                               20

<210> SEQ ID NO 56
<211> LENGTH: 20
<212> TYPE: DNA
<213> ORGANISM: Artificial Sequence
<220> FEATURE:
<223> OTHER INFORMATION: Primer SeqW

<400> SEQUENCE: 56
ggtggctgga gttagacatc                                               20

<210> SEQ ID NO 57
<211> LENGTH: 22
<212> TYPE: DNA
<213> ORGANISM: Artificial Sequence
<220> FEATURE:
<223> OTHER INFORMATION: Primer AP1

<400> SEQUENCE: 57
gtaatacgac tcactatagg gc                                            22

<210> SEQ ID NO 58
<211> LENGTH: 20
<212> TYPE: DNA
<213> ORGANISM: Artificial Sequence
<220> FEATURE:
<223> OTHER INFORMATION: Primer GSP PvDES

<400> SEQUENCE: 58
ctgcgaagac ccagcacagg                                               20

<210> SEQ ID NO 59
<211> LENGTH: 22
<212> TYPE: DNA
<213> ORGANISM: Artificial Sequence
<220> FEATURE:
<223> OTHER INFORMATION: Primer M13-28Rev

<400> SEQUENCE: 59
gtaatacgac tcactatagg gc                                            22

<210> SEQ ID NO 60
<211> LENGTH: 21
<212> TYPE: DNA
<213> ORGANISM: Artificial Sequence
<220> FEATURE:
<223> OTHER INFORMATION: Primer PavDes seq

<400> SEQUENCE: 60
ttgtggcgct caatcatctc c                                             21

<210> SEQ ID NO 61
<211> LENGTH: 1294
<212> TYPE: DNA
<213> ORGANISM: Pavlova lutheri

<400> SEQUENCE: 61
ctttgcgagc gcggcgcaga cgattgcggc ccgtagtgat cgcggtgcgc attgctgtgt   60
```

```
ttctagtttt gctgacgccc ggcccgataa tgacaccttc tcccgtttga aatactaata      120
agtaactata ttataatatt caaaggtggc gactatggat ctccttttct aaagttcagc      180
ggaattggga atcggagaaa tttcgagata tgtcataatc acgtgctcta tctcgaatga      240
accgcggccg gtgagcgatt actcgggaag ccaattccta ttaacgagtc agggggatc       300 tttgaggtga gtcggccacg cagagagagc aaggaatcat cctcatccgc cgttctcgag      360
aaagagccaa gggtgccaac caccttccac gtgagactac acaccgtagg ccgatgggca      420
agggtggaga cggcggcgcg caggcggcga gcgggaccga cgcatctctc gctgaggtga      480
gctccgtcga tagcaagagc gtgcgcgtcg tgctctacgg caagcgcgtg gatgtcacaa      540
agttccagag ggcacacccg ggcgggagca aggtgttccg catcttccag gagcgcgacg      600
cgacggagca gttcgagtct taccactcgc ccaaggccat caagatgatg gagggcatgc      660
tcaagaagtc ggaggatgcg cccgcttccg tgccctgcc ctcgcggtcc accatgggca       720
cggagttcaa ggagatgatt gagcgccaca gagggctgg tctctacgac ccttgcccgt       780
tggacgagct gttcaagctc accatcgtcc ttgcgcccat cttcgtgggc gcctatctcg      840
tgcggagcgg cgtctcgccc ctcgcggcg cgctctccat gggctttggc ttctacctcg       900
acggctggct tgctcacrac tacctgcatc acgcagtctt caagggctcg gtcaacacgc      960
tcgtcaaggc gaacaacgcc atgggatacg ccctcggctt cctccagggc tacgacgtgg     1020
cctggtggcg cgcgcgccat aacacgcacc acgtgtgcac caacgaggat ggttcggacc     1080
cggacatcaa gacggcgccc ctgctcatct acgtgcgaga gaacccgtcc attgccaagc     1140
ggctcaactt cttccagcgc tggcagcagt actactatgt gccgaccatg gccatcctcg     1200
acctctactg gcgcctggag tccatcgcgt acgtggctgt gcgcctgcct aagatgtgga     1260
tgcaggccgc cgctcttgcc gctcactacg cgct                                 1294

<210> SEQ ID NO 62
<211> LENGTH: 1927
<212> TYPE: DNA
<213> ORGANISM: Pavlova lutheri

<400> SEQUENCE: 62
ctttgcgagc gcggcgcaga cgattgcggc ccgtagtgat cgcggtgcgc attgctgtgt       60
ttctagtttt gctgacgccc ggcccgataa tgacaccttc tcccgtttga aatactaata      120
agtaactata ttataatatt caaaggtggc gactatggat ctccttttct aaagttcagc      180
ggaattggga atcggagaaa tttcgagata tgtcataatc acgtgctcta tctcgaatga      240
accgcggccg gtgagcgatt actcgggaag ccaattccta ttaacgagtc agggggatc       300 tttgaggtga gtcggccacg cagagagagc aaggaatcat cctcatccgc cgttctcgag      360
aaagagccaa gggtgccaac caccttccac gtgagactac acaccgtagg ccgatgggca      420
agggtggaga cggcggcgcg caggcggtga gcggaccga cgcgtctctc gctgaggtga       480
gctccgtcga tagcaagagc gtgcacgtcg tgctctacgg caagcgcgtg gatgtcacaa      540
agttccagaa ggcacacccg ggcgggagca aggtgttccg catcttccag gagcgcgacg      600
cgacggagca gttcgagtct taccactcgc ccaaggccat caagatgatg gagggcatgc      660
tcaagaagtc ggaggatgcg cccgcttccg tgccctgcc ctcgcggtcc accatgggca       720
cggagttcaa ggagatgatt gagcgccaca gagggctgg tctctacgac ccttgcccgt       780
tggacgagct gttcaagctc accatcgtcc ttgcgcccat cttcgtgggc gcctatctcg      840
```

```
tgcggagcgg cgtctcgccc ctcgcgggcg cgctctccat gggctttggc ttctacctcg    900
acggctggct tgctcacgac tacctgcatc acgcagtctt caagggctcg gtcaacacgc    960
tcgtcaaggc gaacaacgcc atgggatacg ccctcggctt cctccagggc tacgacgtgg   1020
cctggtggcg cgcgcgccat aacacgcacc acgtgtgcac caacgaggat ggttcggacc   1080
cggacatcaa gacggcgccc ctgctcatct acgtgcgaga gaacccgtcc attgccaagc   1140
ggctcaactt cttccagcgc tggcagcagt actactatgt gccgaccatg gccatcctcg   1200
acctctactg gcgcctggag tccatcgcgt acgtggctgt gcgcctgcct aagatgtgga   1260
tgcaggccgc cgctcttgcc gctcactacg cgctcctgtg ctgggtcttc gcagcgcatc   1320
tcaacctcat ccctctcatg atggttgcac gcggcttcgc gacgggcatc gttgtctttg   1380
caacccacta tggtgaggac atcctcgacc gcgagcacgt cgagggcatg acgctcgtcg   1440
agcagaccgc caagacctcc cgtaacatca cgggcggctg gctagtgaac gtgctcacgg   1500
gcttcatctc cctgcagacc gagcatcacc tcttcccat gatgccacc ggcaacctaa   1560
tgactatcca gcccgaggta cgcgacttct tcaagaagca tggcctcgag taccgcgagg   1620
gcaacctctt ccagtgcgtg caccagaaca tcaaggctct cgccttcgag cacctcctcc   1680
actgagcgtc accactcaag cgtcctaagt gcacaggtac tgtcttctga ccgatggccg   1740
cgcggctccc tcggctggca gtggggccaa cgagtggcct cgcgggatcg ggcacgatcg   1800
ggcctccatg aaacttcagt gttcagagac aagccgacaa cctccgcatc gtgagaaatc   1860
ttttaaagca gtatgttcca tcacgccgct tttgcagtca ataacattac ccaaaaaaaa   1920
aaaaaaa                                                              1927
```

<210> SEQ ID NO 63
<211> LENGTH: 459
<212> TYPE: PRT
<213> ORGANISM: Rhizopus stolonifer (GenBank Accession No. ABB96724)

<400> SEQUENCE: 63

```
Met Ser Thr Leu Asp Arg Gln Ser Ile Phe Thr Ile Lys Glu Leu Glu
1               5                   10                  15

Ser Ile Ser Gln Arg Ile His Asp Gly Asp Glu Glu Ala Met Lys Phe
            20                  25                  30

Ile Ile Ile Asp Lys Lys Val Tyr Asp Val Thr Glu Phe Ile Glu Asp
        35                  40                  45

His Pro Gly Gly Ala Gln Val Leu Leu Thr His Val Gly Lys Asp Ala
    50                  55                  60

Ser Asp Val Phe His Ala Met His Pro Glu Ser Ala Tyr Glu Val Leu
65                  70                  75                  80

Asn Asn Tyr Phe Val Gly Asp Val Gln Glu Thr Val Val Thr Glu Lys
                85                  90                  95

Ser Ser Ser Ala Gln Phe Ala Val Glu Met Arg Gln Leu Arg Asp Gln
            100                 105                 110

Leu Lys Lys Glu Gly Tyr Phe His Ser Ser Lys Leu Phe Tyr Ala Tyr
        115                 120                 125

Lys Val Leu Ser Thr Leu Ala Ile Cys Ile Ala Gly Leu Ser Pro Leu
    130                 135                 140

Tyr Ala Tyr Gly Arg Thr Ser Thr Leu Ala Val Val Ala Ser Ala Ile
145                 150                 155                 160

Thr Val Gly Ile Phe Trp Gln Gln Cys Gly Trp Leu Ala His Asp Phe
                165                 170                 175
```

```
Gly His His Gln Cys Phe Glu Asp Arg Thr Trp Asn Asp Val Leu Val
            180                 185                 190

Val Phe Leu Gly Asn Phe Cys Gln Gly Phe Ser Leu Ser Trp Trp Lys
        195                 200                 205

Asn Lys His Asn Thr His His Ala Ser Thr Asn Val His Gly Gln Asp
    210                 215                 220

Pro Asp Ile Asp Thr Ala Pro Val Leu Leu Trp Asp Glu Tyr Ala Ser
225                 230                 235                 240

Ala Ala Tyr Tyr Ala Ser Leu Asp Gln Glu Pro Thr Met Val Ser Arg
                245                 250                 255

Phe Leu Ala Glu Gln Val Leu Pro His Gln Thr Arg Tyr Phe Phe Phe
            260                 265                 270

Ile Leu Ala Phe Ala Arg Leu Ser Trp Ala Leu Gln Ser Leu Ser Tyr
        275                 280                 285

Ser Phe Lys Lys Glu Ser Ile Asn Lys Ser Arg Gln Leu Asn Leu Phe
    290                 295                 300

Glu Arg Val Cys Ile Val Gly His Trp Ala Leu Ser Ala Phe Cys Ile
305                 310                 315                 320

Tyr Ser Trp Cys Ser Asn Val Tyr His Met Val Leu Phe Phe Leu Val
                325                 330                 335

Ser Gln Ala Thr Thr Gly Tyr Thr Leu Ala Leu Val Phe Ala Leu Asn
            340                 345                 350

His Asn Gly Met Pro Val Ile Thr Glu Glu Lys Ala Glu Ser Met Glu
        355                 360                 365

Phe Phe Glu Ile Gln Val Ile Thr Gly Arg Asp Val Thr Leu Ser Pro
    370                 375                 380

Leu Gly Asp Trp Phe Met Gly Gly Leu Asn Tyr Gln Ile Glu His His
385                 390                 395                 400

Val Phe Pro Asn Met Pro Arg His Asn Leu Pro Thr Val Lys Pro Met
                405                 410                 415

Val Lys Ser Leu Cys Gln Lys Tyr Asp Ile Asn Tyr His Asp Thr Gly
            420                 425                 430

Phe Leu Lys Gly Thr Leu Glu Val Leu Gln Thr Leu Asp Ile Thr Ser
        435                 440                 445

Lys Leu Ser Leu Gln Leu Ser Lys Lys Ser Phe
    450                 455

<210> SEQ ID NO 64
<211> LENGTH: 427
<212> TYPE: PRT
<213> ORGANISM: Pavlova salina
<300> PUBLICATION INFORMATION:
<302> TITLE: SYNTHESIS OF LONG-CHAIN POLYUNSATURATED FATTY ACIDS BY
      RECOMBINANT CELLS
<310> PATENT DOCUMENT NUMBER: WO 2005/103253
<311> PATENT FILING DATE: 2005-04-22
<312> PUBLICATION DATE: 2005-11-03
<313> RELEVANT RESIDUES: (1)..(427)

<400> SEQUENCE: 64

Met Gly Arg Gly Gly Asp Ser Ser Gly Gln Ala His Pro Ala Ala Glu
1               5                   10                  15

Leu Ala Val Pro Ser Asp Arg Ala Glu Val Ser Asn Ala Asp Ser Lys
                20                  25                  30

Ala Leu His Ile Val Leu Tyr Gly Lys Arg Val Asp Val Thr Lys Phe
            35                  40                  45

Gln Arg Thr His Pro Gly Gly Ser Lys Val Phe Arg Ile Phe Gln Asp
```

```
                    50                  55                  60
Arg Asp Ala Thr Glu Gln Phe Glu Ser Tyr His Ser Lys Arg Ala Ile
 65                  70                  75                  80

Lys Met Met Glu Gly Met Leu Lys Lys Ser Glu Asp Ala Pro Ala Asp
                     85                  90                  95

Thr Pro Leu Pro Ser Gln Ser Pro Met Gly Lys Asp Phe Lys Ala Met
                    100                 105                 110

Ile Glu Arg His Val Ala Ala Gly Tyr Tyr Asp Pro Cys Pro Leu Asp
                    115                 120                 125

Glu Leu Phe Lys Leu Ser Leu Val Leu Leu Pro Thr Phe Ala Gly Met
                130                 135                 140

Tyr Met Leu Lys Ala Gly Val Gly Ser Pro Leu Cys Gly Ala Leu Met
145                 150                 155                 160

Val Ser Phe Gly Trp Tyr Leu Asp Gly Trp Leu Ala His Asp Tyr Leu
                    165                 170                 175

His His Ser Val Phe Lys Gly Ser Val Ala Arg Thr Val Gly Trp Asn
                    180                 185                 190

Asn Ala Ala Gly Tyr Phe Leu Gly Phe Val Gln Gly Tyr Ala Val Glu
                    195                 200                 205

Trp Trp Arg Ala Arg His Asn Thr His His Val Cys Thr Asn Glu Asp
210                 215                 220

Gly Ser Asp Pro Asp Ile Lys Thr Ala Pro Leu Leu Ile Tyr Val Arg
225                 230                 235                 240

Asn Lys Pro Ser Ile Ala Lys Arg Leu Asn Ala Phe Gln Arg Tyr Gln
                    245                 250                 255

Gln Tyr Tyr Tyr Val Pro Val Met Ala Ile Leu Asp Leu Tyr Trp Arg
                    260                 265                 270

Leu Glu Ser Ile Ala Tyr Val Ala Met Arg Leu Pro Lys Met Leu Pro
                275                 280                 285

Gln Ala Leu Ala Leu Val Ala His Tyr Ala Ile Val Ala Trp Val Phe
                290                 295                 300

Ala Gly Asn Tyr His Leu Leu Pro Leu Val Thr Val Leu Arg Gly Phe
305                 310                 315                 320

Gly Thr Gly Ile Thr Val Phe Ala Thr His Tyr Gly Glu Asp Ile Leu
                    325                 330                 335

Asp Ala Asp Gln Val Arg His Met Thr Leu Val Glu Gln Thr Ala Leu
                340                 345                 350

Thr Ser Arg Asn Ile Ser Gly Gly Trp Leu Val Asn Val Leu Thr Gly
                355                 360                 365

Phe Ile Ser Leu Gln Thr Glu His His Leu Phe Pro Met Met Pro Thr
370                 375                 380

Gly Asn Leu Met Thr Ile Gln Pro Glu Val Arg Ala Phe Phe Lys Lys
385                 390                 395                 400

His Gly Leu Glu Tyr Arg Glu Gly Asn Leu Ile Glu Cys Val Arg Gln
                    405                 410                 415

Asn Ile Arg Ala Leu Ala Phe Glu His Leu Leu
                420                 425

<210> SEQ ID NO 65
<211> LENGTH: 37
<212> TYPE: DNA
<213> ORGANISM: Artificial Sequence
<220> FEATURE:
<223> OTHER INFORMATION: Primer AP
```

<400> SEQUENCE: 65
ggccacgcgt cgactagtac tttttttttt ttttttt        37

<210> SEQ ID NO 66
<211> LENGTH: 39
<212> TYPE: DNA
<213> ORGANISM: Artificial Sequence
<220> FEATURE:
<223> OTHER INFORMATION: Smart IV oligonucleotide primer

<400> SEQUENCE: 66
aagcagtggt atcaacgcag agtggccatt acggccggg        39

<210> SEQ ID NO 67
<211> LENGTH: 1338
<212> TYPE: DNA
<213> ORGANISM: Mortierella alpina

<400> SEQUENCE: 67

```
atgggaacgg accaaggaaa aaccttcacc tgggaagagc tggcggccca taacaccaag      60
gacgacctac tcttggccat ccgcggcagg gtgtacgatg tcacaaagtt cttgagccgc     120
catcctggtg gagtggacac tctcctgctc ggagctggcc gagatgttac tccggtcttt     180
gagatgtatc acgcgtttgg ggctgcagat gccattatga agaagtacta tgtcggtaca     240
ctggtctcga tgagctgcc catcttcccg gagccaacgg tgttccacaa aaccatcaag     300
acgagagtcg agggctactt tacggatcgg aacattgatc ccaagaatag accagagatc     360
tggggacgat acgctcttat ctttggatcc ttgatcgctt cctactacgc gcagctcttt     420
gtgcctttcg ttgtcgaacg cacatggctt caggtggtgt ttgcaatcat catgggattt     480
gcgtgcgcac aagtcggact caaccctctt catgatgcgt ctcactttc agtgacccac     540 aaccccactg tctggaagat tctgggagcc acgcacgact ttttcaacgg agcatcgtac     600
ctggtgtgga tgtaccaaca tatgctcggc catcacccct acaccaacat tgctggagca     660
gatcccgacg tgtcgacgtc tgagcccgat gttcgtcgta tcaagcccaa ccaaaagtgg     720
tttgtcaacc acatcaacca gcacatgttt gttccttttcc tgtacggact gctggcgttc     780
aaggtgcgca ttcaggacat caacattttg tactttgtca agaccaatga cgctattcgt     840
gtcaatccca tctcgacatg gcacactgtg atgttctggg cggcaaggc tttcttgtc     900 tggtatcgcc tgattgttcc cctgcagtat ctgcccctgg gcaaggtgct gctcttgttc     960
acggtcgcgg acatggtgtc gtcttactgg ctggcgctga ccttccaggc gaaccacgtt    1020
gttgaggaag ttcagtggcc gttgcctgac gagaacggga tcatccaaaa ggactgggca    1080
gctatgcagg tcgagactac gcaggattac gcacacgatt cgcacctctg gaccagcatc    1140
actggcagct tgaactacca ggctgtgcac catctgttcc ccaacgtgtc gcagcaccat    1200
tatcccgata ttctggccat catcaagaac acctgcagcg agtacaaggt tccataccttt    1260 gtcaaggata cgtttttggca agcatttgct tcacatttgg agcacttgcg tgttcttgga    1320
ctccgtccca aggaagag                                                    1338
```

<210> SEQ ID NO 68
<211> LENGTH: 446
<212> TYPE: PRT
<213> ORGANISM: Mortierella alpina

<400> SEQUENCE: 68

Met Gly Thr Asp Gln Gly Lys Thr Phe Thr Trp Glu Glu Leu Ala Ala

-continued

```
1               5                   10                  15
His Asn Thr Lys Asp Leu Leu Leu Ala Ile Arg Gly Arg Val Tyr
            20                  25                  30
Asp Val Thr Lys Phe Leu Ser Arg His Pro Gly Gly Val Asp Thr Leu
            35                  40                  45
Leu Leu Gly Ala Gly Arg Asp Val Thr Pro Val Phe Glu Met Tyr His
50                  55                  60
Ala Phe Gly Ala Ala Asp Ala Ile Met Lys Lys Tyr Tyr Val Gly Thr
65                  70                  75                  80
Leu Val Ser Asn Glu Leu Pro Ile Phe Pro Glu Pro Thr Val Phe His
            85                  90                  95
Lys Thr Ile Lys Thr Arg Val Glu Gly Tyr Phe Thr Asp Arg Asn Ile
            100                 105                 110
Asp Pro Lys Asn Arg Pro Glu Ile Trp Gly Arg Tyr Ala Leu Ile Phe
            115                 120                 125
Gly Ser Leu Ile Ala Ser Tyr Tyr Ala Gln Leu Phe Val Pro Phe Val
            130                 135                 140
Val Glu Arg Thr Trp Leu Gln Val Val Phe Ala Ile Ile Met Gly Phe
145                 150                 155                 160
Ala Cys Ala Gln Val Gly Leu Asn Pro Leu His Asp Ala Ser His Phe
            165                 170                 175
Ser Val Thr His Asn Pro Thr Val Trp Lys Ile Leu Gly Ala Thr His
            180                 185                 190
Asp Phe Phe Asn Gly Ala Ser Tyr Leu Val Trp Met Tyr Gln His Met
            195                 200                 205
Leu Gly His His Pro Tyr Thr Asn Ile Ala Gly Ala Asp Pro Asp Val
210                 215                 220
Ser Thr Ser Glu Pro Asp Val Arg Arg Ile Lys Pro Asn Gln Lys Trp
225                 230                 235                 240
Phe Val Asn His Ile Asn Gln His Met Phe Val Pro Phe Leu Tyr Gly
            245                 250                 255
Leu Leu Ala Phe Lys Val Arg Ile Gln Asp Ile Asn Ile Leu Tyr Phe
            260                 265                 270
Val Lys Thr Asn Asp Ala Ile Arg Val Asn Pro Ile Ser Thr Trp His
            275                 280                 285
Thr Val Met Phe Trp Gly Gly Lys Ala Phe Phe Val Trp Tyr Arg Leu
            290                 295                 300
Ile Val Pro Leu Gln Tyr Leu Pro Leu Gly Lys Val Leu Leu Leu Phe
305                 310                 315                 320
Thr Val Ala Asp Met Val Ser Ser Tyr Trp Leu Ala Leu Thr Phe Gln
            325                 330                 335
Ala Asn His Val Val Glu Glu Val Gln Trp Pro Leu Pro Asp Glu Asn
            340                 345                 350
Gly Ile Ile Gln Lys Asp Trp Ala Ala Met Gln Val Glu Thr Thr Gln
            355                 360                 365
Asp Tyr Ala His Asp Ser His Leu Trp Thr Ser Ile Thr Gly Ser Leu
            370                 375                 380
Asn Tyr Gln Ala Val His His Leu Phe Pro Asn Val Ser Gln His His
385                 390                 395                 400
Tyr Pro Asp Ile Leu Ala Ile Ile Lys Asn Thr Cys Ser Glu Tyr Lys
            405                 410                 415
Val Pro Tyr Leu Val Lys Asp Thr Phe Trp Gln Ala Phe Ala Ser His
            420                 425                 430
```

Leu Glu His Leu Arg Val Leu Gly Leu Arg Pro Lys Glu Glu
        435                 440                 445

<210> SEQ ID NO 69
<211> LENGTH: 6473
<212> TYPE: DNA
<213> ORGANISM: Artificial Sequence
<220> FEATURE:
<223> OTHER INFORMATION: Plasmid pY5-22

<400> SEQUENCE: 69

| | | | | | |
|---|---|---|---|---|---|
| ggtggagctc | cagcttttgt | tccctttagt | gagggttaat | ttcgagcttg | gcgtaatcat | 60 |
| ggtcatagct | gtttcctgtg | tgaaattgtt | atccgctcac | aattccacac | aacgtacgag | 120 |
| ccggaagcat | aaagtgtaaa | gcctggggtg | cctaatgagt | gagctaactc | acattaattg | 180 |
| cgttgcgctc | actgcccgct | ttccagtcgg | gaaacctgtc | gtgccagctg | cattaatgaa | 240 |
| tcggccaacg | cgcggggaga | ggcggtttgc | gtattgggcg | ctcttccgct | tcctcgctca | 300 |
| ctgactcgct | gcgctcggtc | gttcggctgc | ggcgagcgg | atcagctcac | tcaaaggcgg | 360 |
| taatacggtt | atccacagaa | tcaggggata | acgcaggaaa | gaacatgtga | gcaaaaggcc | 420 |
| agcaaaaggc | caggaaccgt | aaaaaggccg | cgttgctggc | gtttttccat | aggctccgcc | 480 |
| cccctgacga | gcatcacaaa | aatcgacgct | caagtcagag | gtggcgaaac | ccgacaggac | 540 |
| tataaagata | ccaggcgttt | ccccctggaa | gctccctcgt | gcgctctcct | gttccgaccc | 600 |
| tgccgcttac | cggatacctg | tccgcctttc | tcccttcggg | aagcgtggcg | ctttctcata | 660 |
| gctcacgctg | taggtatctc | agttcggtgt | aggtcgttcg | ctccaagctg | ggctgtgtgc | 720 |
| acgaaccccc | cgttcagccc | gaccgctgcg | ccttatccgg | taactatcgt | cttgagtcca | 780 |
| acccggtaag | acacgactta | tcgccactgg | cagcagccac | tggtaacagg | attagcagag | 840 |
| cgaggtatgt | aggcggtgct | acagagttct | tgaagtggtg | gcctaactac | ggctacacta | 900 |
| gaaggacagt | atttggtatc | tgcgctctgc | tgaagccagt | taccttcgga | aaaagagttg | 960 |
| gtagctcttg | atccggcaaa | caaaccaccg | ctggtagcgg | tggtttttt | gtttgcaagc | 1020 |
| agcagattac | gcgcagaaaa | aaaggatctc | aagaagatcc | tttgatcttt | tctacggggt | 1080 |
| ctgacgctca | gtggaacgaa | aactcacgtt | aagggatttt | ggtcatgaga | ttatcaaaaa | 1140 |
| ggatcttcac | ctagatcctt | ttaaattaaa | aatgaagttt | taaatcaatc | taaagtatat | 1200 |
| atgagtaaac | ttggtctgac | agttaccaat | gcttaatcag | tgaggcacct | atctcagcga | 1260 |
| tctgtctatt | tcgttcatcc | atagttgcct | gactccccgt | cgtgtagata | actacgatac | 1320 |
| gggagggctt | accatctggc | cccagtgctg | caatgatacc | gcgagaccca | cgctcaccgg | 1380 |
| ctccagattt | atcagcaata | aaccagccag | ccggaagggc | cgagcgcaga | agtggtcctg | 1440 |
| caactttatc | cgcctccatc | cagtctatta | attgttgccg | ggaagctaga | gtaagtagtt | 1500 |
| cgccagttaa | tagtttgcgc | aacgttgttg | ccattgctac | aggcatcgtg | gtgtcacgct | 1560 |
| cgtcgtttgg | tatggcttca | ttcagctccg | gttcccaacg | atcaaggcga | gttacatgat | 1620 |
| cccccatgtt | gtgcaaaaaa | gcggttagct | ccttcggtcc | tccgatcgtt | gtcagaagta | 1680 |
| agttggccgc | agtgttatca | ctcatggtta | tggcagcact | gcataattct | cttactgtca | 1740 |
| tgccatccgt | aagatgcttt | tctgtgactg | gtgagtactc | aaccaagtca | ttctgagaat | 1800 |
| agtgtatgcg | gcgaccgagt | tgctcttgcc | cggcgtcaat | acgggataat | accgcgccac | 1860 |
| atagcagaac | tttaaaagtg | ctcatcattg | gaaaacgttc | ttcggggcga | aaactctcaa | 1920 |
| ggatcttacc | gctgttgaga | tccagttcga | tgtaacccac | tcgtgcaccc | aactgatctt | 1980 |

```
cagcatcttt tactttcacc agcgtttctg ggtgagcaaa acaggaagg caaaatgccg    2040 caaaaaggg aataagggcg acacggaaat gttgaatact catactcttc cttttcaat     2100 attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg gctcccttt agggttccga tttagtgctt    2400
tacggcacct cgaccccaaa aaacttgatt agggtgatgg ttcacgtagt gggccatcgc   2460
cctgatagac ggttttcgc cctttgacgt tggagtccac gttctttaat agtggactct    2520
tgttccaaac tggaacaaca ctcaaccccta tctcggtcta ttcttttgat ttataaggga  2580
ttttgccgat ttcggcctat tggttaaaaa atgagctgat ttaacaaaaa tttaacgcga   2640
attttaacaa atattaacg cttacaattt ccattcgcca ttcaggctgc gcaactgttg    2700
ggaagggcga tcggtgcggg cctcttcgct attacgccag ctggcgaaag ggggatgtgc   2760
tgcaaggcga ttaagttggg taacgccagg gttttcccag tcacgacgtt gtaaaacgac   2820
ggccagtgaa ttgtaatacg actcactata gggcgaattg ggtaccgggc cccccctcga   2880
ggtcgatggt gtcgataagc ttgatatcga attcatgtca cacaaaccga tcttcgcctc   2940
aaggaaacct aattctacat ccgagagact gccgagatcc agtctacact gattaatttt   3000
cgggccaata atttaaaaaa atcgtgttat ataatattat atgtattata tatatacatc   3060
atgatgatac tgacagtcat gtcccattgc taaatagaca gactccatct gccgcctcca   3120
actgatgttc tcaatattta aggggtcatc tcgcattgtt taataataaa cagactccat   3180
ctaccgcctc caaatgatgt tctcaaaata tattgtatga acttattttt attacttagt   3240
attattagac aacttacttg ctttatgaaa aacacttcct atttaggaaa caatttataa   3300
tggcagttcg ttcatttaac aatttatgta gaataaatgt tataaatgcg tatgggaaat   3360
cttaaatatg gatagcataa atgatatctg cattgcctaa ttcgaaatca acagcaacga   3420
aaaaaatccc ttgtacaaca taaatagtca tcgagaaata tcaactatca aagaacagct   3480
attcacacgt tactattgag attattattg gacgagaatc acacactcaa ctgtctttct   3540
ctcttctaga aatacaggta caagtatgta ctattctcat tgttcatact tctagtcatt   3600
tcatcccaca tattccttgg atttctctcc aatgaatgac attctatctt gcaaattcaa   3660
caattataat aagatatacc aaagtagcgg tatagtggca atcaaaaagc ttctctggtg   3720
tgcttctcgt atttattttt attctaatga tccattaaag gtatatattt atttcttgtt   3780
atataatcct tttgtttatt acatgggctg atacataaa ggtattttga tttaatttt    3840 tgcttaaatt caatcccccc tcgttcagtg tcaactgtaa tggtaggaaa ttaccatact   3900
tttgaagaag caaaaaaaat gaaagaaaaa aaaaatcgta tttccaggtt agacgttccg   3960
cagaatctag aatgcggtat gcggtacatt gttcttcgaa cgtaaaagtt gcgctccctg   4020
agatattgta cattttttgct tttcaagta caagtacatc gtacaactat gtactactgt   4080
tgatgcatcc acaacagttt gttttgtttt ttttgtttt tttttttctct aatgattcat   4140 taccgctatg tatacctact tgtacttgta gtaagccggg ttattggcgt tcaattaatc   4200
atagacttat gaatctgcac ggtgtgcgct gcgagttact tttagcttat gcatgctact   4260
tgggtgtaat attgggatct gttcggaaat caacggatgc tcaaccgatt tcgacagtaa   4320
```

| | |
|---|---|
| ttaattaagt catacacaag tcagctttct tcgagcctca tataagtata agtagttcaa | 4380 |
| cgtattagca ctgtacccag catctccgta tcgagaaaca caacaacatg ccccattgga | 4440 |
| cagatcatgc ggatacacag gttgtgcagt atcatacata ctcgatcaga caggtcgtct | 4500 |
| gaccatcata caagctgaac aagcgctcca tacttgcacg ctctctatat acacagttaa | 4560 |
| attacatatc catagtctaa cctctaacag ttaatcttct ggtaagcctc ccagccagcc | 4620 |
| ttctggtatc gcttggcctc ctcaatagga tctcggttct ggccgtacag acctcggccg | 4680 |
| acaattatga tatccgttcc ggtagacatg acatcctcaa cagttcggta ctgctgtccg | 4740 |
| agagcgtctc ccttgtcgtc aagacccacc ccggggtca gaataagcca gtcctcagag | 4800 |
| tcgcccttag gtcggttctg ggcaatgaag ccaaccacaa actcgggtc ggatcgggca | 4860 |
| agctcaatgg tctgcttgga gtactcgcca gtggccagag agcccttgca agacagctcg | 4920 |
| gccagcatga gcagacctct ggccagcttc tcgttgggag aggggactag gaactccttg | 4980 |
| tactgggagt tctcgtagtc agagacgtcc tccttcttct gttcagagac agtttcctcg | 5040 |
| gcaccagctc gcaggccagc aatgattccg gttccgggta caccgtgggc gttggtgata | 5100 |
| tcggaccact cggcgattcg gtgacaccgg tactggtgct tgacagtgtt gccaatatct | 5160 |
| gcgaactttc tgtcctcgaa caggaagaaa ccgtgcttaa gagcaagttc cttgaggggg | 5220 |
| agcacagtgc cggcgtaggt gaagtcgtca atgatgtcga tatggttttt gatcatgcac | 5280 |
| acataaggtc cgaccttatc ggcaagctca atgagctcct tggtggtggt aacatccaga | 5340 |
| gaagcacaca ggttggtttt cttggctgcc acgagcttga gcactcgagc ggcaaaggcg | 5400 |
| gacttgtgga cgttagctcg agcttcgtag gagggcattt tggtggtgaa gaggagactg | 5460 |
| aaataaattt agtctgcaga acttttatc ggaaccttat ctggggcagt gaagtatatg | 5520 |
| ttatggtaat agttacgagt tagttgaact tatagataga ctggactata cggctatcgg | 5580 |
| tccaaattag aaagaacgtc aatggctctc tgggcgtcgc ctttgccgac aaaaatgtga | 5640 |
| tcatgatgaa agccagcaat gacgttgcag ctgatattgt tgtcggccaa ccgcgccgaa | 5700 |
| aacgcagctg tcagacccac agcctccaac gaagaatgta tcgtcaaagt gatccaagca | 5760 |
| cactcatagt tggagtcgta ctccaaaggc ggcaatgacg agtcagacag atactcgtcg | 5820 |
| actcaggcga cgacggaatt cctgcagccc atctgcagaa ttcaggagag accgggttgg | 5880 |
| cggcgtattt gtgtcccaaa aaacagcccc aattgcccca attgacccca aattgaccca | 5940 |
| gtagcgggcc caaccccggc gagagccccc ttcacccac atatcaaacc tcccccggtt | 6000 |
| cccacacttg ccgttaaggg cgtagggtac tgcagtctgg aatctacgct tgttcagact | 6060 |
| ttgtactagt ttctttgtct ggccatccgg gtaacccatg ccggacgcaa aatagactac | 6120 |
| tgaaaatttt tttgctttgt ggttgggact ttagccaagg gtataaaaga ccaccgtccc | 6180 |
| cgaattacct ttcctcttct tttctctctc tccttgtcaa ctcacacccg aaatcgttaa | 6240 |
| gcatttcctt ctgagtataa gaatcattca ccatggatcc actagttcta gagcggccgc | 6300 |
| caccgcggcc cgagattccg gcctcttcgg ccgccaagcg acccgggtgg acgtctagag | 6360 |
| gtacctagca attaacagat agtttgccgg tgataattct cttaacctcc cacactcctt | 6420 |
| tgacataacg atttatgtaa cgaaactgaa atttgaccag atattgtgtc cgc | 6473 |

<210> SEQ ID NO 70
<211> LENGTH: 6970
<212> TYPE: DNA
<213> ORGANISM: Artificial Sequence
<220> FEATURE:
<223> OTHER INFORMATION: Plasmid pY5-22GPD

<400> SEQUENCE: 70

```
tcgacgcagt aggatgtcct gcacgggtct ttttgtgggg tgtggagaaa ggggtgcttg    60
gagatggaag ccggtagaac cgggctgctt gtgcttggag atggaagccg gtagaaccgg   120
gctgcttggg gggatttggg gccgctgggc tccaaagagg ggtaggcatt tcgttggggt   180
tacgtaattg cggcatttgg gtcctgcgcg catgtcccat tggtcagaat tagtccggat   240
aggagactta tcagccaatc acagcgccgg atccacctgt aggttgggtt gggtgggagc   300
accccctccac agagtagagt caaacagcag cagcaacatg atagttgggg gtgtgcgtgt   360
taaaggaaaa aaaagaagct tgggttatat tcccgctcta tttagaggtt gcgggataga   420
cgccgacgga gggcaatggc gccatggaac cttgcggata tcgatacgcc gcggcggact   480
gcgtccgaac cagctccagc agcgtttttt ccgggccatt gagccgactg cgacccccgcc   540
aacgtgtctt ggcccacgca ctcatgtcat gttggtgttg ggaggccact tttttaagtag   600
cacaaggcac ctagctcgca gcaaggtgtc cgaaccaaag aagcggctgc agtggtgcaa   660
acggggcgga aacggcggga aaaagccacg ggggcacgaa ttgaggcacg ccctcgaatt   720
tgagacgagt cacggcccca ttcgcccgcg caatggctcg ccaacgcccg gtcttttgca   780
ccacatcagg ttaccccaag ccaaaccttt gtgttaaaaa gcttaacata ttataccgaa   840
cgtaggtttg gcgggcttg ctccgtctgt ccaaggcaac atttatataa gggtctgcat   900
cgccggctca attgaatctt ttttcttctt ctcttctcta tattcattct tgaattaaac   960
acacatcaat ccgcggccgc caccgcggcc cgagattccg gcctcttcgg ccgccaagcg  1020
acccgggtgg acgtctagag gtacctagca attaacagat agtttgccgg tgataattct  1080
cttaacctcc cacactcctt tgacataacg atttatgtaa cgaaactgaa atttgaccag  1140
atattgtgtc cgcggtggag ctccagcttt tgttcccttt agtgagggtt aatttcgagc  1200
ttggcgtaat catggtcata gctgtttcct gtgtgaaatt gttatccgct cacaattcca  1260
cacaacgtac gagccggaag cataaagtgt aaagcctggg gtgcctaatg agtgagctaa  1320
ctcacattaa ttgcgttgcg ctcactgccc gctttccagt cgggaaacct gtcgtgccag  1380
ctgcattaat gaatcggcca acgcgcgggg agaggcggtt tgcgtattgg gcgctcttcc  1440
gcttcctcgc tcactgactc gctgcgctcg gtcgttcggc tgcggcgagc ggtatcagct  1500
cactcaaagg cggtaatacg gttatccaca gaatcagggg ataacgcagg aaagaacatg  1560
tgagcaaaag gccagcaaaa ggccaggaac cgtaaaaagg ccgcgttgct ggcgtttttc  1620
cataggctcc gcccccctga cgagcatcac aaaaatcgac gctcaagtca gaggtggcga  1680
aacccgacag gactataaag ataccaggcg tttccccctg gaagctccct cgtgcgctct  1740
cctgttccga ccctgccgct taccggatac ctgtccgcct ttctcccttc gggaagcgtg  1800
gcgctttctc atagctcacg ctgtaggtat ctcagttcgg tgtaggtcgt tcgctccaag  1860
ctgggctgtg tgcacgaacc ccccgttcag cccgaccgct gcgccttatc cggtaactat  1920
cgtcttgagt ccaacccggt aagacacgac ttatcgccac tggcagcagc cactggtaac  1980
aggattagca gagcgaggta tgtaggcggt gctacagagt tcttgaagtg gtggcctaac  2040
tacggctaca ctagaaggac agtatttggt atctgcgctc tgctgaagcc agttaccttc  2100
ggaaaaagag ttggtagctc ttgatccggc aaacaaacca ccgctggtag cggtggtttt  2160
tttgtttgca agcagcagat tacgcgcaga aaaaaaggat ctcaagaaga tcctttgatc  2220
ttttctacgg ggtctgacgc tcagtggaac gaaaactcac gttaagggat tttggtcatg  2280
```

```
agattatcaa aaaggatctt cacctagatc ctttaaatt aaaaatgaag ttttaaatca   2340
atctaaagta tatatgagta aacttggtct gacagttacc aatgcttaat cagtgaggca   2400
cctatctcag cgatctgtct atttcgttca tccatagttg cctgactccc cgtcgtgtag   2460
ataactacga tacgggaggg cttaccatct ggcccagtg ctgcaatgat accgcgagac    2520
ccacgctcac cggctccaga tttatcagca ataaaccagc cagccggaag ggccgagcgc   2580
agaagtggtc ctgcaacttt atccgcctcc atccagtcta ttaattgttg ccgggaagct   2640
agagtaagta gttcgccagt taatagtttg cgcaacgttg ttgccattgc tacaggcatc   2700
gtggtgtcac gctcgtcgtt tggtatggct tcattcagct ccggttccca acgatcaagg   2760
cgagttacat gatcccccat gttgtgcaaa aaagcggtta gctccttcgg tcctccgatc   2820
gttgtcagaa gtaagttggc cgcagtgtta tcactcatgg ttatggcagc actgcataat   2880
tctcttactg tcatgccatc cgtaagatgc ttttctgtga ctggtgagta ctcaaccaag   2940
tcattctgag aatagtgtat gcggcgaccg agttgctctt gcccggcgtc aatacgggat   3000
aataccgcgc cacatagcag aactttaaaa gtgctcatca ttggaaaacg ttcttcgggg   3060
cgaaaactct caaggatctt accgctgttg agatccagtt cgatgtaacc cactcgtgca   3120
cccaactgat cttcagcatc ttttactttc accagcgttt ctgggtgagc aaaaacagga   3180
aggcaaaatg ccgcaaaaaa gggaataagg gcgacacgga aatgttgaat actcatactc   3240
ttccttttc aatattattg aagcatttat cagggttatt gtctcatgag cggatacata   3300
tttgaatgta tttagaaaaa taaacaaata ggggttccgc gcacatttcc ccgaaaagtg   3360
ccacctgacg cgcccgtag cggcgcatta agcgcggcgg gtgtggtggt tacgcgcagc   3420
gtgaccgcta cacttgccag cgccctagcg cccgctcctt tcgctttctt cccttccttt   3480
ctcgccacgt tcgccggctt tccccgtcaa gctctaaatc gggggctccc tttagggttc   3540
cgatttagtg ctttacggca cctcgacccc aaaaaacttg attagggtga tggttcacgt   3600
agtgggccat cgccctgata gacggttttt cgccctttga cgttggagtc acgttctttt   3660
aatagtggac tcttgttcca aactggaaca acactcaacc ctatctcggt ctattctttt   3720
gatttataag ggattttgcc gatttcggcc tattggttaa aaaatgagct gatttaacaa   3780
aaatttaacg cgaattttaa caaaatatta acgcttacaa tttccattcg ccattcaggc   3840
tgcgcaactg ttgggaaggg cgatcggtgc gggcctcttc gctattacgc cagctggcga   3900
aaggggatg tgctgcaagg cgattaagtt gggtaacgcc agggttttcc cagtcacgac   3960
gttgtaaaac gacggccagt gaattgtaat acgactcact ataggggaa ttgggtaccg    4020
ggccccccct cgaggtcgat ggtgtcgata agcttgatat cgaattcatg tcacacaaac   4080
cgatcttcgc ctcaaggaaa cctaattcta catccgagag actgccgaga tccagtctac   4140
actgattaat tttcgggcca ataatttaaa aaatcgtgt tatataatat tatatgtatt    4200
atatatatac atcatgatga tactgacagt catgtcccat tgctaaatag acagactcca   4260
tctgccgcct ccaactgatg ttctcaatat ttaaggggtc atctcgcatt gtttaataat   4320
aaacagactc catctaccgc ctccaaatga tgttctcaaa atatattgta tgaacttatt   4380
tttattactt agtattatta gacaacttac ttgctttatg aaaacacttt cctatttagg   4440
aaacaattta taatggcagt tcgttcattt aacaatttat gtagaataaa tgttataaat   4500
gcgtatggga atcttaaat atggatagca taaatgatat ctgcattgcc taattcgaaa    4560
tcaacagcaa cgaaaaaaat cccttgtaca acataaaatag tcatcgagaa atatcaacta   4620
tcaaagaaca gctattcaca cgttactatt gagattatta ttggacgaga atcacacact   4680
```

```
caactgtctt tctctcttct agaaatacag gtacaagtat gtactattct cattgttcat    4740
acttctagtc atttcatccc acatattcct tggatttctc tccaatgaat gacattctat    4800
cttgcaaatt caacaattat aataagatat accaaagtag cggtatagtg gcaatcaaaa    4860
agcttctctg gtgtgcttct cgtatttatt tttattctaa tgatccatta aaggtatata    4920
tttatttctt gttatataat cctttgtttt attacatggg ctggatacat aaaggtattt    4980
tgatttaatt ttttgcttaa attcaatccc ccctcgttca gtgtcaactg taatggtagg    5040
aaattaccat acttttgaag aagcaaaaaa aatgaaagaa aaaaaaatc gtatttccag     5100 gttagacgtt ccgcagaatc tagaatgcgg tatgcggtac attgttcttc gaacgtaaaa    5160
gttgcgctcc ctgagatatt gtacattttt gcttttacaa gtacaagtac atcgtacaac    5220
tatgtactac tgttgatgca tccacaacag tttgttttgt ttttttttgt ttttttttt    5280 tctaatgatt cattaccgct atgtatacct acttgtactt gtagtaagcc gggttattgg    5340
cgttcaatta atcatagact tatgaatctg cacggtgtgc gctgcgagtt actttagct    5400 tatgcatgct acttgggtgt aatattggga tctgttcgga aatcaacgga tgctcaaccg    5460
atttcgacag taattaatta agtcatacac aagtcagctt tcttcgagcc tcatataagt    5520
ataagtagtt caacgtatta gcactgtacc cagcatctcc gtatcgagaa acacaacaac    5580
atgccccatt ggacagatca tgcggataca caggttgtgc agtatcatac atactcgatc    5640
agacaggtcg tctgaccatc atacaagctg aacaagcgct ccatacttgc acgctctcta    5700
tatacacagt taaattacat atccatagtc taacctctaa cagttaatct tctggtaagc    5760
ctcccagcca gccttctggt atcgcttggc ctcctcaata ggatctcggt tctggccgta    5820
cagacctcgg ccgacaatta tgatatccgt tccggtagac atgacatcct caacagttcg    5880
gtactgctgt ccgagagcgt ctcccttgtc gtcaagaccc accccgggg tcagaataag    5940 ccagtcctca gagtcgccct taggtcggtt ctgggcaatg aagccaacca caaactcggg    6000
gtcggatcgg gcaagctcaa tggtctgctt ggagtactcg ccagtggcca gagagcccct    6060
gcaagacagc tcggccagca tgagcagacc tctggccagc ttctcgttgg gagaggggac    6120
taggaactcc ttgtactggg agttctcgta gtcagagacg tcctccttct tctgttcaga    6180
gacagtttcc tcggcaccag ctcgcaggcc agcaatgatt ccggttccgg gtacaccgtg    6240
ggcgttggtg atatcggacc actcggcgat tcggtgacac cggtactggt gcttgacagt    6300
gttgccaata tctgcgaact ttctgtcctc gaacaggaag aaaccgtgct taagagcaag    6360
ttccttgagg gggagcacag tgccggcgta ggtgaagtcg tcaatgatgt cgatatgggt    6420
tttgatcatg cacacataag gtccgacctt atcggcaagc tcaatgagct ccttggtggt    6480
ggtaacatcc agagaagcac acaggttggt tttcttggct gccacgagct tgagcactcg    6540
agcggcaaag gcggacttgt ggacgttagc tcgagcttcg taggagggca ttttggtggt    6600
gaagaggaga ctgaaataaa tttagtctgc agaactttt atcggaacct tatctggggc    6660
agtgaagtat atgttatggt aatagttacg agttagttga acttatagat agactggact    6720
atacggctat cggtccaaat tagaaagaac gtcaatggct ctctgggcgt cgcctttgcc    6780
gacaaaaatg tgatcatgat gaaagccagc aatgacgttg cagctgatat tgttgtcggc    6840
caaccgcgcc gaaaacgcag ctgtcagacc cacagcctcc aacgaagaat gtatcgtcaa    6900
agtgatccaa gcacactcat agttggagtc gtactccaaa ggcggcaatg acgagtcaga    6960
cagatactcg                                                            6970
```

<210> SEQ ID NO 71
<211> LENGTH: 968
<212> TYPE: DNA
<213> ORGANISM: Yarrowia lipolytica
<300> PUBLICATION INFORMATION:
<302> TITLE: GLYCERALDEHYDE-3-PHOSPHATE DEHYDROGENASE AND
      PHOSPHOGLYCERATE MUTASE PROMOTERS FOR GENE EXPRESSION IN
      OLEAGINOUS YEAST
<310> PATENT DOCUMENT NUMBER: US-2005-0014270-A1
<311> PATENT FILING DATE: 2004-06-16
<312> PUBLICATION DATE: 2005-01-20
<313> RELEVANT RESIDUES: (1)..(968)

<400> SEQUENCE: 71

```
tcgacgcagt aggatgtcct gcacgggtct ttttgtgggg tgtggagaaa ggggtgcttg      60
gagatggaag ccggtagaac cgggctgctt gtgcttggag atggaagccg gtagaaccgg     120
gctgcttggg gggatttggg gccgctgggc tccaaagagg ggtaggcatt tcgttggggt     180
tacgtaattg cggcatttgg gtcctgcgcg catgtcccat tggtcagaat tagtccggat     240
aggagactta tcagccaatc acagcgccgg atccacctgt aggttgggtt gggtgggagc     300
acccctccac agagtagagt caaacagcag cagcaacatg atagttgggg gtgtgcgtgt     360
taaaggaaaa aaagaagct tgggttatat tcccgctcta tttagaggtt gcgggataga     420
cgccgacgga gggcaatggc gccatggaac cttgcggata tcgatacgcc gcggcggact     480
gcgtccgaac cagctccagc agcgtttttt ccggccatt gagccgactg cgaccccgcc      540
aacgtgtctt ggcccacgca ctcatgtcat gttggtgttg ggaggccact ttttaagtag     600
cacaaggcac ctagctcgca gcaaggtgtc cgaaccaaag aagcggctgc agtggtgcaa     660
acggggcgga aacggcggga aaaagccacg ggggcacgaa ttgaggcacg ccctcgaatt     720
tgagacgagt cacggcccca ttcgcccgcg caatggctcg ccaacgcccg gtcttttgca     780
ccacatcagg ttaccccaag ccaaaccttt gtgttaaaaa gcttaacata ttataccgaa     840
cgtaggtttg ggcgggcttg ctccgtctgt ccaaggcaac atttatataa gggtctgcat     900
cgccggctca attgaatctt ttttcttctt ctcttctcta tattcattct tgaattaaac     960
acacatca                                                               968
```

<210> SEQ ID NO 72
<211> LENGTH: 8630
<212> TYPE: DNA
<213> ORGANISM: Artificial Sequence
<220> FEATURE:
<223> OTHER INFORMATION: Plasmid pYZDE2-S

<400> SEQUENCE: 72

```
ggtggagctc cagcttttgt tccctttagt gagggttaat tcgagcttg gcgtaatcat       60
ggtcatagct gtttcctgtg tgaaattgtt atccgctcac aattccacac aacgtacgag     120
ccggaagcat aaagtgtaaa gcctggggtg cctaatgagt gagctaactc acattaattg     180
cgttgcgctc actgcccgct ttccagtcgg gaaacctgtc gtgccagctg cattaatgaa     240
tcggccaacg cgcggggaga ggcggtttgc gtattgggcg ctcttccgct tcctcgctca     300
ctgactcgct gcgctcggtc gttcggctgc ggcgagcggt atcagctcac tcaaaggcgg     360
taatacggtt atccacagaa tcaggggata acgcaggaaa gaacatgtga gcaaaaggcc     420
agcaaaaggc caggaaccgt aaaaaggccg cgttgctggc gtttttccat aggctccgcc     480
ccccctgacga gcatcacaaa aatcgacgct caagtcagag gtggcgaaac ccgacaggac     540
tataaagata ccaggcgttt ccccctggaa gctccctcgt gcgctctcct gttccgaccc     600
```

```
tgccgcttac cggatacctg tccgcctttc tcccttcggg aagcgtggcg ctttctcata    660
gctcacgctg taggtatctc agttcggtgt aggtcgttcg ctccaagctg gctgtgtgc    720 acgaaccccc cgttcagccc gaccgctgcg ccttatccgg taactatcgt cttgagtcca    780
acccggtaag acacgactta tcgccactgg cagcagccac tggtaacagg attagcagag    840
cgaggtatgt aggcggtgct acagagttct tgaagtggtg cctaactac ggctacacta    900 gaaggacagt atttggtatc tgcgctctgc tgaagccagt taccttcgga aaaagagttg    960
gtagctcttg atccggcaaa caaaccaccg ctggtagcgg tggtttttt gtttgcaagc   1020 agcagattac gcgcagaaaa aaggatctc aagaagatcc tttgatcttt tctacggggt   1080
ctgacgctca gtggaacgaa aactcacgtt aagggatttt ggtcatgaga ttatcaaaaa   1140
ggatcttcac ctagatcctt ttaaattaaa aatgaagttt taaatcaatc taagtatat   1200 atgagtaaac ttggtctgac agttaccaat gcttaatcag tgaggcacct atctcagcga   1260
tctgtctatt tcgttcatcc atagttgcct gactccccgt cgtgtagata actacgatac   1320
gggagggctt accatctggc cccagtgctg caatgatacc gcgagaccca cgctcaccgg   1380
ctccagattt atcagcaata aaccagccag ccggaagggc cgagcgcaga gtggtcctg   1440 caactttatc cgcctccatc cagtctatta attgttgccg ggaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
ggatcttacc gctgttgaga tccagttcga tgtaacccac tcgtgcaccc aactgatctt   1980
cagcatcttt tactttcacc agcgtttctg ggtgagcaaa aacaggaagg caaaatgccg   2040
caaaaaaggg aataagggcg acacggaaat gttgaatact catactcttc ctttttcaat   2100
attattgaag catttatcag ggttattgtc tcatgagcgg atacatattt gaatgtattt   2160
agaaaaataa acaaataggg gttccgcgca catttccccg aaaagtgcca cctgacgcgc   2220
cctgtagcgg cgcattaagc gcggcgggtg tggtggttac gcgcagcgtg accgctacac   2280
ttgccagcgc cctagcgccc gctcctttcg ctttcttccc ttcctttctc gccacgttcg   2340
ccggctttcc ccgtcaagct ctaaatcggg ggctcccttt agggttccga tttagtgctt   2400
tacggcacct cgaccccaaa aaacttgatt agggtgatgg ttcacgtagt gggccatcgc   2460
cctgatagac ggttttcgc cctttgacgt tggagtccac gttctttaat agtggactct   2520
tgttccaaac tggaacaaca ctcaacccta tctcggtcta ttcttttgat ttataaggga   2580
ttttgccgat ttcggcctat tggttaaaaa atgagctgat ttaacaaaaa tttaacgcga   2640
attttaacaa aatattaacg cttacaattt ccattcgcca ttcaggctgc gcaactgttg   2700
ggaagggcga tcggtgcggg cctcttcgct attacgccag ctggcgaaag ggggatgtgc   2760
tgcaaggcga ttaagttggg taacgccagg gttttcccag tcacgacgtt gtaaaacgac   2820
ggccagtgaa ttgtaatacg actcactata gggcgaattg gtaccgggc cccccctcga   2880 ggtcgatggt gtcgataagc ttgatatcga attcatgtca cacaaaccga tcttcgcctc   2940
```

```
aaggaaacct aattctacat ccgagagact gccgagatcc agtctacact gattaatttt    3000
cgggccaata atttaaaaaa atcgtgttat ataatattat atgtattata tatatacatc    3060
atgatgatac tgacagtcat gtcccattgc taaatagaca gactccatct gccgcctcca    3120
actgatgttc tcaatattta aggggtcatc tcgcattgtt taataataaa cagactccat    3180
ctaccgcctc caaatgatgt tctcaaaata tattgtatga acttattttt attacttagt    3240
attattagac aacttacttg ctttatgaaa aacacttcct atttaggaaa caatttataa    3300
tggcagttcg ttcatttaac aatttatgta gaataaatgt tataaatgcg tatgggaaat    3360
cttaaatatg gatagcataa atgatatctg cattgcctaa ttcgaaatca acagcaacga    3420
aaaaaatccc ttgtacaaca taaatagtca tcgagaaata tcaactatca aagaacagct    3480
attcacacgt tactattgag attattattg gacgagaatc acacactcaa ctgtctttct    3540
ctcttctaga aatacaggta caagtatgta ctattctcat tgttcatact tctagtcatt    3600
tcatcccaca tattccttgg atttctctcc aatgaatgac attctatctt gcaaattcaa    3660
caattataat aagatatacc aaagtagcgg tatagtggca atcaaaaagc ttctctggtg    3720
tgcttctcgt atttattttt attctaatga tccattaaag gtatatattt atttcttgtt    3780
atataatcct tttgtttatt acatgggctg gatacataaa ggtattttga tttaattttt    3840
tgcttaaatt caatcccccc tcgttcagtg tcaactgtaa tggtaggaaa ttaccatact    3900
tttgaagaag caaaaaaaat gaaagaaaaa aaaaatcgta tttccaggtt agacgttccg    3960
cagaatctag aatgcggtat gcggtacatt gttcttcgaa cgtaaaagtt gcgctccctg    4020
agatattgta cattttttgct tttacaagta caagtacatc gtacaactat gtactactgt    4080
tgatgcatcc acaacagttt gttttgtttt ttttttgtttt ttttttttct aatgattcat    4140
taccgctatg tatacctact tgtacttgta gtaagccggg ttattggcgt tcaattaatc    4200
atagacttat gaatctgcac ggtgtgcgct gcgagttact tttagcttat gcatgctact    4260
tgggtgtaat attgggatct gttcggaaat caacggatgc tcaaccgatt tcgacagtaa    4320
taatttgaat cgaatcggag cctaaaatga acccgagtat atctcataaa attctcggtg    4380
agaggtctgt gactgtcagt acaaggtgcc ttcattatgc cctcaacctt accatacctc    4440
actgaatgta gtgtacctct aaaaatgaaa tacagtgcca aaagccaagg cactgagctc    4500
gtctaacgga cttgatatac aaccaattaa aacaaatgaa aagaaataca gttctttgta    4560
tcatttgtaa caattaccct gtacaaacta aggtattgaa atcccacaat attcccaaag    4620
tccacccctt tccaaattgt catgcctaca actcatatac caagcactaa cctaccaaac    4680
accactaaaa ccccacaaaa tatatcttac cgaatataca gtaacaagct accaccacac    4740
tcgttgggtg cagtcgccag cttaaagata tctatccaca tcagccacaa ctcccttcct    4800
ttaataaacc gactacaccc ttggctattg aggttatgag tgaatatact gtagacaaga    4860
cactttcaag aagactgttt ccaaaacgta ccactgtcct ccactacaaa cacacccaat    4920
ctgcttcttc tagtcaaggt tgctacaccg gtaaattata aatcatcatt tcattagcag    4980
ggcagggccc ttttatagta gtcttataca ctagcggacc ctgccggtag accaacccgc    5040
aggcgcgtca gtttgctcct tccatcaatg cgtcgtagaa acgacttact ccttcttgag    5100
cagctccttg accttgttgg caacaagtct ccgacctcgg aggtggagga agagcctccg    5160
atatcggcgg tagtgatacc agcctcgacg gactccttga cggcagcctc aacagcgtca    5220
ccggcgggct tcatgttaag agagaacttg agcatcatgg cggcagacag aatggtggca    5280
atggggttga ccttctgctt gccgagatcg ggggcagatc cgtgacaggg ctcgtacaga    5340
```

```
ccgaacgcct cgttggtgtc gggcagagaa gccagagagg cggagggcag cagacccaga    5400
gaaccgggga tgacggaggc ctcgtcggag atgatatcgc caaacatgtt ggtggtgatg    5460
atgataccat tcatcttgga gggctgcttg atgaggatca tggcggccga gtcgatcagc    5520
tggtggttga gctcgagctg ggggaattcg tccttgagga ctcgagtgac agtctttcgc    5580
caaagtcgag aggaggccag cacgttggcc ttgtcaagag accacacggg aagaggggggg   5640 ttgtgctgaa gggccaggaa ggcggccatt cgggcaattc gctcaacctc aggaacggag    5700
taggtctcgg tgtcggaagc gacgccagat ccgtcatcct cctttcgctc tccaaagtag    5760 ataccctccga cgagctctcg gacaatgatg aagtcggtgc cctcaacgtt tcggatgggg   5820
gagagatcgg cgagcttggg cgacagcagc tggcagggtc gcaggttggc gtacaggttc    5880
aggtcctttc gcagcttgag gagaccctgc tcgggtcgca cgtcggttcg tccgtcggga    5940
gtggtccata cggtgttggc agcgcctccg acagcaccga gcataataga gtcagccttt    6000
cggcagatgt cgagagtagc gtcggtgatg ggctcgccct ccttctcaat ggcagctcct    6060
ccaatgagtc ggtcctcaaa cacaaactcg gtgccggagg cctcagcaac agacttgagc    6120
accttgacgg cctcggcaat cacctcgggg ccacagaagt cgccgccgag aagaacaatc    6180
ttcttggagt cagtcttggt cttcttagtt tcgggttcca ttgtggatgt gtgtggttgt    6240
atgtgtgatg tggtgtgtgg agtgaaaatc tgtggctggc aaacgctctt gtatatatac    6300
gcacttttgc ccgtgctatg tggaagacta aacctccgaa gattgtgact caggtagtgc    6360
ggtatcggct agggacccaa accttgtcga tgccgatagc gctatcgaac gtaccccagc    6420
cggccgggag tatgtcggag gggacatacg agatcgtcaa gggtttgtgg ccaactggta    6480
aatttaaatg atgtcgacgc agtaggatgt cctgcacggg tcttttttgtg gggtgtggag    6540 aaagggtgc ttggagatgg aagccggtag aaccgggctg cttgtgcttg gagatggaag    6600
ccggtagaac cgggctgctt ggggggattt ggggccgctg ggctccaaag aggggtaggc    6660
atttcgttgg ggttacgtaa ttgcggcatt tgggtcctgc gcgcatgtcc cattggtcag    6720
aattagtccg gataggagac ttatcagcca atcacagcgc cggatccacc tgtaggttgg    6780
gttgggtggg agcacccctc cacagagtag agtcaaacag cagcagcaac atgatagttg    6840
ggggtgtgcg tgttaaagga aaaaaaagaa gcttgggtta tattcccgct ctatttagag    6900
gttgcgggat agacgccgac ggagggcaat ggcgccatgg aaccttgcgg atatcgatac    6960
gccgcggcgg actgcgtccg aaccagctcc agcagcgttt tttccgggcc attgagccga    7020
ctgcgacccc gccaacgtgt cttggcccac gcactcatgt catgttggtg ttgggaggcc    7080 acttttttaag tagcacaagg cacctagctc gcagcaaggt gtccgaacca agaagcggc    7140 tgcagtggtg caaacgggc ggaacgcgcg ggaaaaagcc acgggggcac gaattgaggc    7200
acgccctcga atttgagacg agtcacggcc ccattcgccc gcgcaatggc tcgccaacgc    7260
ccggtctttt gcaccacatc aggttacccc aagccaaacc tttgtgttaa aaagcttaac    7320
atattatacc gaacgtaggt ttgggcgggc ttgctccgtc tgtccaaggc aacatttata    7380
taagggtctg catcgccggc tcaattgaat cttttttctt cttctcttct ctatattcat    7440
tcttgaatta aacacacatc aatccatggc aaacagcagc gtgtgggatg atgtggtggg    7500
ccgcgtggag accggcgtgg accagtggat ggatggcgcc aagccgtacg cactcaccga    7560
tgggctcccg atgatggacg tgtccaccat gctggcattc gaggtgggat acatggccat    7620
gctgctcttc ggcatcccga tcatgaagca gatggagaag ccttttgagc tcaagaccat    7680
```

```
caagctcttg cacaacttgt ttctcttcgg actttccttg tacatgtgcg tggagaccat     7740
ccgccaggct atcctcggag gctacaaagt gtttggaaac gacatggaga agggcaacga    7800
gtctcatgct cagggcatgt ctcgcatcgt gtacgtgttc tacgtgtcca aggcatacga    7860
gttcttggat accgccatca tgatcctttg caagaagttc aaccaggttt ccttcttgca    7920
tgtgtaccac catgccactc attttgcca tctggtgggc tatccgccaa gtacgctcca     7980
ggaggtgatg cgtactttt cagtgatcct caactctttc gtgcacaccg tcatgtacgg     8040
catactactt cttctcctcc caagggttcg ggttcgtgaa gccaatcaag ccgtacatca    8100
ccacccttca gatgacccag ttcatggcaa tgcttgtgca gtccttgtac gactacctct    8160
tcccatgcga ctacccacag gctcttgtgc agctccttgg agtgtacatg atcaccttgc    8220
ttgccctctt cggcaacttt tttgtgcaga gctatcttaa aaagccaaaa aagagcaaga    8280
ccaactaaaa ctgcctgcat gatatgccgc tcgccggcgt tcgaattgac tcagaaagcg    8340
agttaaggcg acacgcaaac tctatatttt ttcaaacgtg ttgccgtcac tcattcgcca    8400
tctgtttact acgtgtctgt tcaatgagca tgttcttgaa tctaaagaat ctcgaatgtt    8460
ttttaaaaaa agaattcgat atcaagctta cgcgtcgacc cgggtggacg tctagaggta    8520
cctagcaatt aacagatagt ttgccggtga taattctctt aacctccac actcctttga     8580 cataacgatt tatgtaacga aactgaaatt tgaccagata ttgtgtccgc                8630

<210> SEQ ID NO 73
<211> LENGTH: 18
<212> TYPE: DNA
<213> ORGANISM: Artificial Sequence
<220> FEATURE:
<223> OTHER INFORMATION: Primer GPDsense

<400> SEQUENCE: 73
atacgagatc gtcaaggg                                                    18

<210> SEQ ID NO 74
<211> LENGTH: 26
<212> TYPE: DNA
<213> ORGANISM: Artificial Sequence
<220> FEATURE:
<223> OTHER INFORMATION: Primer GPDantisense

<400> SEQUENCE: 74
gcggccgcgg attgatgtgt gtttaa                                           26

<210> SEQ ID NO 75
<211> LENGTH: 6339
<212> TYPE: DNA
<213> ORGANISM: Artificial Sequence
<220> FEATURE:
<223> OTHER INFORMATION: Plasmid pKR136
<220> FEATURE:
<221> NAME/KEY: misc_feature
<222> LOCATION: (4078)..(4078)
<223> OTHER INFORMATION: n is a, c, g, or t

<400> SEQUENCE: 75
ggccgcgaca caagtgtgag agtactaaat aaatgctttg gttgtacgaa atcattacac      60
taaataaaat aatcaaagct tatatatgcc ttccgctaag gccgaatgca agaaaattgg    120
ttctttctcg ttatcttttg ccacttttac tagtacgtat taattactac ttaatcatct    180
ttgtttacgc ctcattatat ccgtacgtcg agtcgacctg caggcatgca agcttggcgt    240
aatcatggtc atagctgttt cctgtgtgaa attgttatcc gctcacaatt ccacacaaca    300
```

-continued

```
tacgagccgg aagcataaag tgtaaagcct ggggtgccta atgagtgagc taactcacat    360
taattgcgtt gcgctcactg cccgctttcc agtcgggaaa cctgtcgtgc cagctgcatt    420
aatgaatcgg ccaacgcgcg gggagaggcg gtttgcgtat tgggcgctct tccgcttcct    480
cgctcactga ctcgctgcgc tcggtcgttc ggctgcggcg agcggtatca gctcactcaa    540
aggcggtaat acggttatcc acagaatcag gggataacgc aggaaagaac atgtgagcaa    600
aaggccagca aaaggccagg aaccgtaaaa aggccgcgtt gctggcgttt ttccataggc    660
tccgcccccc tgacgagcat cacaaaaatc gacgctcaag tcagaggtgg cgaaacccga    720
caggactata aagataccag gcgtttcccc ctggaagctc cctcgtgcgc tctcctgttc    780
cgaccctgcc gcttaccgga tacctgtccg cctttctccc ttcgggaagc gtggcgcttt    840
ctcatagctc acgctgtagg tatctcagtt cggtgtaggt cgttcgctcc aagctgggct    900
gtgtgcacga accccccgtt cagcccgacc gctgcgcctt atccggtaac tatcgtcttg    960
agtccaaccc ggtaagacac gacttatcgc cactggcagc agccactggt aacaggatta   1020
gcagagcgag gtatgtaggc ggtgctacag agttcttgaa gtggtggcct aactacggct   1080
acactagaag gacagtattt ggtatctgcg ctctgctgaa gccagttacc ttcggaaaaa   1140
gagttggtag ctcttgatcc ggcaaacaaa ccaccgctgg tagcggtggt ttttttgttt   1200
gcaagcagca gattacgcgc agaaaaaaag gatctcaaga agatcctttg atcttttcta   1260
cggggtctga cgctcagtgg aacgaaaact cacgttaagg gattttggtc atgagattat   1320
caaaaaggat cttcacctag atccttttaa attaaaaatg aagttttaaa tcaatctaaa   1380
gtatatatga gtaaacttgg tctgacagtt accaatgctt aatcagtgag gcacctatct   1440
cagcgatctg tctatttcgt tcatccatag ttgcctgact ccccgtcgtg tagataacta   1500
cgatacggga gggcttacca tctggcccca gtgctgcaat gataccgcga gacccacgct   1560
caccggctcc agatttatca gcaataaacc agccagccgg aagggccgag cgcagaagtg   1620
gtcctgcaac tttatccgcc tccatccagt ctattaattg ttgccgggaa gctagagtaa   1680
gtagttcgcc agttaatagt ttgcgcaacg ttgttgccat tgctacaggc atcgtggtgt   1740
cacgctcgtc gtttggtatg gcttcattca gctccggttc ccaacgatca aggcgagtta   1800
catgatcccc catgttgtgc aaaaaagcgg ttagctcctt cggtcctccg atcgttgtca   1860
gaagtaagtt ggccgcagtg ttatcactca tggttatggc agcactgcat aattctctta   1920
ctgtcatgcc atccgtaaga tgcttttctg tgactggtga gtactcaacc aagtcattct   1980
gagaatagtg tatgcggcga ccgagttgct cttgcccggc gtcaatacgg gataataccg   2040
cgccacatag cagaacttta aaagtgctca tcattggaaa acgttcttcg ggcgaaaac   2100 tctcaaggat cttaccgctg ttgagatcca gttcgatgta acccactcgt gcacccaact   2160
gatcttcagc atcttttact ttcaccagcg tttctgggtg agcaaaaaca ggaaggcaaa   2220
atgccgcaaa aaagggaata agggcgacac ggaaatgttg aatactcata ctcttccttt   2280
ttcaatatta ttgaagcatt tatcagggtt attgtctcat gagcggatac atatttgaat   2340
gtatttagaa aaataaacaa ataggggttc cgcgcacatt tccccgaaaa gtgccacctg   2400
acgtctaaga aaccattatt atcatgacat taacctataa aaataggcgt atcacgaggc   2460
cctttcgtct cgcgcgtttc ggtgatgacg gtgaaaacct ctgacacatg cagctcccgg   2520
agacggtcac agcttgtctg taagcggatg ccgggagcag acaagcccgt cagggcgcgt   2580
cagcgggtgt tggcgggtgt cggggctggc ttaactatgc ggcatcagag cagattgtac   2640
```

-continued

```
tgagagtgca ccatatgcgg tgtgaaatac cgcacagatg cgtaaggaga aaataccgca    2700
tcaggcgcca ttcgccattc aggctgcgca actgttggga agggcgatcg gtgcgggcct    2760
cttcgctatt acgccagctg gcgaaagggg gatgtgctgc aaggcgatta agttgggtaa    2820
cgccagggtt ttcccagtca cgacgttgta aaacgacggc cagtgaattc gagctcggta    2880
cccggggatc ctctagacgt acgtcctcga agagaagggt taataacaca ttttttaaca    2940
tttttaacac aaattttagt tatttaaaaa tttattaaaa aatttaaaat aagaagagga    3000
actctttaaa taaatctaac ttacaaaatt tatgattttt aataagtttt caccaataaa    3060
aaatgtcata aaaatatgtt aaaaagtata ttatcaatat tctctttatg ataaataaaa    3120
agaaaaaaaa aataaaagtt aagtgaaaat gagattgaag tgactttagg tgtgtataaa    3180
tatatcaacc ccgccaacaa tttatttaat ccaaatatat tgaagtatat tattccatag    3240
cctttatttta tttatatatt tattatataa aagctttatt tgttctaggt tgttcatgaa    3300
atatttttt ggttttatct ccgttgtaag aaaatcatgt gctttgtgtc gccactcact    3360
attgcagctt tttcatgcat tggtcagatt gacggttgat tgtattttg ttttttatgg    3420
ttttgtgtta tgacttaagt cttcatctct ttatctcttc atcaggtttg atggttacct    3480
aatatggtcc atgggtacat gcatggttaa attaggtggc caactttgtt gtgaacgata    3540
gaattttttt tatattaagt aaactatttt tatattatga ataataata aaaaaaatat    3600
tttatcatta ttaacaaaat catattagtt aatttgttaa ctctataata aaagaaatac    3660
tgtaacattc acattacatg gtaacatctt tccacccttt catttgtttt tgtttgatg    3720
actttttttc ttgtttaaat ttatttccct tcttttaaat ttggaataca ttatcatcat    3780
atataaacta aaatactaaa aacaggatta cacaaatgat aaataataac acaaatattt    3840
ataaatctag ctgcaatata tttaaactag ctatatcgat attgtaaaat aaaactagct    3900
gcattgatac tgataaaaaa atatcatgtg ctttctggac tgatgatgca gtatacttt    3960
gacattgcct ttattttatt tttcagaaaa gctttcttag ttctgggttc ttcattattt    4020
gtttcccatc tccattgtga attgaatcat ttgcttcgtg tcacaaatac aatttagnta    4080
ggtacatgca ttggtcagat tcacggttta ttatgtcatg acttaagttc atggtagtac    4140
attacctgcc acgcatgcat tatattggtt agatttgata ggcaaatttg gttgtcaaca    4200
atataaatat aaataatgtt tttatattac gaaataacag tgatcaaaac aaacagtttt    4260
atctttatta acaagatttt gttttttgttt gatgacgttt tttaatgttt acgctttccc    4320
ccttcttttg aatttagaac actttatcat cataaaatca aatactaaaa aaattacata    4380
tttcataaat aataacacaa atatttttaa aaaatctgaa ataataatga acaatattac    4440
atattatcac gaaaattcat taataaaaat attatataaa taaaatgtaa tagtagttat    4500
atgtaggaaa aaagtactgc acgcataata tatacaaaaa gattaaaatg aactattata    4560
aataataaca ctaaattaat ggtgaatcat atcaaaataa tgaaaagta aataaaattt    4620
gtaattaact tctatatgta ttacacacac aaataataaa taatagtaaa aaaaattatg    4680
ataaatattt accatctcat aagatattta aaataatgat aaaaatatag attattttt    4740
atgcaactag ctagccaaaa agagaacacg ggtatatata aaaagagtac ctttaaattc    4800
tactgtactt cctttattcc tgacgttttt atatcaagtg gacatacgtg aagatttaa    4860
ttatcagtct aaatatttca ttagcactta atacttttct gttttattcc tatcctataa    4920
gtagtcccga ttctcccaac attgcttatt cacacaacta actaagaaag tcttccatag    4980
cccccccaagc ggccgcatgg gaacggacca aggaaaaacc ttcacctggg aagagctggc    5040
```

-continued

| | |
|---|---|
| ggcccataac accaaggacg acctactctt ggccatccgc ggcagggtgt acgatgtcac | 5100 |
| aaagttcttg agccgccatc ctggtggagt ggacactctc ctgctcggag ctggccgaga | 5160 |
| tgttactccg gtctttgaga tgtatcacgc gtttggggct gcagatgcca ttatgaagaa | 5220 |
| gtactatgtc ggtacactgg tctcgaatga gctgcccatc ttcccggagc aacggtgtt | 5280 |
| ccacaaaacc atcaagacga gagtcgaggg ctactttacg gatcggaaca ttgatcccaa | 5340 |
| gaatagacca gagatctggg gacgatacgc tcttatcttt ggatccttga tcgcttccta | 5400 |
| ctacgcgcag ctctttgtgc ctttcgttgt cgaacgcaca tggcttcagg tggtgtttgc | 5460 |
| aatcatcatg ggatttgcgt gcgcacaagt cggactcaac cctcttcatg atgcgtctca | 5520 |
| cttttcagtg acccacaacc ccactgtctg aagattctg ggagccacgc acgacttttt | 5580 |
| caacggagca tcgtacctgg tgtggatgta ccaacatatg ctcggccatc acccctacac | 5640 |
| caacattgct ggagcagatc ccgacgtgtc gacgtctgag cccgatgttc gtcgtatcaa | 5700 |
| gcccaaccaa aagtggtttg tcaaccacat caaccagcac atgtttgttc ctttcctgta | 5760 |
| cggactgctg gcgttcaagg tgcgcattca ggacatcaac attttgtact tgtcaagac | 5820 |
| caatgacgct attcgtgtca atcccatctc gacatggcac actgtgatgt tctggggcgg | 5880 |
| caaggctttc tttgtctggt atcgcctgat tgttcccctg cagtatctgc ccctgggcaa | 5940 |
| ggtgctgctc ttgttcacgg tcgcggacat ggtgtcgtct tactggctgg cgctgacctt | 6000 |
| ccaggcgaac cacgttgttg aggaagttca gtggccgttg cctgacgaga cgggatcat | 6060 |
| ccaaaaggac tgggcagcta tgcaggtcga gactacgcag gattacgcac acgattcgca | 6120 |
| cctctggacc agcatcactg gcagcttgaa ctaccaggct gtgcaccatc tgttccccaa | 6180 |
| cgtgtcgcag caccattatc ccgatattct ggccatcatc aagaacacct gcagcgagta | 6240 |
| caaggttcca taccttgtca aggatacgtt ttggcaagca tttgcttcac atttggagca | 6300 |
| cttgcgtgtt cttggactcc gtcccaagga agagtaggc | 6339 |

<210> SEQ ID NO 76
<211> LENGTH: 8319
<212> TYPE: DNA
<213> ORGANISM: Artificial Sequence
<220> FEATURE:
<223> OTHER INFORMATION: Plasmid pY98

<400> SEQUENCE: 76

| | |
|---|---|
| ggccgccacc gcggcccgag attccggcct cttcggccgc caagcgaccc gggtggacgt | 60 |
| ctagaggtac ctagcaatta acagatagtt tgccggtgat aattctctta acctcccaca | 120 |
| ctcctttgac ataacgattt atgtaacgaa actgaaattt gaccagatat tgtgtccgcg | 180 |
| gtggagctcc agcttttgtt ccctttagtg agggttaatt tcgagcttgg cgtaatcatg | 240 |
| gtcatagctg tttcctgtgt gaaattgtta tccgctcaca attccacaca acgtacgagc | 300 |
| cggaagcata aagtgtaaag cctggggtgc ctaatgagtg agctaactca cattaattgc | 360 |
| gttgcgctca ctgcccgctt tccagtcggg aaacctgtcg tgccagctgc attaatgaat | 420 |
| cggccaacgc gcggggagag gcggtttgcg tattgggcgc tcttccgctt cctcgctcac | 480 |
| tgactcgctg cgctcggtcg ttcggctgcg gcgagcggta tcagctcact caaaggcggt | 540 |
| aatacggtta tccacagaat cagggggataa cgcaggaaag aacatgtgag caaaaggcca | 600 |
| gcaaaaggcc aggaaccgta aaaaggccgc gttgctggcg ttttttccata ggctccgccc | 660 |
| ccctgacgag catcacaaaa atcgacgctc aagtcagagg tggcgaaacc cgacaggact | 720 |

```
ataaagatac caggcgtttc cccctggaag ctccctcgtg cgctctcctg ttccgaccct    780
gccgcttacc ggatacctgt ccgcctttct ccttcggga agcgtggcgc tttctcatag    840
ctcacgctgt aggtatctca gttcggtgta ggtcgttcgc tccaagctgg gctgtgtgca    900
cgaaccccc gttcagcccg accgctgcgc cttatccggt aactatcgtc ttgagtccaa    960
cccggtaaga cacgacttat cgccactggc agcagccact ggtaacagga ttagcagagc   1020
gaggtatgta ggcggtgcta cagagttctt gaagtggtgg cctaactacg gctacactag   1080
aaggacagta tttggtatct gcgctctgct gaagccagtt accttcggaa aaagagttgg   1140
tagctcttga tccggcaaac aaaccaccgc tggtagcggt ggtttttttg tttgcaagca   1200
gcagattacg cgcagaaaaa aaggatctca agaagatcct ttgatctttt ctacggggtc   1260
tgacgctcag tggaacgaaa actcacgtta agggattttg gtcatgagat tatcaaaaag   1320
gatcttcacc tagatccttt taaattaaaa atgaagtttt aaatcaatct aaagtatata   1380
tgagtaaact tggtctgaca gttaccaatg cttaatcagt gaggcaccta tctcagcgat   1440
ctgtctattt cgttcatcca tagttgcctg actccccgtc gtgtagataa ctacgatacg   1500
ggagggctta ccatctggcc ccagtgctgc aatgataccg cgagacccac gctcaccggc   1560
tccagattta tcagcaataa accagccagc cggaagggcc gagcgcagaa gtggtcctgc   1620
aactttatcc gcctccatcc agtctattaa ttgttgccgg gaagctagag taagtagttc   1680
gccagttaat agtttcgcca acgttgttgc cattgctaca ggcatcgtgg tgtcacgctc   1740
gtcgtttggt atggcttcat tcagctccgg ttcccaacga tcaaggcgag ttacatgatc   1800
ccccatgttg tgcaaaaaag cggttagctc cttcggtcct ccgatcgttg tcagaagtaa   1860
gttggccgca gtgttatcac tcatggttat ggcagcactg cataattctc ttactgtcat   1920
gccatccgta agatgctttt ctgtgactgg tgagtactca accaagtcat tctgagaata   1980
gtgtatgcgg cgaccgagtt gctcttgccc ggcgtcaata cgggataata ccgcgccaca   2040
tagcagaact ttaaaagtgc tcatcattgg aaaacgttct cggggcgaaa actctcaag    2100
gatcttaccg ctgttgagat ccagttcgat gtaacccact cgtgcaccca actgatcttc   2160
agcatctttt actttcacca gcgtttctgg gtgagcaaaa acaggaaggc aaaatgccgc   2220
aaaaaaggga ataagggcga cacggaaatg ttgaatactc atactcttcc ttttttcaata   2280
ttattgaagc atttatcagg gttattgtct catgagcgga tacatatttg aatgtattta   2340
gaaaaataaa caaatagggg ttccgcgcac atttccccga aaagtgccac ctgacgcgcc   2400
ctgtagcggc gcattaagcg cggcgggtgt ggtggttacg cgcagcgtga ccgctacact   2460
tgccagcgcc ctagcgcccg ctcctttcgc tttcttccct tcctttctcg ccacgttcgc   2520
cggctttccc cgtcaagctc taaatcgggg ctccctttta gggttccgat ttagtgcttt   2580
acggcacctc gaccccaaaa aacttgatta gggtgatggt tcacgtagtg gccatcgcc    2640
ctgatagacg gtttttcgcc ctttgacgtt ggagtccacg ttctttaata gtggactctt   2700
gttccaaact ggaacaacac tcaaccctat ctcggtctat tcttttgatt tataagggat   2760
tttgccgatt tcggcctatt ggttaaaaaa tgagctgatt taacaaaaat ttaacgcgaa   2820
ttttaacaaa atattaacgc ttacaatttc cattcgccat tcaggctgcg caactgttgg   2880
gaagggcgat cggtgcgggc ctcttcgcta ttacgccagc tggcgaaagg gggatgtgct   2940
gcaaggcgat taagttgggt aacgccaggg ttttcccagt cacgacgttg taaaacgacg   3000
gccagtgaat tgtaatacga ctcactatag ggcgaattgg gtaccgggcc cccctcgag   3060
gtcgatggtg tcgataagct tgatatcgaa ttcatgtcac acaaaccgat cttcgcctca   3120
```

```
aggaaaccta attctacatc cgagagactg ccgagatcca gtctacactg attaattttc    3180
gggccaataa tttaaaaaaa tcgtgttata taatattata tgtattatat atatacatca    3240
tgatgatact gacagtcatg tcccattgct aaatagacag actccatctg ccgcctccaa    3300
ctgatgttct caatatttaa ggggtcatct cgcattgttt aataataaac agactccatc    3360
taccgcctcc aaatgatgtt ctcaaaatat attgtatgaa cttattttta ttacttagta    3420
ttattagaca acttacttgc tttatgaaaa acacttccta tttaggaaac aatttataat    3480
ggcagttcgt tcatttaaca atttatgtag aataaatgtt ataaatgcgt atgggaaatc    3540
ttaaatatgg atagcataaa tgatatctgc attgcctaat tcgaaatcaa cagcaacgaa    3600
aaaaatccct tgtacaacat aaatagtcat cgagaaatat caactatcaa agaacagcta    3660
ttcacacgtt actattgaga ttattattgg acgagaatca cacactcaac tgtctttctc    3720
tcttctagaa atacaggtac aagtatgtac tattctcatt gttcatactt ctagtcattt    3780
catcccacat attccttgga tttctctcca atgaatgaca ttctatcttg caaattcaac    3840
aattataata agatatacca agtagcggt atagtggcaa tcaaaaagct tctctggtgt    3900
gcttctcgta tttatttta ttctaatgat ccattaaagg tatatattta ttcttgtta    3960 tataatcctt ttgtttatta catgggctgg atacataaag gtattttgat ttaattttt    4020 gcttaaattc aatcccccct cgttcagtgt caactgtaat ggtaggaaat taccatactt    4080
ttgaagaagc aaaaaaatg aaagaaaaaa aaatcgtat ttccaggtta gacgttccgc    4140
agaatctaga atgcggtatg cggtacattg ttcttcgaac gtaaaagttg cgctccctga    4200
gatattgtac attttttgctt ttacaagtac aagtacatcg tacaactatg tactactgtt    4260
gatgcatcca caacagtttg tttttgtttt ttttgttttt ttttttttcta atgattcatt    4320 accgctatgt atacctactt gtacttgtag taagccgggt tattggcgtt caattaatca    4380
tagacttatg aatctgcacg gtgtgcgctg cgagttactt ttagcttatg catgctactt    4440
gggtgtaata ttgggatctg ttcggaaatc aacggatgct caaccgattt cgacagtaat    4500
taattaagtc atacacaagt cagctttctt cgagcctcat ataagtataa gtagttcaac    4560
gtattagcac tgtacccagc atctccgtat cgagaaacac aacaacatgc cccattggac    4620
agatcatgcg gatacacagg ttgtgcagta tcatacatac tcgatcagac aggtcgtctg    4680
accatcatac aagctgaaca agcgctccat acttgcacgc tctctatata cacagttaaa    4740
ttacatatcc atagtctaac ctctaacagt taatcttctg gtaagcctcc cagccagcct    4800
tctggtatcg cttggcctcc tcaataggat ctcggttctg gccgtacaga cctcggccga    4860
caattatgat atccgttccg gtagacatga catcctcaac agttcggtac tgctgtccga    4920
gagcgtctcc cttgtcgtca agacccaccc cggggggtcag aataagccag tcctcagagt    4980
cgcccttagg tcggttctgg gcaatgaagc caaccacaaa ctcggggtcg gatcgggcaa    5040
gctcaatggt ctgcttggag tactcgccag tggccagaga gcccttgcaa gacagctcgg    5100
ccagcatgag cagacctctg gccagcttct cgttgggaga ggggactagg aactccttgt    5160
actgggagtt ctcgtagtca gagacgtcct ccttcttctg ttcagagaca gtttcctcgg    5220
caccagctcg caggccagca atgattccgg ttccgggtac accgtgggcg ttggtgatat    5280
cggaccactc ggcgattcgg tgacaccggt actggtgctt gacagtgttg ccaatatctg    5340
cgaacttcct gtcctcgaac aggaagaaac cgtgcttaag agcaagttcc ttgaggggga    5400
gcacagtgcc ggcgtaggtg aagtcgtcaa tgatgtcgat atgggttttg atcatgcaca    5460
```

```
cataaggtcc gaccttatcg gcaagctcaa tgagctcctt ggtggtggta acatccagag   5520
aagcacacag gttggttttc ttggctgcca cgagcttgag cactcgagcg gcaaaggcgg   5580
acttgtggac gttagctcga gcttcgtagg agggcatttt ggtggtgaag aggagactga   5640
aataaattta gtctgcagaa cttttttatcg gaaccttatc tggggcagtg aagtatatgt   5700
tatggtaata gttacgagtt agttgaactt atagatagac tggactatac ggctatcggt   5760
ccaaattaga agaacgtca atggctctct gggcgtcgcc tttgccgaca aaaatgtgat   5820
catgatgaaa gccagcaatg acgttgcagc tgatattgtt gtcggccaac cgcgccgaaa   5880
acgcagctgt cagacccaca gcctccaacg aagaatgtat cgtcaaagtg atccaagcac   5940
actcatagtt ggagtcgtac tccaaaggcg gcaatgacga gtcagacaga tactcgtcga   6000
cgcagtagga tgtcctgcac gggtcttttt gtggggtgtg gagaaagggg tgcttggaga   6060
tggaagccgg tagaaccggg ctgcttgtgc ttggagatgg aagccggtag aaccgggctg   6120
cttggggga tttggggccg ctgggctcca aagaggggta ggcatttcgt tggggttacg   6180
taattgcggc atttgggtcc tgcgcgcatg tcccattggt cagaattagt ccggatagga   6240
gacttatcag ccaatcacag cgccggatcc acctgtaggt tgggttgggt gggagcaccc   6300
ctccacagag tagagtcaaa cagcagcagc aacatgatag ttgggggtgt gcgtgttaaa   6360
ggaaaaaaaa gaagcttggg ttatattccc gctctattta gaggttgcgg gatagacgcc   6420
gacggagggc aatggcgcca tggaaccttg cggatatcga tacgccgcgg cggactgcgt   6480
ccgaaccagc tccagcagcg ttttttccgg gccattgagc cgactgcgac cccgccaacg   6540
tgtcttggcc cacgcactca tgtcatgttg gtgttgggag gccactttt aagtagcaca   6600
aggcacctag ctcgcagcaa ggtgtccgaa ccaaagaagc ggctgcagtg gtgcaaacgg   6660
ggcggaaacg gcgggaaaaa gccacgggg cacgaattga ggcacgccct cgaatttgag   6720
acgagtcacg gcccattcg cccgcgcaat ggctcgccaa cgcccggtct tttgcaccac   6780
atcaggttac cccaagccaa acctttgtgt taaaaagctt aacatattat accgaacgta   6840
ggtttgggcg ggcttgctcc gtctgtccaa ggcaacattt atataagggt ctgcatcgcc   6900
ggctcaattg aatcttttt cttcttctct tctctatatt cattcttgaa ttaaacacac   6960
atcaatccgc ggccgcatgg gaacggacca aggaaaaacc ttcacctggg aagagctggc   7020
ggcccataac accaaggacg acctactctt ggccatccgc ggcagggtgt acgatgtcac   7080
aaagttcttg agccgccatc ctggtggagt ggacactctc ctgctcggag ctggccgaga   7140
tgttactccg gtcttttgaga tgtatcacgc gtttggggct gcagatgcca ttatgaagaa   7200
gtactatgtc ggtacactgg tctcgaatga gctgcccatc ttcccggagc caacggtgtt   7260
ccacaaaacc atcaagacga gagtcgaggg ctactttacg gatcggaaca ttgatcccaa   7320
gaatagacca gagatctggg gacgatacgc tcttatcttt ggatccttga tcgcttccta   7380
ctacgcgcag ctcttgtgc ctttcgttgt cgaacgcaca tggcttcagg tggtgtttgc   7440
aatcatcatg ggatttgcgt gcgcacaagt cggactcaac cctcttcatg atgcgtctca   7500
cttttcagtg acccacaacc ccactgtctg gaagattctg ggagccacgc acgactttt   7560
caacggagca tcgtacctgg tgtggatgta ccaacatatg ctcggccatc acccctacac   7620
caacattgct ggagcagatc ccgacgtgtc gacgtctgag cccgatgttc gtcgtatcaa   7680
gcccaaccaa aagtggtttg tcaaccacat caaccagcac atgtttgttc ctttcctgta   7740
cggactgctg gcgttcaagg tgcgcattca ggacatcaac attttgtact tgtcaagac   7800
caatgacgct attcgtgtca atcccatctc gacatggcac actgtgatgt tctggggcgg   7860
```

```
caaggctttc tttgtctggt atcgcctgat tgttccctg cagtatctgc ccctgggcaa    7920
ggtgctgctc ttgttcacgg tcgcggacat ggtgtcgtct tactggctgg cgctgacctt    7980
ccaggcgaac cacgttgttg aggaagttca gtggccgttg cctgacgaga acgggatcat    8040
ccaaaaggac tgggcagcta tgcaggtcga gactacgcag gattacgcac acgattcgca    8100
cctctggacc agcatcactg gcagcttgaa ctaccaggct gtgcaccatc tgttccccaa    8160
cgtgtcgcag caccattatc ccgatattct ggccatcatc aagaacacct gcagcgagta    8220
caaggttcca taccttgtca aggatacgtt ttggcaagca tttgcttcac atttggagca    8280
cttgcgtgtt cttggactcc gtcccaagga agagtaggc                          8319
```

<210> SEQ ID NO 77
<211> LENGTH: 774
<212> TYPE: DNA
<213> ORGANISM: Euglena gracilis

<400> SEQUENCE: 77

```
atggaggtgg tgaatgaaat agtctcaatt gggcaggaag ttttacccaa agttgattat      60
gcccaactct ggagtgatgc cagtcactgt gaggtgcttt acttgtccat cgcatttgtc     120
atcttgaagt tcactcttgg ccccccttggt ccaaaaggtc agtctcgtat gaagtttgtt    180
ttcaccaatt acaaccttct catgtccatt tattcgttgg gatcattcct ctcaatggca     240
tatgccatgt acaccatcgg tgttatgtct gacaactgcg agaaggcttt tgacaacaac     300
gtcttcagga tcaccacgca gttgttctat ttgagcaagt tcctggagta tattgactcc     360
ttctatttgc cactgatggg caagcctctg acctggttgc aattcttcca tcatttgggg     420
gcaccgatgg atatgtggct gttctataat taccgaaatg aagctgtttg gattttttgtg    480
ctgttgaatg gtttcatcca ctggatcatg tacggttatt attggaccag attgatcaag    540
ctgaagttcc ccatgccaaa atccctgatt acatcaatgc agatcattca attcaatgtt    600
ggtttctaca ttgtctggaa gtacaggaac attccctgtt atcgccaaga tgggatgagg    660
atgtttggct ggttcttcaa ttactttttat gttggcacag tcttgtgttt gttcttgaat    720
ttctatgtgc aaacgtatat cgtcaggaag cacaagggag ccaaaaagat tcag          774
```

<210> SEQ ID NO 78
<211> LENGTH: 1263
<212> TYPE: DNA
<213> ORGANISM: Euglena gracilis

<400> SEQUENCE: 78

```
atgaagtcaa agcgccaagc gcttcccctt acaattgatg gaacaacata tgatgtgtct      60
gcctgggtca atttccaccc tggtggtgcg gaaattatag agaattacca aggaagggat     120
gccactgatg ccttcatggt tatgcactct caagaagcct tcgacaagct caagcgcatg     180
cccaaaatca atcccagttc tgagttgcca cccaggctg cagtgaatga agctcaagag      240
gatttccgga agctccgaga agagttgatc gcaactggca tgtttgatgc ctcccccctc    300
tggtactcat acaaaatcag caccacactg ggccttggag tgctgggtta tttcctgatg    360
gttcagtatc agatgtattt cattggggca gtgttgcttg gatgcacta tcaacagatg    420
ggctggcttt ctcatgacat ttgccaccac cagactttca gaaccggaa ctggaacaac    480
ctcgtgggac tggtatttgg caatggtctg caaggttttt ccgtgacatg gtggaaggac    540
agacacaatg cacatcattc ggcaaccaat gttcaagggc acgaccctga tattgacaac    600
```

```
ctcccccctct tagcctggtc tgaggatgac gtcacacggg cgtcaccgat ttcccgcaag    660
ctcattcagt tccagcagta ctatttcttg gtcatctgta tcttgttgcg gttcatttgg    720
tgtttccaga gcgtgttgac cgtgcgcagt ttgaaggaca gagataacca attctatcgc    780
tctcagtata agaaggaggc cattggcctc gccctgcact ggaccttgaa gaccctgttc    840
cacttattct ttatgcccag catcctcaca tcgctgttgg tgttttttcgt ttcggagctg    900 gttggcggct tcggcattgc gatcgtggtg ttcatgaacc actcccact ggagaagatc    960 ggggactcag tctgggatgg ccatggattc tcggttggcc agatccatga ccatgaac   1020 attcggcgag ggattatcac agattggttt tcggaggct tgaattacca gattgagcac  1080
catttgtggc cgaccctccc tcgccacaac ctgacagcgg ttagctacca ggtggaacag  1140
ctgtgccaga agcacaacct gccgtatcgg aacccgctgc ccatgaagg gttggtcatc  1200 ctgctgcgct atctggcggt gttcgcccgg atggcggaga agcaacccgc ggggaaggct  1260
cta                                                                1263

<210> SEQ ID NO 79
<211> LENGTH: 30
<212> TYPE: DNA
<213> ORGANISM: Artificial Sequence
<220> FEATURE:
<223> OTHER INFORMATION: Primer oEugEL1-1

<400> SEQUENCE: 79
agcggccgca ccatggaggt ggtgaatgaa                                    30

<210> SEQ ID NO 80
<211> LENGTH: 30
<212> TYPE: DNA
<213> ORGANISM: Artificial Sequence
<220> FEATURE:
<223> OTHER INFORMATION: Primer oEugEL1-2

<400> SEQUENCE: 80
tgcggccgct cactgaatct ttttggctcc                                    30

<210> SEQ ID NO 81
<211> LENGTH: 4311
<212> TYPE: DNA
<213> ORGANISM: Artificial Sequence
<220> FEATURE:
<223> OTHER INFORMATION: Plasmid pKR906

<400> SEQUENCE: 81
agcggccgca ccatggaggt ggtgaatgaa atagtctcaa ttgggcagga agttttaccc    60
aaagttgatt atgcccaact ctggagtgat gccagtcact gtgaggtgct tacttgtcc   120 atcgcatttg tcatcttgaa gttcactctt ggccccttg gtccaaaagg tcagtctcgt   180
atgaagtttg ttttcaccaa ttacaacctt ctcatgtcca tttattcgtt gggatcattc   240
ctctcaatgg catatgccat gtacaccatc ggtgttatgt ctgacaactg cgagaaggct   300
tttgacaaca acgtcttcag gatcaccacg cagttgttct atttgagcaa gttcctggag   360
tatattgact ccttctattt gccactgatg ggcaagcctc tgacctggtt gcaattcttc   420
catcatttgg gggcaccgat ggatatgtgg ctgttctata attaccgaaa tgaagctgtt   480 tggattttg tgctgttgaa tggtttcatc cactggatca tgtacggtta ttattggacc   540
agattgatca agctgaagtt ccccatgcca aaatccctga ttcatcaat gcagatcatt   600 caattcaatg ttggtttcta cattgtctgg aagtacagga acattccctg ttatcgccaa   660
```

```
gatgggatga ggatgtttgg ctggttcttc aattactttt atgttggcac agtcttgtgt    720
ttgttcttga atttctatgt gcaaacgtat atcgtcagga agcacaaggg agccaaaaag    780
attcagtgag cggccgcacc tgaattccag cacactggcg gccgttacta gtggatccga    840
gctcggtacc aagcttgatg catagcttga gtattctaac cgtcaccta aatagcttgg    900 cgtaatcatg gtcatagctg tttcctgtgt gaaattgtta tccgctcaca attccacaca    960
acatacgagc cggaagcata aagtgtaaag cctggggtgc ctaatgagtg agctaactca   1020
cattaattgc gttgcgctca ctgcccgctt tccagtcggg aaacctgtcg tgccagctgc   1080
attaatgaat cggccaacgc gcggggagag gcggtttgcg tattgggcgc tcttccgctt   1140
cctcgctcac tgactcgctg cgctcggtcg ttcggctgcg gcgagcggta tcagctcact   1200 caaaggcgg aatacggtta tccacagaat caggggataa cgcaggaaag aacatgtgag   1260
caaaaggcca gcaaaagccc aggaaccgta aaaaggccgc gttgctggcg ttttttccata   1320 ggctccgccc ccctgacgag catcacaaaa atcgacgctc aagtcagagg tggcgaaacc   1380
cgacaggact ataaagatac caggcgtttc ccctggaag ctccctcgtg cgctctcctg   1440
ttccgaccct gccgcttacc ggatacctgt ccgcctttct cccttcggga agcgtggcgc   1500
tttctcatag ctcacgctgt aggtatctca gttcggtgta ggtcgttcgc tccaagctgg   1560
gctgtgtgca cgaaccccc gttcagcccg accgctgcgc cttatccggt aactatcgtc   1620
ttgagtccaa cccggtaaga cacgacttat cgccactggc agcagccact ggtaacagga   1680
ttagcagagc gaggtatgta ggcggtgcta cagagttctt gaagtggtgg cctaactacg   1740
gctacactag aaggacagta tttggtatct gcgctctgct gaagccagtt accttcggaa   1800
aaagagttgg tagctcttga tccggcaaac aaaccaccgc tggtagcggt ggttttttg    1860 tttgcaagca gcagattacg cgcagaaaaa aaggatctca agaagatcct ttgatctttt   1920
ctacggggtc tgacgctcag tggaacgaaa actcacgtta agggattttg gtcatgagat   1980
tatcaaaaag gatcttcacc tagatccttt taaattaaaa atgaagtttt agcacgtgtc   2040
agtcctgctc ctcggccacg aagtgcacg agttgccggc cgggtcgcgc agggcgaact   2100
cccgccccca cggctgctcg ccgatctcgg tcatggccgg cccggaggcg tcccggaagt   2160
tcgtggacac gacctccgac cactcggcgt acagctcgtc caggccgcgc acccacaccc   2220
aggccagggt gttgtccggc accacctggt cctggaccgc gctgatgaac agggtcacgt   2280
cgtcccggac acaccggcg aagtcgtcct ccacgaagtc ccgggagaac ccgagccggt   2340
cggtccagaa ctcgaccgct ccggcgacgt cgcgcgcggt gagcaccgga acggcactgg   2400
tcaacttggc catggtggcc ctcctcacgt gctattattg aagcatttat cagggttatt   2460
gtctcatgag cggatacata tttgaatgta tttagaaaaa taaacaaata ggggttccgc   2520
gcacatttcc ccgaaaagtg ccacctgtat gcggtgtgaa ataccgcaca gatgcgtaag   2580
gagaaaatac cgcatcagga aattgtaagc gttaataatt cagaagaact cgtcaagaag   2640
gcgatagaag gcgatgcgct gcgaatcggg agcggcgata ccgtaaagca cgaggaagcg   2700
gtcagcccat tcgccgccaa gctcttcagc aatatcacgg gtagccaacg ctatgtcctg   2760
atagcggtcc gccacaccca gccggccaca gtcgatgaat ccagaaaagc ggccattttc   2820
caccatgata ttcggcaagc aggcatcgcc atgggtcacg acgagatcct cgccgtcggg   2880
catgctcgcc ttgagcctgg cgaacagttc ggctggcgcg agccctgat gctcttcgtc   2940 cagatcatcc tgatcgacaa gaccggcttc catccgagta cgtgctcgct cgatgcgatg   3000
```

| | |
|---|---:|
| tttcgcttgg tggtcgaatg ggcaggtagc cggatcaagc gtatgcagcc gccgcattgc | 3060 |
| atcagccatg atggatactt tctcggcagg agcaaggtga gatgacagga gatcctgccc | 3120 |
| cggcacttcg cccaatagca gccagtccct tcccgcttca gtgacaacgt cgagcacagc | 3180 |
| tgcgcaagga acgccgtcg tggccagcca cgatagccgc gctgcctcgt cttgcagttc | 3240 |
| attcagggca ccggacaggt cggtcttgac aaaaagaacc gggcgcccct gcgctgacag | 3300 |
| ccggaacacg gcggcatcag agcagccgat tgtctgttgt gcccagtcat agccgaatag | 3360 |
| cctctccacc caagcggccg gagaacctgc gtgcaatcca tcttgttcaa tcatgcgaaa | 3420 |
| cgatcctcat cctgtctctt gatcagagct tgatccctg cgccatcaga tccttggcgg | 3480 |
| cgagaaagcc atccagttta ctttgcaggg cttcccaacc ttaccagagg gcgccccagc | 3540 |
| tggcaattcc ggttcgcttg ctgtccataa aaccgcccag tctagctatc gccatgtaag | 3600 |
| cccactgcaa gctacctgct ttctctttgc gcttgcgttt tcccttgtcc agatagccca | 3660 |
| gtagctgaca ttcatccggg gtcagcaccg tttctgcgga ctggctttct acgtgaaaag | 3720 |
| gatctaggtg aagatccttt ttgataatct catgcctgac atttatattc cccagaacat | 3780 |
| caggttaatg gcgttttga tgtcattttc gcggtggctg agatcagcca cttcttcccc | 3840 |
| gataacggag accggcacac tggccatatc ggtggtcatc atgcgccagc tttcatcccc | 3900 |
| gatatgcacc accgggtaaa gttcacggga gactttatct gacagcagac gtgcactggc | 3960 |
| caggggatc accatccgtc gccccggcgt gtcaataata tcactctgta catccacaaa | 4020 |
| cagacgataa cggctctctc ttttataggt gtaaaccta aactgccgta cgtataggct | 4080 |
| gcgcaactgt tgggaagggc gatcggtgcg ggcctcttcg ctattacgcc agctggcgaa | 4140 |
| agggggatgt gctgcaaggc gattaagttg ggtaacgcca gggttttccc agtcacgacg | 4200 |
| ttgtaaaacg acggccagtg aattgtaata cgactcacta tagggcgaat gggccctct | 4260 |
| agatgcatgc tcgagcggcc gccagtgtga tggatatctg cagaattcag g | 4311 |

<210> SEQ ID NO 82
<211> LENGTH: 7085
<212> TYPE: DNA
<213> ORGANISM: Artificial Sequence
<220> FEATURE:
<223> OTHER INFORMATION: Plasmid pKR72

<400> SEQUENCE: 82

| | |
|---|---:|
| gtacggatcc gtcgacggcg cgcccgatca tccggatata gttcctcctt tcagcaaaaa | 60 |
| accccctcaag acccgtttag aggccccaag gggttatgct agttattgct cagcggtggc | 120 |
| agcagccaac tcagcttcct ttcgggcttt gttagcagcc ggatcgatcc aagctgtacc | 180 |
| tcactattcc tttgccctcg acgagtgct ggggcgtcgg tttccactat cggcgagtac | 240 |
| ttctacacag ccatcggtcc agacggccgc gcttctgcgg gcgatttgtg tacgcccgac | 300 |
| agtcccggct ccggatcgga cgattgcgtc gcatcgaccc tgcgcccaag ctgcatcatc | 360 |
| gaaattgccg tcaaccaagc tctgatagag ttggtcaaga ccaatgcgga gcatatacgc | 420 |
| ccggagccgc ggcgatcctg caagctccgg atgcctccgc tcgaagtagc gcgtctgctg | 480 |
| ctccatacaa gccaaccacg gcctccagaa gaagatgttg gcgacctcgt attgggaatc | 540 |
| cccgaacatc gcctcgctcc agtcaatgac cgctgttatg cggccattgt ccgtcaggac | 600 |
| attgttggag ccgaaatccg cgtgcacgag gtgccggact cggggcagt cctcggccca | 660 |
| aagcatcagc tcatcgagag cctgcgcgac ggacgcactg acggtgtcgt ccatcacagt | 720 |
| ttgccagtga tacacatggg gatcagcaat cgcgcatatg aaatcacgcc atgtagtgta | 780 |

```
ttgaccgatt ccttgcggtc cgaatgggcc gaacccgctc gtctggctaa gatcggccgc      840
agcgatcgca tccatagcct ccgcgaccgg ctgcagaaca gcgggcagtt cggtttcagg      900
caggtcttgc aacgtgacac cctgtgcacg gcgggagatg caataggtca ggctctcgct      960
gaattcccca atgtcaagca cttccggaat cgggagcgcg gccgatgcaa agtgccgata     1020
aacataacga tctttgtaga aaccatcggc gcagctattt acccgcagga catatccacg     1080
ccctcctaca tcgaagctga aagcacgaga ttcttcgccc tccgagagct gcatcaggtc     1140
ggagacgctg tcgaactttt cgatcagaaa cttctcgaca gacgtcgcgg tgagttcagg     1200
cttttccatg ggtatatctc cttcttaaag ttaaacaaaa ttatttctag agggaaaccg     1260
ttgtggtctc cctatagtga gtcgtattaa tttcgcggga tcgagatcga tccaattcca     1320
atcccacaaa aatctgagct taacagcaca gttgctcctc tcagagcaga atcgggtatt     1380
caacaccctc atatcaacta ctacgttgtg tataacggtc cacatgccgg tatatacgat     1440 gactgggggtt gtacaaaggc ggcaacaaac ggcgttcccg gagttgcaca caagaaattt     1500
gccactatta cagaggcaag agcagcagct gacgcgtaca caacaagtca gcaaacagac     1560
aggttgaact tcatccccaa aggagaagct caactcaagc ccaagagctt tgctaaggcc     1620
ctaacaagcc caccaaagca aaaagcccac tggctcacgc taggaaccaa aaggcccagc     1680
agtgatccag ccccaaaaga gatctccttt gccccggaga ttacaatgga cgatttcctc     1740
tatctttacg atctaggaag gaagttcgaa ggtgaaggtg acgacactat gttcaccact     1800
gataatgaga aggttagcct cttcaatttc agaaagaatg ctgacccaca gatggttaga     1860
gaggcctacg cagcaggtct catcaagacg atctacccga gtaacaatct ccaggagatc     1920 aaatacctte ccaagaaggt taaagatgca gtcaaaagat tcaggactaa ttgcatcaag     1980
aacacagaga aagacatatt tctcaagatc agaagtacta ttccagtatg gacgattcaa     2040
ggcttgcttc ataaaccaag gcaagtaata gagattggag tctctaaaaa ggtagttcct     2100
actgaatcta aggccatgca tggagtctaa gattcaaatc gaggatctaa cagaactcgc     2160
cgtgaagact ggcgaacagt tcatacagag tcttttacga ctcaatgaca agaagaaaat     2220
cttcgtcaac atggtggagc acgacactct ggtctactcc aaaaatgtca agatacagt      2280 ctcagaagac caagggctta ttgagacttt tcaacaaagg ataatttcgg gaaacctcct     2340
cggattccat tgcccagcta tctgtcactt catcgaaagg acagtagaaa aggaaggtgg     2400
ctcctacaaa tgccatcatt gcgataaagg aaaggctatc attcaagatg cctctgccga     2460
cagtggtccc aaagatggac ccccacccac gaggagcatc gtggaaaaag aagacgttcc     2520
aaccacgtct tcaaagcaag tggattgatg tgacatctcc actgacgtaa gggatgacgc     2580
acaatcccac tatccttcgc aagacccttc ctctatataa ggaagttcat ttcatttgga     2640
gaggacacgc tcgagctcat ttctctatta cttcagccat aacaaagaa ctcttttctc      2700 ttcttattaa accatgaaaa agcctgaact caccgcgacg tctgtcgaga agtttctgat     2760
cgaaaagttc gacagcgtct ccgacctgat gcagctctcg gagggcgaag aatctcgtgc     2820
tttcagcttc gatgtaggag ggcgtggata tgtcctgcgg gtaaatagct gcgccgatgg     2880
tttctacaaa gatcgttatg tttatcggca ctttgcatcg gccgcgctcc cgattccgga     2940
agtgcttgac attggggaat tcagcgagag cctgacctat tgcatctccc gccgtgcaca     3000
gggtgtcacg ttgcaagacc tgcctgaaac cgaactgccc gctgttctgc agccggtcgc     3060
ggaggccatg gatgcgatcg ctgcggccga tcttagccag acgagcgggt tcggcccatt     3120
```

```
cggaccgcaa ggaatcggtc aatacactac atggcgtgat tcatatgcg cgattgctga   3180
tccccatgtg tatcactggc aaactgtgat ggacgacacc gtcagtgcgt ccgtcgcgca   3240
ggctctcgat gagctgatgc tttgggccga ggactgcccc gaagtccggc acctcgtgca   3300
cgcggatttc ggctccaaca atgtcctgac ggacaatggc cgcataacag cggtcattga   3360
ctggagcgag gcgatgttcg gggattccca atacgaggtc gccaacatct tcttctggag   3420
gccgtggttg gcttgtatgg agcagcagac gcgctacttc gagcggaggc atccggagct   3480
tgcaggatcg ccgcggctcc gggcgtatat gctccgcatt ggtcttgacc aactctatca   3540
gagcttggtt gacggcaatt tcgatgatgc agcttgggcg cagggtcgat gcgacgcaat   3600
cgtccgatcc ggagccggga ctgtcgggcg tacacaaatc gcccgcagaa gcgcggccgt   3660
ctggaccgat ggctgtgtag aagtactcgc cgatagtgga aaccgacgcc ccagcactcg   3720
tccgagggca aggaatagt gaggtaccta agaaggagt gcgtcgaagc agatcgttca    3780
aacatttggc aataaagttt cttaagattg aatcctgttg ccggtcttgc gatgattatc   3840
atataatttc tgttgaatta cgttaagcat gtaataatta acatgtaatg catgacgtta   3900
tttatgagat gggttttat gattagagtc ccgcaattat acatttaata cgcgatagaa    3960
aacaaaatat agcgcgcaaa ctaggataaa ttatcgcgcg cggtgtcatc tatgttacta   4020
gatcgatgtc gaatcgatca acctgcatta atgaatcggc caacgcgcgg ggagaggcgg   4080
tttgcgtatt gggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcaatgctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt tttttgtttg caagcagcag attacgcgca gaaaaaaagg   4860
atctcaagaa gatcctttga tcttttctac ggggtctgac gctcagtgga acgaaaactc   4920
acgttaaggg attttggtca tgacattaac ctataaaaat aggcgtatca cgaggccctt   4980
tcgtctcgcg cgtttcggtg atgacggtga aaacctctga cacatgcagc tcccggagac   5040
ggtcacagct tgtctgtaag cggatgccgg gagcagacaa gcccgtcagg gcgcgtcagc   5100
gggtgttggc gggtgtcggg gctggcttaa ctatgcggca tcagagcaga ttgtactgag   5160
agtgcaccat atggacatat tgtcgttaga acgcggctac aattaataca taaccttatg   5220
tatcatacac atacgattta ggtgacacta tagaacggcg cgccaagctt gttgaaacat   5280
ccctgaagtg tctcatttta ttttatttat ctttgctga taaaaaata aataaaaga     5340
agctaagcac acggtcaacc attgctctac tgctaaaagg gttatgtgta gtgttttact   5400
gcataaaatta tgcagcaaac aagacaactc aaattaaaaa atttcctttg cttgttttt   5460
tgttgtctct gacttgactt tcttgtggaa gttggttgta taaggattgg gacaccattg   5520
```

```
tccttcttaa tttaatttta ttctttgctg ataaaaaaaa aaatttcata tagtgttaaa    5580
taataatttg ttaaataacc aaaaagtcaa atatgtttac tctcgtttaa ataattgaga    5640
ttcgtccagc aaggctaaac gattgtatag atttatgaca atatttactt ttttatagat    5700
aaatgttata ttataataaa tttatataca tatattatat gttatttatt attatttaa    5760 atccttcaat attttatcaa accaactcat aattttttt ttatctgtaa gaagcaataa    5820
aattaaatag acccacttta aggatgatcc aaccttata cagagtaaga gagttcaaat    5880 agtaccettt catatacata tcaactaaaa tattagaaat atcatggatc aaaccttata    5940
aagacattaa ataagtggat aagtataata tataaatggg tagtatataa tatataaatg    6000
gatacaaact tctctctta taattgttat gtctccttaa catcctaata taatacataa    6060
gtgggtaata tataatatat aaatggagac aaacttcttc cattataatt gttatgtctt    6120
cttaacactt atgtctcgtt cacaatgcta aggttagaat tgtttagaaa gtcttatagt    6180
acacatttgt ttttgtacta tttgaagcat tccataagcc gtcacgattc agatgattta    6240
taataataag aggaaattta tcatagaaca ataaggtgca tagatagagt gttaatatat    6300
cataacatcc tttgtttatt catagaagaa gtgagatgga gctcagttat tatactgtta    6360
catggtcgga tacaatattc catgctctcc atgagctctt acacctacat gcattttagt    6420
tcatacttgc ggccgcagta tatcttaaat tctttaatac ggtgtactag gatattgaac    6480
tggttcttga tgatgaaaac ctgggccgag attgcagcta tttatagtca taggtcttgt    6540
taacatgcat ggacatttgg ccacggggtg gcatgcagtt tgacgggtgt tgaaataaac    6600
aaaaatgagg tggcggaaga gaatacgagt ttgaggttgg gttagaaaca acaaatgtga    6660
gggctcatga tgggttgagt tggtgaatgt tttgggctgc tcgattgaca cctttgtgag    6720
tacgtgttgt tgtgcatggc ttttggggtc cagttttttt ttcttgacgc ggcgatcctg    6780
atcagctagt ggataagtga tgtccactgt gtgtgattgc gttttttgttt gaattttatg    6840 aacttagaca ttgctatgca aaggatactc tcattgtgtt ttgtcttctt ttgttccttg    6900
gcttttctct atgatccaag agactagtca gtgttgtggc attcgagact accaagatta    6960
attatgatgg gggaaggata agtaactgat tagtacggac tgttaccaaa ttaattaata    7020
agcggcaaat gaagggcatg gatcaaaagc ttggatctcc tgcaggatct ggccggccgg    7080
atctc    7085
```

<210> SEQ ID NO 83
<211> LENGTH: 2540
<212> TYPE: DNA
<213> ORGANISM: Artificial Sequence
<220> FEATURE:
<223> OTHER INFORMATION: Plasmid pKS102

<400> SEQUENCE: 83

```
cgatcatccg gatatagttc ctcctttcag caaaaaaccc ctcaagaccc gtttagaggc      60 cccaagggt tatgctagtt attgctcagc ggtggcagca gccaactcag cttcctttcg     120
ggctttgtta gcagccggat cgatccaagc tgtacctcac tattcctttg ccctcggacg     180
agtgctgggg cgtcggtttc cactatcggc gagtacttct acacagccat cggtccagac     240
ggccgcgctt ctgcgggcga tttgtgtacg cccgacagtc ccggctccgg atcggacgat     300
tgcgtcgcat cgaccctgcg cccaagctgc atcatcgaaa ttgccgtcaa ccaagctctg     360
atagagttgg tcaagaccaa tgcggagcat atacgcccgg agccgcggcg atcctgcaag     420
```

```
ctccggatgc ctccgctcga agtagcgcgt ctgctgctcc atacaagcca accacggcct      480
ccagaagaag atgttggcga cctcgtattg ggaatcccg aacatcgcct cgctccagtc       540
aatgaccgct gttatgcggc cattgtccgt caggacattg ttggagccga atccgcgtg       600
cacgaggtgc cggacttcgg ggcagtcctc ggcccaaagc atcagctcat cgagagcctg      660
cgcgacggac gcactgacgg tgtcgtccat cacagtttgc cagtgataca catggggatc      720
agcaatcgcg catatgaaat cacgccatgt agtgtattga ccgattcctt gcggtccgaa      780
tgggccgaac ccgctcgtct ggctaagatc ggccgcagcg atcgcatcca tagcctccgc      840
gaccggctgc agaacagcgg gcagttcggt ttcaggcagg tcttgcaacg tgacaccctg      900
tgcacggcgg gagatgcaat aggtcaggct ctcgctgaat tccccaatgt caagcacttc      960
cggaatcggg agcgcggccg atgcaaagtg ccgataaaca taacgatctt tgtagaaacc     1020
atcggcgcag ctatttaccc gcaggacata tccacgccct cctacatcga agctgaaagc     1080
acgagattct tcgccctccg agagctgcat caggtcggag acgctgtcga acttttcgat     1140
cagaaacttc tcgacagacg tcgcggtgag ttcaggcttt tccatgggta tatctccttc     1200
ttaaagttaa acaaaattat ttctagaggg aaaccgttgt ggtctcccta tagtgagtcg     1260
tattaatttc gcgggatcga gatctgatca acctgcatta atgaatcggc caacgcgcgg     1320
ggagaggcgg tttgcgtatt gggcgctctt ccgcttcctc gctcactgac tcgctgcgct     1380
cggtcgttcg gctgcggcga gcggtatcag ctcactcaaa ggcggtaata cggttatcca     1440
cagaatcagg ggataacgca ggaaagaaca tgtgagcaaa aggccagcaa aaggccagga     1500
accgtaaaaa ggccgcgttg ctggcgtttt tccataggct ccgcccccct gacgagcatc     1560
acaaaaatcg acgctcaagt cagaggtggc gaaacccgac aggactataa agataccagg     1620
cgtttccccc tggaagctcc ctcgtgcgct ctcctgttcc gaccctgccg cttaccggat     1680
acctgtccgc ctttctccct tcgggaagcg tggcgctttc tcaatgctca cgctgtaggt     1740
atctcagttc ggtgtaggtc gttcgctcca agctgggctg tgtgcacgaa ccccccgttc     1800
agcccgaccg ctgcgcctta tccggtaact atcgtcttga gtccaacccg gtaagacacg     1860
acttatcgcc actggcagca gccactggta acaggattag cagagcgagg tatgtaggcg     1920
gtgctacaga gttcttgaag tggtggccta actacggcta cactagaagg acagtatttg     1980
gtatctgcgc tctgctgaag ccagttacct tcggaaaaag agttggtagc tcttgatccg     2040
gcaaacaaac caccgctggt agcggtggtt ttttgtttg caagcagcag attacgcgca     2100
gaaaaaaagg atctcaagaa gatcctttga tcttttctac ggggtctgac gctcagtgga     2160
acgaaaactc acgttaaggg attttggtca tgacattaac ctataaaaat aggcgtatca     2220
cgaggccctt tcgtctcgcg cgtttcggtg atgacggtga aaacctctga cacatgcagc     2280
tcccggagac ggtcacagct tgtctgtaag cggatgccgg gagcagacaa gcccgtcagg     2340
gcgcgtcagc gggtgttggc gggtgtcggg gctggcttaa ctatgcggca tcagagcaga     2400
ttgtactgag agtgcaccat atggacatat tgtcgttaga acgcggctac aattaataca     2460
taaccttatg tatcatacac atacgattta ggtgacacta tagaacggcg cgccaagctt     2520
ggatccgtcg acggcgcgcc                                                  2540
```

<210> SEQ ID NO 84
<211> LENGTH: 4359
<212> TYPE: DNA
<213> ORGANISM: Artificial Sequence
<220> FEATURE:
<223> OTHER INFORMATION: Plasmid pKR197

<400> SEQUENCE: 84

```
cgcgcccgat catccggata tagttcctcc tttcagcaaa aaaccccctca agacccgttt    60
agaggcccca aggggttatg ctagttattg ctcagcggtg gcagcagcca actcagcttc   120
ctttcgggct ttgttagcag ccggatcgat ccaagctgta cctcactatt cctttgccct   180
cggacgagtg ctgggcgtc ggtttccact atcggcgagt acttctacac agccatcggt    240
ccagacggcc gcgcttctgc gggcgatttg tgtacgcccg acagtcccgg ctccggatcg   300
gacgattgcg tcgcatcgac cctgcgccca agctgcatca tcgaaattgc cgtcaaccaa   360
gctctgatag agttggtcaa gaccaatgcg gagcatatac gcccggagcc gcggcgatcc   420
tgcaagctcc ggatgcctcc gctcgaagta gcgcgtctgc tgctccatac aagccaacca   480
cggcctccag aagaagatgt tggcgacctc gtattgggaa tccccgaaca tcgcctcgct   540
ccagtcaatg accgctgtta tgcggccatt gtccgtcagg acattgttgg agccgaaatc   600
cgcgtgcacg aggtgccgga cttcggggca gtcctcggcc caaagcatca gctcatcgag   660
agcctgcgcg acggacgcac tgacggtgtc gtccatcaca gtttgccagt gatacacatg   720
gggatcagca atcgcgcata tgaaatcacg ccatgtagtg tattgaccga ttccttgcgg   780
tccgaatggg ccgaacccgc tcgtctggct aagatcggcc gcagcgatcg catccatagc   840
ctccgcgacc ggctgcagaa cagcgggcag ttcggtttca ggcaggtctt gcaacgtgac   900
accctgtgca cggcgggaga tgcaataggt caggctctcg ctgaattccc caatgtcaag   960
cacttccgga atcgggagcg cggccgatgc aaagtgccga taaacataac gatctttgta  1020
gaaaccatcg gcgcagctat ttacccgcag gacatatcca cgccctccta catcgaagct  1080
gaaagcacga gattcttcgc cctccgagag ctgcatcagg tcggagacgc tgtcgaactt  1140
ttcgatcaga aacttctcga cagacgtcgc ggtgagttca ggcttttcca tgggtatatc  1200
tccttcttaa agttaaacaa aattatttct agagggaaac cgttgtggtc tccctatagt  1260
gagtcgtatt aatttcgcgg gatcgagatc tgatcaacct gcattaatga atcggccaac  1320
gcgcggggag aggcggtttg cgtattgggc gctcttccgc ttcctcgctc actgactcgc  1380
tgcgctcggt cgttcggctg cggcgagcgg tatcagctca ctcaaaggcg gtaatacggt  1440
tatccacaga atcaggggat aacgcaggaa agaacatgtg agcaaaaggc cagcaaaagg  1500
ccaggaaccg taaaaaggcc gcgttgctgg cgtttttcca taggctccgc cccccctgacg  1560
agcatcacaa aaatcgacgc tcaagtcaga ggtggcgaaa cccgacagga ctataaagat  1620
accaggcgtt ccccctgga agctccctcg tgcgctctcc tgttccgacc ctgccgctta  1680
ccggatacct gtccgccttt ctcccttcgg gaagcgtggc gctttctcaa tgctcacgct  1740
gtaggtatct cagttcggtg taggtcgttc gctccaagct gggctgtgtg cacgaacccc  1800
ccgttcagcc cgaccgctgc gccttatccg gtaactatcg tcttgagtcc aacccggtaa  1860
gacacgactt atcgccactg gcagcagcca ctggtaacag gattagcaga gcgaggtatg  1920
taggcggtgc tacagagttc ttgaagtggt ggcctaacta cggctacact agaaggacag  1980
tatttggtat ctgcgctctg ctgaagccag ttaccttcgg aaaaagagtt ggtagctctt  2040
gatccggcaa acaaaccacc gctggtagcg gtggtttttt tgtttgcaag cagcagatta  2100
cgcgcagaaa aaaaggatct caagaagatc ctttgatctt ttctacgggg tctgacgctc  2160
agtggaacga aaactcacgt taagggattt tggtcatgac attaacctat aaaaataggc  2220
gtatcacgag gccctttcgt ctcgcgcgtt tcggtgatga cggtgaaaac ctctgacaca  2280
```

```
tgcagctccc ggagacggtc acagcttgtc tgtaagcgga tgccgggagc agacaagccc    2340
gtcagggcgc gtcagcgggt gttggcgggt gtcggggctg gcttaactat gcggcatcag    2400
agcagattgt actgagagtg caccatatgg acatattgtc gttagaacgc ggctacaatt    2460
aatacataac cttatgtatc atacacatac gatttaggtg acactataga acggcgcgcc    2520
aagcttgttg aaacatccct gaagtgtctc attttatttt atttattctt tgctgataaa    2580
aaaataaaat aaaagaagct aagcacacgg tcaaccattg ctctactgct aaagggtta    2640 tgtgtagtgt tttactgcat aaattatgca gcaaacaaga caactcaaat taaaaaattt    2700
cctttgcttg ttttttttgtt gtctctgact tgactttctt gtggaagttg gttgtataag    2760
gattgggaca ccattgtcct tcttaattta attttattct ttgctgataa aaaaaaaaat    2820
ttcatatagt gttaaataat aatttgttaa ataaccaaaa agtcaaatat gtttactctc    2880
gtttaaataa ttgagattcg tccagcaagg ctaaacgatt gtatagattt atgacaatat    2940 ttacttttt atagataaat gttatattat aataaattta tatacatata ttatatgtta    3000
tttattatta tttttaaatcc ttcaatattt tatcaaacca actcataatt ttttttttat    3060
ctgtaagaag caataaaatt aaatagaccc actttaagga tgatccaacc tttatacaga    3120
gtaagagagt tcaaatagta ccctttcata tacatatcaa ctaaaatatt agaaatatca    3180
tggatcaaac cttataaaga cattaaataa gtggataagt ataatatata aatgggtagt    3240
atataatata taaatggata caaacttctc tctttataat tgttatgtct ccttaacatc    3300
ctaatataat acataagtgg gtaatatata atatataaat ggagacaaac ttcttccatt    3360
ataattgtta tgtcttctta acacttatgt ctcgttcaca atgctaaggt tagaattgtt    3420
tagaaagtct tatagtacac atttgttttt gtactatttg aagcattcca taagccgtca    3480
cgattcagat gatttataat aataagagga aatttatcat agaacaataa ggtgcataga    3540
tagagtgtta atatatcata acatcctttg tttattcata gaagaagtga gatggagctc    3600
agttattata ctgttacatg gtcggataca atattccatg ctctccatga gctcttacac    3660
ctacatgcat tttagttcat acttgcggcc gcagtatatc ttaaattctt taatacggtg    3720
tactaggata ttgaactggt tcttgatgat gaaaacctgg gccgagattg cagctattta    3780
tagtcatagg tcttgttaac atgcatggac atttggccac ggggtggcat gcagtttgac    3840
gggtgttgaa ataaacaaaa atgaggtggc ggaagagaat acgagtttga ggttgggtta    3900
gaaacaacaa atgtgagggc tcatgatggg ttgagttggt gaatgttttg ggctgctcga    3960
ttgacacctt tgtgagtacg tgttgttgtg catggctttt ggggtccagt ttttttttct    4020
tgacgcggcg atcctgatca gctagtggat aagtgatgtc cactgtgtgt gattgcgttt    4080
ttgtttgaat tttatgaact tagacattgc tatgcaaagg atactctcat tgtgtttttgt    4140 cttcttttgt tccttggctt tttcttatga tccaagagac tagtcagtgt tgtggcattc    4200
gagactacca agattaatta tgatggggga aggataagta actgattagt acggactgtt    4260
accaaattaa ttaataagcg gcaaatgaag ggcatggatc aaaagcttgg atctcctgca    4320
ggatctggcc ggccggatct cgtacggatc cgtcgacgg                          4359
```

<210> SEQ ID NO 85
<211> LENGTH: 5147
<212> TYPE: DNA
<213> ORGANISM: Artificial Sequence
<220> FEATURE:
<223> OTHER INFORMATION: Plasmid pKR911

<400> SEQUENCE: 85

| | |
|---|---|
| ggccgcaagt atgaactaaa atgcatgtag gtgtaagagc tcatggagag catggaatat | 60 |
| tgtatccgac catgtaacag tataataact gagctccatc tcacttcttc tatgaataaa | 120 |
| caaaggatgt tatgatatat taacactcta tctatgcacc ttattgttct atgataaatt | 180 |
| tcctcttatt attataaatc atctgaatcg tgacggctta tggaatgctt caaatagtac | 240 |
| aaaaacaaat gtgtactata agactttcta aacaattcta accttagcat tgtgaacgag | 300 |
| acataagtgt taagaagaca taacaattat aatggaagaa gtttgtctcc atttatatat | 360 |
| tatatattac ccacttatgt attatattag gatgttaagg agacataaca attataaaga | 420 |
| gagaagtttg tatccattta tatattatat actacccatt tatatattat acttatccac | 480 |
| ttatttaatg tctttataag gtttgatcca tgatatttct aatattttag ttgatatgta | 540 |
| tatgaaaggg tactatttga actctcttac tctgtataaa ggttggatca tccttaaagt | 600 |
| gggtctattt aattttattg cttcttacag ataaaaaaaa aattatgagt tggtttgata | 660 |
| aaatattgaa ggatttaaaa taataataaa taacatataa tatatgtata taaatttatt | 720 |
| ataatataac atttatctat aaaaaagtaa atattgtcat aaatctatac aatcgtttag | 780 |
| ccttgctgga cgaatctcaa ttatttaaac gagagtaaac atatttgact ttttggttat | 840 |
| ttaacaaatt attatttaac actatatgaa attttttttt ttatcagcaa agaataaaat | 900 |
| taaattaaga aggacaatgg tgtcccaatc cttatacaac caacttccac aagaaagtca | 960 |
| agtcagagac aacaaaaaaa caagcaaagg aaatttttta atttgagttg tcttgtttgc | 1020 |
| tgcataattt atgcagtaaa acactacaca taacccttttt agcagtagag caatggttga | 1080 |
| ccgtgtgctt agcttctttt attttatttt tttatcagca aagaataaat aaaataaaat | 1140 |
| gagacacttc agggatgttt caacaagctt ggcgcgccgt tctatagtgt cacctaaatc | 1200 |
| gtatgtgtat gatacataag gttatgtatt aattgtagcc gcgttctaac gacaaatatgt | 1260 |
| ccatatggtg cactctcagt acaatctgct ctgatgccgc atagttaagc cagccccgac | 1320 |
| acccgccaac acccgctgac gcgccctgac gggcttgtct gctcccggca tccgcttaca | 1380 |
| gacaagctgt gaccgtctcc gggagctgca tgtgtcagag gttttcaccg tcatcaccga | 1440 |
| aacgcgcgag acgaaagggc ctcgtgatac gcctattttt ataggttaat gtcatgacca | 1500 |
| aaatccctta acgtgagttt tcgttccact gagcgtcaga ccccgtagaa aagatcaaag | 1560 |
| gatcttcttg agatcctttt tttctgcgcg taatctgctg cttgcaaaca aaaaaaccac | 1620 |
| cgctaccagc ggtggtttgt ttgccggatc aagagctacc aactcttttt ccgaaggtaa | 1680 |
| ctggcttcag cagagcgcag ataccaaata ctgtccttct agtgtagccg tagttaggcc | 1740 |
| accacttcaa gaactctgta gcaccgccta catacctcgc tctgctaatc ctgttaccag | 1800 |
| tggctgctgc cagtggcgat aagtcgtgtc ttaccgggtt ggactcaaga cgatagttac | 1860 |
| cggataaggc gcagcggtcg ggctgaacgg ggggttcgtg cacacagccc agcttggagc | 1920 |
| gaacgaccta caccgaactg agatacctac agcgtgagca ttgagaaagc gccacgcttc | 1980 |
| ccgaagggag aaaggcggac aggtatccgg taagcggcag ggtcggaaca ggagagcgca | 2040 |
| cgagggagct tccaggggga aacgcctggt atctttatag tcctgtcggg tttcgccacc | 2100 |
| tctgacttga gcgtcgattt tgtgatgct cgtcaggggg gcggagccta tggaaaaacg | 2160 |
| ccagcaacgc ggccttttta cggttcctgg ccttttgctg gccttttgct cacatgttct | 2220 |
| ttcctgcgtt atcccctgat tctgtggata accgtattac cgcctttgag tgagctgata | 2280 |
| ccgctcgccg cagccgaacg accgagcgca gcgagtcagt gagcgaggaa gcggaagagc | 2340 |

```
gcccaatacg caaaccgcct ctccccgcgc gttggccgat tcattaatgc aggttgatca  2400
gatctcgatc ccgcgaaatt aatacgactc actataggga gaccacaacg gtttccctct  2460
agaaataatt ttgtttaact ttaagaagga gatataccca tggaaaagcc tgaactcacc  2520
gcgacgtctg tcgagaagtt tctgatcgaa aagttcgaca cgtctccga cctgatgcag  2580 ctctcggagg gcgaagaatc tcgtgctttc agcttcgatg taggagggcg tggatatgtc  2640
ctgcgggtaa atagctgcgc cgatggtttc tacaaagatc gttatgttta tcggcacttt  2700
gcatcggccg cgctcccgat tccggaagtg cttgacattg gggaattcag cgagagcctg  2760
acctattgca tctcccgccg tgcacagggt gtcacgttgc aagacctgcc tgaaaccgaa  2820
ctgcccgctg ttctgcagcc ggtcgcggag gctatggatg cgatcgctgc ggccgatctt  2880
agccagacga gcgggttcgg cccattcgga ccgcaaggaa tcggtcaata cactacatgg  2940
cgtgatttca tatgcgcgat tgctgatccc catgtgtatc actggcaaac tgtgatggac  3000
gacaccgtca gtgcgtccgt cgcgcaggct ctcgatgagc tgatgctttg ggccgaggac  3060
tgccccgaag tccggcacct cgtgcacgcg gatttcggct ccaacaatgt cctgacggac  3120
aatggccgca taacagcggt cattgactgg agcgaggcga tgttcgggga ttcccaatac  3180
gaggtcgcca acatcttctt ctggaggccg tggttggctt gtatggagca gcagacgcgc  3240
tacttcgagc ggaggcatcc ggagcttgca ggatcgccgc ggctccgggc gtatatgctc  3300
cgcattggtc ttgaccaact ctatcagagc ttggttgacg gcaatttcga tgatgcagct  3360
tgggcgcagg gtcgatgcga cgcaatcgtc cgatccggag ccgggactgt cgggcgtaca  3420
caaatcgccc gcagaagcgc ggccgtctgg accgatggct gtgtagaagt actcgccgat  3480
agtggaaacc gacgcccag cactcgtccg agggcaaagg aatagtgagg tacagcttgg  3540
atcgatccgc ctgctaacaa agcccgaaag gaagctgagt tggctgctgc caccgctgag  3600
caataactag cataacccct tggggcctct aaacgggtct gagggggttt tttgctgaaa  3660
ggaggaacta tatccggatg atcgggcgcg ccgtcgacgg atccgtacga gatccggccg  3720
gccagatcct gcaggagatc caagcttttg atccatgccc ttcatttgcc gcttattaat  3780
taatttggta acagtccgta ctaatcagtt acttatcctt cccccatcat aattaatctt  3840
ggtagtctcg aatgccacaa cactgactag tctcttggat cataagaaaa agccaaggaa  3900
caaaagaaga caaaacacaa tgagagtatc ctttgcatag caatgtctaa gttcataaaa  3960
ttcaaacaaa aacgcaatca cacacagtgg acatcactta tccactagct gatcaggatc  4020
gccgcgtcaa gaaaaaaaaa ctggacccca aaagcatgc acaacaacac gtactcacaa  4080
aggtgtcaat cgagcagccc aaaacattca ccaactcaac ccatcatgag ccctcacatt  4140
tgttgtttct aacccaacct caaactcgta ttctcttccg ccacctcatt tttgtttatt  4200
tcaacacccg tcaaactgca tgccaccccg tggccaaatg tccatgcatg ttaacaagac  4260
ctatgactat aaatagctgc aatctcggcc caggttttca tcatcaagaa ccagttcaat  4320
atcctagtac accgtattaa agaatttaag atatactgcg gccgcaccat ggaggtggtg  4380
aatgaaatag tctcaattgg gcaggaagtt ttacccaaag ttgattatgc ccaactctgg  4440
agtgatgcca gtcactgtga ggtgctttac ttgtccatcg catttgtcat cttgaagttc  4500
actcttggcc cccttggtcc aaaaggtcag tctcgtatga agtttgtttt caccaattac  4560
aaccttctca tgtccattta ttcgtttggga tcattcctct caatggcata tgccatgtac  4620
accatcggtg ttatgtctga caactgcgag aaggcttttg acaacaacgt cttcaggatc  4680
accacgcagt tgttctattt gagcaagttc ctggagtata ttgactcctt ctatttgcca  4740
```

-continued

```
ctgatgggca agcctctgac ctggttgcaa ttcttccatc atttggggc accgatggat      4800 atgtggctgt tctataatta ccgaaatgaa gctgtttgga ttttgtgct gttgaatggt      4860 ttcatccact ggatcatgta cggttattat tggaccagat tgatcaagct gaagttcccc     4920
atgccaaaat ccctgattac atcaatgcag atcattcaat tcaatgttgg tttctacatt    4980
gtctggaagt acaggaacat tccctgttat cgccaagatg ggatgaggat gtttggctgg     5040
ttcttcaatt acttttatgt tggcacagtc ttgtgtttgt tcttgaattt ctatgtgcaa     5100
acgtatatcg tcaggaagca aagggagcc aaaaagattc agtgagc                    5147
```

<210> SEQ ID NO 86
<211> LENGTH: 6559
<212> TYPE: DNA
<213> ORGANISM: Artificial Sequence
<220> FEATURE:
<223> OTHER INFORMATION: Plasmid pKR680
<220> FEATURE:
<221> NAME/KEY: misc_feature
<222> LOCATION: (4340)..(4340)
<223> OTHER INFORMATION: n is a, c, g, or t

<400> SEQUENCE: 86

```
ggccgcgaca caagtgtgag agtactaaat aaatgctttg gttgtacgaa atcattacac       60
taaataaaat aatcaaagct tatatatgcc ttccgctaag gccgaatgca agaaattgg       120 ttctttctcg ttatcttttg ccacttttac tagtacgtat taattactac ttaatcatct      180
ttgtttacgg ctcattatat ccggtctaga ggatccaagg ccgcgaagtt aaaagcaatg      240
ttgtcacttg tcgtactaac acatgatgtg atagtttatg ctagctagct ataacataag     300
ctgtctctga gtgtgttgta tattaataaa gatcatcact ggtgaatggt gatcgtgtac      360
gtaccctact tagtaggcaa tggaagcact tagagtgtgc tttgtgcatg gccttgcctc      420
tgttttgaga cttttgtaat gttttcgagt ttaaatcttt gcctttgcgt acgtgggcgg      480
atccccgggg ctgcaggaat tcactggccg tcgttttaca acgtcgtgac tgggaaaacc     540
ctggcgttac ccaacttaat cgccttgcag cacatccccc tttcgccagc tggcgtaata    600
gcgaagaggc ccgcaccgat cgcccttccc aacagttgcg cagcctgaat ggcgaatggc    660
gcctgatgcg gtattttctc cttacgcatc tgtgcggtat ttcacaccgc atatggtgca    720
ctctcagtac aatctgctct gatgccgcat agttaagcca gccccgacac cgccaacac    780 ccgctgacgc gccctgacgg gcttgtctgc tcccggcatc cgcttacaga caagctgtga    840
ccgtctccgg gagctgcatg tgtcagaggt tttaccgtc atcaccgaaa cgcgcgagac     900
gaaagggcct cgtgatacgc ctattttat aggttaatgt catgataata atggtttctt      960
agacgtcagg tggcactttt cggggaaatg tgcgcggaac ccctatttgt ttattttct    1020 aaatacattc aaatatgtat ccgctcatga acaataacc ctgataaatg cttcaataat    1080
attgaaaaag gaagagtatg agtattcaac atttccgtgt cgcccttatt cccttttttg    1140 cggcatttg ccttcctgtt tttgctcacc cagaaacgct ggtgaaagta aaagatgctg    1200
aagatcagtt gggtgcacga gtgggttaca tcgaactgga tctcaacagc ggtaagatcc    1260
ttgagagttt tcgccccgaa gaacgttttc caatgatgag cacttttaaa gttctgctat    1320
gtggcgcggt attatcccgt attgacgccg ggcaagagca actcggtcgc cgcatacact    1380
attctcagaa tgacttggtt gagtactcac cagtcacaga aaagcatctt acggatggca    1440
tgacagtaag agaattatgc agtgctgcca taaccatgag tgataacact gcggccaact    1500
```

```
tacttctgac aacgatcgga ggaccgaagg agctaaccgc ttttttgcac aacatggggg    1560
atcatgtaac tcgccttgat cgttgggaac cggagctgaa tgaagccata ccaaacgacg    1620
agcgtgacac cacgatgcct gtagcaatgg caacaacgtt gcgcaaacta ttaactggcg    1680
aactacttac tctagcttcc cggcaacaat taatagactg gatggaggcg gataaagttg    1740
caggaccact tctgcgctcg gcccttccgg ctggctggtt tattgctgat aaatctggag    1800
ccggtgagcg tgggtctcgc ggtatcattg cagcactggg gccagatggt aagccctccc    1860
gtatcgtagt tatctacacg acggggagtc aggcaactat ggatgaacga atagacaga    1920 tcgctgagat aggtgcctca ctgattaagc attggtaact gtcagaccaa gtttactcat    1980
atatacttta gattgattta aacttcatt tttaatttaa aaggatctag gtgaagatcc    2040
tttttgataa tctcatgacc aaaatccctt aacgtgagtt ttcgttccac tgagcgtcag    2100
accccgtaga aaagatcaaa ggatcttctt gagatccttt ttttctgcgc gtaatctgct    2160
gcttgcaaac aaaaaaacca ccgctaccag cggtggtttg tttgccggat caagagctac    2220
caactctttt tccgaaggta actggcttca gcagagcgca gataccaaat actgtccttc    2280
tagtgtagcc gtagttaggc caccacttca agaactctgt agcaccgcct acatacctcg    2340
ctctgctaat cctgttacca gtggctgctg ccagtggcga taagtcgtgt cttaccgggt    2400
tggactcaag acgatagtta ccggataagg cgcagcggtc gggctgaacg ggggggttcgt    2460 gcacacagcc cagcttggag cgaacgacct acaccgaact gagatacgta cagcgtgagc    2520
tatgagaaag cgccacgctt cccgaaggga gaaaggcgga caggtatccg gtaagcggca    2580
gggtcggaac aggagagcgc acgagggagc ttccagggggg aaacgcctgg tatctttata    2640
gtcctgtcgg gtttcgccac ctctgacttg agcgtcgatt tttgtgatgc tcgtcagggg    2700
ggcggagcct atggaaaaac gccagcaacg cggccttttt acggttcctg ccttttgct    2760 ggcctttgtg tcacatgttc tttcctgcgt tatcccctga ttctgtggat aaccgtatta    2820 ccgccttttga gtgagctgat accgctcgcc gcagccgaac gaccgagcgc agcgagtcag    2880
tgagcgagga agcggaagag cgcccaatac gcaaaccgcc tctccccgcg cgttggccga    2940
ttcattaatg cagctggcac gacaggtttc ccgactggaa agcgggcagt gagcgcaacg    3000
caattaatgt gagttagctc actcattagg cacccccaggc tttacacttt atgcttccgg    3060
ctcgtatgtt gtgtggaatt gtgagcggat aacaatttca cacaggaaac agctatgacc    3120
atgattacgc caagcttgca tgcctgcagg tcgactcgac gtacgtcctc gaagagaagg    3180
gttaataaca cattttttaa catttttaac acaattttta gttatttaaa aatttattaa    3240
aaaatttaaa ataagaagag gaactcttta aataaatcta acttacaaaa tttatgattt    3300
ttaataagtt ttcaccaata aaaaatgtca taaaaatatg ttaaaaagta tattatcaat    3360
attctcttta tgataaataa aaagaaaaaa aaaataaaag ttaagtgaaa atgagattga    3420
agtgacttta ggtgtgtata aatatatcaa ccccgccaac aatttattta atccaaatat    3480
attgaagtat attattccat agcctttatt tatttatata tttattatat aaaagcttta    3540
tttgttctag gttgttcatg aaatattttt ttggttttat ctccgttgta agaaaatcat    3600 gtgcttgtg tcgccactca ctattgcagc ttttcatgc attggtcaga ttgacggttg    3660
attgtatttt tgtttttat ggttttgtgt tatgacttaa gtcttcatct ctttatctct    3720
tcatcaggtt tgatggttac ctaatatggt ccatgggtac atgcatggtt aaattaggtg    3780
gccaactttg ttgtgaacga tagaattttt tttattaa gtaaactatt tttatattat    3840
gaaataataa taaaaaaaat attttatcat tattaacaaa atcatattag ttaatttgtt    3900
```

```
aactctataa taaaagaaat actgtaacat tcacattaca tggtaacatc tttccaccct    3960
ttcatttgtt ttttgtttga tgactttttt tcttgtttaa atttatttcc cttcttttaa    4020
atttggaata cattatcatc atatataaac taaaatacta aaaacaggat tacacaaatg    4080
ataaataata acacaaatat ttataaatct agctgcaata tatttaaact agctatatcg    4140
atattgtaaa ataaaactag ctgcattgat actgataaaa aaatatcatg tgctttctgg    4200
actgatgatg cagtatactt ttgacattgc ctttatttta ttttcagaa  aagctttctt    4260
agttctgggt tcttcattat ttgtttccca tctccattgt gaattgaatc atttgcttcg    4320
tgtcacaaat acaatttagn taggtacatg cattggtcag attcacggtt tattatgtca    4380
tgacttaagt tcatggtagt acattacctg ccacgcatgc attatattgg ttagatttga    4440
taggcaaatt tggttgtcaa caatataaat ataataatg ttttatatt acgaaataac      4500
agtgatcaaa acaaacagtt ttatctttat taacaagatt ttgttttgt ttgatgacgt     4560
tttttaatgt ttacgctttc cccttctttt gaatttaga acactttatc atcataaaat     4620
caaatactaa aaaattaca tatttcataa ataataacac aaatatttt aaaaaatctg      4680
aaataataat gaacaatatt acatattatc acgaaaattc attaataaaa atattatata    4740
aataaaatgt aatagtagtt atatgtagga aaaagtact gcacgcataa tatatacaaa     4800
aagattaaaa tgaactatta taaataataa cactaaatta atggtgaatc atatcaaaat    4860
aatgaaaaag taaataaaat ttgtaattaa cttctatatg tattacacac acaaataata    4920
aataatagta aaaaaaatta tgataaatat ttaccatctc ataagatatt taaaataatg    4980
ataaaaatat agattatttt ttatgcaact agctagccaa aaagagaaca cgggtatata    5040
taaaagagt  accttaaat  tctactgtac ttcctttatt cctgacgttt ttatatcaag    5100
tggacatacg tgaagatttt aattatcagt ctaaatattt cattagcact taatactttt    5160
ctgttttatt cctatcctat aagtagtccc gattctccca acattgctta ttcacacaac    5220
taactaagaa agtcttccat agccccccaa gcggccgcgg gaattcgatt gaaatgaagt    5280
caaagcgcca agcgcttccc cttacaattg atggaacaac atatgatgtg tctgcctggg    5340
tcaatttcca ccctggtggt gcggaaatta tagagaatta ccaaggaagg gatgccactg    5400
atgccttcat ggttatgcac tctcaagaag ccttcgacaa gctcaagcgc atgcccaaaa    5460
tcaatcccag ttctgagttg ccaccccagg ctgcagtgaa tgaagctcaa gaggatttcc    5520
ggaagctccg agaagagttg atcgcaactg gcatgtttga tgcctccccc ctctggtact    5580
catacaaaat cagcaccaca ctgggccttg gagtgctggg ttatttcctg atggttcagt    5640
atcagatgta tttcattggg gcagtgttgc ttgggatgca ctatcaacag atgggctggc    5700
tttctcatga catttgccac caccagactt caagaaccg  gaactggaac aacctcgtgg    5760
gactggtatt tggcaatggt ctgcaaggtt tttccgtgac atggtggaag gacagacaca    5820
atgcacatca ttcggcaacc aatgttcaag ggcacgaccc tgatattgac aacctccccc    5880
tcttagcctg gtctgaggat gacgtcacac gggcgtcacc gatttcccgc aagctcattc    5940
agttccagca gtactatttc ttggtcatct gtatcttgtt gcggttcatt tggtgtttcc    6000
agagcgtgtt gaccgtgcgc agtttgaagg acagagataa ccaattctat cgctctcagt    6060
ataagaagga ggccattggc ctcgccctgc actggaccct gaagaccctg ttccacttat    6120
tctttatgcc cagcatcctc acatcgctgt tggtgttttt cgtttcggag ctggttggcg    6180
gcttcggcat tgcgatcgtg gtgttcatga accactaccc actggagaag atcggggact    6240
```

```
cagtctggga tggccatgga ttctcggttg ccagatcca tgagaccatg aacattcggc    6300
gagggattat cacagattgg tttttcggag gcttgaatta ccagattgag caccatttgt    6360
ggccgaccct ccctcgccac aacctgacag cggttagcta ccaggtggaa cagctgtgcc    6420
agaagcacaa cctgccgtat cggaacccgc tgccccatga agggttggtc atcctgctgc    6480
gctatctggc ggtgttcgcc cggatggcgg agaagcaacc cgcggggaag gctctataag    6540
gaatcactag tgaattcgc                                                 6559
```

<210> SEQ ID NO 87
<211> LENGTH: 9014
<212> TYPE: DNA
<213> ORGANISM: Artificial Sequence
<220> FEATURE:
<223> OTHER INFORMATION: Plasmid pKR913
<220> FEATURE:
<221> NAME/KEY: misc_feature
<222> LOCATION: (7839)..(7839)
<223> OTHER INFORMATION: n is a, c, g, or t

<400> SEQUENCE: 87

```
gtacgagatc cggccggcca gatcctgcag gagatccaag cttttgatcc atgcccttca      60
tttgccgctt attaattaat ttggtaacag tccgtactaa tcagttactt atccttcccc     120
catcataatt aatcttggta gtctcgaatg ccacaacact gactagtctc ttggatcata     180
agaaaaagcc aaggaacaaa agaagacaaa acacaatgag agtatccttt gcatagcaat     240
gtctaagttc ataaaattca acaaaaacg caatcacaca cagtggacat cacttatcca      300
ctagctgatc aggatcgccg cgtcaagaaa aaaaactgg accccaaaag ccatgcacaa      360
caacacgtac tcacaaaggt gtcaatcgag cagcccaaaa cattcaccaa ctcaacccat     420
catgagccct cacatttgtt gtttctaacc caacctcaaa ctcgtattct cttccgccac     480 ctcattttg tttatttcaa cacccgtcaa actgcatgcc acccgtggc caaatgtcca       540 tgcatgttaa caagacctat gactataaat agctgcaatc tcggcccagg ttttcatcat     600
caagaaccag ttcaatatcc tagtacaccg tattaaagaa tttaagatat actgcggccg     660
caccatggag gtggtgaatg aaatagtctc aattgggcag gaagttttac ccaaagttga     720
ttatgcccaa ctctggagtg atgccagtca ctgtgaggtg ctttacttgt ccatcgcatt     780
tgtcatcttg aagttcactc ttggccccct tggtccaaaa ggtcagtctc gtatgaagtt     840
tgttttcacc aattacaacc ttctcatgtc catttattcg ttgggatcat tcctctcaat     900
ggcatatgcc atgtacacca tcggtgttat gtctgacaac tgcgagaagg cttttgacaa     960
caacgtcttc aggatcacca cgcagttgtt ctatttgagc aagttcctgg agtatattga    1020
ctccttctat ttgccactga tgggcaagcc tctgacctgg ttgcaattct tccatcattt    1080
gggggcaccg atggatatgt ggctgttcta taattaccga aatgaagctg tttggatttt    1140
tgtgctgttg aatggtttca tccactggat catgtacggt tattattgga ccagattgat    1200
caagctgaag ttccccatgc caaaatccct gattacatca atgcagatca ttcaattcaa    1260 tgttggttttc tacattgtct ggaagtacag gaacattccc tgttatcgcc aagatgggat    1320
gaggatgttt ggctggttct tcaattactt ttatgttggc acagtcttgt gtttgttctt    1380
gaatttctat gtgcaaacgt atatcgtcag gaagcacaag ggagccaaaa agattcagtg    1440
agcggccgca agtatgaact aaaatgcatg taggtgtaag agctcatgga gagcatggaa    1500
tattgtatcc gaccatgtaa cagtataata actgagctcc atctcacttc ttctatgaat    1560
aaacaaagga tgttatgata tattaacact ctatctatgc accttattgt tctatgataa    1620
```

```
atttcctctt attattataa atcatctgaa tcgtgacggc ttatggaatg cttcaaatag    1680
tacaaaaaca aatgtgtact ataagacttt ctaaacaatt ctaaccttag cattgtgaac    1740
gagacataag tgttaagaag acataacaat tataatggaa gaagtttgtc tccatttata    1800
tattatatat tacccactta tgtattatat taggatgtta aggagacata acaattataa    1860
agagagaagt ttgtatccat ttatatatta tatactaccc atttatatat tatacttatc    1920
cacttattta atgtctttat aaggtttgat ccatgatatt tctaatattt tagttgatat    1980
gtatatgaaa gggtactatt tgaactctct tactctgtat aaaggttgga tcatccttaa    2040
agtgggtcta tttaatttta ttgcttctta cagataaaaa aaaaattatg agttggtttg    2100
ataaaatatt gaaggattta aaataataat aaataacata taatatatgt atataaattt    2160
attataatat aacatttatc tataaaaaag taaatattgt cataaatcta tacaatcgtt    2220
tagccttgct ggacgaatct caattatttta aacgagagta aacatatttg acttttttggt    2280 tatttaacaa attattattt aacactatat gaaattttt tttttatcag caaagaataa    2340
aattaaatta agaaggacaa tggtgtccca atccttatac aaccaacttc cacaagaaag    2400
tcaagtcaga gacaacaaaa aaacaagcaa aggaaattt ttaatttgag ttgtcttgtt    2460
tgctgcataa tttatgcagt aaaacactac acataaccct tttagcagta gagcaatggt    2520
tgaccgtgtg cttagcttct tttattttat tttttatca gcaaagaata aataaaataa    2580
aatgagacac ttcagggatg tttcaacaag cttggcgcgc cgttctatag tgtcacctaa    2640
atcgtatgtg tatgatacat aaggttatgt attaattgta gccgcgttct aacgacaata    2700
tgtccatatg gtgcactctc agtacaatct gctctgatgc cgcatagtta agccagcccc    2760
gacacccgcc aacacccgct gacgcgccct gacgggcttg tctgctcccg gcatccgctt    2820
acagacaagc tgtgaccgtc tccgggagct gcatgtgtca gaggttttca ccgtcatcac    2880
cgaaacgcgc gagacgaaag gcctcgtga tacgcctatt tttataggtt aatgtcatga    2940
ccaaaatccc ttaacgtgag ttttcgttcc actgagcgtc agaccccgta gaaaagatca    3000
aaggatcttc ttgagatcct ttttttctgc gcgtaatctg ctgcttgcaa acaaaaaaac    3060
caccgctacc agcggtggtt tgtttgccgg atcaagagct accaactctt tttccgaagg    3120
taactggctt cagcagagcg cagataccaa atactgtcct tctagtgtag ccgtagttag    3180
gccaccactt caagaactct gtagcaccgc ctacatacct cgctctgcta atcctgttac    3240
cagtggctgc tgccagtggc gataagtcgt gtcttaccgg gttggactca agacgatagt    3300
taccggataa ggcgcagcgg tcgggctgaa cggggggttc gtgcacacag cccagcttgg    3360
agcgaacgac ctacaccgaa ctgagatacc tacagcgtga gcattgagaa agcgccacgc    3420
ttcccgaagg gagaaaggcg gacaggtatc cggtaagcgg cagggtcgga acaggagagc    3480
gcacgaggga gcttccaggg ggaaacgcct ggtatcttta tagtcctgtc gggtttcgcc    3540
acctctgact tgagcgtcga tttttgtgat gctcgtcagg gggcggagc ctatggaaaa    3600 acgccagcaa cgcggccttt ttacggttcc tggccttttg ctggcctttt gctcacatgt    3660
tctttcctgc gttatcccct gattctgtgg ataaccgtat taccgccttt gagtgagctg    3720
ataccgctcg ccgcagccga acgaccgagc gcagcgagtc agtgagcgag gaagcggaag    3780
agcgcccaat acgcaaaccg cctctccccg cgcgttggcc gattcattaa tgcaggttga    3840
tcagatctcg atcccgcgaa attaatacga ctcactatag ggagaccaca cggtttccc    3900 tctagaaata attttgttta actttaagaa ggagatatac catggaaaa gcctgaactc    3960
```

```
accgcgacgt ctgtcgagaa gtttctgatc gaaaagttcg acagcgtctc cgacctgatg    4020
cagctctcgg agggcgaaga atctcgtgct ttcagcttcg atgtaggagg gcgtggatat    4080
gtcctgcggg taaatagctg cgccgatggt ttctacaaag atcgttatgt ttatcggcac    4140
tttgcatcgg ccgcgctccc gattccgaa gtgcttgaca ttggggaatt cagcgagagc    4200
ctgacctatt gcatctcccg ccgtgcacag ggtgtcacgt tgcaagacct gcctgaaacc    4260
gaactgcccg ctgttctgca gccggtcgcg gaggctatgg atgcgatcgc tgcggccgat    4320
cttagccaga cgagcgggtt cggcccattc ggaccgcaag gaatcggtca atacactaca    4380
tggcgtgatt tcatatgcgc gattgctgat ccccatgtgt atcactggca aactgtgatg    4440
gacgacaccg tcagtgcgtc cgtcgcgcag gctctcgatg agctgatgct ttgggccgag    4500
gactgccccg aagtccggca cctcgtgcac gcggatttcg gctccaacaa tgtcctgacg    4560
gacaatggcc gcataacagc ggtcattgac tggagcgagg cgatgttcgg ggattcccaa    4620
tacgaggtcg ccaacatctt cttctggagg ccgtggttgg cttgtatgga gcagcagacg    4680
cgctacttcg agcggaggca tccggagctt gcaggatcgc cgcggctccg ggcgtatatg    4740
ctccgcattg gtcttgacca actctatcag agcttggttg acggcaattt cgatgatgca    4800
gcttgggcgc agggtcgatg cgacgcaatc gtccgatccg gagccgggac tgtcgggcgt    4860
acacaaatcg cccgcagaag cgcggccgtc tggaccgatg gctgtgtaga agtactcgcc    4920
gatagtggaa accgacgccc cagcactcgt ccgagggcaa aggaatagtg aggtacagct    4980
tggatcgatc cggctgctaa caaagcccga aggaagctg agttggctgc tgccaccgct    5040
gagcaataac tagcataacc ccttggggcc tctaaacggg tcttgagggg ttttttgctg    5100
aaaggaggaa ctatatccgg atgatcgggc gcgccgtcga cggatccgta cgcaaaggca    5160
aagatttaaa ctcgaaaaca ttacaaaagt ctcaaaacag aggcaaggcc atgcacaaag    5220
cacactctaa gtgcttccat tgcctactaa gtagggtacg tacacgatca ccattcacca    5280
gtgatgatct ttattaatat acaacacact cagagacagc ttatgttata gctagctagc    5340
ataaactatc acatcatgtg ttagtacgac aagtgacaac attgctttta acttcgcggc    5400
cttggatcct ctagaccgga tataatgagc cgtaaacaaa gatgattaag tagtaattaa    5460
tacgtactag taaaagtggc aaaagataac gagaaagaac caatttcttt gcattcggcc    5520
ttagcggaag gcatatataa gctttgatta tttatttag tgtaatgatt tcgtacaacc    5580
aaagcattta tttagtactc tcacacttgt gtcgcggccg cgaattcact agtgattcct    5640
tatagagcct tccccgcggg ttgcttctcc gccatccggg cgaacaccgc cagatagcgc    5700
agcaggatga ccaacccttc atgggcagc gggttccgat acggcaggtt gtgcttctgg    5760
cacagctgtt ccacctggta gctaaccgct gtcaggttgt ggcgagggag ggtcggccac    5820
aaatggtgct caatctggta attcaagcct ccgaaaaacc aatctgtgat aatccctcgc    5880
cgaatgttca tggtctcatg gatctggcca accgagaatc catggccatc ccagactgag    5940
tccccgatct tctccagtgg gtagtggttc atgaacacca cgatcgcaat gccgaagccg    6000
ccaaccagct ccgaaacgaa aaacaccaac agcgatgtga ggatgctggg cataaagaat    6060
aagtggaaca gggtcttcaa ggtccagtgc agggcgaggc caatggcctc cttcttatac    6120
tgagagcgat agaattggtt atctctgtcc ttcaaactgc gcacggtcaa cacgctctgg    6180
aaacaccaaa tgaaccgcaa caagatacag atgaccaaga aatagtactg ctggaactga    6240
atgagcttgc gggaaatcgg tgacgcccgt gtgacgtcat cctcagacca ggctaagagg    6300
gggaggttgt caatatcagg gtcgtgccct tgaacattgg ttgccgaatg atgtgcattg    6360
```

```
tgtctgtcct tccaccatgt cacggaaaaa ccttgcagac cattgccaaa taccagtccc    6420
acgaggttgt tccagttccg gttcttgaaa gtctggtggt ggcaaatgtc atgagaaagc    6480
cagcccatct gttgatagtg catcccaagc aacactgccc caatgaaata catctgatac    6540
tgaaccatca ggaaataacc cagcactcca aggcccagtg tggtgctgat tttgtatgag    6600
taccagaggg gggaggcatc aaacatgcca gttgcgatca actcttctcg gagcttccgg    6660
aaatcctctt gagcttcatt cactgcagcc tggggtggca actcagaact gggattgatt    6720
ttgggcatgc gcttgagctt gtcgaaggct tcttgagagt gcataaccat gaaggcatca    6780
gtggcatccc ttccttggta attctctata atttccgcac caccagggtg gaaattgacc    6840
caggcagaca catcatatgt tgttccatca attgtaaggg gaagcgcttg gcgctttgac    6900
ttcatttcaa tcgaattccc gcggccgctt gggggctat ggaagacttt cttagttagt    6960
tgtgtgaata agcaatgttg ggagaatcgg gactacttat aggataggaa taaaacagaa    7020
aagtattaag tgctaatgaa atatttagac tgataattaa aatcttcacg tatgtccact    7080
tgatataaaa acgtcaggaa taaggaagt acagtagaat ttaaaggtac tcttttata    7140 tatacccgtg ttctcttttt ggctagctag ttgcataaaa aataatctat atttttatca    7200
ttattttaaa tatcttatga gatggtaaat atttatcata attttttta ctattattta    7260 ttatttgtgt gtgtaataca tatagaagtt aattacaaat tttatttact ttttcattat    7320
tttgatatga ttcaccatta atttagtgtt attatttata atagttcatt ttaatctttt    7380
tgtatatatt atgcgtgcag tactttttc ctacatataa ctactattac attttattta    7440
tataatattt ttattaatga attttcgtga taatatgtaa tattgttcat tattatttca    7500
gattttttaa aaatatttgt gttattattt atgaaatatg taatttttt agtatttgat    7560 tttatgatga taaagtgttc taaattcaaa agaaggggga aagcgtaaac attaaaaaac    7620
gtcatcaaac aaaaacaaaa tcttgttaat aaagataaaa ctgtttgttt tgatcactgt    7680
tatttcgtaa tataaaaaca ttatttatat ttatattgtt gacaaccaaa tttgcctatc    7740
aaatctaacc aatataatgc atgcgtggca ggtaatgtac taccatgaac ttaagtcatg    7800
acataataaa ccgtgaatct gaccaatgca tgtacctanc taaattgtat ttgtgacacg    7860
aagcaaatga ttcaattcac aatggagatg ggaaacaaat aatgaagaac ccagaactaa    7920
gaaagctttt ctgaaaaata aaataaaggc aatgtcaaaa gtatactgca tcatcagtcc    7980
agaaagcaca tgatattttt ttatcagtat caatgcagct agttttattt tacaatatcg    8040
atatagctag tttaaatata ttgcagctag atttataaat atttgtgtta ttatttatca    8100
tttgtgtaat cctgttttta gtattttagt ttatatatga tgataatgta ttccaaattt    8160
aaaagaaggg aaataaattt aaacaagaaa aaaagtcatc aaacaaaaaa caaatgaaag    8220
ggtggaaaga tgttaccatg taatgtgaat gttacagtat ttctttatt atagagttaa    8280 caaattaact aatatgattt tgttaataat gataaaatat tttttttatt attatttcat    8340
aatataaaaa tagtttactt aatataaaaa aaattctatc gttcacaaca aagttggcca    8400
cctaatttaa ccatgcatgt acccatggac catattaggt aaccatcaaa cctgatgaag    8460
agataaagag atgaagactt aagtcataac acaaaaccat aaaaaacaaa aatacaatca    8520
accgtcaatc tgaccaatgc atgaaaaagc tgcaatagtg agtggcgaca caaagcacat    8580
gattttctta caacggagat aaaaccaaaa aaatatttca tgaacaacct agaacaaata    8640 aagctttat ataataaata tataaataaa taaaggctat ggaataatat acttcaatat    8700
```

-continued

| | |
|---|---|
| atttggatta aataaattgt tggcgggggtt gatatattta tacacaccta aagtcacttc | 8760 |
| aatctcattt tcacttaact tttatttttt ttttcttttt atttatcata aagagaatat | 8820 |
| tgataaatata ctttttaaca tattttatg acatttttta ttggtgaaaa cttattaaaa | 8880 |
| atcataaatt ttgtaagtta gatttattta aagagttcct cttcttattt taaatttttt | 8940 |
| aataaatttt taaataacta aaatttgtgt taaaaatgtt aaaaaatgtg ttattaaccc | 9000 |
| ttctcttcga ggac | 9014 |

<210> SEQ ID NO 88
<211> LENGTH: 5561
<212> TYPE: DNA
<213> ORGANISM: Artificial Sequence
<220> FEATURE:
<223> OTHER INFORMATION: Plasmid pKR767

<400> SEQUENCE: 88

| | |
|---|---|
| catggtcaat caatgagacg ccaacttctt aatctattga gacctgcagg tctagaaggg | 60 |
| cggatcccccg ggtaccgagc tcgaattcac tggccgtcgt tttacaacgt cgtgactggg | 120 |
| aaaaccctgg cgttacccaa cttaatcgcc ttgcagcaca tccccctttc gccagctggc | 180 |
| gtaatagcga agaggcccgc accgatcgcc cttcccaaca gttgcgcagc ctgaatggcg | 240 |
| aatggcgcct gatgcggtat tttctcctta cgcatctgtg cggtatttca caccgcatat | 300 |
| ggtgcactct cagtacaatc tgctctgatg ccgcatagtt aagccagccc cgacacccgc | 360 |
| caacacccgc tgacgcgccc tgacgggctt gtctgctccc ggcatccgct tacagacaag | 420 |
| ctgtgaccgt ctccgggagc tgcatgtgtc agaggttttc accgtcatca ccgaaacgcg | 480 |
| cgagacgaaa gggcctcgtg atacgcctat ttttataggt taatgtcatg ataataatgg | 540 |
| tttcttagac gtcaggtggc acttttcggg gaaatgtgcg cggaacccct atttgtttat | 600 |
| ttttctaaat acattcaaat atgtatccgc tcatgagaca ataaccctga taaatgcttc | 660 |
| aataatattg aaaaaggaag agtatgagta ttcaacattt ccgtgtcgcc cttattccct | 720 |
| tttttgcggc attttgcctt cctgtttttg ctcacccaga aacgctggtg aaagtaaaag | 780 |
| atgctgaaga tcagttgggt gcacgagtgg gttacatcga actggatctc aacagcggta | 840 |
| agatccttga gagttttcgc cccgaagaac gttttccaat gatgagcact tttaaagttc | 900 |
| tgctatgtgg cgcggtatta tcccgtattg acgccgggca agagcaactc ggtcgccgca | 960 |
| tacactattc tcagaatgac ttggttgagt actcaccagt cacagaaaag catcttacgg | 1020 |
| atggcatgac agtaagagaa ttatgcagtg ctgccataac catgagtgat aacactgcgg | 1080 |
| ccaacttact tctgacaacg atcggaggac cgaaggagct aaccgctttt ttgcacaaca | 1140 |
| tgggggatca tgtaactcgc cttgatcgtt gggaaccgga gctgaatgaa gccataccaa | 1200 |
| acgacgagcg tgacaccacg atgcctgtag caatggcaac aacgttgcgc aaactattaa | 1260 |
| ctggcgaact acttactcta gcttcccggc aacaattaat agactggatg gaggcggata | 1320 |
| aagttgcagg accacttctg cgctcggccc ttccggctgg ctggtttatt gctgataaat | 1380 |
| ctggagccgg tgagcgtggg tctcgcggta tcattgcagc actggggcca gatggtaagc | 1440 |
| cctcccgtat cgtagttatc tacacgacgg ggagtcaggc aactatggat gaacgaaata | 1500 |
| gacagatcgc tgagataggt gcctcactga ttaagcattg gtaactgtca gaccaagttt | 1560 |
| actcatatat actttagatt gatttaaaac ttcatttta atttaaaagg atctaggtga | 1620 |
| agatcctttt tgataatctc atgaccaaaa tcccttaacg tgagttttcg ttccactgag | 1680 |
| cgtcagaccc cgtagaaaag atcaaggat cttcttgaga tcctttttttt ctgcgcgtaa | 1740 |

```
tctgctgctt gcaaacaaaa aaaccaccgc taccagcggt ggtttgtttg ccggatcaag    1800
agctaccaac tctttttccg aaggtaactg gcttcagcag agcgcagata ccaaatactg    1860
tccttctagt gtagccgtag ttaggccacc acttcaagaa ctctgtagca ccgcctacat    1920
acctcgctct gctaatcctg ttaccagtgg ctgctgccag tggcgataag tcgtgtctta    1980
ccggggttgga ctcaagacga tagttaccgg ataaggcgca gcggtcgggc tgaacggggg    2040
gttcgtgcac acagcccagc ttggagcgaa cgacctacac cgaactgaga tacctacagc    2100
gtgagctatg agaaagcgcc acgcttcccg aagggagaaa ggcggacagg tatccggtaa    2160
gcggcagggt cggaacagga gagcgcacga gggagcttcc aggggaaac gcctggtatc    2220
tttatagtcc tgtcgggttt cgccacctct gacttgagcg tcgattttg tgatgctcgt    2280
cagggggcg gagcctatgg aaaaacgcca gcaacgcggc cttttacgg ttcctggcct    2340
tttgctggcc ttttgctcac atgttctttc ctgcgttatc ccctgattct gtggataacc    2400
gtattaccgc ctttgagtga gctgataccg ctcgccgcag ccgaacgacc gagcgcagcg    2460
agtcagtgag cgaggaagcg gaagagcgcc caatacgcaa accgcctctc cccgcgcgtt    2520
ggccgattca ttaatgcagc tggcacgaca ggtttcccga ctggaaagcg ggcagtgagc    2580
gcaacgcaat taatgtgagt tagctcactc attaggcacc ccaggcttta cactttatgc    2640
ttccggctcg tatgttgtgt ggaattgtga gcggataaca atttcacaca ggaaacagct    2700
atgaccatga ttacgccaag cttgcatgcc tgcaggctag cctaagtacg tactcaaaat    2760
gccaacaaat aaaaaaaaag ttgctttaat aatgccaaaa caattaata aaacacttac    2820
aacaccggat ttttttaat taaatgtgc catttaggat aaatagttaa tattttaat    2880
aattatttaa aaagccgtat ctactaaat gatttttatt tggttgaaaa tattaatatg    2940
tttaaatcaa cacaatctat caaaattaaa ctaaaaaaaa aataagtgta cgtggttaac    3000
attagtacag taatataaga ggaaaatgag aaattaagaa attgaaagcg agtctaattt    3060
ttaaattatg aacctgcata tataaaagga aagaaagaat ccaggaagaa aagaaatgaa    3120
accatgcatg gtcccctcgt catcacgagt ttctgccatt tgcaatagaa acactgaaac    3180
acctttctct ttgtcactta attgagatgc cgaagccacc tcacaccatg aacttcatga    3240
ggtgtagcac ccaaggcttc catagccatg catactgaag aatgtctcaa gctcagcacc    3300
ctacttctgt gacgtgtccc tcattcacct tcctctcttc cctataaata accacgcctc    3360
aggttctccg cttcacaact caaacattct ctccattggt ccttaaacac tcatcagtca    3420
tcaccgcggc gcatgggaa cggaccaagg aaaaaccttc acctgggaag agctggcggc    3480
ccataacacc aaggacgacc tactcttggc catccgcggc agggtgtacg atgtcacaaa    3540
gttcttgagc cgccatcctg gtggagtgga cactctcctg ctcggagctg ccgagatgt    3600
tactccggtc tttgagatgt atcacgcgtt tggggctgca gatgccatta tgaagaagta    3660
ctatgtcggt acactggtct cgaatgagct gcccatcttc ccggagccaa cggtgttcca    3720
caaaaccatc aagacgagag tcgagggcta ctttacggat cggaacattg atcccaagaa    3780
tagaccagag atctggggac gatacgctct tatctttgga tccttgatcg cttcctacta    3840
cgcgcagctc tttgtgcctt tcgttgtcga acgcacatgg cttcaggtgg tgtttgcaat    3900
catcatggga tttgcgtgcg cacaagtcgg actcaaccct cttcatgatg cgtctcactt    3960
ttcagtgacc cacaaccccca ctgtctggaa gattctggga gccacgcacg actttttcaa    4020
cggagcatcg tacctggtgt ggatgtacca acatatgctc ggccatcacc cctacaccaa    4080
```

```
cattgctgga gcagatcccg acgtgtcgac gtctgagccc gatgttcgtc gtatcaagcc    4140
caaccaaaag tggtttgtca accacatcaa ccagcacatg tttgttcctt tcctgtacgg    4200
actgctggcg ttcaaggtgc gcattcagga catcaacatt ttgtactttg tcaagaccaa    4260
tgacgctatt cgtgtcaatc ccatctcgac atggcacact gtgatgttct ggggcggcaa    4320
ggctttcttt gtctggtatc gcctgattgt tcccctgcag tatctgcccc tgggcaaggt    4380
gctgctcttg ttcacggtcg cggacatggt gtcgtcttac tggctggcgc tgaccttcca    4440
ggcgaaccac gttgttgagg aagttcagtg gccgttgcct gacgagaacg ggatcatcca    4500
aaaggactgg gcagctatgc aggtcgagac tacgcaggat tacgcacacg attcgcacct    4560
ctggaccagc atcactggca gcttgaacta ccaggctgtg caccatctgt tccccaacgt    4620
gtcgcagcac cattatcccg atattctggc catcatcaag aacacctgca gcgagtacaa    4680
ggttccatac cttgtcaagg atacgttttg gcaagcattt gcttcacatt tggagcactt    4740
gcgtgttctt ggactccgtc caaggaaga gtaggcggcc gcatttcgca ccaaatcaat    4800
gaaagtaata atgaaaagtc tgaataagaa tacttaggct tagatgcctt tgttacttgt    4860 gtaaataac ttgagtcatg tacctttggc ggaaacagaa taaataaaag gtgaaattcc    4920
aatgctctat gtataagtta gtaatactta atgtgttcta cggttgtttc aatatcatca    4980
aactctaatt gaaactttag aaccacaaat ctcaatcttt tcttaatgaa atgaaaaatc    5040
ttaattgtac catgtttatg ttaaacacct tacaattggt tggagaggag gaccaaccga    5100
tgggacaaca ttgggagaaa gagattcaat ggagatttgg ataggagaac aacattcttt    5160
ttcacttcaa tacaagatga gtgcaacact aaggatatgt atgagacttt cagaagctac    5220
gacaacatag atgagtgagg tggtgattcc tagcaagaaa gacattagag gaagccaaaa    5280
tcgaacaagg aagacatcaa gggcaagaga caggaccatc catctcagga aaaggagctt    5340
tgggatagtc cgagaagttg tacaagaaat ttttggagg gtgagtgatg cattgctggt    5400
gactttaact caatcaaaat tgagaaagaa agaaaaggga gggggctcac atgtgaatag    5460
aagggaaacg ggagaatttt acagttttga tctaatgggc atcccagcta gtggtaacat    5520
attcaccatg tttaaccttc acgtacgtct agaggatccc c                        5561
```

<210> SEQ ID NO 89
<211> LENGTH: 11889
<212> TYPE: DNA
<213> ORGANISM: Artificial Sequence
<220> FEATURE:
<223> OTHER INFORMATION: Plasmid pKR916
<220> FEATURE:
<221> NAME/KEY: misc_feature
<222> LOCATION: (7810)..(7810)
<223> OTHER INFORMATION: n is a, c, g, or t

<400> SEQUENCE: 89

```
ggagatccaa gcttttgatc catgcccttc atttgccgct tattaattaa tttggtaaca      60
gtccgtacta atcagttact tatccttccc ccatcataat taatcttggt agtctcgaat     120
gccacaacac tgactagtct cttggatcat aagaaaagc caaggaacaa agaagacaa      180 aacacaatga gagtatcctt tgcatagcaa tgtctaagtt cataaaattc aaacaaaaac     240
gcaatcacac acagtggaca tcacttatcc actagctgat caggatcgcc gcgtcaagaa     300
aaaaaaactg gaccccaaaa gccatgcaca acaacacgta ctcacaaagg tgtcaatcga     360
gcagcccaaa acattcacca actcaaccca tcatgagccc tcacatttgt tgtttctaac     420
ccaacctcaa actcgtattc tcttccgcca cctcattttt gtttatttca acacccgtca     480
```

```
aactgcatgc cacccegtgg ccaaatgtcc atgcatgtta acaagaccta tgactataaa    540
tagctgcaat ctcggcccag ttttcatca tcaagaacca gttcaatatc ctagtacacc    600
gtattaaaga atttaagata tactgcggcc gcaccatgga ggtggtgaat gaaatagtct    660
caattgggca ggaagtttta cccaaagttg attatgccca actctggagt gatgccagtc    720
actgtgaggt gctttacttg tccatcgcat ttgtcatctt gaagttcact cttggcccc   780
ttggtccaaa aggtcagtct cgtatgaagt ttgttttcac caattacaac cttctcatgt   840
ccatttattc gttgggatca ttcctctcaa tggcatatgc catgtacacc atcggtgtta   900
tgtctgacaa ctgcgagaag cttttgaca acaacgtctt caggatcacc acgcagttgt    960
tctatttgag caagttcctg gagtatattg actccttcta tttgccactg atgggcaagc   1020
ctctgacctg gttgcaattc ttccatcatt tgggggcacc gatggatatg tggctgttct   1080
ataattaccg aaatgaagct gtttggattt ttgtgctgtt gaatggtttc atccactgga   1140
tcatgtacgt ttattattgg accagattga tcaagctgaa gttccccatg ccaaaatccc   1200
tgattacatc aatgcagatc attcaattca atgttggttt ctacattgtc tggaagtaca   1260
ggaacattcc ctgttatcgc caagatggga tgaggatgtt tggctggttc ttcaattact   1320
tttatgttgg cacagtcttg tgtttgttct tgaatttcta tgtgcaaacg tatatcgtca   1380
ggaagcacaa gggagccaaa aagattcagt gagcggccgc aagtatgaac taaaatgcat   1440
gtaggtgtaa gagctcatgg agagcatgga atattgtatc cgaccatgta acagtataat   1500
aactgagctc catctcactt cttctatgaa taaacaaagg atgttatgat atattaacac   1560
tctatctatg caccttattg ttctatgata aatttcctct tattattata aatcatctga   1620
atcgtgacgg cttatggaat gcttcaaata gtacaaaaac aaatgtgtac tataagactt   1680
tctaaacaat tctaacctta gcattgtgaa cgagacataa gtgttaagaa gacataacaa   1740
ttataatgga agaagtttgt ctccatttat atattatata ttaccactt atgtattata   1800
ttaggatgtt aaggagacat aacaattata agagagaag tttgtatcca tttatatatt   1860
atatactacc catttatata ttatacttat ccactattt aatgtcttta taaggtttga   1920
tccatgatat ttctaatatt ttagttgata tgtatatgaa agggtactat ttgaactctc   1980
ttactctgta taaaggttgg atcatcctta aagtgggtct atttaatttt attgcttctt   2040
acagataaaa aaaaaattat gagttggttt gataaaatat tgaaggattt aaaataataa   2100
taaataacat ataatatatg tatataaatt tattataata taacatttat ctataaaaaa   2160
gtaaatattg tcataaatct atacaatcgt ttagccttgc tggacgaatc tcaattattt   2220
aaacgagagt aaacatattt gactttttgg ttatttaaca aattattatt taacactata   2280
tgaaattttt ttttttatca gcaaagaata aaattaaatt aagaaggaca atggtgtccc   2340
aatccttata caaccaactt ccacaagaaa gtcaagtcag agacaacaaa aaacaagca   2400
aaggaaattt tttaatttga gttgtcttgt ttgctgcata atttatgcag taaaacacta   2460
cacataaccc ttttagcagt agagcaatgg ttgaccgtgt gcttagcttc ttttattta    2520
ttttttttatc agcaaagaat aaataaaata aaatgagaca cttcagggat gtttcaacaa   2580
gcttggcgcg ccgttctata gtgtcaccta atcgtatgt gtatgataca taaggttatg    2640
tattaattgt agccgcgttc taacgacaat atgtccatat ggtgcactct cagtacaatc   2700
tgctctgatg ccgcatagtt aagccagccc cgacacccgc caacacccgc tgacgcgccc   2760
tgacgggctt gtctgctccc ggcatccgct tacagacaag ctgtgaccgt ctccgggagc   2820
```

```
tgcatgtgtc agaggttttc accgtcatca ccgaaacgcg cgagacgaaa gggcctcgtg    2880
atacgcctat ttttataggt taatgtcatg accaaaatcc cttaacgtga gttttcgttc    2940
cactgagcgt cagacccgt agaaaagatc aaaggatctt cttgagatcc ttttttttctg    3000 cgcgtaatct gctgcttgca acaaaaaaaa ccaccgctac cagcggtggt ttgtttgccg    3060
gatcaagagc taccaactct tttccgaag gtaactggct tcagcagagc gcagatacca    3120
aatactgtcc ttctagtgta gccgtagtta ggccaccact tcaagaactc tgtagcaccg    3180
cctacatacc tcgctctgct aatcctgtta ccagtggctg ctgccagtgg cgataagtcg    3240
tgtcttaccg ggttggactc aagacgatag ttaccggata aggcgcagcg gtcgggctga    3300
acggggggtt cgtgcacaca gcccagcttg gagcgaacga cctacaccga actgagatac    3360
ctacagcgtg agcattgaga aagcgccacg cttcccgaag ggagaaaggc ggacaggtat    3420
ccggtaagcg gcagggtcgg aacaggagag cgcacgaggg agcttccagg gggaaacgcc    3480
tggtatcttt atagtcctgt cgggtttcgc cacctctgac ttgagcgtcg attttttgtga    3540 tgctcgtcag gggggcggag cctatggaaa aacgccagca acgcggcctt tttacggttc    3600
ctggcctttt gctggccttt tgctcacatg ttctttcctg cgttatcccc tgattctgtg    3660
gataaccgta ttaccgcctt tgagtgagct gataccgctc gccgcagccg aacgaccgag    3720
cgcagcgagt cagtgagcga ggaagcggaa gagcgcccaa tacgcaaacc gcctctcccc    3780
gcgcgttggc cgattcatta atgcaggttg atcagatctc gatcccgcga aattaatacg    3840
actcactata gggagaccac aacggtttcc ctctagaaat aattttgttt aactttaaga    3900
aggagatata cccatggaaa agcctgaact caccgcgacg tctgtcgaga gtttctgat    3960 cgaaaagttc gacagcgtct ccgacctgat gcagctctcg gagggcgaag aatctcgtgc    4020
tttcagcttc gatgtaggag ggcgtggata tgtcctgcgg gtaaatagct gcgccgatgg    4080
tttctacaaa gatcgttatg tttatcggca ctttgcatcg gccgcgctcc cgattccgga    4140
agtgcttgac attggggaat tcagcgagag cctgacctat tgcatctccc gccgtgcaca    4200
gggtgtcacg ttgcaagacc tgcctgaaac cgaactgccc gctgttctgc agccggtcgc    4260
ggaggctatg gatgcgatcg ctgcggccga tcttagccag acgagcgggt tcggcccatt    4320
cggaccgcaa ggaatcggtc aatacactac atggcgtgat ttcatatgcg cgattgctga    4380
tccccatgtg tatcactggc aaactgtgat ggacgacacc gtcagtgcgt ccgtcgcgca    4440
ggctctcgat gagctgatgc tttgggccga ggactgcccc gaagtccggc acctcgtgca    4500
cgcggatttc ggctccaaca atgtcctgac ggacaatggc cgcataacag cggtcattga    4560
ctggagcgag gcgatgttcg ggattccca atacgaggtc gccaacatct tcttctggag    4620
gccgtggttg gcttgtatgg agcagcagac gcgctacttc gagcggaggc atccggagct    4680
tgcaggatcg ccgcggctcc gggcgtatat gctccgcatt ggtcttgacc aactctatca    4740
gagcttggtt gacggcaatt tcgatgatgc agcttgggcg cagggtcgat gcgacgcaat    4800
cgtccgatcc ggagccggga ctgtcgggcg tacacaaatc gcccgcagaa gcgcggccgt    4860
ctggaccgat ggctgtgtag aagtactcgc cgatagtgga aaccgacgcc ccagcactcg    4920
tccgagggca aaggaatagt gaggtacagc ttggatcgat ccggctgcta acaaagcccg    4980
aaaggaagct gagttggctg ctgccaccgc tgagcaataa ctagcataac cccttggggc    5040
ctctaaacgg gtcttgaggg gttttttgct gaaaggagga actatatccg gatgatcggg    5100
cgcgccgtcg acggatccgt acgcaaaggc aaagatttaa actcgaaaac attacaaaag    5160
tctcaaaaca gaggcaaggc catgcacaaa gcacactcta agtgcttcca ttgcctacta    5220
```

```
agtagggtac gtacacgatc accattcacc agtgatgatc tttattaata tacaacacac  5280
tcagagacag cttatgttat agctagctag cataaactat cacatcatgt gttagtacga  5340
caagtgacaa cattgctttt aacttcgcgg ccttggatcc tctagaccgg atataatgag  5400
ccgtaaacaa agatgattaa gtagtaatta atacgtacta gtaaaagtgg caaaagataa  5460
cgagaaagaa ccaatttctt tgcattcggc cttagcggaa ggcatatata agctttgatt  5520
attttattta gtgtaatgat ttcgtacaac caaagcattt atttagtact ctcacacttg  5580
tgtcgcggcc gcgaattcac tagtgattcc ttatagagcc ttcccgcgg gttgcttctc  5640 cgccatccgg gcgaacaccg ccagatagcg cagcaggatg accaaccctt catggggcag  5700
cgggttccga tacggcaggt tgtgcttctg gcacagctgt tccacctggt agctaaccgc  5760
tgtcaggttg tggcgaggga gggtcggcca caaatggtgc tcaatctggt aattcaagcc  5820
tccgaaaaac caatctgtga taatccctcg ccgaatgttc atggtctcat ggatctggcc  5880
aaccgagaat ccatggccat cccagactga gtccccgatc ttctccagtg ggtagtggtt  5940
catgaacacc acgatcgcaa tgccgaagcc gccaaccagc tccgaaacga aaacaccaa  6000 cagcgatgtg aggatgctgg gcataaagaa taagtggaac agggtcttca aggtccagtg  6060
cagggcgagg ccaatggcct ccttcttata ctgagagcga tagaattggt tatctctgtc  6120
cttcaaactg cgcacggtca acacgctctg gaaacaccaa atgaaccgca acaagataca  6180
gatgaccaag aaatagtact gctggaactg aatgagcttg cgggaaatcg gtgacgcccg  6240
tgtgacgtca tcctcagacc aggctaagag ggggaggttg tcaatatcag ggtcgtgccc  6300
ttgaacattg gttgccgaat gatgtgcatt gtgtctgtcc ttccaccatg tcacggaaaa  6360
accttgcaga ccattgccaa ataccagtcc cacgaggttg ttccagttcc ggttcttgaa  6420
agtctggtgg tggcaaatgt catgagaaag ccagcccatc tgttgatagt gcatcccaag  6480
caacactgcc ccaatgaaat acatctgata ctgaaccatc aggaaataac ccagcactcc  6540
aaggcccagt gtggtgctga ttttgtatga gtaccagagg ggggaggcat caaacatgcc  6600
agttgcgatc aactcttctc ggagcttccg gaaatcctct tgagcttcat tcactgcagc  6660
ctggggtggc aactcagaac tgggattgat tttgggcatg cgcttgagct tgtcgaaggc  6720
ttcttgagag tgcataacca tgaaggcatc agtggcatcc cttccttggt aattctctat  6780
aatttccgca ccaccagggt ggaaattgac ccaggcagac acatcatatg ttgttccatc  6840
aattgtaagg ggaagcgctt ggcgctttga cttcatttca atcgaattcc cgcggccgct  6900 tgggggggcta tggaagactt tcttagttag ttgtgtgaat aagcaatgtt gggagaatcg  6960
ggactactta taggatagga ataaaacaga aaagtattaa gtgctaatga aatatttaga  7020
ctgataatta aaatcttcac gtatgtccac ttgatataaa aacgtcagga ataaaggaag  7080
tacagtagaa tttaaaggta ctcttttat atatacccgt gttctctttt tggctagcta  7140
gttgcataaa aaataatcta tattttatc attattttaa atatcttatg agatggtaaa  7200
tatttatcat aattttttt actattattt attatttgtg tgtgtaatac atatagaagt  7260
taattacaaa ttttatttac tttttcatta ttttgatatg attcaccatt aatttagtgt  7320
tattatttat aatagttcat tttaatcttt ttgtatatat tatgcgtgca gtactttttt  7380
cctacatata actactatta cattttattt atataatatt tttattaatg aattttcgtg  7440
ataatatgta atattgttca ttattattc agattttta aaaatatttg tgttattatt  7500
tatgaaatat gtaattttt tagtatttga ttttatgatg ataaagtgtt ctaaattcaa  7560
```

```
aagaaggggg aaagcgtaaa cattaaaaaa cgtcatcaaa caaaaacaaa atcttgttaa      7620
taaagataaa actgtttgtt ttgatcactg ttatttcgta atataaaaac attatttata      7680
tttatattgt tgacaaccaa atttgcctat caaatctaac caatataatg catgcgtggc      7740
aggtaatgta ctaccatgaa cttaagtcat gacataataa accgtgaatc tgaccaatgc      7800
atgtacctan ctaaattgta tttgtgacac gaagcaaatg attcaattca caatggagat      7860
gggaaacaaa taatgaagaa cccagaacta agaaagcttt tctgaaaaat aaaataaagg      7920
caatgtcaaa agtatactgc atcatcagtc cagaaagcac atgatatttt tttatcagta      7980
tcaatgcagc tagttttatt ttacaatatc gatatagcta gtttaaatat attgcagcta      8040
gatttataaa tatttgtgtt attatttatc atttgtgtaa tcctgttttt agtattttag      8100
tttatatatg atgataatgt attccaaatt taaagaagg gaaataaatt taaacaagaa        8160
aaaaagtcat caaacaaaaa acaaatgaaa gggtggaaag atgttaccat gtaatgtgaa      8220
tgttacagta tttctttat tatagagtta acaaattaac taatatgatt tgttaataa        8280 tgataaaata ttttttttat tattatttca taatataaaa atagtttact taatataaaa      8340
aaaattctat cgttcacaac aaagttggcc acctaattta accatgcatg tacccatgga      8400
ccatattagg taaccatcaa acctgatgaa gagataaaga gatgaagact taagtcataa      8460
cacaaaacca taaaaacaa aaatacaatc aaccgtcaat ctgaccaatg catgaaaaag        8520
ctgcaatagt gagtggcgac acaaagcaca tgattttctt acaacggaga taaaaccaaa      8580
aaaatatttc atgaacaacc tagaacaaat aaagcttta tataataaat atataaataa        8640
ataaaggcta tggaataata tacttcaata tatttggatt aaataaattg ttggcggggt      8700
tgatatattt atacacacct aaagtcactt caatctcatt ttcacttaac tttatttt         8760 ttttctttt tatttatcat aaagagaata ttgataatat actttttaac atattttat        8820 gacatttttt attggtgaaa acttattaaa aatcataaat tttgtaagtt agatttattt      8880
aaagagttcc tcttcttatt ttaaatttt taataaattt ttaaataact aaaatttgtg       8940
ttaaaaatgt taaaaatgt gttattaacc cttctcttcg aggacgtacg agatccggcc       9000
ggccagatcc tgcaggtctc aatagattaa gaagttggcg tctcattgat tgaccatggg      9060
ggatcctcta gacgtacgtg aaggttaaac atggtgaata tgttaccact agctgggatg      9120
cccattagat caaaactgta aaattctccc gtttcccttc tattcacatg tgagccccct      9180 ccctttttctt tctttctcaa ttttgattga gttaaagtca ccagcaatgc atcactcacc     9240
ctccaaaaaa tttcttgtac aacttctcgg actatcccaa agctccttt cctgagatgg       9300 atggtcctgt ctcttgccct tgatgtcttc cttgttcgat tttggcttcc tctaatgtct      9360
ttcttgctag gaatcaccac ctcactcatc tatgttgtcg tagcttctga aagtctcata     9420
catatcctta gtgttgcact catcttgtat tgaagtgaaa aagaatgttg ttctcctatc      9480
caaatctcca ttgaatctct ttctcccaat gttgtcccat cggttggtcc tcctctccaa      9540
ccaattgtaa ggtgtttaac ataaacatgg tacaattaag attttcatt tcattaagaa       9600 aagattgaga tttgtggttc taaagtttca attagagttt gatgatattg aaacaaccgt      9660
agaacacatt aagtattact aacttataca tagagcattg gaatttcacc tttatttat       9720 tctgtttccg ccaaaggtac atgactcaag ttattttaca caagtaacaa aggcatctaa      9780
gcctaagtat tcttattcag acttttcatt attactttca ttgatttggt gcgaaatgcg      9840
gccgccacta cttccttggg acggagtcca agaacacgca agtgctccaa atgtgaagca      9900
aatgcttgcc aaaacgtatc cttgacaagg tatggaacct tgtactcgct gcaggtgttc      9960
```

```
ttgatgatgg ccagaatatc gggataatgg tgctgcgaca cgttggggaa cagatggtgc    10020
acagcctggt agttcaagct gccagtgatg ctggtccaga ggtgcgaatc gtgtgcgtaa    10080
tcctgcgtag tctcgacctg catagctgcc cagtccttt  ggatgatccc gttctcgtca    10140
ggcaacggcc actgaacttc ctcaacaacg tggttcgcct ggaaggtcag cgccagccag    10200
taagacgaca ccatgtccgc gaccgtgaac aagagcagca ccttgcccag ggcagatac     10260 tgcaggggaa caatcaggcg ataccagaca agaaagcct  tgccgcccca gaacatcaca    10320
gtgtgccatg tcgagatggg attgacacga atagcgtcat tggtcttgac aaagtacaaa    10380
atgttgatgt cctgaatgcg cacctttgaac gccagcagtc cgtacaggaa aggaacaaac   10440
atgtgctggt tgatgtggtt gacaaaccac tttttggttgg gcttgatacg acgaacatcg   10500
ggctcagacg tcgacacgtc gggatctgct ccagcaatgt tggtgtaggg gtgatggccg    10560
agcatatgtt ggtacatcca ccaccaggtac gatgctccgt tgaaaaagtc gtgcgtggct   10620
cccagaatct tccagacagt ggggttgtgg gtcactgaaa agtgagacgc atcatgaaga    10680
gggttgagtc cgacttgtgc gcacgcaaat cccatgatga ttgcaaacac cacctgaagc    10740
catgtgcgtt cgacaacgaa aggcacaaag agctgcgcgt agtaggaagc gatcaaggat    10800
ccaaagataa gagcgtatcg tccccagatc tctggtctat tcttgggatc aatgttccga    10860
tccgtaaagt agccctcgac tctcgtcttg atggttttgt ggaacaccgt tggctccggg    10920
aagatgggca gctcattcga gaccagtgta ccgacatagt acttcttcat aatggcatct    10980
gcagccccaa acgcgtgata catctcaaag accggagtaa catctcggcc agctccgagc    11040
aggagagtgt ccactccacc aggatggcgg ctcaagaact ttgtgacatc gtacaccctg    11100
ccgcggatgg ccaagagtag gtcgtccttg gtgttatggg ccgccagctc ttcccaggtg    11160 aaggttttc  cttggtccgt tcccatgcgg ccgcggtgat gactgatgag tgtttaagga    11220
ccaatggaga gaatgtttga gttgtgaagc ggagaacctg aggcgtggtt atttataggg    11280
aagagaggaa ggtgaatgag ggacacgtca cagaagtagg gtgctgagct tgagacattc    11340
ttcagtatgc atggctatgg aagccttggg tgctacacct catgaagttc atggtgtgag    11400
gtggcttcgg catctcaatt aagtgacaaa gagaaaggtg tttcagtgtt tctattgcaa    11460
atggcagaaa ctcgtgatga cgaggggacc atgcatggtt tcatttcttt tcttcctgga   11520
ttctttcttt cctttttatat atgcaggttc ataattaaa aattagactc gctttcaatt   11580
tcttaatttc tcattttcct cttatattac tgtactaatg ttaaccacgt acacttattt   11640 ttttttagt  ttaattttga tagattgtgt tgatttaaac atattaatat tttcaaccaa   11700
ataaaaatca ttttagtaga tacggctttt taaataatta ttaaaaatat taactattta   11760
tcctaaatgg cacattttaa ttaaaaaaaa tccggtgttg taagtgtttt attaatttgt   11820
tttggcatta ttaaagcaac ttttttttta tttgttggca ttttgagtac gtacttaggc   11880
tagcctgca                                                            11889
```

<210> SEQ ID NO 90
<211> LENGTH: 5661
<212> TYPE: DNA
<213> ORGANISM: Artificial Sequence
<220> FEATURE:
<223> OTHER INFORMATION: Plasmid pKR974

<400> SEQUENCE: 90

```
gtacgtctag aggatccccc atggtcaatc aatgagacgc caacttctta atctattgag       60
```

-continued

```
acctgcaggt ctagaagggc ggatccccgg gtaccgagct cgaattcact ggccgtcgtt      120
ttacaacgtc gtgactggga aaaccctggc gttacccaac ttaatcgcct tgcagcacat      180
ccccctttcg ccagctggcg taatagcgaa gaggcccgca ccgatcgccc ttcccaacag      240
ttgcgcagcc tgaatggcga atggcgcctg atgcggtatt ttctccttac gcatctgtgc      300
ggtatttcac accgcatatg gtgcactctc agtacaatct gctctgatgc cgcatagtta      360
agccagcccc gacacccgcc aacacccgct gacgcgccct gacgggcttg tctgctcccg      420
gcatccgctt acagacaagc tgtgaccgtc tccgggagct gcatgtgtca gaggttttca      480
ccgtcatcac cgaaacgcgc gagacgaaag ggcctcgtga tacgcctatt tttataggtt      540
aatgtcatga taataatggt ttcttagacg tcaggtggca cttttcgggg aaatgtgcgc      600 ggaacccta tttgtttatt tttctaaata cattcaaata tgtatccgct catgagacaa      660
taaccctgat aaatgcttca ataatattga aaaggaaga gtatgagtat tcaacatttc      720
cgtgtcgccc ttattccctt ttttgcggca ttttgcctc ctgttttgc tcacccagaa      780 acgctggtga agtaaaaga tgctgaagat cagttgggtg cacgagtggg ttacatcgaa      840
ctggatctca acagcggtaa gatccttgag agttttcgcc ccgaagaacg ttttccaatg      900
atgagcactt ttaaagttct gctatgtggc gcggtattat cccgtattga cgccgggcaa      960
gagcaactcg gtcgccgcat acactattct cagaatgact tggttgagta ctcaccagtc      1020
acagaaaagc atcttacgga tggcatgaca gtaagagaat tatgcagtgc tgccataacc      1080
atgagtgata acactgcggc caacttactt ctgacaacga tcggaggacc gaaggagcta      1140 accgctttt tgcacaacat gggggatcat gtaactcgcc ttgatcgttg ggaaccggag      1200
ctgaatgaag ccataccaaa cgacgagcgt gacaccacga tgcctgtagc aatggcaaca      1260
acgttgcgca aactattaac tggcgaacta cttactctag cttcccggca acaattaata      1320
gactggatgg aggcggataa agttgcagga ccacttctgc gctcggccct tccggctggc      1380
tggtttattg ctgataaatc tggagccggt gagcgtgggt ctcgcggtat cattgcagca      1440
ctggggccag atggtaagcc ctcccgtatc gtagttatct acacgacggg gagtcaggca      1500
actatggatg aacgaaatag acagatcgct gagataggtg cctcactgat taagcattgg      1560
taactgtcag accaagttta ctcatatata ctttagattg atttaaaact tcatttttaa      1620
tttaaaagga tctaggtgaa gatcctttt gataatctca tgaccaaaat cccttaacgt      1680
gagttttcgt tccactgagc gtcagacccc gtagaaaaga tcaaaggatc ttcttgagat      1740 ccttttttc tgcgcgtaat ctgctgcttg caaacaaaaa aaccaccgct accagcggtg      1800
gtttgtttgc cggatcaaga gctaccaact cttttccga aggtaactgg cttcagcaga      1860
gcgcagatac caaatactgt ccttctagtg tagccgtagt taggccacca cttcaagaac      1920
tctgtagcac cgcctacata cctcgctctg ctaatcctgt taccagtggc tgctgccagt      1980
ggcgataagt cgtgtcttac cgggttggac tcaagacgat agttaccgga taaggcgcag      2040
cggtcgggct gaacggggggt tcgtgcaca cagcccagct tggagcgaac gacctacacc      2100
gaactgagat acctacagcg tgagctatga gaaagcgcca cgcttcccga agggagaaag      2160
gcggacaggt atccggtaag cggcagggtc ggaacaggag agcgcacgag ggagcttcca      2220
gggggaaacg cctggtatct ttatagtcct gtcgggtttc gccacctctg acttgagcgt      2280
cgatttttgt gatgctcgtc aggggggcgg agcctatgga aaaacgccag caacgcggcc      2340 ttttacggt tcctggcctt ttgctggcct tttgctcaca tgttctttcc tgcgttatcc      2400
cctgattctg tggataaccg tattaccgcc tttgagtgag ctgataccgc tcgccgcagc      2460
```

```
cgaacgaccg agcgcagcga gtcagtgagc gaggaagcgg aagagcgccc aatacgcaaa    2520
ccgcctctcc ccgcgcgttg gccgattcat taatgcagct ggcacgacag gtttcccgac    2580
tggaaagcgg gcagtgagcg caacgcaatt aatgtgagtt agctcactca ttaggcaccc    2640
caggctttac actttatgct tccggctcgt atgttgtgtg gaattgtgag cggataacaa    2700
tttcacacag gaaacagcta tgaccatgat tacgccaagc ttgcatgcct gcaggctagc    2760
ctaagtacgt actcaaaatg ccaacaaata aaaaaaagt tgctttaata atgccaaaac    2820
aaattaataa aacacttaca acaccggatt tttttaatt aaaatgtgcc atttaggata    2880
aatagttaat attttaata attatttaaa agccgtatc tactaaaatg attttattt     2940 ggttgaaaat attaatatgt ttaaatcaac acaatctatc aaaattaaac taaaaaaaaa    3000
ataagtgtac gtggttaaca ttagtacagt aatataagag gaaaatgaga aattaagaaa    3060
ttgaaagcga gtctaatttt taaattatga acctgcatat ataaaaggaa agaaagaatc    3120
caggaagaaa agaaatgaaa ccatgcatgg tcccctcgtc atcacgagtt tctgccattt    3180
gcaatagaaa cactgaaaca cctttctctt tgtcacttaa ttgagatgcc gaagccacct    3240
cacaccatga acttcatgag gtgtagcacc caaggcttcc atagccatgc atactgaaga    3300
atgtctcaag ctcagcaccc tacttctgtg acgtgtccct cattcacctt cctctcttcc    3360
ctataaataa ccacgcctca ggttctccgc ttcacaactc aaacattctc tccattggtc    3420
cttaaacact catcagtcat caccgcggcc gccaattcat ggccccgcag acggagctcc    3480
gccagcgcca cgccgccgtc gccgagacgc cggtggccgg caagaaggcc tttacatggc    3540
aggaggtcgc gcagcacaac acggcggcct cggcctggat cattatccgc ggcaaggtct    3600
acgacgtgac cgagtgggcc aacaagcacc ccggcggccg cgagatggtg ctgctgcacg    3660
ccggtcgcga ggccaccgac acgttcgact cgtaccaccc gttcagcgac aaggccgagt    3720
cgatcttgaa caagtatgag attggcacgt tcacgggccc gtccgagttt ccgaccttca    3780
agccggacac gggcttctac aaggagtgcc gcaagcgcgt tggcgagtac ttcaagaaga    3840
acaacctcca tccgcaggac ggcttcccgg gcctctggcg catgatggtc gtgtttgcgg    3900
tcgccggcct cgccttgtac ggcatgcact tttcgactat ctttgcgctg cagctcgcgg    3960
ccgcggcgct cttttggcgtc tgccaggcgc tgccgctgct ccacgtcatg cacgactcgt    4020
cgcacgcgtc gtacaccaac atgccgttct tccattacgt cgtcggccgc tttgccatgg    4080
actggtttgc cggcggctcg atggtgtcat ggctcaacca gcacgtcgtg gccaccaca    4140 tctacacgaa cgtcgcgggc tcggacccgg atcttccggt caacatggac ggcgacatcc    4200
gccgcatcgt gaaccgccag gtgttccagc ccatgtacgc attccagcac atctaccttc    4260
cgccgctcta tggcgtgctt ggcctcaagt tccgcatcca ggacttcacc gacacgttcg    4320
gctcgcacac gaacggcccg atccgcgtca cccgcacgc gctctcgacg tggatggcca    4380
tgatcagctc caagtcgttc tgggccttct accgcgtgta ccttccgctt gccgtgctcc    4440
agatgcccat caagacgtac cttgcgatct tcttcctcgc cgagtttgtc acgggctggt    4500
acctcgcgtt caacttccaa gtaagccatg tctcgaccga gtgcggctac ccatgcggcg    4560
acgaggccaa gatggcgctc caggacgagt gggcagtctc gcaggtcaag acgtcggtcg    4620
actacgccca tggctcgtgg atgacgacgt tccttgccgg cgcgctcaac taccaggtcg    4680
tgcaccactt gttccccagc gtgtcgcagt accactaccc ggcgatcgcg cccatcatcg    4740
tcgacgtctg caaggagtac aacatcaagt acgccatctt gccggacttt acggcggcgt    4800
```

```
tcgttgccca cttgaagcac ctccgcaaca tgggccagca gggcatcgcc gccacgatcc    4860
acatgggcta actcgagctc agctagatcg cggccgcatt tcgcaccaaa tcaatgaaag    4920
taataatgaa aagtctgaat aagaatactt aggcttagat gcctttgtta cttgtgtaaa    4980
ataacttgag tcatgtacct tggcggaaaa cagaataaaa aaaggtgaaa attccaatgc    5040
tctatgtata agttagtaat acttaatgtg ttctacggtt gtttcaatat catcaaactc    5100
taattgaaac tttagaacca caaatctcaa tcttttctta tgaaatgaaa aatcttaat     5160 tgtaccatgt ttatgttaaa caccttacaa ttaattggtt ggagaggagg accaaccgat    5220
gggacaacat tgggagaaag agattcaatg gagatttgga taggagaaca acattctttt    5280
tcacttcaat acaagatgag tgcaacacta aggatatgta tgagactttc agaagctacg    5340
acaacataga tgagtgaggt ggtgattcct agcaagaaag acattagagg aagccaaaat    5400
cgaacaagga agacatcaag gcaagagac  aggaccatcc atctcaggaa aaggagcttt    5460
gggatagtcc gagaagttgt acaagaaatt ttttggaggg tgagtgatgc attgctggtg    5520
actttaactc aatcaaaatt gagaaagaaa gaaaagggag gggctcaca tgtgaataga    5580 agggaaacgg gagaatttta cagttttgat ctaatgggca tcccagctag tggtaacata    5640
ttcaccatgt ttaaccttca c                                              5661

<210> SEQ ID NO 91
<211> LENGTH: 5578
<212> TYPE: DNA
<213> ORGANISM: Artificial Sequence
<220> FEATURE:
<223> OTHER INFORMATION: Plasmid pKR1032

<400> SEQUENCE: 91
ggccgcattt cgcaccaaat caatgaaagt aataatgaaa agtctgaata agaatactta      60
ggcttagatg cctttgttac ttgtgtaaaa taacttgagt catgtacctt ggcggaaaac     120
agaataaata aaaggtgaaa ttccaatgct ctatgtataa gttagtaata cttaatgtgt     180
tctacggttg tttcaatatc atcaaactct aattgaaact ttagaaccac aaatctcaat     240
cttttcttaa tgaaatgaaa aatcttaatt gtaccatgtt tatgttaaac accttacaat     300
taattggttg agaggagga ccaaccgatg gacaacatt gggagaaaga gattcaatgg      360
agatttggat aggagaacaa cattcttttt cacttcaata caagatgagt gcaacactaa     420
ggatatgtat gagactttca gaagctacga acatagat gagtgaggtg gtgattccta      480
gcaagaaaga cattagagga agccaaaatc gaacaaggaa gacatcaagg caagagaca      540 ggaccatcca tctcaggaaa aggagctttg ggatagtccg agaagttgta caagaaattt     600 tttggaggt gagtgatgca ttgctggtga ctttaactca atcaaaattg agaaagaaag      660
aaaagggagg gggctcacat gtgaatagaa gggaaacggg agaattttac agttttgatc     720
taatgggcat cccagctagt ggtaacatat tcaccatgtt taaccttcac gtacgtctag     780
aggatccccc atggtcaatc aatgagacgc aacttctta atctattgag acctgcaggt      840
ctagaagggc ggatccccgg gtaccgagct cgaattcact ggccgtcgtt ttacaacgtc     900
gtgactggga aaaccctggc gttacccaac ttaatcgcct tgcagcacat ccccctttcg     960
ccagctggcg taatagcgaa gaggcccgca ccgatcgccc ttcccaacag ttgcgcagcc    1020
tgaatggcga atggcgcctg atgcggtatt ttctccttac gcatctgtgc ggtatttcac    1080
accgcatatg gtgcactctc agtacaatct gctctgatgc cgcatagtta agccagcccc    1140
gacacccgcc aacacccgct gacgcgccct gacgggcttg tctgctcccg gcatccgctt    1200
```

```
acagacaagc tgtgaccgtc tccgggagct gcatgtgtca gaggttttca ccgtcatcac    1260
cgaaacgcgc gagacgaaag ggcctcgtga tacgcctatt tttataggtt aatgtcatga    1320
taataatggt ttcttagacg tcaggtggca cttttcgggg aaatgtgcgc ggaaccccta    1380
tttgtttatt tttctaaata cattcaaata tgtatccgct catgagacaa taaccctgat    1440
aaatgcttca ataatattga aaaggaaga gtatgagtat tcaacatttc cgtgtcgccc    1500
ttattccctt ttttgcggca ttttgccttc ctgttttttgc tcacccagaa acgctggtga    1560
aagtaaaaga tgctgaagat cagttgggtg cacgagtggg ttacatcgaa ctggatctca    1620
acagcggtaa gatccttgag agttttcgcc ccgaagaacg ttttccaatg atgagcactt    1680
ttaaagttct gctatgtggc gcggtattat cccgtattga cgccgggcaa gagcaactcg    1740
gtcgccgcat acactattct cagaatgact tggttgagta ctcaccagtc acagaaaagc    1800
atcttacgga tggcatgaca gtaagagaat tatgcagtgc tgccataacc atgagtgata    1860
acactgcggc caacttactt ctgacaacga tcggaggacc gaaggagcta accgcttttt    1920
tgcacaacat gggggatcat gtaactcgcc ttgatcgttg ggaaccggag ctgaatgaag    1980
ccataccaaa cgacgagcgt gacaccacga tgcctgtagc aatggcaaca acgttgcgca    2040
aactattaac tggcgaacta cttactctag cttcccggca acaattaata gactggatgg    2100
aggcggataa agttgcagga ccacttctgc gctcggccct tccggctggc tggtttattg    2160
ctgataaatc tggagccggt gagcgtgggt ctcgcggtat cattgcagca ctggggccag    2220
atggtaagcc ctcccgtatc gtagttatct acacgacggg gagtcaggca actatggatg    2280
aacgaaatag acagatcgct gagataggtg cctcactgat taagcattgg taactgtcag    2340
accaagttta ctcatatata ctttagattg atttaaaact tcatttttaa tttaaaagga    2400
tctaggtgaa gatccttttt gataatctca tgaccaaaat cccttaacgt gagttttcgt    2460
tccactgagc gtcagacccc gtagaaaaga tcaaaggatc ttcttgagat cctttttttc    2520
tgcgcgtaat ctgctgcttg caaacaaaaa aaccaccgct accagcggtg gtttgtttgc    2580
cggatcaaga gctaccaact ctttttccga aggtaactgg cttcagcaga gcgcagatac    2640
caaatactgt ccttctagtg tagccgtagt taggccacca cttcaagaac tctgtagcac    2700
cgcctacata cctcgctctg ctaatcctgt taccagtggc tgctgccagt ggcgataagt    2760
cgtgtcttac cgggttggac tcaagacgat agttaccgga taaggcgcag cggtcgggct    2820 gaacggggggg ttcgtgcaca cagcccagct tggagcgaac gacctacacc gaactgagat    2880
acctacagcg tgagctatga gaaagcgcca cgcttcccga agggagaaag gcggacaggt    2940
atccggtaag cggcagggtc ggaacaggag agcgcacgag ggagcttcca ggggggaaacg    3000 cctggtatct ttatagtcct gtcgggtttc gccacctctg acttgagcgt cgatttttgt    3060
gatgctcgtc agggggggcgg agcctatgga aaaacgccag caacgcggcc ttttttacggt    3120 tcctggcctt ttgctggcct tttgctcaca tgttctttcc tgcgttatcc cctgattctg    3180
tggataaccg tattaccgcc tttgagtgag ctgataccgc tcgccgcagc cgaacgaccg    3240
agcgcagcga gtcagtgagc gaggaagcgg aagagcgccc aatacgcaaa ccgcctctcc    3300
ccgcgcgttg gccgattcat taatgcagct ggcacgacag gtttcccgac tggaaagcgg    3360
gcagtgagcg caacgcaatt aatgtgagtt agctcactca ttaggcaccc caggctttac    3420
actttatgct tccggctcgt atgttgtgtg gaattgtgag cggataacaa tttcacacag    3480
gaaacagcta tgaccatgat tacgccaagc ttgcatgcct gcaggctagc ctaagtacgt    3540
```

```
actcaaaatg ccaacaaata aaaaaaaagt tgctttaata atgccaaaac aaattaataa    3600
aacacttaca acaccggatt tttttttaatt aaaatgtgcc atttaggata aatagttaat    3660
atttttaata attatttaaa aagccgtatc tactaaaatg atttttattt ggttgaaaat    3720
attaatatgt ttaaatcaac acaatctatc aaaattaaac taaaaaaaaa ataagtgtac    3780
gtggttaaca ttagtacagt aatataagag gaaaatgaga aattaagaaa ttgaaagcga    3840
gtctaatttt taaattatga acctgcatat ataaaaggaa agaaagaatc caggaagaaa    3900
agaaatgaaa ccatgcatgg tccctcgtc atcacgagtt tctgccattt gcaatagaaa    3960
cactgaaaca cctttctctt tgtcacttaa ttgagatgcc gaagccacct cacaccatga    4020
acttcatgag gtgtagcacc caaggcttcc atagccatgc atactgaaga atgtctcaag    4080
ctcagcaccc tacttctgtg acgtgtccct cattcacctt cctctcttcc ctataaataa    4140
ccacgcctca ggttctccgc ttcacaactc aaacattctc tccattggtc cttaaacact    4200
catcagtcat caccgcggcc gcaaaccatg gctctcagtc ttaccacaga acagctgtta    4260
gaacgccctg atttggttgc gattgatggc atcctctacg accttgaagg gcttgccaaa    4320
gttcatccag gaggagattt gattctcgct tctggtgcct ctgatgcctc ccctctcttt    4380
tattcaatgc atccatacgt caaaccggag aattccaaat tgcttcaaca gttcgtccga    4440
gggaagcatg accgcacctc gaaggacatt gtctacacgt atgattctcc cttcgcacaa    4500
gacgttaagg ggacaatgcg cgaggtgatg aaagggagga actggtacgc aaccctggc    4560
ttctggctgc gcaccgttgg gatcatcgcc gtgacggcct tttgcgagtg gcactgggct    4620
accacgggga tggtgctgtg gggcctgttg actggattca tgcacatgca gatcggctta    4680
tccatccagc atgatgcgtc ccacgggggcc atcagcaaga agccttgggt caacgccctc    4740
ttcgcctacg gcattgacgt catcggatcg tcccggtgga tttggctgca gtcgcacatc    4800
atgcggcacc acacctacac caaccagcac ggcctcgacc tggatgcgga gtcggcagag    4860
ccgttcctgg tgttccacaa ctaccccgcc gcaaacaccg cccgaaagtg gttccaccgc    4920
ttccaagctt ggtacatgta ccttgtgctg ggggcatacg gggtatcgct ggtgtacaac    4980
ccgctctaca ttttccggat gcagcacaat gacaccatcc cagagtctgt cacggccatg    5040
cgggaaaatg gctttctgcg gcgctaccgc acacttgcat tcgtgatgcg agcttttctc    5100
atcttccgga ccgcattctt gccctggtac ctcactggga cctcattgct gatcaccatt    5160
cctctggtgc ccaccgcaac tggtgccttc ttgacgttct tcttcatttt gtcccacaat    5220
tttgatggct ccgaacggat ccccgacaag aactgcaagg ttaagagatc tgagaaggac    5280
gttgaggctg accaaattga ctggtatcgg gcgcaggtgg agacgtcctc cacatacggt    5340
ggccccatcg ccatgttctt cactggcggt ctcaatttcc agatcgagca ccacctcttt    5400
ccccggatgt cgtcttggca ctaccccttc gtccagcagg cggtccggga gtgttgcgaa    5460
cgccatggag tgcgatatgt tttctaccct accatcgtcg gcaacatcat ctccaccctg    5520
aagtacatgc ataaggtggg tgtcgtccac tgcgtgaagg acgcacagga ttcctaag     5578
```

<210> SEQ ID NO 92
<211> LENGTH: 11907
<212> TYPE: DNA
<213> ORGANISM: Artificial Sequence
<220> FEATURE:
<223> OTHER INFORMATION: Plasmid pKR1037
<220> FEATURE:
<221> NAME/KEY: misc_feature
<222> LOCATION: (7810)..(7810)
<223> OTHER INFORMATION: n is a, c, g, or t

<400> SEQUENCE: 92

```
ggagatccaa gcttttgatc catgcccttc atttgccgct tattaattaa tttggtaaca    60
gtccgtacta atcagttact tatccttccc ccatcataat taatcttggt agtctcgaat   120
gccacaacac tgactagtct cttggatcat aagaaaaagc caaggaacaa aagaagacaa   180
aacacaatga gagtatcctt tgcatagcaa tgtctaagtt cataaaattc aaacaaaaac   240
gcaatcacac acagtggaca tcacttatcc actagctgat caggatcgcc gcgtcaagaa   300
aaaaaaactg acccccaaaa gccatgcaca acaacacgta ctcacaaagg tgtcaatcga   360
gcagcccaaa acattcacca actcaaccca tcatgagccc tcacatttgt tgtttctaac   420
ccaacctcaa actcgtattc tcttccgcca cctcattttt gtttatttca acacccgtca   480
aactgcatgc caccccgtgg ccaaatgtcc atgcatgtta acaagaccta tgactataaa   540
tagctgcaat ctcggcccag ttttcatca tcaagaacca gttcaatatc ctagtacacc   600
gtattaaaga atttaagata tactgcggcc gcaccatgga ggtggtgaat gaaatagtct   660
caattgggca ggaagtttta cccaaagttg attatgccca actctggagt gatgccagtc   720
actgtgaggt gctttacttg tccatcgcat ttgtcatctt gaagttcact cttggccccc   780
ttggtccaaa aggtcagtct cgtatgaagt ttgttttcac caattacaac cttctcatgt   840
ccatttattc gttgggatca ttcctctcaa tggcatatgc catgtacacc atcggtgtta   900
tgtctgacaa ctgcgagaag gcttttgaca acaacgtctt caggatcacc acgcagttgt   960
tctatttgag caagttcctg gagtatattg actccttcta tttgccactg atgggcaagc  1020
ctctgacctg gttgcaattc ttccatcatt tgggggcacc gatggatatg tggctgttct  1080
ataattaccg aaatgaagct gtttggattt ttgtgctgtt gaatggtttc atccactgga  1140
tcatgtacgg ttattattgg accagattga tcaagctgaa gttccccatg ccaaaatccc  1200
tgattacatc aatgcagatc attcaattca atgttggttt ctacattgtc tggaagtaca  1260
ggaacattcc ctgttatcgc caagatggga tgaggatgtt tggctggttc ttcaattact  1320
tttatgttgg cacagtcttg tgtttgttct tgaatttcta tgtgcaaacg tatatcgtca  1380
ggaagcacaa gggagccaaa aagattcagt gagcggccgc aagtatgaac taaaatgcat  1440
gtaggtgtaa gagctcatgg agagcatgga atattgtatc cgaccatgta acagtataat  1500
aactgagctc catctcactt cttctatgaa taaacaaagg atgttatgat atattaacac  1560
tctatctatg caccttattg ttctatgata aatttcctct tattattata aatcatctga  1620
atcgtgacgg cttatggaat gcttcaaata gtacaaaaac aaatgtgtac tataagactt  1680
tctaaacaat tctaaccta gcattgtgaa cgagacataa gtgttaagaa gacataacaa  1740
ttataatgga agaagtttgt ctccatttat atattatata ttacccactt atgtattata  1800
ttaggatgtt aaggagacat aacaattata agagagaag tttgtatcca tttatatatt  1860
atatactacc catttatata ttatacttat ccacttattt aatgtcttta taggtttga   1920
tccatgatat ttctaatatt ttagttgata tgtatatgaa agggtactat ttgaactctc  1980
ttactctgta taaaggttgg atcatcctta aagtgggtct attaattttt attgcttctt  2040
acagataaaa aaaaattat gagttggttt gataaaatat tgaaggattt aaataataa   2100
taaataacat ataatatatg tatataaatt tattataata taacatttat ctataaaaaa  2160
gtaaatattg tcataaatct atacaatcgt ttagccttgc tggacgaatc tcaattattt  2220
aaacgagagt aaacatattt gacttttgg ttatttaaca aattattatt taacactata  2280
```

```
tgaaattttt ttttttatca gcaaagaata aaattaaatt aagaaggaca atggtgtccc     2340
aatccttata caaccaactt ccacaagaaa gtcaagtcag agacaacaaa aaaacaagca     2400
aaggaaattt tttaatttga gttgtcttgt ttgctgcata atttatgcag taaaacacta     2460
cacataaccc ttttagcagt agagcaatgg ttgaccgtgt gcttagcttc ttttattta     2520 tttttttatc agcaaagaat aaataaaata aaatgagaca cttcagggat gtttcaacaa     2580
gcttggcgcg ccgttctata gtgtcaccta atcgtatgt gtatgataca taaggttatg     2640
tattaattgt agccgcgttc taacgacaat atgtccatat ggtgcactct cagtacaatc     2700
tgctctgatg ccgcatagtt aagccagccc cgacacccgc caacacccgc tgacgcgccc     2760
tgacgggctt gtctgctccc ggcatccgct tacagacaag ctgtgaccgt ctccgggagc     2820
tgcatgtgtc agaggttttc accgtcatca ccgaaacgcg cgagacgaaa gggcctcgtg     2880
atacgcctat ttttataggt taatgtcatg accaaaatcc cttaacgtga gttttcgttc     2940
cactgagcgt cagaccccgt agaaaagatc aaaggatctt cttgagatcc ttttttctg      3000 cgcgtaatct gctgcttgca acaaaaaaa ccaccgctac cagcggtggt ttgtttgccg     3060
gatcaagagc taccaactct ttttccgaag gtaactggct tcagcagagc gcagatacca     3120
aatactgtcc ttctagtgta gccgtagtta ggccaccact tcaagaactc tgtagcaccg     3180
cctacatacc tcgctctgct aatcctgtta ccagtggctg ctgccagtgg cgataagtcg     3240
tgtcttaccg ggttggactc aagacgatag ttaccggata aggcgcagcg gtcgggctga     3300 acgggggggtt cgtgcacaca gcccagcttg gagcgaacga cctacaccga actgagatac     3360
ctacagcgtg agcattgaga aagcgccacg cttcccgaag ggagaaaggc ggacaggtat     3420
ccggtaagcg gcagggtcgg aacaggagag cgcacgaggg agcttccagg gggaaacgcc     3480
tggtatcttt atagtcctgt cgggtttcgc cacctctgac ttgagcgtcg attttttgtga     3540 tgctcgtcag ggggggcggag cctatggaaa aacgccagca acgcggcctt tttacggttc     3600
ctggcctttt gctggccttt tgctcacatg ttctttcctg cgttatcccc tgattctgtg     3660
gataaccgta ttaccgcctt tgagtgagct gataccgctc gccgcagccg aacgaccgag     3720
cgcagcgagt cagtgagcga ggaagcggaa gagcgcccaa tacgcaaacc gcctctcccc     3780
gcgcgttggc cgattcatta atgcaggttg atcagatctc gatcccgcga aattaatacg     3840
actcactata gggagaccac aacggtttcc ctctagaaat aattttgttt aactttaaga     3900
aggagatata cccatggaaa agcctgaact caccgcgacg tctgtcgaga gtttctgat      3960 cgaaaagttc gacagcgtct ccgacctgat gcagctctcg gagggcgaag aatctcgtgc     4020
tttcagcttc gatgtaggag ggcgtggata tgtcctgcgg gtaaatagct gcgccgatgg     4080
tttctacaaa gatcgttatg tttatcggca ctttgcatcg gccgcgctcc cgattccgga     4140
agtgcttgac attggggaat tcagcgagag cctgacctat tgcatctccc gccgtgcaca     4200
gggtgtcacg ttgcaagacc tgcctgaaac cgaactgccc gctgttctgc agccggtcgc     4260
ggaggctatg gatgcgatcg ctgcggccga tcttagccag acgagcgggt tcggcccatt     4320
cggaccgcaa ggaatcggtc aatacactac atggcgtgat ttcatatgcg cgattgctga     4380
tccccatgtg tatcactggc aaactgtgat ggacgacacc gtcagtgcgt ccgtcgcgca     4440
ggctctcgat gagctgatgc tttgggccga ggactgcccc gaagtccggc acctcgtgca     4500
cgcggatttc ggctccaaca atgtcctgac ggacaatggc cgcataacag cggtcattga     4560
ctggagcgag gcgatgttcg gggattccca atacgaggtc gccaacatct tcttctggag     4620
gccgtggttg gcttgtatgg agcagcagac gcgctacttc gagcggaggc atccggagct     4680
```

| | | | | | |
|---|---|---|---|---|---|
| tgcaggatcg | ccgcggctcc | gggcgtatat | gctccgcatt | ggtcttgacc | aactctatca | 4740 |
| gagcttggtt | gacggcaatt | tcgatgatgc | agcttgggcg | cagggtcgat | gcgacgcaat | 4800 |
| cgtccgatcc | ggagccggga | ctgtcgggcg | tacacaaatc | gcccgcagaa | gcgcggccgt | 4860 |
| ctggaccgat | ggctgtgtag | aagtactcgc | cgatagtgga | aaccgacgcc | ccagcactcg | 4920 |
| tccgagggca | aaggaatagt | gaggtacagc | ttggatcgat | ccggctgcta | acaaagcccg | 4980 |
| aaaggaagct | gagttggctg | ctgccaccgc | tgagcaataa | ctagcataac | cccttggggc | 5040 |
| ctctaaacgg | gtcttgaggg | gttttttgct | gaaaggagga | actatatccg | gatgatcggg | 5100 |
| cgcgccgtcg | acggatccgt | acgcaaaggc | aaagatttaa | actcgaaaac | attacaaaag | 5160 |
| tctcaaaaca | gaggcaaggc | catgcacaaa | gcacactcta | agtgcttcca | ttgcctacta | 5220 |
| agtagggtac | gtacacgatc | accattcacc | agtgatgatc | tttattaata | tacaacacac | 5280 |
| tcagagacag | cttatgttat | agctagctag | cataaactat | cacatcatgt | gttagtacga | 5340 |
| caagtgacaa | cattgctttt | aacttcgcgg | ccttggatcc | tctagaccgg | atataatgag | 5400 |
| ccgtaaacaa | agatgattaa | gtagtaatta | atacgtacta | gtaaaagtgg | caaaagataa | 5460 |
| cgagaaagaa | ccaatttctt | tgcattcggc | cttagcggaa | ggcatatata | agctttgatt | 5520 |
| attttattta | gtgtaatgat | ttcgtacaac | caaagcattt | atttagtact | ctcacacttg | 5580 |
| tgtcgcggcc | gcgaattcac | tagtgattcc | ttatagagcc | ttccccgcgg | gttgcttctc | 5640 |
| cgccatccgg | gcgaacaccg | ccagatagcg | cagcaggatg | accaacccct | catggggcag | 5700 |
| cgggttccga | tacggcaggt | tgtgcttctg | gcacagctgt | tccacctggt | agctaaccgc | 5760 |
| tgtcaggttg | tggcgaggga | gggtcggcca | caaatggtgc | tcaatctggt | aattcaagcc | 5820 |
| tccgaaaaac | caatctgtga | taatccctcg | ccgaatgttc | atggtctcat | ggatctggcc | 5880 |
| aaccgagaat | ccatggccat | cccagactga | gtccccgatc | ttctccagtg | ggtagtggtt | 5940 |
| catgaacacc | acgatcgcaa | tgccgaagcc | gccaaccagc | tccgaaacga | aaaacaccaa | 6000 |
| cagcgatgtg | aggatgctgg | gcataaagaa | taagtggaac | agggtcttca | aggtccagtg | 6060 |
| cagggcgagg | ccaatggcct | ccttcttata | ctgagagcga | tagaattggt | tatctctgtc | 6120 |
| cttcaaactg | cgcacggtca | acacgctctg | gaaacaccaa | atgaaccgca | acaagataca | 6180 |
| gatgaccaag | aaatagtact | gctggaactg | aatgagcttg | cgggaaatcg | gtgacgcccg | 6240 |
| tgtgacgtca | tcctcagacc | aggctaagag | ggggaggttg | tcaatatcag | ggtcgtgccc | 6300 |
| ttgaacattg | gttgccgaat | gatgtgcatt | gtgtctgtcc | ttccaccatg | tcacggaaaa | 6360 |
| accttgcaga | ccattgccaa | ataccagtcc | cacgaggttg | ttccagttcc | ggttcttgaa | 6420 |
| agtctggtgg | tggcaaatgt | catgagaaag | ccagcccatc | tgttgatagt | gcatcccaag | 6480 |
| caacactgcc | ccaatgaaat | acatctgata | ctgaaccatc | aggaaataac | ccagcactcc | 6540 |
| aaggcccagt | gtggtgctga | ttttgtatga | gtaccagagg | ggggaggcat | caaacatgcc | 6600 |
| agttgcgatc | aactcttctc | ggagcttccg | gaaatcctct | tgagcttcat | tcactgcagc | 6660 |
| ctggggtggc | aactcagaac | tgggattgat | tttgggcatg | cgcttgagct | tgtcgaaggc | 6720 |
| ttcttgagag | tgcataacca | tgaaggcatc | agtggcatcc | cttccttggt | aattctctat | 6780 |
| aatttccgca | ccaccagggt | ggaaattgac | ccaggcagac | acatcatatg | ttgttccatc | 6840 |
| aattgtaagg | ggaagcgctt | ggcgctttga | cttcatttca | atcgaattcc | cgcggccgct | 6900 |
| tgggggggcta | tggaagactt | tcttagttag | ttgtgtgaat | aagcaatgtt | gggagaatcg | 6960 |
| ggactactta | taggatagga | ataaaacaga | aaagtattaa | gtgctaatga | aatatttaga | 7020 |

```
ctgataatta aaatcttcac gtatgtccac ttgatataaa aacgtcagga ataaaggaag    7080
tacagtagaa tttaaaggta ctcttttat atatacccgt gttctctttt tggctagcta     7140
gttgcataaa aaataatcta tattttatc attattttaa atatcttatg agatggtaaa     7200
tatttatcat aattttttt actattattt attatttgtg tgtgtaatac atatagaagt     7260
taattacaaa ttttatttac tttttcatta ttttgatatg attcaccatt aatttagtgt    7320
tattatttat aatagttcat tttaatcttt ttgtatatat tatgcgtgca gtacttttt     7380
cctacatata actactatta cattttattt atataatatt tttattaatg aattttcgtg    7440
ataatatgta atattgttca ttattatttc agatttttta aaaatatttg tgttattatt    7500
tatgaaatat gtaatttttt tagtatttga ttttatgatg ataaagtgtt ctaaattcaa    7560
aagaaggggg aaagcgtaaa cattaaaaaa cgtcatcaaa caaaaacaaa atcttgttaa    7620
taaagataaa actgtttgtt ttgatcactg ttatttcgta atataaaaac attatttata    7680
tttatattgt tgacaaccaa atttgcctat caaatctaac caatataatg catgcgtggc    7740
aggtaatgta ctaccatgaa cttaagtcat gacataataa accgtgaatc tgaccaatgc    7800
atgtacctan ctaaattgta tttgtgacac gaagcaaatg attcaattca caatggagat    7860
gggaaacaaa taatgaagaa cccagaacta agaaagcttt tctgaaaaat aaaataaagg    7920
caatgtcaaa agtatactgc atcatcagtc cagaaagcac atgatatttt tttatcagta    7980
tcaatgcagc tagttttatt ttacaatatc gatatagcta gtttaaatat attgcagcta    8040
gatttataaa tatttgtgtt attatttatc atttgtgtaa tcctgttttt agtattttag    8100
tttatatatg atgataatgt attccaaatt taaagaagg gaaataaatt taaacaagaa     8160
aaaaagtcat caaacaaaaa acaaatgaaa gggtggaaag atgttaccat gtaatgtgaa    8220
tgttacagta tttcttttat tatagagtta acaaattaac taatatgatt ttgttaataa    8280
tgataaaata ttttttttat tattatttca taatataaaa atagtttact taatataaaa    8340
aaaattctat cgttcacaac aaagttggcc acctaattta accatgcatg tacccatgga    8400
ccatattagg taaccatcaa acctgatgaa gagataaaga gatgaagact taagtcataa    8460
cacaaaacca taaaaaacaa aaatacaatc aaccgtcaat ctgaccaatg catgaaaaag    8520
ctgcaatagt gagtggcgac acaaagcaca tgattttctt acaacggaga taaaccaaa     8580
aaaatatttc atgaacaacc tagaacaaat aaagctttta tataataaat atataaataa    8640
ataaaggcta tggaataata tacttcaata tatttggatt aaataaattg ttggcggggt    8700
tgatatattt atacacacct aaagtcactt caatctcatt ttcacttaac ttttattttt    8760
tttttctttt tatttatcat aaagagaata ttgataatat acttttaac atattttat     8820
gacatttttt attggtgaaa acttattaaa aatcataaat tttgtaagtt agatttattt    8880
aaagagttcc tcttcttatt ttaaattttt taataaattt ttaaataact aaaatttgtg    8940
ttaaaaatgt taaaaatgt gttattaacc cttctcttcg aggacgtacg agatccggcc     9000
ggccagatcc tgcaggtctc aatagattaa gaagttggcg tctcattgat tgaccatggg    9060
ggatcctcta gacgtacgtg aaggttaaac atggtgaata tgttaccact agctgggatg    9120
cccattagat caaactgta aaattctccc gtttcccttc tattcacatg tgagccccct     9180
cccttttctt tctttctcaa ttttgattga gttaaagtca ccagcaatgc atcactcacc    9240
ctccaaaaaa tttcttgtac aacttctcgg actatcccaa agctcctttt cctgagatgg    9300
atggtcctgt ctcttgccct tgatgtcttc cttgttcgat tttggcttcc tctaatgtct    9360
ttcttgctag gaatcaccac ctcactcatc tatgttgtcg tagcttctga aagtctcata    9420
```

```
catatcctta gtgttgcact catcttgtat tgaagtgaaa aagaatgttg ttctcctatc   9480
caaatctcca ttgaatctct ttctcccaat gttgtcccat cggttggtcc tcctctccaa   9540
ccaattaatt gtaaggtgtt taacataaac atggtacaat taagatttt  catttcatta   9600 agaaaagatt gagatttgtg gttctaaagt ttcaattaga gtttgatgat attgaaacaa   9660
ccgtagaaca cattaagtat tactaactta tacatagagc attggaattt cacctttat    9720 ttattctgtt tccgccaaag gtacatgact caagttattt tacacaagta acaaaggcat   9780
ctaagcctaa gtattcttat tcagactttt cattattact ttcattgatt tggtgcgaaa   9840
tgcggccgct taggaatcct gtgcgtcctt cacgcagtgg acgacaccca ccttatgcat   9900
gtacttcagg gtggagatga tgttgccgac gatggtaggg tagaaaacat atcgcactcc   9960
atggcgttcg caacactccc ggaccgcctg ctggacgaag gggtagtgcc aagacgacat  10020
ccggggaaag aggtggtgct cgatctggaa attgagaccg ccagtgaaga acatggcgat  10080
ggggccaccg tatgtggagg acgtctccac ctgcgcccga taccagtcaa tttggtcagc  10140
ctcaacgtcc ttctcagatc tcttaacctt gcagttcttg tcgggatcc  gttcggagcc  10200 atcaaaattg tgggacaaaa tgaagaagaa cgtcaagaag gcaccagttg cggtgggcac  10260
cagaggaatg gtgatcagca atgaggtccc agtgaggtac cagggcaaga atgcggtccg  10320
gaagatgaag aaagctcgca tcacgaatgc aagtgtgcgg tagcgccgca gaaagccatt  10380
ttcccgcatg gccgtgacag actctgggat ggtgtcattg tgctgcatcc ggaaaatgta  10440
gagcgggttg tacaccagcg atacccgta  tgccccagc  acaaggtaca tgtaccaagc  10500
ttggaagcgg tggaaccact ttcgggcggt gtttgcggcg gggtagttgt ggaacaccag  10560
gaacggctct gccgactccg catccaggtc gaggccgtgc tggttggtgt aggtgtggtg  10620
ccgcatgatg tgcgactgca gccaaatcca ccgggacgat ccgatgacgt caatgccgta  10680
ggcgaagagg gcgttgaccc aaggcttctt gctgatggcc ccgtgggacg catcatgctg  10740
gatggataag ccgatctgca tgtgcatgaa tccagtcaac aggccccaca gcaccatccc  10800
cgtggtagcc cagtgccact cgcaaaaggc cgtcacggcg atgatcccaa cggtgcgcag  10860
ccagaagcca ggggttgcgt accagttcct cccttcatc  acctcgcgca ttgtccgctt  10920
aacgtcttgt gcaagggag  aatcatacgt gtagacaatg tccttcgagg tgcggtcatg  10980
cttccctcgg acgaactgtt gaagcaattt ggaattctcc ggtttgacgt atggatgcat  11040
tgaataaaag agaggggagg catcagaggc accagaagcg agaatcaaat ctcctcctgg  11100
atgaactttg gcaagcccct caaggtcgta gaggatgcca tcaatcgcaa ccaaatcagg  11160
gcgttctaac agctgttctg tggtaagact gagagccatg gtttgcggcc gcggtgatga  11220
ctgatgagtg tttaaggacc aatggagaga atgtttgagt tgtgaagcgg agaacctgag  11280
gcgtggttat ttatagggaa gagaggaagg tgaatgaggg acacgtcaca gaagtagggt  11340
gctgagcttg agacattctt cagtatgcat ggctatggaa gccttgggtg ctacacctca  11400
tgaagttcat ggtgtgaggt ggcttcggca tctcaattaa gtgacaaaga gaaaggtgtt  11460
tcagtgtttc tattgcaaat ggcagaaact cgtgatgacg aggggaccat gcatggtttc  11520 atttctttc  ttcctggatt cttctcttcc ttttatatat gcaggttcat aatttaaaaa  11580
ttagactcgc tttcaatttc ttaatttctc attttcctct tatattactg tactaatgtt  11640
aaccacgtac acttattttt tttttagttt aattttgata gattgtgttg atttaaacat  11700
attaatattt tcaaccaaat aaaaatcatt ttagtagata cggcttttta aataattatt  11760
```

| | | |
|---|---|---|
| aaaaatatta actatttatc ctaaatggca cattttaatt aaaaaaaatc cggtgttgta | 11820 | |
| agtgttttat taatttgttt tggcattatt aaagcaactt tttttttatt tgttggcatt | 11880 | |
| ttgagtacgt acttaggcta gcctgca | 11907 | |

<210> SEQ ID NO 93
<211> LENGTH: 8671
<212> TYPE: DNA
<213> ORGANISM: Artificial Sequence
<220> FEATURE:
<223> OTHER INFORMATION: Plasmid pKR328

<400> SEQUENCE: 93

| | |
|---|---|
| ggatctggcc ggccggatct cgtacggatc cgtcgacggc gcgcccgatc atccggatat | 60 |
| agttcctcct ttcagcaaaa aaccccctcaa gacccgttta gaggccccaa ggggttatgc | 120 |
| tagttattgc tcagcggtgg cagcagccaa ctcagcttcc tttcgggctt tgttagcagc | 180 |
| cggatcgatc caagctgtac ctcactattc ctttgccctc ggacgagtgc tggggcgtcg | 240 |
| gtttccacta tcggcgagta cttctacaca gccatcggtc cagacggccg cgcttctgcg | 300 |
| ggcgatttgt gtacgcccga cagtcccggc tccggatcgg acgattgcgt cgcatcgacc | 360 |
| ctgcgcccaa gctgcatcat cgaaattgcc gtcaaccaag ctctgataga gttggtcaag | 420 |
| accaatgcgg agcatatacg cccggagccg cggcgatcct gcaagctccg gatgcctccg | 480 |
| ctcgaagtag cgcgtctgct gctccataca agccaaccac ggcctccaga agaagatgtt | 540 |
| ggcgacctcg tattgggaat ccccgaacat cgcctcgctc cagtcaatga ccgctgttat | 600 |
| gcggccattg tccgtcagga cattgttgga gccgaaatcc gcgtgacga ggtgccggac | 660 |
| ttcgggcag tcctcggccc aaagcatcag ctcatcgaga gcctgcgcga cggacgcact | 720 |
| gacggtgtcg tccatcacag tttgccagtg atacacatgg ggatcagcaa tcgcgcatat | 780 |
| gaaatcacgc catgtagtgt attgaccgat tccttgcggt ccgaatgggc cgaacccgct | 840 |
| cgtctggcta agatcggccg cagcgatcgc atccatagcc tccgcgaccg gctgcagaac | 900 |
| agcgggcagt tcggtttcag gcaggtcttg caacgtgaca ccctgtgcac ggcgggagat | 960 |
| gcaataggtc aggctctcgc tgaattcccc aatgtcaagc acttccggaa tcgggagcgc | 1020 |
| ggccgatgca aagtgccgat aaacataacg atctttgtag aaaccatcgg cgcagctatt | 1080 |
| tacccgcagg acatatccac gccctcctac atcgaagctg aaagcacgag attcttcgcc | 1140 |
| ctccgagagc tgcatcaggt cggagacgct gtcgaacttt tcgatcagaa acttctcgac | 1200 |
| agacgtcgcg gtgagttcag gcttttccat gggtatatct ccttcttaaa gttaaacaaa | 1260 |
| attatttcta gagggaaacc gttgtggtct ccctatagtg agtcgtatta atttcgcggg | 1320 |
| atcgagatcg atccaattcc aatcccacaa aaatctgagc ttaacagcac agttgctcct | 1380 |
| ctcagagcag aatcgggtat tcaacaccct catatcaact actacgttgt gtataacggt | 1440 |
| ccacatgccg gtatatacga tgactggggt tgtacaaagg cggcaacaaa cggcgttccc | 1500 |
| ggagttgcac acaagaaatt tgccactatt acagaggcaa gagcagcagc tgacgcgtac | 1560 |
| acaacaagtc agcaaacaga caggttgaac ttcatcccca aggagaaagc tcaactcaag | 1620 |
| cccaagagct tgctaaggc cctaacaagc ccaccaaagc aaaagcccca ctggctcacg | 1680 |
| ctaggaacca aaaggcccag cagtgatcca gccccaaaag atctccttt gccccggag | 1740 |
| attacaatgg acgatttcct ctatctttac gatctaggaa ggaagttcga aggtgaaggt | 1800 |
| gacgacacta tgttcaccac tgataatgag aaggttagcc tcttcaattt cagaaagaat | 1860 |
| gctgacccac agatggttag agaggcctac gcagcaggtc tcatcaagac gatctacccg | 1920 |

```
agtaacaatc tccaggagat caaataccct cccaagaagg ttaaagatgc agtcaaaaga   1980
ttcaggacta attgcatcaa gaacacagag aaagacatat ttctcaagat cagaagtact   2040
attccagtat ggacgattca aggcttgctt cataaaccaa ggcaagtaat agagattgga   2100
gtctctaaaa aggtagttcc tactgaatct aaggccatgc atggagtcta agattcaaat   2160
cgaggatcta acagaactcg ccgtgaagac tggcgaacag ttcatacaga gtcttttacg   2220
actcaatgac aagaagaaaa tcttcgtcaa catggtggag cacgcactc tggtctactc   2280
caaaaatgtc aaagatacag tctcagaaga ccaagggct attgagactt tcaacaaag    2340
gataatttcg ggaaacctcc tcggattcca ttgcccagct atctgtcact tcatcgaaag   2400
gacagtagaa aaggaaggtg gctcctacaa atgccatcat tgcgataaag gaaaggctat   2460
cattcaagat gcctctgccg acagtggtcc caaagatgga cccccacca cgaggagcat    2520
cgtggaaaaa gaagacgttc caaccacgtc ttcaaagcaa gtggattgat gtgacatctc   2580
cactgacgta agggatgacg cacaatccca ctatccttcg caagaccctt cctctatata   2640
aggaagttca tttcatttgg agaggacacg ctcgagctca tttctctatt acttcagcca   2700
taacaaaaga actcttttct cttcttatta aaccatgaaa aagcctgaac tcaccgcgac   2760
gtctgtcgag aagtttctga tcgaaaagtt cgacagcgtc tccgacctga tgcagctctc   2820
ggagggcgaa gaatctcgtg ctttcagctt cgatgtagga gggcgtggat atgtcctgcg   2880
ggtaaatagc tgcgccgatg gtttctacaa agatcgttat gtttatcggc actttgcatc   2940
ggccgcgctc ccgattccgg aagtgcttga cattggggaa ttcagcgaga gcctgaccta   3000
ttgcatctcc cgccgtgcac agggtgtcac gttgcaagac ctgcctgaaa ccgaactgcc   3060
cgctgttctg cagccggtcg cggaggccat ggatgcgatc gctgcggccg atcttagcca   3120
gacgagcggg ttcggcccat tcggaccgca aggaatcggt caatacacta catggcgtga   3180
tttcatatgc gcgattgctg atccccatgt gtatcactgg caaactgtga tggacgacac   3240
cgtcagtgcg tccgtcgcgc aggctctcga tgagctgatg ctttgggccg aggactgccc   3300
cgaagtccgg cacctcgtgc acgcggattt cggctccaac aatgtcctga cggacaatgg   3360
ccgcataaca gcggtcattg actggagcga ggcgatgttc ggggattccc aatacgaggt   3420
cgccaacatc ttcttctgga ggccgtggtt ggcttgtatg gagcagcaga cgcgctactt   3480
cgagcggagg catccggagc ttgcaggatc gccgcggctc cgggcgtata tgctccgcat   3540
tggtcttgac caactctatc agagcttggt tgacggcaat ttcgatgatg cagcttgggc   3600
gcagggtcga tgcgacgcaa tcgtccgatc cggagccggg actgtcgggc gtacacaaat   3660
cgcccgcaga agcgcggccg tctggaccga tggctgtgta aagtactcg ccgatagtgg    3720
aaaccgacgc cccagcactc gtccgagggc aaaggaatag tgaggtacct aaagaaggag   3780
tgcgtcgaag cagatcgttc aaacatttgg caataaagtt tcttaagatt gaatcctgtt   3840
gccggtcttg cgatgattat catataattt ctgttgaatt acgttaagca tgtaataatt   3900
aacatgtaat gcatgacgtt atttatgaga tgggttttta tgattagagt cccgcaatta   3960
tacatttaat acgcgataga aaacaaaata tagcgcgcaa actaggataa attatcgcgc   4020
gcggtgtcat ctatgttact agatcgatgt cgaatcgatc aacctgcatt aatgaatcgg   4080
ccaacgcgcg gggagaggcg gtttgcgtat tgggcgctct tccgcttcct cgctcactga   4140
ctcgctgcgc tcggtcgttc ggctgcggcg agcggtatca gctcactcaa aggcggtaat   4200
acggttatcc acagaatcag gggataaacgc aggaaagaac atgtgagcaa aaggccagca   4260
```

```
aaaggccagg aaccgtaaaa aggccgcgtt gctggcgttt ttccataggc tccgccccccc   4320 tgacgagcat cacaaaaatc gacgctcaag tcagaggtgg cgaaacccga caggactata    4380
aagataccag gcgtttcccc ctggaagctc cctcgtgcgc tctcctgttc cgaccctgcc    4440
gcttaccgga tacctgtccg cctttctccc ttcgggaagc gtggcgcttt ctcaatgctc    4500
acgctgtagg tatctcagtt cggtgtaggt cgttcgctcc aagctgggct gtgtgcacga    4560
accccccgtt cagcccgacc gctgcgcctt atccggtaac tatcgtcttg agtccaaccc    4620
ggtaagacac gacttatcgc cactggcagc agccactggt aacaggatta gcagagcgag    4680
gtatgtaggc ggtgctacag agttcttgaa gtggtggcct aactacggct acactagaag    4740
gacagtattt ggtatctgcg ctctgctgaa gccagttacc ttcggaaaaa gagttggtag    4800
ctcttgatcc ggcaaacaaa ccaccgctgg tagcggtggt ttttttgttt gcaagcagca    4860
gattacgcgc agaaaaaaag gatctcaaga agatcctttg atcttttcta cggggtctga    4920
cgctcagtgg aacgaaaact cacgttaagg gattttggtc atgacattaa cctataaaaa    4980
taggcgtatc acgaggccct ttcgtctcgc gcgtttcggt gatgacggtg aaaacctctg    5040
acacatgcag ctcccggaga cggtcacagc ttgtctgtaa gcggatgccg ggagcagaca    5100
agcccgtcag ggcgcgtcag cgggtgttgg cgggtgtcgg gctggctta actatgcggc     5160 atcagagcag attgtactga gagtgcacca tatggacata ttgtcgttag aacgcggcta    5220
caattaatac ataaccttat gtatcataca catacgattt aggtgacact atagaacggc    5280
gcgccaagct tggatctcct gcagcccggg ggatccgccc acgtacggta ccatctgcta    5340
atattttaaa tcacatgcaa gagaggaggc atggttccat tttctacctt cacattattt    5400
gagaaaaacg aacttgttct gtgttttatt tttgcccttc acattagtac aacgtggaag    5460
actcatggtt acacagaatc atacataagt acaatgcttg tccctaagaa aacaagcact    5520
cgttgtattg aacctttacg gctcatgcgg ccgcgaattc actagtgatt gaattcgcgg    5580
ccgcttagtc cgacttggcc ttggcggccg cggccgactc tttgagcgtg aagatctgcg    5640
ccgtctcggg cacagcgccg tagttgacaa agaggtgcgc ggtcttgaag aaggccgtga    5700
tgatgggctc gtcgttcctg cgcacgaggt gcgggtacgc ggccgcaaag tgcttggtgg    5760
cttcgttgag cttgtagtgc ggaatgatcg ggaacaagtg gtggacctgg tgcgtgccaa    5820
tgtggtggct caggttgtcc acgaacgcgc cgtacgagcg gtcgacgctc gagaggttgc    5880
ccttgacgta cgtccactcc gagtcgccgt accacggcgt cgcttcgtcg ttgtggtgca    5940
agaaggtcgt aatgacgagg aacgaagcaa agacaaagag cggcgcatag tagtagaggc    6000
ccatgacggc aaagccgagc gagtatgtga ggtacgcgta cgcggcgaag aaggcggccc    6060
agacgccgag cgcacgatg acggccgacg cgcggcgaag gaggagcggg tcccacgggt     6120
caaagtggct catcgtgcgc ggggcatacc cgaccttcaa gtagacaaac cacgcaccgc    6180
cgagcgtgta gacccattgg cgcacgtcct ggaggtcctt gaccgaccgg tgcgggtaaa    6240
agatctcgtc cttatcaatg ttgcccgtgt tcttgtggtg gtggcggtgc gtcacgcgcc    6300
agctctcgaa cggcgtcaaa atcgcagagt gcatgatgca gccgatgata agttgacgc     6360 tgtggtagcg cgagaaggcc gagtggccgc agtcgtggcc gaccgtgaag aagcccagca    6420
agatgacgcc ctgcacgtag atgtaggtgg cgcaaacgag cgcgtggagc agaacgttat    6480
cggcaatgaa cggcgtcgag cgcgccgcgt agagcagcgc cgccgaggcc gacgcgttga    6540
agatcgcgcg ggccgtgtag tagagcgaga ggccgaggtt cgactcaaag cacgcgttcg    6600
ggatcgagtg cttgagctcc gtgagcgtcg ggaactcgac cttcgtctta tcctcagtca    6660
```

```
tgcggccgct gaagtattgc ttcttagtta acctttcctt tctctctcag ctatgtgaat    6720
tcattttgct ttcgtcacaa tttatatagt gaaattggat ctttggagtt aacgccttca    6780
caggattatc gtgttagaac aatgcttttt catgttctaa ttagtagtac attacaaatg    6840
tgcactctat tcaataagca tcttttggca cgttaataaa tcatgtgaaa aaaaaatact    6900
actatttcaa agaaagtgtt gtaaaaagaa acggaaagag agctggcttc agttgttgag    6960
acttgtttgc tagtaaaaat ggtgtgaaga gtgattcatg gtgaggtggt ttttcgtccc    7020
tttctgtttg catgaaaaac aaatggcaag agatgacgta ggattccttc ccttaacgat    7080
tatctgtttt taatttcaaa tatacatata ggaatttatg aattactaag gttgtaaaat    7140
atgctggtca tttatttatg ctaaaatat ttttttttct cgtaaatata aaatatttta    7200
aaatttattt ttatcatatt ttttatcctt ataaaattat gtgtacaacc tatataaaaa    7260
aatatcatat ttaatattga ttatatgttt aatcaatata aaaaatcatt atcatatatt    7320
tagatttatt cgaatataca tctaaacaaa aaataacata ttttaatttt atgaagaaaa    7380
aaaaatattt tatcctttat ttatttaaga ttaattaata gttatgtatt gtggaaagac    7440
ttttacacat gcaatagata tactgaatca attagatgcc aatgctgagt tggaaatcac    7500
ttgaggaggg gaggagactt gccaatgctt ttcagtttca tttaaatgat ttagtggagg    7560
agatagagta gtgataaagg catgccccaa ttttggagtg tatatatgag tggaaataag    7620
agagggatag agagaaaaaa taagagagt aaaaataatt aatgtgaaat gatatgataa    7680
aaaaataaag aaagagataa agagaaaaat gaaatgagag atagatgaaa tagagagtag    7740
atacatgttt gtttaggttt tttttaggaa ataacacatt ttttctcat cacttattac    7800 tcactgtcaa tttcctctct ttcaatcata atgatatgat ttgtttaaca aaaatgtgaa    7860
aaaacatata aagtaaaata ttttataaa ttgataaata aaaatttaca aaatttattt    7920
cttattaaat tgaatagaaa atgaaagaaa agaaagaaa aagtatatat aaaatgatat    7980
agctttaaaa agaataaatt tttcatatca gtcttttttt aataatttag aaatatttaa    8040
gtatatagca aaaatataat gtactttaca tatgcataaa taataatttg aaaatagaac    8100
taatagaata gagaaaaaag taatataata attaactata tgaaaattta gaagggacaa    8160 tattttaat taagaatata aacaatattt cttttcatgt aatgagggac ggatgtacgg    8220
ggccagtgtt ggagtcaaag ccaaaatagt cacggggaaa ttaatgcact gcatgactat    8280
tcgaaaaaat tcactagcct tacttagatg ttagattaat agctaggggg tgcagataat    8340
tttgaaaggc atgaaaaaca ttaatttgta cattgcaagc ttttgatgac aagctttgca    8400
attgttcaca ctaccttatg ccatttataa atagagtgat tggcatatga aggaaatcat    8460
gagagtcgaa gcgaaaaaca aagcttgaga gtgtaggaaa aatacagttt ttttggtaaa    8520
aatacagtat ttgaatagga gcgaaaaata tcctttcaaa atgatccttt tctttttttt    8580 ttttttctt gttgttcttg gtcagttatt caaaggaaaa gggattgaaa taaaaacttg    8640
catgtgggat cgtacgtcga gtcgacctgc a                                  8671
```

<210> SEQ ID NO 94
<211> LENGTH: 1413
<212> TYPE: DNA
<213> ORGANISM: Saprolegnia diclina

<400> SEQUENCE: 94

```
atggccccgc agacggagct ccgccagcgc cacgccgccg tcgccgagac gccggtggcc    60
```

```
ggcaagaagg cctttacatg gcaggaggtc gcgcagcaca acacggcggc ctcggcctgg    120
atcattatcc gcggcaaggt ctacgacgtg accgagtggg ccaacaagca ccccggcggc    180
cgcgagatgg tgctgctgca cgccggtcgc gaggccaccg acacgttcga ctcgtaccac    240
ccgttcagcg acaaggccga gtcgatcttg aacaagtatg agattggcac gttcacgggc    300
ccgtccgagt ttccgacctt caagccggac acgggcttct acaaggagtg ccgcaagcgc    360
gttggcgagt acttcaagaa gaacaacctc catccgcagg acggcttccc gggcctctgg    420
cgcatgatgg tcgtgtttgc ggtcgccggc ctcgccttgt acggcatgca cttttcgact    480
atctttgcgc tgcagctcgc ggccgcggcg ctctttggcg tctgccaggc gctgccgctg    540
ctccacgtca tgcacgactc gtcgcacgcg tcgtacacca acatgccgtt cttccattac    600
gtcgtcggcc gctttgccat ggactggttt gccggcggct cgatggtgtc atggctcaac    660
cagcacgtcg tgggccacca catctacacg aacgtcgcgg gctcggaccc ggatcttccg    720
gtcaacatgg acggcgacat ccgccgcatc gtgaaccgcc aggtgttcca gcccatgtac    780
gcattccagc acatctacct tccgccgctc tatggcgtgc ttggcctcaa gttccgcatc    840
caggacttca ccgacacgtt cggctcgcac acgaacggcc cgatccgcgt caacccgcac    900
gcgctctcga cgtggatggc catgatcagc tccaagtcgt tctgggcctt ctaccgcgtg    960
taccttccgc ttgccgtgct ccagatgccc atcaagacgt accttgcgat cttcttcctc   1020
gccgagtttg tcacgggctg gtacctcgcg ttcaacttcc aagtaagcca tgtctcgacc   1080
gagtgcggct acccatgcgg cgacgaggcc aagatggcgc tccaggacga gtgggcagtc   1140
tcgcaggtca agacgtcggt cgactacgcc catggctcgt ggatgacgac gttccttgcc   1200
ggcgcgctca actaccaggt cgtgcaccac ttgttcccca gcgtgtcgca gtaccactac   1260
ccggcgatcg cgcccatcat cgtcgacgtc tgcaaggagt acaacatcaa gtacgccatc   1320
ttgccggact ttacggcggc gttcgttgcc cacttgaagc acctccgcaa catgggccag   1380
cagggcatcg ccgccacgat ccacatgggc taa                                1413
```

DELTA-5 DESATURASE AND ITS USE IN MAKING POLYUNSATURATED FATTY ACIDS

This application claims the benefit of U.S. Provisional Patent Application 60/801,172, filed May 17, 2006, the entire contents of which are herein incorporated by reference.

FIELD OF THE INVENTION

This invention is in the field of biotechnology. More specifically, this invention pertains to the identification of nucleic acid fragments encoding a delta-5 fatty acid desaturase enzyme and the use of this desaturase in making long chain polyunsaturated fatty acids (PUFAs).

BACKGROUND OF THE INVENTION

The importance of PUFAs is undisputed. For example, certain PUFAs are important biological components of healthy cells and are recognized as: "essential" fatty acids that cannot be synthesized de novo in mammals and instead must be obtained either in the diet or derived by further desaturation and elongation of linoleic acid (LA; 18:2 omega-6) or α-linolenic acid (ALA; 18:3 omega-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain omega-3 PUFAs produces cardiovascular protective effects (Dyerberg, J. et al., Amer. J. Clin. Nutr., 28:958-966 (1975); Dyerberg, J. et al., Lancet, 2(8081):117-119 (Jul. 15, 1978); Shimokawa, H., World Rev. Nutr. Diet, 88:100-108 (2001); von Schacky, C. and Dyerberg, J., World Rev. Nutr. Diet, 88:90-99 (2001)). And, numerous other studies document wide-ranging health benefits conferred by administration of omega-3 and/or omega-6 PUFAs against a variety of symptoms and diseases (e.g., asthma, psoriasis, eczema, diabetes, cancer).

A variety of different hosts including plants, algae, fungi and yeast are being investigated as means for commercial PUFA production. Genetic engineering has demonstrated that the natural abilities of some hosts (even those natively limited to LA and ALA fatty acid production) can be substantially altered to result in high-level production of various long-chain omega-3/omega-6 PUFAs. Whether this is the result of natural abilities or recombinant technology, production of arachidonic acid (ARA; 20:4 omega-6), eicosapentaenoic acid (EPA; 20:5 omega-3) and docosahexaenoic acid (DHA; 22:6 omega-3) may all require expression of a delta-5 desaturase.

Most delta-5 desaturase enzymes identified so far have the primary ability to convert dihomo-gamma-linolenic acid (DGLA; 20:3 omega-6) to ARA, with secondary activity in converting eicosatetraenoic acid (ETA; 20:4 omega-3) to EPA (where DHA is subsequently synthesized from EPA following reaction with an additional $C_{20/22}$ elongase and a delta-4 desaturase). The delta-5 desaturase has a role in both the delta-6 desaturase/delta-6 elongase pathway (which is predominantly found in algae, mosses, fungi, nematodes and humans and which is characterized by the production of gamma-linolenic acid (GLA; 18:3 omega-6) and/or stearidonic acid (STA; 18:4 omega-3)) and the delta-9 elongase/delta-8 desaturase pathway (which operates in some organisms, such as euglenoid species and which is characterized by the production of eicosadienoic acid (EDA; 20:2 omega-6) and/or eicosatrienoic acid (ETrA; 20:3 omega-3)) (FIG. 1).

Based on the role delta-5 desaturase enzymes play in the synthesis of e.g., ARA, EPA and DHA, there has been considerable effort to identify and characterize these enzymes from various sources. As such, numerous delta-5 desaturases have been disclosed in both the open literature (e.g., GenBank Accession No. AF199596, No. AF226273, No. AF320509, No. AB072976, No. AF489588, No. AJ510244, No. AF419297, No. AF07879, No. AF067654 and No. AB022097) and the patent literature (e.g., U.S. Pat. Nos. 5,972,664 and 6,075,183). Also, commonly owned, co-pending application having Provisional Application No. 60/801,119 (filed May 17, 2006) discloses amino acid and nucleic acid sequences for a delta-5 desaturase enzyme from Peridium sp. CCMP626, while commonly owned, co-pending application having Provisional Application No. 60/915,733 (BB1614) (filed May 3, 2007) discloses amino acid and nucleic acid sequences for a delta-5 desaturase enzyme from Euglena anabaena.

The instant invention concerns the identification and isolation of additional genes encoding delta-5 desaturases from Euglena gracilis that would be suitable for heterologous expression in a variety of host organisms for use in the production of omega-3/omega-6 fatty acids.

SUMMARY OF THE INVENTION

The present invention concerns an isolated polynucleotide comprising:
  (a) a nucleotide sequence encoding a polypeptide having delta-5 desaturase activity, wherein the polypeptide has at least 70%, 75%, 80%, 85%, 90%, 95%, or 100% amino acid identity, based on the Clustal W method of alignment, when compared to an amino acid sequence as set forth in SEQ ID NO:2;
  (b) a nucleotide sequence encoding a polypeptide having delta-5 desaturase activity, wherein the nucleotide sequence has at least 70%, 75%, 80%, 85%, 90%, 95%, or 100% sequence identity, based on the BLASTN method of alignment, when compared to a nucleotide sequence as set forth in SEQ ID NO:1 or SEQ ID NO:3;
  (c) a nucleotide sequence encoding a polypeptide having delta-5 desaturase activity, wherein the nucleotide sequence hybridizes under stringent conditions to a nucleotide sequence as set forth in SEQ ID NO:1 or SEQ ID NO:3; or
  (d) a complement of the nucleotide sequence of (a), (b) or (c), wherein the complement and the nucleotide sequence consist of the same number of nucleotides and are 100% complementary.

In a second embodiment, the invention concerns a recombinant DNA construct comprising any of the isolated polynucleotides of the invention operably linked to at least one regulatory sequence.

In a third embodiment, the invention concerns a cell comprising in its genome the recombinant DNA construct of the invention. Such cells can be plant cells or yeast cells.

In a fourth embodiment, the invention concerns a method for transforming a cell, comprising transforming a cell with a recombinant construct of the invention or an isolated polynucleotide of the invention and selecting those cells transformed with the recombinant construct or the isolated polynucleotide.

In a fifth embodiment, the invention concerns transgenic seed comprising in its genome the recombinant construct of the invention or a transgenic seed obtained from a plant made by a method of the invention. Also of interest is oil or by-products obtained from such transgenic seeds.

In a sixth embodiment, the invention concerns a method for making long-chain polyunsaturated fatty acids in a plant cell comprising:
(a) transforming a cell with the recombinant construct of the invention; and
(b) selecting those transformed cells that make long-chain polyunsaturated fatty acids.

In a seventh embodiment, the invention concerns a method for producing at least one polyunsaturated fatty acid in an oilseed plant cell comprising:
(a) transforming an oilseed plant cell with a first recombinant DNA construct comprising an isolated polynucleotide encoding at least one delta-5 desaturase polypeptide, operably linked to at least one regulatory sequence and at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase;
(b) regenerating an oilseed plant from the transformed cell of step (a); and
(c) selecting those seeds obtained from the plants of step (b) having an altered level of polyunsaturated fatty acids when compared to the level in seeds obtained from a nontransformed oilseed plant.

In an eighth embodiment, the invention concerns an oilseed plant comprising in its genome the recombinant construct of the invention. Suitable oilseed plants include, but are not limited to, soybean, *Brassica* species, sunflower, maize, cotton, flax and safflower.

In a ninth embodiment, the invention concerns an oilseed plant comprising:
(a) a first recombinant DNA construct comprising an isolated polynucleotide encoding at least one delta-5 desaturase polypeptide, operably linked to at least one regulatory sequence; and
(b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase.

Also of interest are transgenic seeds obtained from such oilseed plants as well as oil or by-products obtained from these transgenic seeds. A preferred by-product is lecithin.

In a tenth embodiment, the invention concerns food or feed incorporating an oil or seed of the invention or food or feed comprising an ingredient derived from the processing of the seeds.

In an eleventh embodiment, the invention concerns progeny plants obtained from obtained from a plant made by the method of the invention or an oilseed plant of the invention.

BRIEF DESCRIPTION OF THE DRAWINGS AND SEQUENCE LISTINGS

FIG. 3 shows a portion of an alignment between and among delta-5 desaturase proteins and delta-8 desaturase proteins using a Clustal W analysis (MegAlign™ program of DNAS-TAR software).

Figure 4:
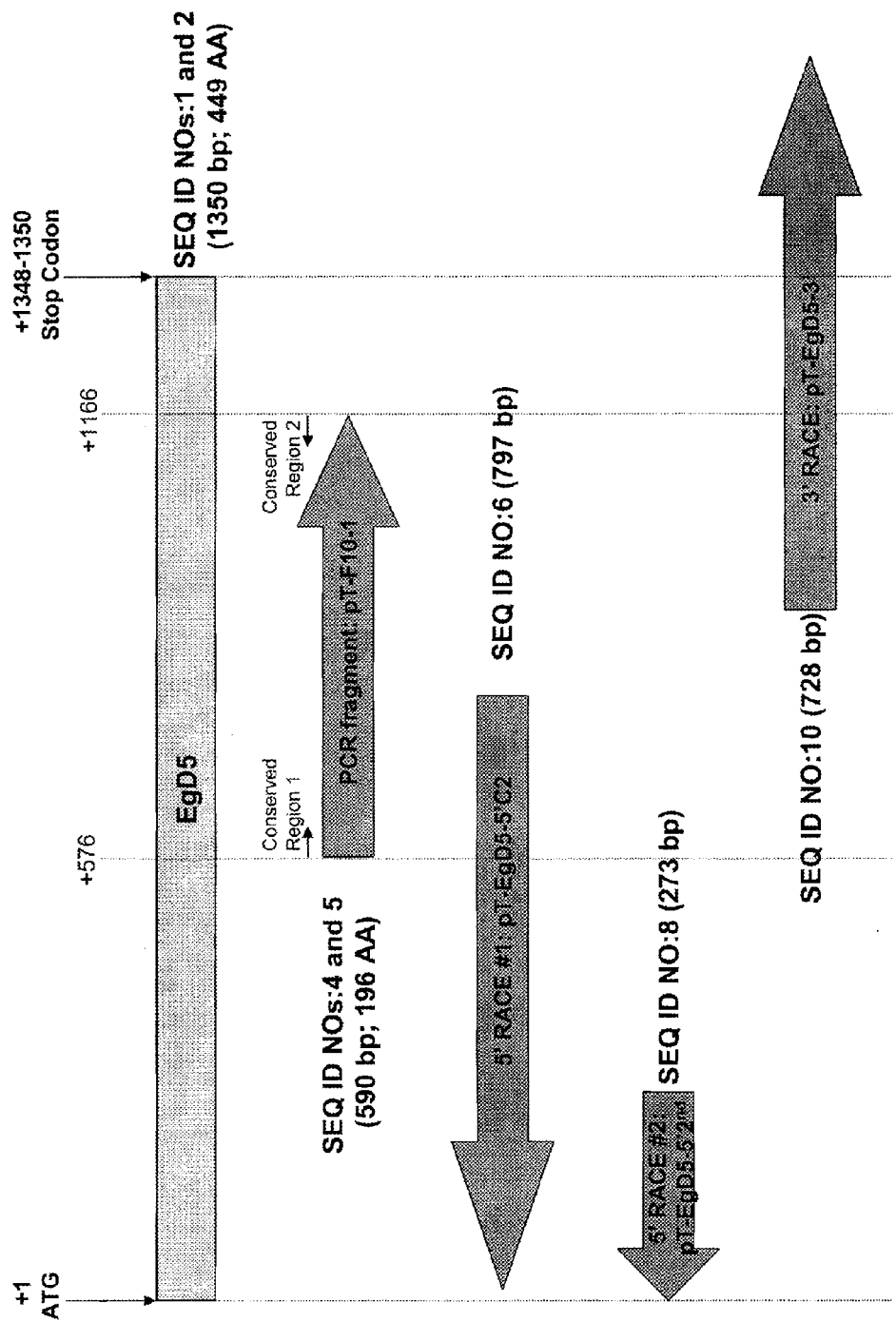

FIG. 4 graphically represents the relationship between SEQ ID NOs:1, 2, 4, 5, 6, 8 and 10, each of which relates to the *Euglena gracilis* delta-5 desaturase.

Figure 5:
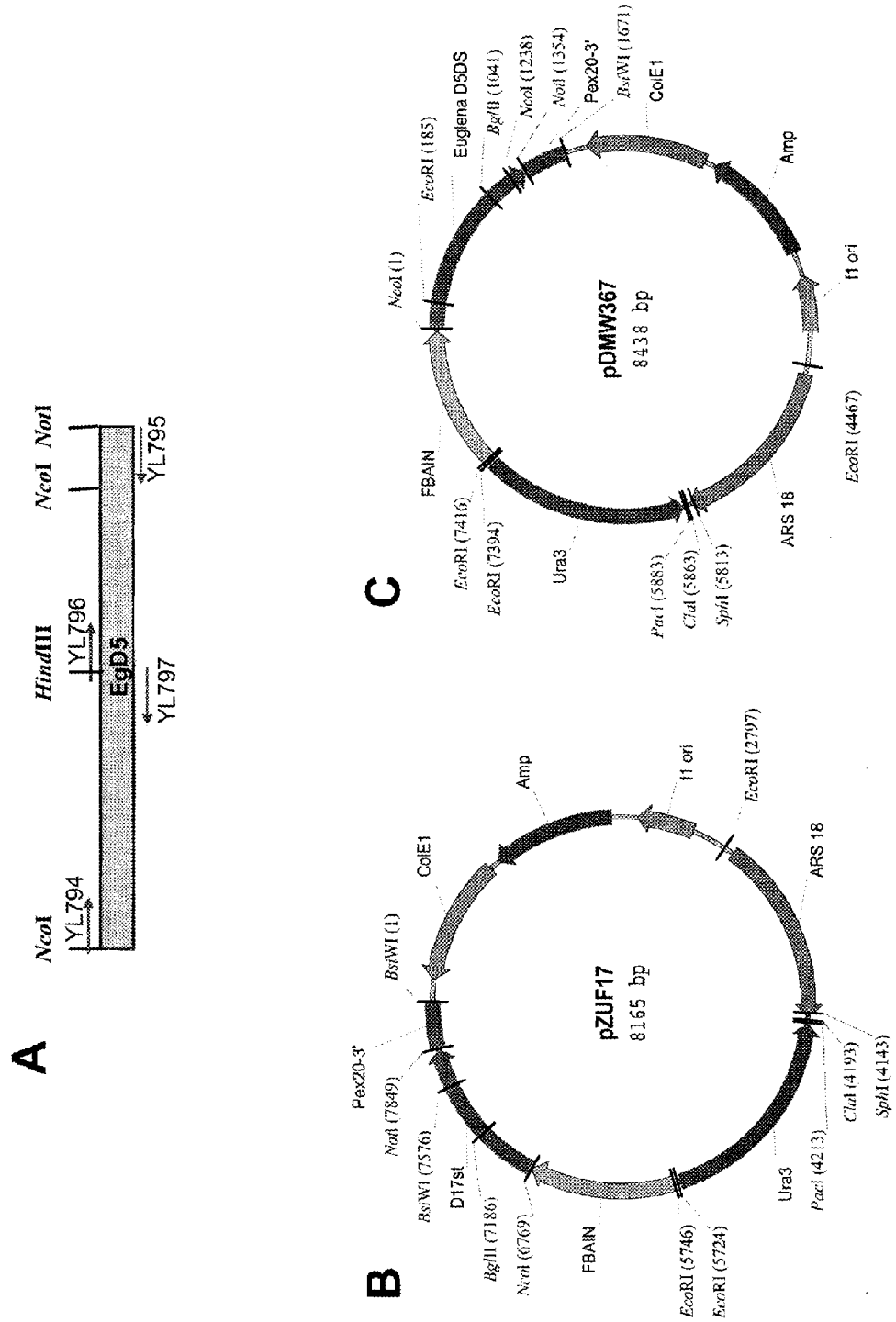

FIG. 5A illustrates the cloning strategy utilized for amplification of the *Euglena gracilis* delta-5 desaturase gene (EgD5). FIG. 5B is a plasmid map of pZUF17, while FIG. 5C is a plasmid map of pDMW367.

Figure 6:
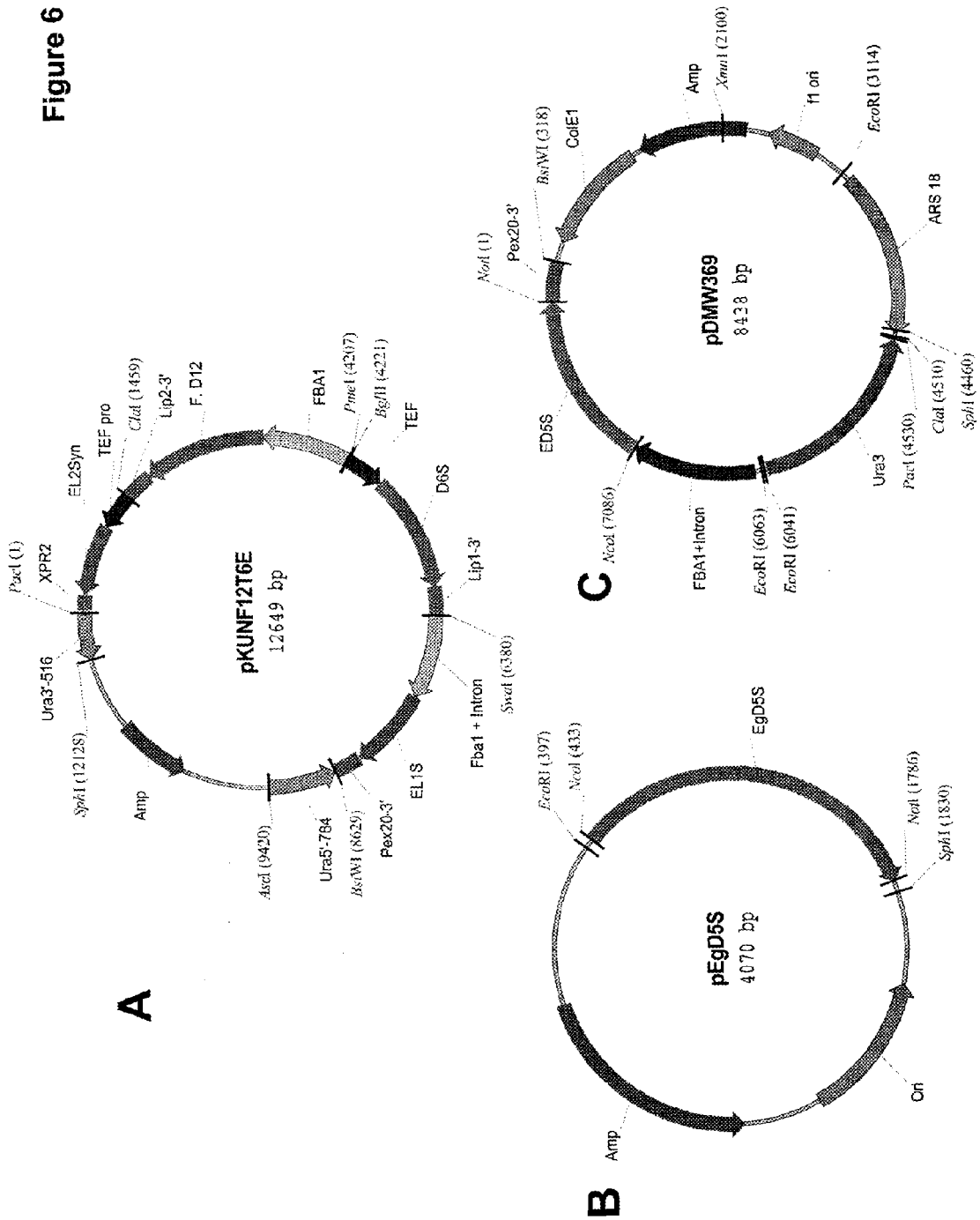

FIG. 6 provides plasmid maps for the following: (A) pKUNF12T6E; (B) pEgD5S; and, (C) pDMW369.

FIG. 7 shows a comparison of the DNA sequence of the *Euglena gracilis* delta-5 desaturase gene (designated as "EgD5"; SEQ ID NO:1) and the synthetic gene (designated as "EgD5S"; SEQ ID NO:3) codon-optimized for expression in *Yarrowia lipolytica*.

Figure 8A:
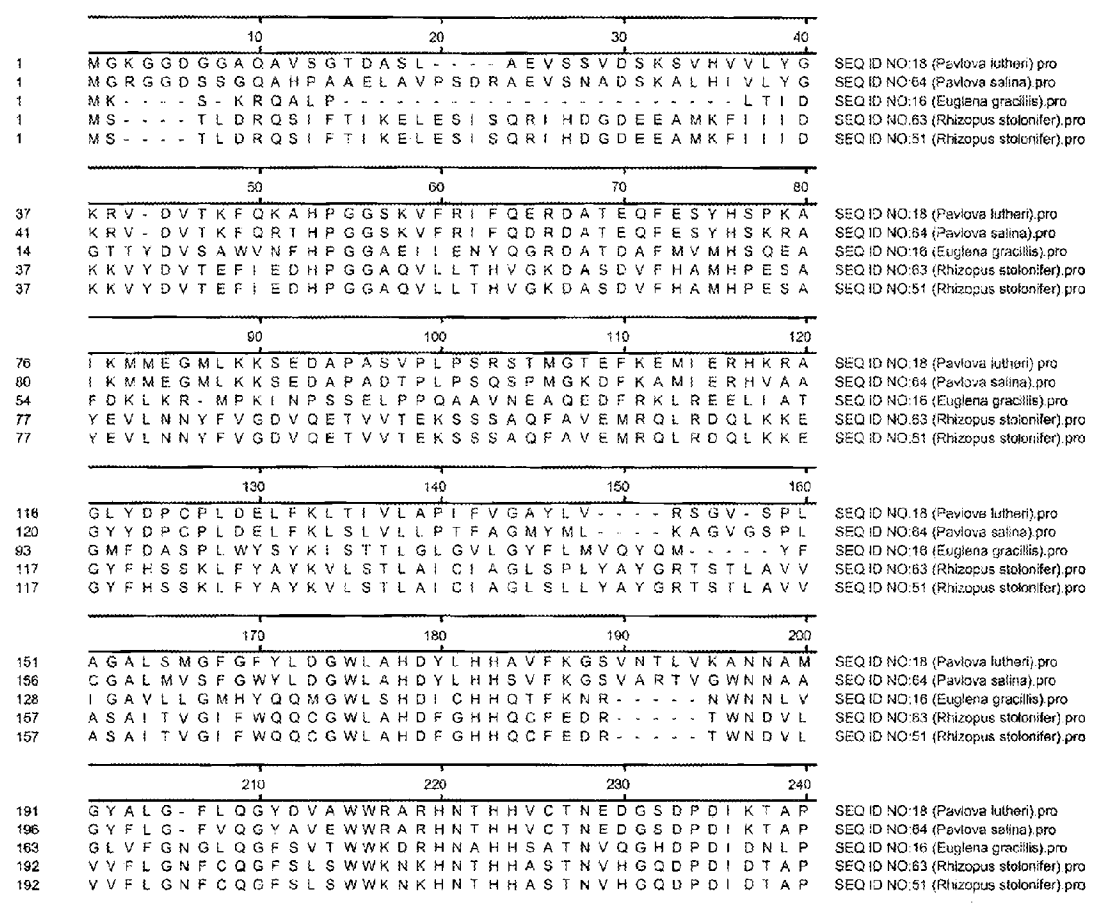
Figure 8B:
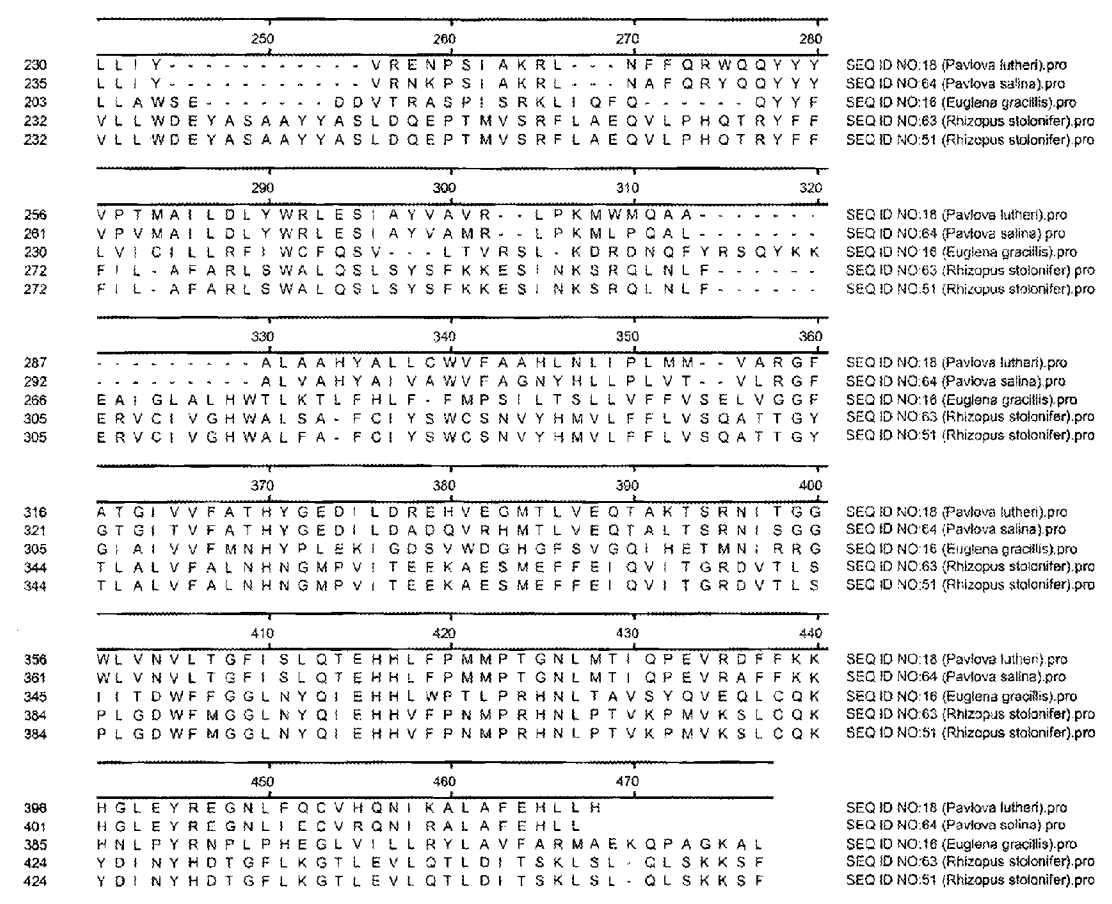

FIGS. 8A and 8B show a Clustal V alignment (with default parameters) of a *Pavlova lutheri* delta-8 desaturase (SEQ ID NO:18), a *Pavlova salina* delta-8 desaturase (SEQ ID NO:64), a *Euglena gracilis* delta-8 desaturase (SEQ ID NO:16) and two different *Rhizopus stolonifer* delta-6 fatty acid desaturases (SEQ ID NOs:51 and 63).

Figure 9:
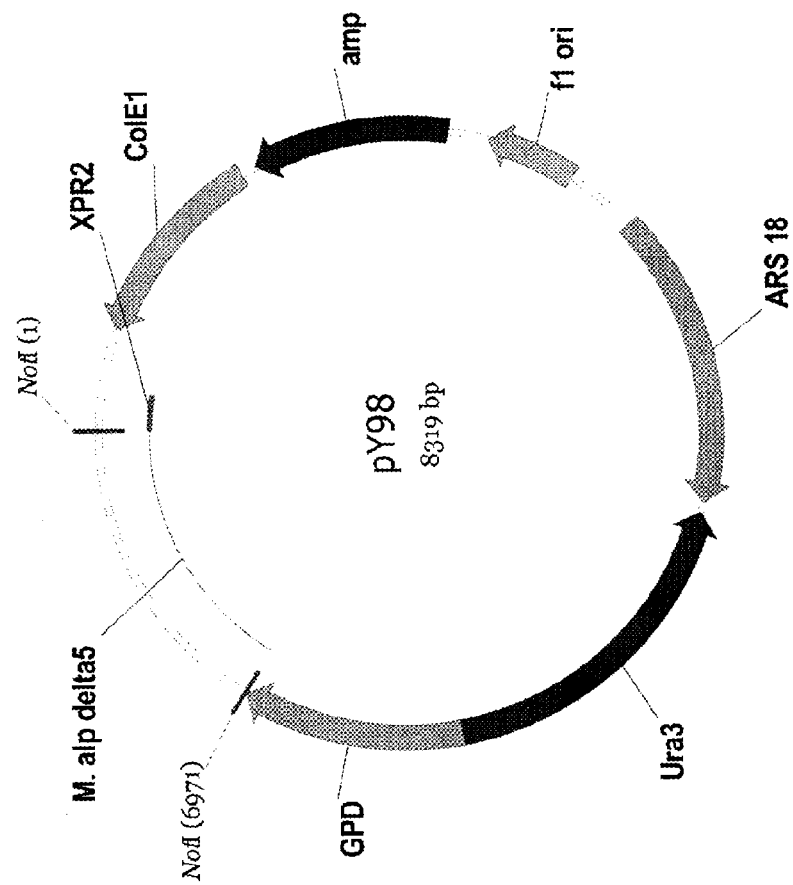

FIG. 9 provides a plasmid map for pY98.

FIG. 10A provides the fatty acid profiles for *Yarrowia lipolytica* expressing pY98 (SEQ ID NO:76; comprising a *Mortierella alpina* delta-5 desaturase gene designated as "MaD5") or pDMW367 (SEQ ID NO:23; comprising the *Euglena gracilis* delta-5 desaturase gene designated as "EgD5") and fed various substrates. FIG. 10B provides a comparison of the omega-3 and omega-6 substrate specificity of MaD5 versus EgD5.

Figure 11:
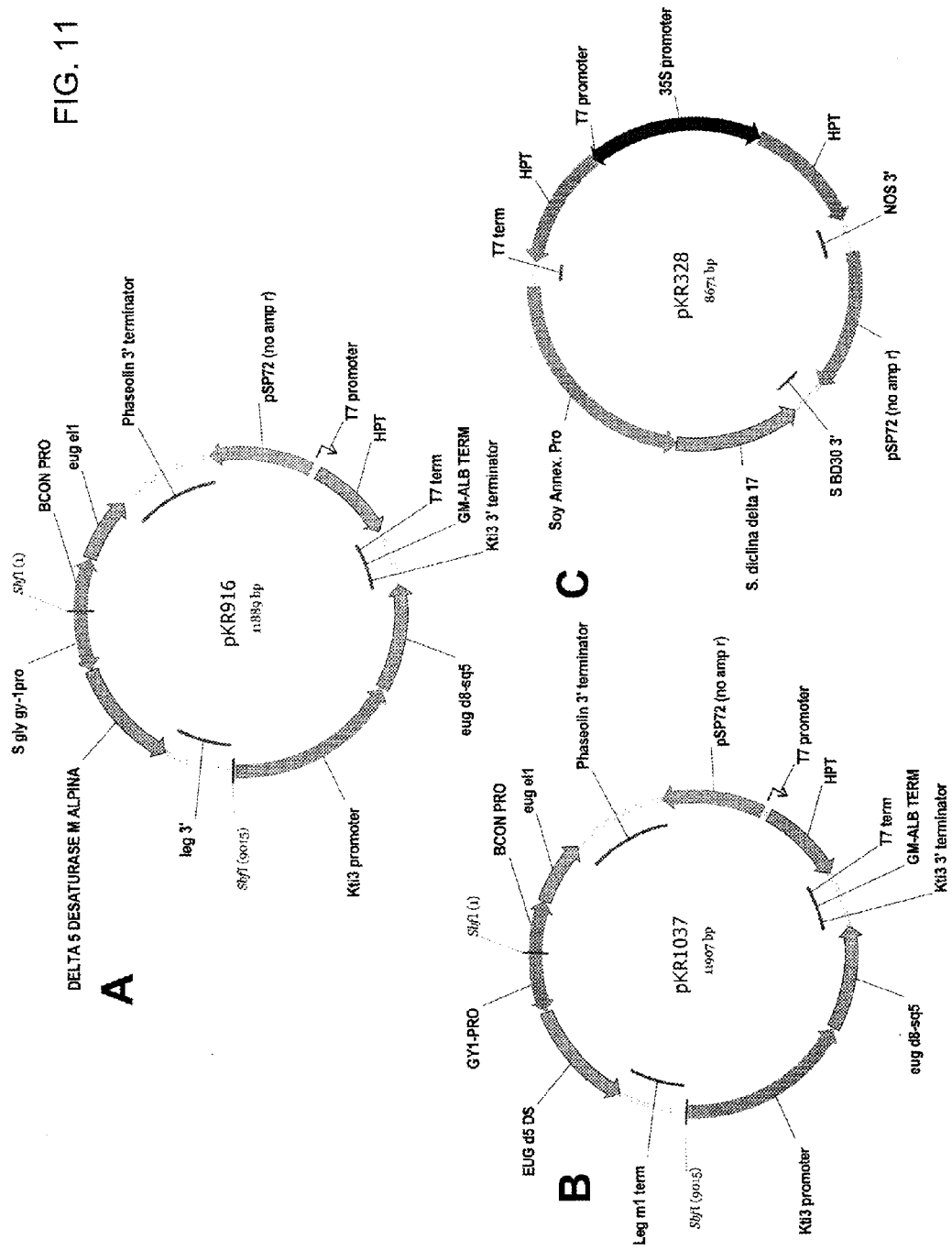

FIG. 11 provides plasmid maps for the following: (A) pKR916; (B) pKR1037; and, (C) pKR328.

FIG. 12A provides the average fatty acid profiles for ten events having the highest delta-5 desaturase activity when the *Mortierella alpina* enzyme (MaD5) is transformed into soybean embryos. FIG. 12B provides the average fatty acid profiles for ten events having the highest delta-5 desaturase activity when the *Euglena gracilis* enzyme (EgD5) is transformed into soybean embryos. Fatty acids are identified as 16:0 (palmitate), 18:0 (stearic acid), 18:1 (oleic acid), LA, ALA, EDA, SCI, DGLA, ARA, ERA, JUP, ETA and EPA. Fatty acids listed as "others" include: 18:2 (5, 9), GLA, STA, 20:0, 20:1(11), 20:2 (7, 11) or 20:2 (8, 11) and DPA. Each of these "other" fatty acids is present at a relative abundance of less than 3.0% of the total fatty acids. Fatty acid compositions for an individual embryo were expressed as the weight percent (wt. %) of total fatty acids and the average fatty acid composition is an average of six individual embryos for each event. FIG. 12B shows that the activity of EgD5 in soy embryos is very high with an average conversion (Correct % delta-5 desat) from 77% to 99% in the top ten events.

Figure 13:
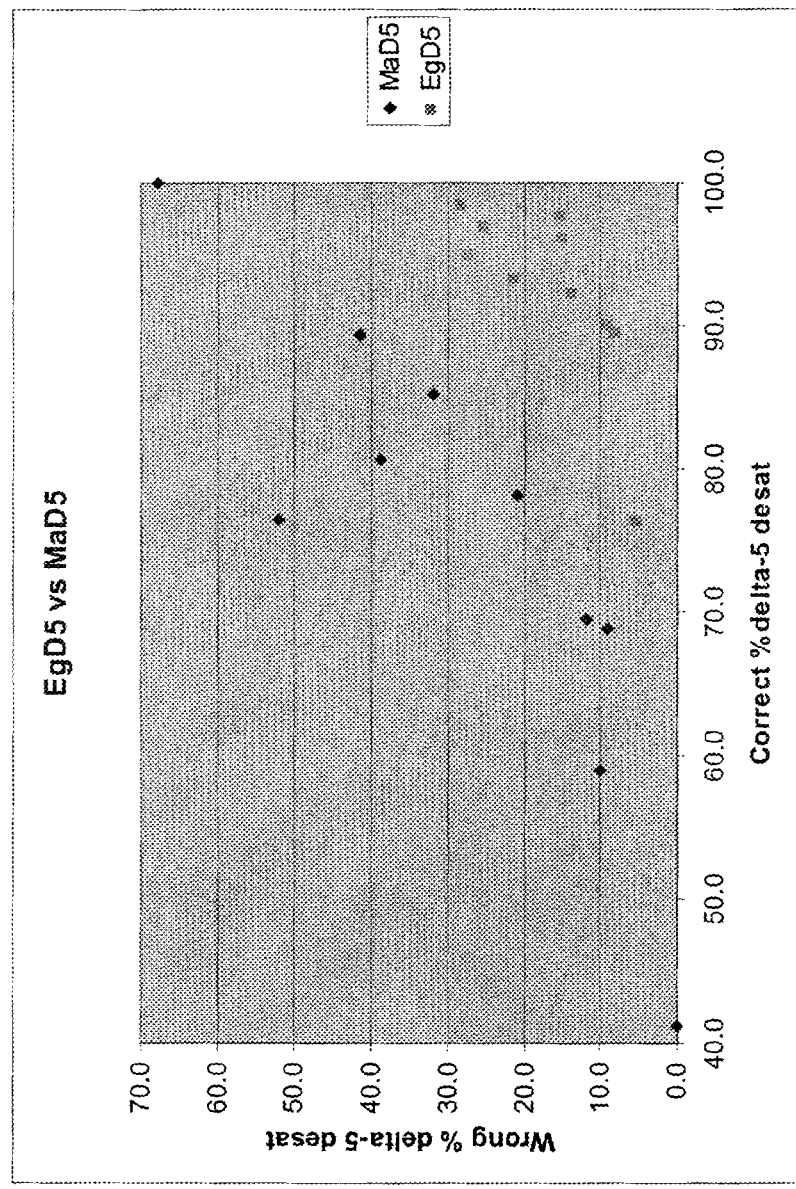

FIG. 13 provides the activity of the delta-5 desaturase for the "correct" substrates ("Correct % delta-5 desat") as plotted on the x-axis versus the activity of the delta-5 desaturase for the "wrong" substrates ("Wrong % delta-5 desat") as plotted on the y-axis for MaD5 (see FIG. 12A) and EgD5 (see FIG. 12B). The substrate specificity of EgD5 has a preference for the "correct" substrates over the "wrong" substrates when compared to MaD5.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

SEQ ID NOs:1-26, 48, 49, 51-54, 61-64, 67-72 and 75-76 are ORFs encoding genes or proteins (or portions thereof), or plasmids, as identified in Table 1.

TABLE 1

Summary Of Nucleic Acid And Protein SEQ ID Numbers

| Description and Abbreviation | Nucleic acid SEQ ID NO. | Protein SEQ ID NO. |
|---|---|---|
| *Euglena gracilis* delta-5 desaturase ("EgD5") | 1 (1350 bp) | 2 (449 AA) |
| Synthetic delta-5 desaturase, derived from *Euglena gracilis*, codon-optimized for expression in *Yarrowia lipolytica* ("EgD5S") | 3 (1350 bp) | 2 (449 AA) |
| *Euglena gracilis* EgD5 - fragment of pT-F10-1 | 4 (590 bp) | 5 (196 AA) |
| *Euglena gracilis* EgD5 - fragment of pT-EgD5-5'C2 | 6 (797 bp) | — |
| *Euglena gracilis* EgD5-5' sequence relative to SEQ ID NO: 4 | 7 (559 bp) | — |
| *Euglena gracilis* EgD5 - fragment of pT-EgD5-5'2$^{nd}$ | 8 (273 bp) | — |
| *Euglena gracilis* EgD5 - 5' sequence relative to SEQ ID NO: 6 | 9 (20 bp) | — |
| *Euglena gracilis* EgD5 - fragment of pT-EgD5-3' | 10 (728 bp) | — |
| *Euglena gracilis* EgD5 - 3' sequence relative to SEQ ID NO: 4 | 11 (464 bp) | — |
| *Pythium irregulare* delta-5 desaturase (GenBank Accession No. AAL13311) | — | 12 (456 AA) |
| *Phytophthora megasperma* delta-5 desaturase (GenBank Accession No. CAD53323) | — | 13 (477 AA) |
| *Phaeodactylum tricornutum* delta-5 desaturase (GenBank Accession No. AAL92562) | — | 14 (469 AA) |
| *Dictyostelium discoideum* delta-5 desaturase (GenBank Accession No. XP_640331) | — | 15 (467 AA) |
| *Euglena gracilis* delta-8 desaturase (PCT Publications No. WO 2006/012325 and No. WO 2006/012326) | — | 16 (421 AA) |
| *Pavlova lutheri* (CCMP459) delta-8 desaturase | 17 (1269 bp) | 18 (423 AA) |
| Conserved Region 1 | — | 19 (7 AA) |
| Conserved Region 2 | — | 20 (7 AA) |
| *Thalassiosira pseudonana* delta-8 sphingolipid desaturase (GenBank Accession No. AAX14502) | — | 21 (476 AA) |
| Plasmid pZUF17 | 22 (8165 bp) | — |
| Plasmid pDMW367 | 23 (8438 bp) | — |
| Plasmid pKUNF12T6E | 24 (12,649 bp) | — |
| Synthetic C$_{18/20}$ elongase gene derived from *Thraustochytrium aureum* (U.S. Pat. No. 6,677,145), codon-optimized for expression in *Yarrowia lipolytica* ("EL2S") | 25 (819 bp) | 26 (272 AA) |
| Plasmid pEgD5S | 48 (4070 bp) | — |
| Plasmid pDMW369 | 49 (8438 bp) | — |
| *Rhizopus stolonifer* delta-6 fatty acid desaturase (NCBI Accession No. AAX22052) | — | 51 (459 AA) |
| *Pavlova lutheri* delta-8 desaturase - portion of cDNA insert from clone eps1c.pk002.f22 (5' end of cDNA insert) | 52 (695 bp) | — |
| *Pavlova lutheri* delta-8 desaturase - fully sequenced EST eps1c.pk002.f22:fis (full insert sequence) | 53 (1106 bp) | — |
| *Pavlova lutheri* delta-8 desaturase-translation of nucleotides 1-864 of fully sequenced EST eps1c.pk002.f22:fis (full insert sequence; SEQ ID NO: 53) | — | 54 (287 AA) |
| *Pavlova lutheri* delta-8 desaturase - full 5' end sequence from genome walking | 61 (1294 bp) | — |
| *Pavlova lutheri* delta-8 desaturase-assembled sequence | 62 (1927 bp) | — |
| *Rhizopus stolonifer* delta-6 fatty acid desaturase (NCBI Accession No. ABB96724) | — | 63 (459 AA) |
| *Pavlova salina* delta-8 desaturase | — | 64 (427 AA) |
| *Mortierella alpina* delta-5 desaturase | 67 (1338 bp) | 68 (446 AA) |
| Plasmid pY5-22 | 69 (6473 bp) | — |
| Plasmid pY5-22GPD | 70 (6970 bp) | — |
| *Yarrowia lipolytica* glyceraldehyde-3-phosphate dehydrogenase promoter (GPD) | 71 (968 bp) | — |
| Plasmid pYZDE2-S | 72 (8630 bp) | — |
| Plasmid pKR136 | 75 (6339 bp) | — |
| Plasmid pY98 | 76 (8319 bp) | — |
| *Euglena gracilis* delta-9 elongase ("EgD9e") | 77 (774 bp) | — |
| *Euglena gracilis* delta-8 desaturase ("EgD8") | 78 (1263 bp) | — |
| Plasmid pKR906 | 81 (4311 bp) | — |
| Plasmid pKR72 | 82 (7085 bp) | — |
| Plasmid pKS102 | 83 (2540 bp) | — |
| Plasmid pKR197 | 84 (4359 bp) | — |
| Plasmid pKR911 | 85 (5147 bp) | — |
| Plasmid pKR680 | 86 (6559 bp) | — |
| Plasmid pKR913 | 87 (9014 bp) | — |
| Plasmid pKR767 | 88 (5561 bp) | — |
| Plasmid pKR916 | 89 (11,889 bp) | — |
| Plasmid pKR974 | 90 (5661 bp) | — |
| Plasmid pKR1032 | 91 (5578 bp) | — |
| Plasmid pKR1037 | 92 (11,907 bp) | — |
| Plasmid pKR328 | 93 (8671 bp) | — |
| *Saprolegnia diclina* delta-5 desaturase ("SdD5") | 94 (1413 bp) | — |

SEQ ID NOs:27-30 correspond to degenerate oligonucleotide primers 5-1A, 5-1B, 5-1C and 5-1D, respectively, that encode Conserved Region 1.

SEQ ID NOs:31-34 correspond to degenerate oligonucleotide primers 5-5AR, 5-5BR, 5-5CR and 5-5DR, respectively, that encode Conserved Region 2.

SEQ ID NOs:35-40 correspond to primers ODMW480, CDSIII 5' primer, ODMW479, DNR CDS 5', YL791 and YL792, respectively, used for 5' RACE.

SEQ ID NOs:41-43 correspond to primers ODMW469, AUAP and ODMW470, respectively, used for 3' RACE.

SEQ ID NOs:44-47 correspond to primers YL794, YL797, YL796 and YL795, respectively, used for amplification of the full length cDNA of EgD5.

SEQ ID NO:50 corresponds to primer T7, used for sequencing the Pavlova lutheri (CCMP459) cDNA library.

SEQ ID NOs:55 and 56 correspond to primers SeqE and SeqW, respectively, used for sequencing Pavlova lutheri (CCMP459) clones.

SEQ ID NOs:57 and 58 correspond to the universal primer AP1 and primer GSP PvDES, respectively, used for amplification of genomic Pavlova lutheri (CCMP459) DNA.

SEQ ID NOs:59 and 60 correspond to primers M13-28Rev and PavDES seq, respectively, used for sequencing Pavlova lutheri (CCMP459) genomic inserts.

SEQ ID NOs:65 and 66 correspond to AP primer and Smart IV oligonucleotide primer, respectively, used for Euglena gracilis cDNA synthesis.

SEQ ID NOs:73 and 74 are primers GPDsense and GPDantisense, respectively, used for amplifying the GPD promoter.

SEQ ID NOs:79 and 80 correspond to primers oEugEL1-1 and oEugEL1-2, respectively, used to amplify a Euglena gracilis delta-9 elongase (EgD9e).

DETAILED DESCRIPTION OF THE INVENTION

All patents, patent applications, and publications cited herein are incorporated by reference in their entirety. This specifically includes the following commonly owned, co-pending applications: U.S. Pat. Nos. 7,125,672, 7,189,559, 7,192,762, 7,198,937, 7,202,356, U.S. patent applications Ser. No. 10/840579 and Ser. No. 10/840325 (filed May 6, 2004) now U.S. Pat. No. 7,238,482 and 7,214,491, U.S. patent application Ser. No. 10/869630 (filed Jun. 16, 2004) now U.S. Pat. No. 7,259,255, U.S. patent application Ser. No. 10/882760 (filed Jul. 1, 2004) now U.S. Pat. No. 7,267,976, U.S. patent applications Ser. No. 10/985254 and Ser. No. 10/985691 (filed Nov. 10, 2004) now U.S. Pat. No. 7,659,120, and 7,504,259, U.S. patent application Ser. No. 11/024544 (filed Dec. 29, 2004) now U.S. Pat. No. 7,273,746, U.S. patent application Ser. No. 11/166993 (filed Jun. 24, 2005) now U.S. Pat. No. 7,256,033, U.S. patent application Ser. No. 11/183664 (filed Jul. 18, 2005) now U.S. Pat. No. 7,459,546, U.S. patent application Ser. No. 11/185,301 (filed Jul. 20, 2005), U.S. patent application Ser. No. 11/190750 (filed Jul. 27, 2005), U.S. patent application Ser. No. 11/198975 (filed Aug. 8, 2005) now U.S. Pat. No. 7,465,564, U.S. patent application Ser. No. 11/225354 (filed Sep. 13, 2005) now U.S. Pat. No. 7,264,949, U.S. patent application Ser. No. 11/253882 (filed Oct. 19, 2005) now U.S. Pat. No. 7,470,532, U.S. patent applications Ser. No. 11/264784 and 11/264737 (filed Nov. 1, 2005) now U.S. Pat. No. 7,588,931 and 7,550,286, U.S. patent application Ser. No. 11/265761 (filed Nov. 2, 2005), U.S. patent application Ser. No. 60/795810 (filed Apr. 28, 2006), U.S. patent application Ser. No. 60/793575 (filed Apr. 20, 2006), U.S. patent application Ser. No. 60/796637 (filed May 2, 2006), U.S. patent applications Ser. No. 60/801172 and Ser. No. 60/801119(filed May 17, 2006), U.S. Patent Application Ser. No. 60/853563 (filed Oct. 23, 2006), U.S. patent application Ser. No. 60/855,177 (filed Oct. 30, 2006), U.S. patent applications Ser. No. 11/601563 and Ser. No. 11/601564 (filed Nov. 16, 2006), wherein No. 11/601564 is now U.S. Pat. No. 7,645,604, U.S. patent application Ser. No. 11/635258 (filed Dec. 7, 2006) now U.S. Pat. No. 7,709,239, U.S. patent application Ser. No. 11/613420 (filed Dec. 20, 2006), U.S. patent application Ser. No. 60/909790 (filed Apr. 3, 2007), U.S. patent application Ser. No. 60/910831 (filed Apr. 10, 2007) and U.S. patent application Ser. No. 60/915733, (filed May 3, 2007). This additionally includes the following Applicants' Assignee's co-pending applications: U.S. Patent Publication No. 2005/0136519, now U.S. Pat. No. 7,238,482, concerning the production of PUFAs in plants; and, U.S. Pat. No. 7,129,089, concerning annexin promoters and their use in expression of transgenes in plants.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In accordance with the subject invention, Applicants identify a novel Euglena gracilis delta-5 desaturase enzyme and gene encoding the same that may be used for the manipulation of biochemical pathways for the production of healthful PUFAs. Thus, the subject invention finds many applications.

PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary).

Supplementation of humans or animals with PUFAs produced by recombinant means can result in increased levels of the added PUFAs, as well as their metabolic progeny. For example, treatment with EPA can result not only in increased levels of EPA, but also downstream products of EPA such as eicosanoids (i.e., prostaglandins, leukotrienes, thromboxanes). Complex regulatory mechanisms can make it desirable to combine various PUFAs, or add different conjugates of PUFAs, in order to prevent, control or overcome such mechanisms to achieve the desired levels of specific PUFAs in an individual.

Definitions

In this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

The term "invention" or "present invention" as used herein is not meant to be limiting to any one specific embodiment of the invention but applies generally to any and all embodiments of the invention as described in the claims and specification.

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (omega-6 or n-6) versus "omega-3 fatty acids" (omega-3 or n-3) are provided in U.S. Patent Publication No. 2005/0136519.

Fatty acids are described herein by a simple notation system of "X:Y", wherein X is number of carbon (C) atoms in the particular fatty acid and Y is the number of double bonds. The number following the fatty acid designation indicates the position of the double bond from the carboxyl end of the fatty acid with the "c" affix for the cis-configuration of the double bond (e.g., palmitic acid (16:0), stearic acid (18:0), oleic acid (18:1, 9c), petroselinic acid (18:1, 6c), LA (18:2, 9c, 12c), GLA (18:3, 6c, 9c, 12c) and ALA (18:3, 9c, 12c, 15c)). Unless otherwise specified, 18:1, 18:2 and 18:3 refer to oleic, LA and ALA fatty acids, respectively. If not specifically written as otherwise, double bonds are assumed to be of the cis configuration. For instance, the double bonds in 18:2 (9, 12) would be assumed to be in the cis configuration.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of omega-3 and omega-6 fatty acids and their precursors, the abbreviations that will be used throughout the specification and each compounds' chemical name.

TABLE 2

Nomenclature of Polyunsaturated Fatty Acids And Precursors

| Common Name | Abbreviation | Chemical Name | Shorthand Notation |
| --- | --- | --- | --- |
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 omega-6 |
| γ-Linoleic | GLA | cis-6,9,12-octadecatrienoic | 18:3 omega-6 |
| Eicosadienoic | EDA | cis-11,14-eicosadienoic | 20:2 omega-6 |
| Dihomo-γ-Linoleic | DGLA | cis-8,11,14-eicosatrienoic | 20:3 omega-6 |
| Arachidonic | ARA | cis-5,8,11,14-eicosatetraenoic | 20:4 omega-6 |
| α-Linolenic | ALA | cis-9,12,15-octadecatrienoic | 18:3 omega-3 |
| Stearidonic | STA | cis-6,9,12,15-octadecatetraenoic | 18:4 omega-3 |
| Eicosatrienoic | ETrA or ERA | cis-11,14,17-eicosatrienoic | 20:3 omega-3 |
| Sciadonic | SCI | cis-5,11,14-eicosatrienoic | 20:3b omega-6 |
| Juniperonic | JUP | cis-5,11,14,17-eicosatetraenoic | 20:4b omega-3 |
| Eicosatetraenoic | ETA | cis-8,11,14,17-eicosatetraenoic | 20:4 omega-3 |
| Eicosapentaenoic | EPA | cis-5,8,11,14,17-eicosapentaenoic | 20:5 omega-3 |
| Docosapentaenoic | DPA | cis-7,10,13,16,19-docosapentaenoic | 22:5 omega-3 |
| Docosahexaenoic | DHA | cis-4,7,10,13,16,19-docosahexaenoic | 22:6 omega-3 |

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see PCT Publication No. WO 2006/052870). Briefly, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzymes" refer to any of the following enzymes (and genes which encode said enzymes) associated with the biosynthesis of a PUFA, including: a delta-4 desaturase, a delta-5 desaturase, a delta-6 desaturase, a delta-12 desaturase, a delta-15 desaturase, a delta-17 desaturase, a delta-9 desaturase, a delta-8 desaturase, a delta-9 elongase, a $C_{14/16}$ elongase, a $C_{16/18}$ elongase, a $C_{18/20}$ elongase and/or a $C_{20/22}$ elongase.

Figure 1:
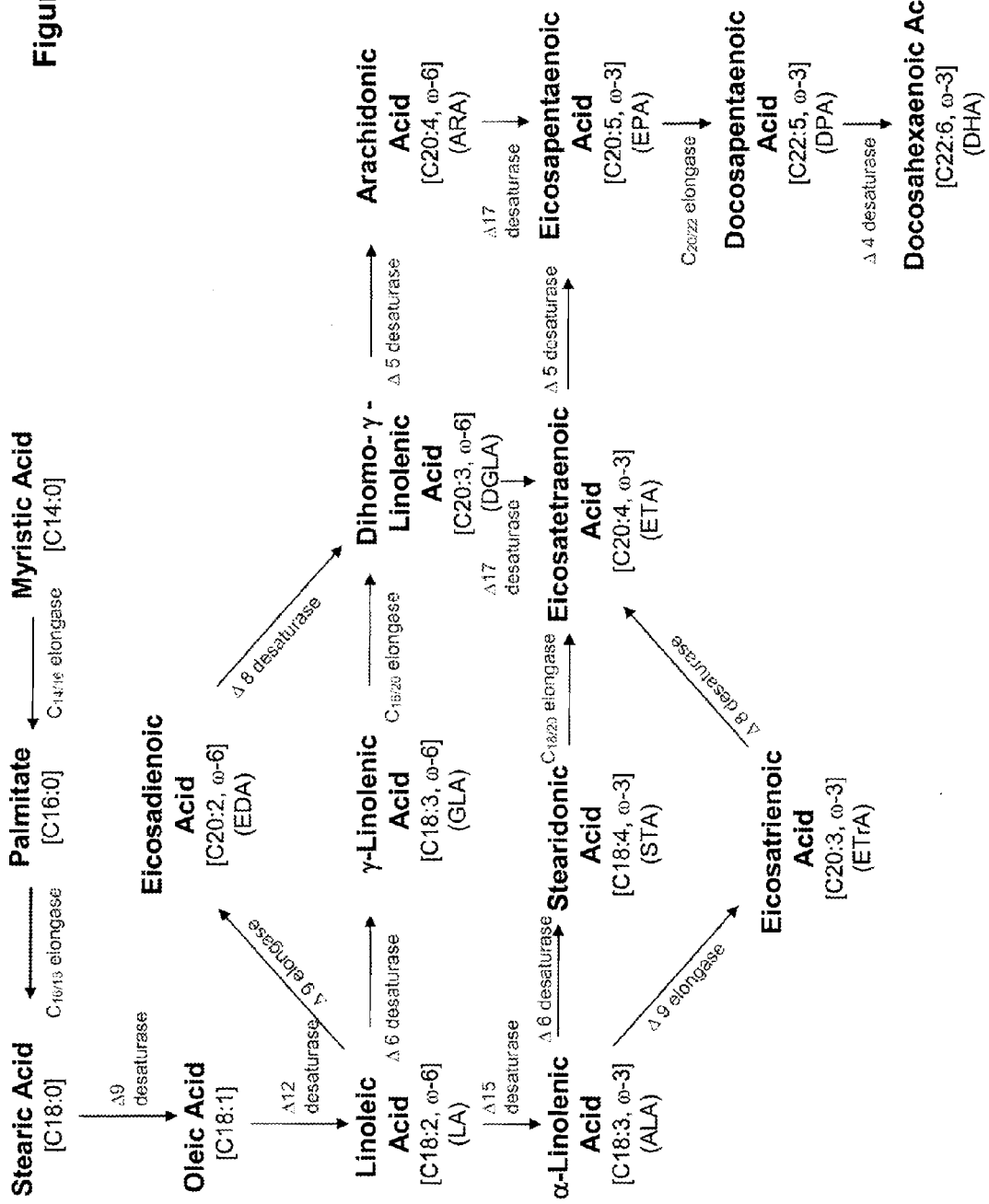
FIG. 1 illustrates the omega-3/omega-6 fatty acid biosynthetic pathway.

The term "omega-3/omega-6 fatty acid biosynthetic pathway" refers to a set of genes which, when expressed under the appropriate conditions encode enzymes that catalyze the production of either or both omega-3 and omega-6 fatty acids. Typically the genes involved in the omega-3/omega-6 fatty acid biosynthetic pathway encode PUFA biosynthetic pathway enzymes. A representative pathway is illustrated in FIG. 1, providing for the conversion of myristic acid through various intermediates to DHA, which demonstrates how both omega-3 and omega-6 fatty acids may be produced from a common source. The pathway is naturally divided into two portions where one portion will generate omega-3 fatty acids and the other portion, only omega-6 fatty acids. That portion that only generates omega-3 fatty acids will be referred to herein as the omega-3 fatty acid biosynthetic pathway, whereas that portion that generates only omega-6 fatty acids will be referred to herein as the omega-6 fatty acid biosynthetic pathway.

The term "functional" as used herein in context with the omega-3/omega-6 fatty acid biosynthetic pathway means that some (or all) of the genes in the pathway express active enzymes, resulting in in vivo catalysis or substrate conversion. It should be understood that "omega-3/omega-6 fatty acid biosynthetic pathway" or "functional omega-3/omega-6 fatty acid biosynthetic pathway" does not imply that all the genes listed in the above paragraph are required, as a number of fatty acid products will only require the expression of a subset of the genes of this pathway.

The term "delta-6 desaturase/delta-6 elongase pathway" will refer to a PUFA biosynthetic pathway that minimally includes at least one delta-6 desaturase and at least one $C_{18/20}$ elongase, thereby enabling biosynthesis of DGLA and/or ETA from LA and ALA, respectively, with GLA and/or STA as intermediate fatty acids. With expression of other desaturases and elongases, ARA, EPA, DPA and DHA may also be synthesized.

The term "delta-9 elongase/delta-8 desaturase pathway" will refer to a PUFA biosynthetic pathway that minimally includes at least one delta-9 elongase and at least one delta-8 desaturase, thereby enabling biosynthesis of DGLA and/or ETA from LA and ALA, respectively, with EDA and/or ETrA as intermediate fatty acids. With expression of other desaturases and elongases, ARA, EPA, DPA and DHA may also be synthesized.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the delta-9 elongase/delta-8 desaturase pathway, EDA, ETrA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the delta-9 elongase/delta-8 desaturase pathway, sciadonic acid (SCI) and juniperonic acid (JUP) also can be produced by the action of a delta-5 desaturase on either EDA or ETrA, respectively. They are considered to be "by-product fatty acids" since neither can be further converted to EPA by the action of other metabolic pathway enzymes.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are delta-5 desaturases that catalyze the conversion of DGLA to ARA and/or ETA to EPA. Other desaturases include: 1.) delta-17 desaturases that desaturate a fatty acid between the $17^{th}$ and $18^{th}$ carbon atom numbered from the carboxyl-terminal end of the molecule and which, for example, catalyze the conversion of ARA to EPA and/or DGLA to ETA; 2.) delta-6 desaturases that catalyze the conversion of LA to GLA and/or ALA to STA; 3.) delta-12 desaturases that catalyze the conversion of oleic acid to LA; 4.) delta-15 desaturases that catalyze the conversion of LA to ALA and/or GLA to STA; 5.) delta-4 desaturases that catalyze the conversion of DPA to DHA; 6.) delta-8 desaturases that catalyze the conversion of EDA to DGLA and/or ETrA to ETA; and, 7.) delta-9 desaturases that catalyze the conversion of palmitate to palmitoleic acid (16:1) and/or stearate to oleic acid. In the art, delta-15 and delta-17 desaturases are also occasionally referred to as "omega-3 desaturases", "w-3 desaturases", and/or "omega-3 desaturases", based on their ability to convert omega-6 fatty acids into their omega-3 counterparts (e.g., conversion of LA into ALA and ARA into EPA, respectively). In some embodiments, it is most desirable to empirically determine the specificity of a particular fatty acid desaturase by transforming a suitable host with the gene for the fatty acid desaturase and determining its effect on the fatty acid profile of the host.

The term "delta-5 desaturase" refers to an enzyme that desaturates a fatty acid between the fifth and sixth carbon atom numbered from the carboxyl-terminal end of the molecule. Preferably, a delta-5 desaturase converts dihomo-gamma-linolenic acid [20:3, DGLA] to arachidonic acid [20:4, ARA] or converts eicosatetraenoic acid [20:4, ETA] to eicosapentaenoic acid [20:5, EPA].

For the purposes herein, the term "EgD5" refers to a delta-5 desaturase enzyme (SEQ ID NO:2) isolated from *Euglena gracilis*, encoded by SEQ ID NO:1 herein. Similarly, the term "EgD5S" refers to a synthetic delta-5 desaturase derived from *Euglena gracilis* that is codon-optimized for expression in *Yarrowia lipolytica* (i.e., SEQ ID NOs:3 and 2).

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, as described in U.S. Patent Publication No. 2005/0132442. Examples of reactions catalyzed by elongase systems are the conversion of GLA to DGLA, STA to ETA and EPA to DPA. In general, the substrate selectivity of elongases is somewhat broad but segregated by both chain length and the degree and type of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase (also known as a delta-6 elongase as the terms can be used interchangeably) will utilize a $C_{18}$ substrate (e.g., GLA, STA) and a $C_{20/22}$ elongase will utilize a $C_{20}$ substrate (e.g., EPA). In like manner, a delta-9 elongase is able to catalyze the conversion of LA and ALA to EDA and ETrA, respectively. It is important to note that some elongases have broad specificity and thus a single enzyme may be capable of catalyzing several elongase reactions (e.g., thereby acting as both a $C_{16-18}$ elongase and a $C_{18/20}$ elongase).

The term "oleaginous" refers to those organisms that tend to store their energy source in the form of lipid (Weete, In: Fungal Lipid Biochemistry, $2^{nd}$ Ed., Plenum, 1980). The term "oleaginous yeast" refers to those microorganisms classified as yeasts that can make oil. Generally, the cellular oil or TAG content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "Euglenophyceae" refers to a group of unicellular colorless or photosynthetic flagellates ("euglenoids") found living in freshwater, marine, soil and parasitic environments. The class is characterized by solitary unicells, wherein most are free-swimming and have two flagella (one of which may be nonemergent) arising from an anterior invagination known as a reservoir. Photosynthetic euglenoids contain one to many chloroplasts, which vary from minute disks to expanded plates or ribbons. Colorless euglenoids depend on osmotrophy or phagotrophy for nutrient assimilation. About 1000 species have been described and classified into about 40 genera and 6 orders. Examples of Euglenophyceae include, but are no means limited to, the following genera: *Euglena, Eutreptiella* and *Tetruetreptia*.

The term "conservative amino acid substitution" refers to a substitution of an amino acid residue in a given protein with another amino acid, without altering the chemical or functional nature of that protein. For example, it is well known in the art that alterations in a gene that result in the production of a chemically equivalent amino acid at a given site (but that do not affect the structural and functional properties of the encoded, folded protein) are common. For the purposes of the present invention, "conservative amino acid substitutions" are defined as exchanges within one of the following five groups:

1. small aliphatic, nonpolar or slightly polar residues: Ala [A], Ser [S], Thr [T] (Pro [P], Gly [G]);
2. polar, negatively charged residues and their amides: Asp [D], Asn [N], Glu [E], Gln [Q];
3. polar, positively charged residues: His [H], Arg [R], Lys [K];
4. large aliphatic, nonpolar residues: Met [M], Leu [L], Ile [I], Val [V] (Cys [C]); and,
5. large aromatic residues: Phe [F], Tyr [Y], Trp [W].

Conservative amino acid substitutions generally maintain: 1) the structure of the polypeptide backbone in the area of the substitution; 2) the charge or hydrophobicity of the molecule at the target site; or 3) the bulk of the side chain. Additionally, in many cases, alterations of the N-terminal and C-terminal portions of the protein molecule would also not be expected to alter the activity of the protein.

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deosycytidylate, "G" for guanylate or deoxyguanylate, "U" for uridlate, "T" for deosythymidylate, "R" for purines (A or G), "Y" for pyrimidiens (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth et al., *Anal. Biochem.* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular euglenoid proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the invention herein also includes isolated nucleic acid fragments that are complementary to the complete sequences as reported in the accompanying Sequence Listing, as well as those substantially similar nucleic acid sequences.

The terms "homology" and "homologous" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the present invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions (e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant euglenoid polypeptide as set forth in SEQ ID NO:2. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

The term "allele" refers to one of several alternative forms of a gene occupying a given locus on a chromosome. When all the alleles present at a given locus on a chromosome are the same, then that plant is homozygous at that locus. If the alleles present at a given locus on a chromosome differ, then that plant is heterozygous at that locus.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

A promoter sequence may consist of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. New promoters of various types useful in plant cells are constantly being discovered; numerous examples may be found in the compilation by Okamuro, J. K., and Goldberg, R. B., *Biochemistry of Plants*, 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.*, 3:225-236 (1995)).

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; PCT Publication No. WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragments of the invention. Expression may also refer to translation of mRNA into a polypeptide.

"Mature" protein refers to a post-translationally processed polypeptide, i.e., one from which any pre- or propeptides present in the primary translation product have been removed. "Precursor" protein refers to the primary product of translation of mRNA, i.e., with pre- and propeptides still present. Pre- and propeptides may be (but are not limited to) intracellular localization signals.

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a specific vector containing a foreign gene and having elements in addition to the foreign gene that allow for enhanced expression of that gene in a foreign host.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and, 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS*, 5:151-153 (1989); Higgins, D. G. et al., *Comput. Appl. Biosci.*, 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the ClustalV program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS*, 5:151-153 (1989); Higgins, D. G. et al., *Comput. Appl. Biosci.*, 8:189-191 (1992)) and found in the MegAlign™ v6.1 program of the LASERGENE bioinformatics computing suite (DNASTAR Inc.). Default parameters for multiple alignment correspond to GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB. After alignment of the sequences using the Clustal W program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Although preferred ranges are described above, any integer amino acid identity from 39% to 100% may be useful in describing the present invention, such as 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), *Meeting Date* 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized. With regard to the BLASTP algorithm used herein, default parameters will include the Robinson and Robinson amino acid frequencies (Robinson A. B., Robinson L. R., *Proc. Natl Acad. Sci. U.S.A.*, 88:8880-8884 (1991)), the BLOSUM62 scoring matrix and the gap cost $A(g)=11+g$.

The term "plant parts" includes differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or group of tissues that constitute a morphologically and functionally distinct part of a plant.

The term "genome" refers to the following: (1) the entire complement of genetic material (genes and non-coding sequences) present in each cell of an organism, or virus or organelle; (2) a complete set of chromosomes inherited as a (haploid) unit from one parent.

Standard recombinant DNA and molecular cloning techniques used herein are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., a mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (Vaucheret et al., *Plant J.* 16:651-659 (1998); Gura, *Nature* 404:804-808 (2000)). The overall efficiency of this phenomenon is low, and the extent of the RNA reduction is widely variable. More recent work has described the use of "hairpin" structures that incorporate all, or part, of an mRNA encoding sequence in a complementary orientation that results in a potential "stem-loop" structure for the expressed RNA (PCT Publication No. WO 99/53050, published Oct. 21, 1999; PCT Publication No. WO 02/00904, published Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083, published Aug. 20, 1998). Both of these co-suppressing phenomena have not been elucidated mechanistically, although genetic evidence has begun to unravel this complex situation (Elmayan et al., *Plant Cell* 10:1747-1757 (1998)).

An Overview Microbial Biosynthesis of Fatty Acids and Triacylglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: 1.) the esterification of one molecule of acyl-CoA to glycerol-3-phosphate via an acyltransferase to produce lysophosphatidic acid; 2.) the esterification of a second molecule of acyl-CoA via an acyltransferase to yield 1,2-diacylglycerol phosphate (commonly identified as phosphatidic acid); 3.) removal of a phosphate by phosphatidic acid phosphatase to yield 1,2-diacylglycerol (DAG); and, 4.) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to omega-3/omega-6 fatty acids involves elongation of the carbon chain through the addition of carbon atoms and desaturation of the molecule through the addition of double bonds. This requires a series of special desaturation and elongation enzymes present in the endoplasmic reticulim membrane. However, as seen in FIG. 1 and as described below, there are often multiple alternate pathways for production of a specific omega-3/omega-6 fatty acid.

Specifically, all pathways require the initial conversion of oleic acid to LA, the first of the omega-6 fatty acids, by a delta-12 desaturase. Then, using the "delta-6 desaturase/delta-6 elongase pathway", omega-6 fatty acids are formed as follows: (1) LA is converted to GLA by a delta-6 desaturase;

(2) GLA is converted to DGLA by a $C_{18/20}$ elongase; and, (3) DGLA is converted to ARA by a delta-5 desaturase. Alternatively, the "delta-6 desaturase/delta-6 elongase pathway" can be utilized for formation of omega-3 fatty acids as follows: (1) LA is converted to ALA, the first of the omega-3 fatty acids, by a delta-15 desaturase; (2) ALA is converted to STA by a delta-6 desaturase; (3) STA is converted to ETA by a $C_{18/20}$ elongase; (4) ETA is converted to EPA by a delta-5 desaturase; (5) EPA is converted to DPA by a $C_{20/22}$ elongase; and, (6) DPA is converted to DHA by a delta-4 desaturase. Optionally, omega-6 fatty acids may be converted to omega-3 fatty acids; for example, ETA and EPA are produced from DGLA and ARA, respectively, by delta-17 desaturase activity.

Alternate pathways for the biosynthesis of omega-3/ omega-6 fatty acids utilize a delta-9 elongase and delta-8 desaturase. More specifically, LA and ALA may be converted to EDA and ETrA, respectively, by a delta-9 elongase; then, a delta-8 desaturase converts EDA to DGLA and/or ETrA to ETA.

It is contemplated that the particular functionalities required to be expressed in a specific host organism for production of omega-3/omega-6 fatty acids will depend on the host cell (and its native PUFA profile and/or desaturase/elongase profile), the availability of substrate, and the desired end product(s). One skilled in the art will be able to identify various candidate genes encoding each of the enzymes desired for omega-3/omega-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or, 4.) co-factors required by the polypeptide. The expressed polypeptide preferably has parameters compatible with the biochemical environment of its location in the host cell (see PCT Publication No. WO 2004/101757 for additional details).

In additional embodiments, it will also be useful to consider the conversion efficiency of each particular desaturase and/or elongase. More specifically, since each enzyme rarely functions with 100% efficiency to convert substrate to product, the final lipid profile of un-purified oils produced in a host cell will typically be a mixture of various PUFAs consisting of the desired omega-3/omega-6 fatty acid, as well as various upstream intermediary PUFAs. Thus, each enzyme's conversion efficiency is also a variable to consider, when optimizing biosynthesis of a desired fatty acid.

With each of the considerations above in mind, candidate genes having the appropriate desaturase and elongase activities (e.g., delta-6 desaturases, $C_{18/20}$ elongases, delta-5 desaturases, delta-17 desaturases, delta-15 desaturases, delta-9 desaturases, delta-12 desaturases, $C_{14/16}$ elongases, $C_{16/18}$ elongases, delta-9 elongases, delta-8 desaturases, delta-4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Sequence Identification of a Novel *Euglena gracilis* Delta-5 Desaturase

In the present invention, a nucleotide sequence (SEQ ID NO:1) has been isolated from *Euglena gracilis* encoding a delta-5 desaturase (SEQ ID NO:2), designated herein as "EgD5".

Comparison of the EgD5 nucleotide base and deduced amino acid sequences to public databases reveals that the most similar known sequences are about 39% identical to the amino acid sequence of EgD5 reported herein over a length of 449 amino acids using a ClustalW alignment method. More preferred amino acid fragments are at least about 70%-80% identical to the sequences herein, where those sequences that are at least about 80%-90% identical are particularly suitable and those sequences that are at least about 90%-95% identical are most preferred. Similarly, preferred EgD5 encoding nucleic acid sequences corresponding to the instant ORF are those encoding active proteins and which are at least about 70%-80% identical to the nucleic acid sequences of EgD5 reported herein, where those sequences that are at least about 80%-90% identical are particularly suitable and those sequences that are at least about 90%-95% identical are most preferred.

In alternate embodiments, the instant EgD5 desaturase sequence can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having e.g., desaturase activity can be synthesized in whole or in part using the codons preferred in the host species.

In one preferred embodiment of the invention herein, EgD5 was codon-optimized for expression in *Yarrowia lipolytica*. This was possible by first determining the *Y. lipolytica* codon usage profile (see PCT Publication No. WO 04/101757 and U.S. Pat. No. 7,125,672) and identifying those codons that were preferred. Then, for further optimization of gene expression in *Y. lipolytica*, the consensus sequence around the 'ATG' initiation codon was determined. This optimization resulted in modification of 196 bp of the 1350 bp coding region (14.5%) and optimization of 189 codons of the total 449 codons (42%). None of the modifications in the codon-optimized gene ("EgD5S"; SEQ ID NO:3) changed the amino acid sequence of the encoded protein (SEQ ID NO:2). As described in Example 11, the codon-optimized gene was 36% more efficient desaturating DGLA to ARA than the wildtype gene, when expressed in *Y. lipolytica*.

One skilled in the art would be able to use the teachings herein to create various other codon-optimized delta-5 desaturase proteins suitable for optimal expression in alternate hosts (i.e., other than *Yarrowia lipolytica*), based on the wildtype EgD5 sequence. Accordingly, the instant invention relates to any codon-optimized delta-5 desaturase protein that is derived from the wildtype EgD5 (i.e., encoded by SEQ ID NO:2). This includes, but is not limited to, the nucleotide sequence set forth in SEQ ID NO:3, which encodes a synthetic delta-5 desaturase protein (i.e., EgD5S) that was codon-optimized for expression in *Yarrowia lipolytica*.

Identification and Isolation of Homologs

Any of the instant desaturase sequences (i.e., EgD5, EgD5S) or portions thereof may be used to search for delta-5 desaturase homologs in the same or other bacterial, algal, fungal, euglenoid or plant species using sequence analysis software. In general, such computer software matches similar sequences by assigning degrees of homology to various substitutions, deletions, and other modifications.

Alternatively, any of the instant desaturase sequences or portions thereof may also be employed as hybridization reagents for the identification of delta-5 homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the delta-5 desaturase nucleic acid fragments described herein (or any homologs identified thereof) may be used to isolate genes encoding homologous proteins from the same or other bacterial, algal, fungal, euglenoid or plant species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Natl. Acad. Sci. U.S.A.*, 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, genes encoding similar proteins or polypeptides to the delta-5 desaturases described herein could be isolated directly by using all or a portion of the instant nucleic acid fragments as DNA hybridization probes to screen libraries from e.g., any desired yeast or fungus using methodology well known to those skilled in the art (wherein those organisms producing ARA [or derivatives thereof] would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *Proc. Natl Acad. Sci. U.S.A.*, 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *Proc. Natl. Acad. Sci. U.S.A.*, 86:5673 (1989); Loh et al., *Science*, 243:217 (1989)).

In other embodiments, any of the delta-5 desaturase nucleic acid fragments described herein (or any homologs identified thereof) may be used for creation of new and improved fatty acid desaturases. As is well known in the art, in vitro mutagenesis and selection, chemical mutagenesis, "gene shuffling" methods or other means can be employed to obtain mutations of naturally occurring desaturase genes. Alternatively, improved fatty acids may be synthesized by domain swapping, wherein a functional domain from any of the delta-5 desaturase nucleic acid fragments described herein are exchanged with a functional domain in an alternate desaturase gene to thereby result in a novel protein.

Methods for Production of Various Omega-3 and/or Omega-6 Fatty Acids

It is expected that introduction of chimeric genes encoding the delta-5 desaturases described herein (i.e., EgD5, EgD5S or other mutant enzymes, codon-optimized enzymes or homologs thereof), under the control of the appropriate promoters, will result in increased production of ARA and/or EPA in the transformed host organism, respectively. As such, the present invention encompasses a method for the direct production of PUFAs comprising exposing a fatty acid substrate (i.e., DGLA or ETA) to the desaturase enzymes described herein (e.g., EgD5, EgD5S), such that the substrate is converted to the desired fatty acid product (i.e., ARA or EPA, respectively).

More specifically, it is an object of the present invention to provide a method for the production of ARA in a host cell (e.g., oleaginous yeast, soybean), wherein the host cell comprises:
  (i) an isolated nucleotide molecule encoding a delta-5 desaturase polypeptide having at least 39% identity when compared to a polypeptide having an amino acid sequence as set forth in SEQ ID NO:2, based on BLASTP algorithms or Clustal W alignment methods; and,
  (ii) a source of dihomo-γ-linoleic acid;
wherein the host cell is grown under conditions such that the delta-5 desaturase is expressed and the DGLA is converted to ARA, and wherein the ARA is optionally recovered.

The person of skill in the art will recognize that the broad substrate range of the delta-5 desaturase may additionally allow for the use of the enzyme for the conversion of ETA to EPA. Accordingly the invention provides a method for the production of EPA, wherein the host cell comprises:
  (i) an isolated nucleotide molecule encoding a delta-5 desaturase polypeptide having at least 39% identity when compared to a polypeptide having an amino acid sequence as set forth in SEQ ID NO:2, based on BLASTP algorithms or Clustal W alignment methods; and,
  (ii) a source of eicosatetraenoic acid;
wherein the host cell is grown under conditions such that the delta-5 desaturase is expressed and the ETA is converted to EPA, and wherein the EPA is optionally recovered.

Alternatively, each delta-5 desaturase gene and its corresponding enzyme product described herein can be used indirectly for the production of omega-3 fatty acids (see U.S. Patent Publication No. 2005/0136519). Indirect production of omega-3/omega-6 PUFAs occurs wherein the fatty acid substrate is converted indirectly into the desired fatty acid product, via means of an intermediate step(s) or pathway intermediate(s). Thus, it is contemplated that the delta-5 desaturases described herein (e.g., EgD5, EgD5S or other mutant enzymes, codon-optimized enzymes or homologs thereof) may be expressed in conjunction with additional genes encoding enzymes of the PUFA biosynthetic pathway (e.g., delta-6 desaturases, $C_{18/20}$ elongases, delta-17 desaturases, delta-15 desaturases, delta-9 desaturases, delta-12 desaturases, $C_{14/16}$ elongases, $C_{16/18}$ elongases, delta-9 elongases, delta-8 desaturases, delta-4 desaturases, $C_{20/22}$ elongases) to result in higher levels of production of longer-chain omega-3 fatty acids (e.g., EPA, DPA and DHA). The particular genes included within a particular expression cassette will depend on the host cell (and its PUFA profile and/or desaturase/elongase profile), the availability of substrate and the desired end product(s).

In alternative embodiments, it may be useful to disrupt a host organism's native delta-5 desaturase, based on the complete sequences described herein, the complement of those complete sequences, substantial portions of those sequences, codon-optimized desaturases derived therefrom and those sequences that are substantially homologous thereto.

Plant Expression Systems, Cassettes and Vectors, and Transformation

In one embodiment, this invention concerns a recombinant construct comprising any one of the delta-5 desaturase polynucleotides of the invention operably linked to at least one regulatory sequence suitable for expression in a plant. A promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the delta-5 desaturase coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the alpha prime subunit of beta conglycinin promoter, the Kunitz trypsin inhibitor 3 promoter, the annexin promoter, the glycinin Gy1 promoter, the beta subunit of beta conglycinin promoter, the P34/Gly Bd m 30K promoter, the albumin promoter, the Leg A1 promoter and the Leg A2 promoter.

The annexin, or P34, promoter is described in PCT Publication No. WO 2004/071178 (published Aug. 26, 2004). The level of activity of the annexin promoter is comparable to that of many known strong promoters, such as: (1) the CaMV 35S promoter (Atanassova et al., *Plant Mol. Biol.* 37:275-285 (1998); Battraw and Hall, *Plant Mol. Biol.* 15:527-538 (1990); Holtorf et al., *Plant Mol. Biol.* 29:637-646 (1995); Jefferson et al., *EMBO J.* 6:3901-3907 (1987); Wilmink et al., *Plant Mol. Biol.* 28:949-955 (1995)); (2) the *Arabidopsis* oleosin promoters (Plant et al., *Plant Mol. Biol.* 25:193-205

(1994); Li, Texas A&M University Ph.D. dissertation, pp. 107-128 (1997)); (3) the *Arabidopsis* ubiquitin extension protein promoters (Callis et al., *J Biol. Chem.* 265(21):12486-93 (1990)); (4) a tomato ubiquitin gene promoter (Rollfinke et al., *Gene.* 211(2):267-76 (1998)); (5) a soybean heat shock protein promoter (Schoffl et al., *Mol Gen Genet.* 217(2-3): 246-53 (1989)); and, (6) a maize H3 histone gene promoter (Atanassova et al., *Plant Mol Biol.* 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.* 10:112-122 (1989); Ellerstrom et al., *Plant Mol. Biol.* 32:1019-1027 (1996); Keddie et al., *Plant Mol. Biol.* 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific delta-5 desaturase coding sequence, the promoter is then operably linked in a sense orientation using conventional means well known to those skilled in the art.

Standard recombinant DNA and molecular cloning techniques used herein are well known in the art and are described more fully in Sambrook, J. et al., In *Molecular Cloning: A Laboratory Manual;* $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In *Current Protocols in Molecular Biology*; John Wiley and Sons: New York, 1990 (hereinafter "Ausubel et al., 1990").

Once the recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long-chain PUFA which is then optionally recovered and purified.

The recombinant constructs of the invention may be introduced into one plant cell; or, alternatively, each construct may be introduced into separate plant cells.

Expression in a plant cell may be accomplished in a transient or stable fashion as is described above.

The desired long-chain PUFAs can be expressed in seed. Also within the scope of this invention are seeds or plant parts obtained from such transformed plants.

Plant parts include differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or a group of tissues that constitute a morphologically and functionally distinct part of a plant. The term "genome" refers to the following: (1) the entire complement of genetic material (genes and non-coding sequences) that is present in each cell of an organism, or virus or organelle; and/or (2) a complete set of chromosomes inherited as a (haploid) unit from one parent.

Thus, this invention also concerns a method for transforming a cell, comprising transforming a cell with the recombinant construct of the invention and selecting those cells transformed with the recombinant construct of the invention.

Also of interest is a method for producing a transformed plant comprising transforming a plant cell with the delta-5 desaturase polynucleotides of the instant invention and regenerating a plant from the transformed plant cell.

Methods for transforming dicots (primarily by use of *Agrobacterium tumefaciens*) and obtaining transgenic plants have been published, among others, for: cotton (U.S. Pat. No. 5,004,863; U.S. Pat. No. 5,159,135); soybean (U.S. Pat. No. 5,569,834; U.S. Pat. No. 5,416,011); *Brassica* (U.S. Pat. No. 5,463,174); peanut (Cheng et al. *Plant Cell Rep.* 15:653-657 (1996); McKently et al. *Plant Cell Rep.* 14:699-703 (1995)); papaya (Ling, K. et al. *Bio/technology* 9:752-758 (1991)); and pea (Grant et al. *Plant Cell Rep.* 15:254-258 (1995)). For a review of other commonly used methods of plant transformation see Newell, C. A. (*Mol. Biotechnol.* 16:53-65 (2000)). One of these methods of transformation uses *Agrobacterium rhizogenes* (Tepfler, M. and Causse-Delbart, F. *Microbiol. Sci.* 4:24-28 (1987)). Transformation of soybeans using direct delivery of DNA has been published using PEG fusion (PCT Publication No. WO 92/17598), electroporation (Chowrira, G. M. et al., *Mol. Biotechnol.* 3:17-23 (1995); Christou, P. et al., *Proc. Natl. Acad. Sci.* U.S.A. 84:3962-3966 (1987)), microinjection and particle bombardement (McCabe, D. E. et. al., *Bio/Technology* 6:923 (1988); Christou et al., *Plant Physiol.* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for: the construction, manipulation and isolation of macromolecules (e.g., DNA molecules, plasmids, etc.); the generation of recombinant DNA fragments and recombinant expression constructs; and, the screening and isolating of clones. See, for example: Sambrook et al., Molecular Cloning: A Laboratory Manual, Cold Spring Harbor: NY (1989); Maliga et al., Methods in Plant Molecular Biology, Cold Spring Harbor: NY (1995); Birren et al., Genome Analysis: Detecting Genes, Vol. 1, Cold Spring Harbor: NY (1998); Birren et al., Genome Analysis:

Analyzing DNA, Vol. 2, Cold Spring Harbor: NY (1998); Plant Molecular Biology: A Laboratory Manual, eds. Clark, Springer: NY (1997).

Examples of oilseed plants include, but are not limited to: soybean, *Brassica* species, sunflower, maize, cotton, flax and safflower.

Examples of PUFAs having at least twenty carbon atoms and four or more carbon-carbon double bonds include, but are not limited to, omega-3 fatty acids such as EPA, DPA and DHA and the omega-6 fatty acid ARA. Seeds obtained from such plants are also within the scope of this invention as well as oil obtained from such seeds.

Thus, in one embodiment this invention concerns an oilseed plant comprising:
 (a) a first recombinant DNA construct comprising an isolated polynucleotide encoding a delta-5 desaturase polypeptide, operably linked to at least one regulatory sequence; and,
 (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-9 elongase, a delta-12 desaturase, a delta-15 desaturase, a delta-17 desaturase, a $C_{14/16}$ elongase, a $C_{16/18}$ elongase, a $C_{18/20}$ elongase and a $C_{20/22}$ elongase.

Additional desaturases are discussed, for example, in U.S. Pat. Nos. 6,075,183, 5,968,809, 6,136,574, 5,972,664, 6,051,754, 6,410,288 and PCT Publication Nos. WO 98/46763, WO 98/46764, WO 00/12720 and WO 00/40705.

The choice of combination of cassettes used depends in part on the PUFA profile and/or desaturase/elongase profile of the oilseed plant cells to be transformed and the long-chain PUFA which is to be expressed.

In another aspect, this invention concerns a method for making long-chain PUFAs in a plant cell comprising:
 (a) transforming a cell with the recombinant construct of the invention; and,
 (b) selecting those transformed cells that make long-chain PUFAs.

In still another aspect, this invention concerns a method for producing at least one PUFA in a soybean cell comprising:
 (a) transforming a soybean cell with a first recombinant DNA construct comprising:
  (i) an isolated polynucleotide encoding a delta-5 desaturase polypeptide, operably linked to at least one regulatory sequence; and,
  (ii) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-9 elongase, a delta-12 desaturase, a delta-15 desaturase, a delta-17 desaturase, a $C_{14/16}$ elongase, a $C_{16/18}$ elongase, a $C_{18/20}$ elongase and a $C_{20/22}$ elongase;
 (b) regenerating a soybean plant from the transformed cell of step (a); and,
 (c) selecting those seeds obtained from the plants of step (b) having an altered level of PUFAs when compared to the level in seeds obtained from a nontransformed soybean plant.

In other preferred embodiments, the at least one additional recombinant DNA construct encodes a polypeptide having delta-9 elongase activity, e.g., the delta-9 elongase isolated or derived from *Isochrysis galbana* (GenBank Accession No. AF390174; IgD9e) or the delta-9 elongase isolated or derived from *Euglena gracilis*.

In other preferred embodiments, the at least one additional recombinant DNA construct encodes a polypeptide having delta-8 desaturase activity. For example, PCT Publication No. WO 2005/103253 (published Apr. 22, 2005) discloses amino acid and nucleic acid sequences for a delta-8 desaturase enzyme from *Pavlova salina* (see also U.S. Publication No. 2005/0273885). Sayanova et al. (*FEBS Lett.* 580:1946-1952 (2006)) describes the isolation and characterization of a cDNA from the free living soil amoeba *Acanthamoeba castellanii* that, when expressed in *Arabidopsis*, encodes a $C_{20}$ delta-8 desaturase. Also, Applicants' Assignee's co-pending application having Provisional Application No. 60/795,810 filed Apr. 28, 2006 (Attorney Docket No. BB-1566) discloses amino acid and nucleic acid sequences for a delta-8 desaturase enzyme from *Pavlova lutheri* (CCMP459). U.S. Provisional Application No. 60/853,563 (filed Oct. 23, 2006; Attorney Docket No. BB-1574) discloses amino acid and nucleic acid sequences for a delta-8 desaturase enzyme from *Tetruetreptia pomquetensis* CCMP1491, *Eutreptiella* sp. CCMP389 and *Eutreptiella cf_gymnastica* CCMP1594.

Microbial Expression Systems, Cassettes and Vectors, and Transformation

The delta-5 desaturase genes and gene products described herein (i.e., EgD5, or other mutant enzymes, codon-optimized enzymes or homologs thereof) may also be produced in heterologous microbial host cells, particularly in the cells of oleaginous yeasts (e.g., *Yarrowia lipolytica*).

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors or DNA cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed microbial host cell, although it is to be understood that such control regions need not be derived from the genes native to the specific species chosen as a production host.

Initiation control regions or promoters which are useful to drive expression of the instant delta-5 desaturase ORFs in the desired microbial host cell are numerous and familiar to those skilled in the art. Virtually any promoter capable of directing expression of these genes in the selected host cell is suitable for the present invention. Expression in a microbial host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see PCT Publication Nos. WO 2004/101757 and WO 2006/052870 for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, when the microbial host is a yeast cell, the termination region is derived from a yeast gene (particularly *Saccharomyces, Schizosaccharomyces, Candida, Yarrowia* or *Kluyveromyces*). The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included. Although not intended to be limiting, termination regions useful in the disclosure herein include: ~100 bp of the 3' region of the *Yarrowia lipolytica* extracellular protease (XPR; GenBank Accession No. M17741); the acyl-coA oxidase (Aco3: GenBank Accession No. AJ001301 and No. CAA04661; Pox3: GenBank Accession No. XP_503244) terminators; the Pex20 (GenBank Accession No. AF054613) terminator; the Pex16 (GenBank Accession No. U75433) terminator; the Lip1 (GenBank Accession No. Z50020) terminator; the Lip2 (GenBank Accession No. AJ012632) terminator; and the 3-oxoacyl-coA thiolase (OCT; GenBank Accession No. X69988) terminator.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the microbial host cell. More specifically, some of the molecular features that have been manipulated to control gene expression include: (1) the nature of the relevant transcriptional promoter and terminator sequences; (2) the number of copies of the cloned gene and whether the gene is plasmid-borne or integrated into the genome of the host cell; (3) the final cellular location of the synthesized foreign protein; (4) the efficiency of translation and correct folding of the protein in the host organism; (5) the intrinsic stability of the mRNA and protein of the cloned gene within the host cell; and (6) the codon usage within the cloned gene, such that its frequency approaches the frequency of preferred codon usage of the host cell. Each of these types of modifications are encompassed in the present invention, as means to further optimize expression of the delta-5 desaturase described herein.

Once the DNA encoding a polypeptide suitable for expression in an appropriate microbial host cell (e.g., oleaginous yeast) has been obtained (e.g., a chimeric gene comprising a promoter, ORF and terminator), it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

In the present invention, the preferred method of expressing genes in *Yarrowia lipolytica* is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the delta-12 desaturase gene locus (PCT Publication No. WO2004/104167), the Lip1 gene locus (GenBank Accession No. Z50020) and/or the Lip2 gene locus (GenBank Accession No. AJ012632)].

Advantageously, the Ura3 gene can be used repeatedly in combination with 5-fluoroorotic acid (5-fluorouracil-6-carboxylic acid monohydrate; "5-FOA") selection (infra), to readily permit genetic modifications to be integrated into the *Yarrowia* genome in a facile manner.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a microbial host cell by any standard technique. These techniques include transformation (e.g., lithium acetate transformation [*Methods in Enzymology*, 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. Pat. No. 4,880,741 and U.S. Pat. No. 5,071,764 and Chen, D. C. et al. (*Appl. Microbiol. Biotechnol.*, 48(2): 232-235 (1997)).

For convenience, a host cell that has been manipulated by any method to take up a DNA sequence (e.g., an expression cassette) will be referred to as "transformed" or "recombinant" herein. Thus, the term "transformed" and "recombinant" are used interchangeably herein. The transformed host will have at least one copy of the expression construct and may have two or more, depending upon whether the gene is integrated into the genome, amplified or is present on an extrachromosomal element having multiple copy numbers.

The transformed host cell can be identified by various selection techniques, as described in PCT Publication Nos. WO 2004/101757 and WO 2006/052870. Preferred selection methods for use herein are resistance to kanamycin, hygromycin and the amino glycoside G418, as well as ability to grow on media lacking uracil, leucine, lysine, tryptophan or histidine. In alternate embodiments, 5-FOA is used for selection of yeast Ura– mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of Ura⁻ mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura– phenotype, wherein selection occurs based on 5-FOA resistance. Then, a cluster of multiple chimeric genes and a new Ura3 gene can be integrated into a different locus of the Yarrowia genome to thereby produce a new strain having a Ura+ phenotype. Subsequent integration produces a new Ura3– strain (again identified using 5-FOA selection), when the introduced Ura3 gene is knocked out. Thus, the Ura3 gene (in combination with 5-FOA selection) can be used as a selection marker in multiple rounds of transformation.

Following transformation, substrates suitable for the instant delta-5 desaturase (and, optionally other PUFA enzymes that are co-expressed within the host cell) may be produced by the host either naturally or transgenically, or they may be provided exogenously.

Microbial host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. Based on the needs of the Applicants' Assignee, the genes described in the instant invention will be expressed in an oleaginous yeast (and in particular *Yarrowia lipolytica*); however, it is contemplated that because transcription, translation and the protein biosynthetic apparatus is highly conserved, any bacteria, yeast, algae and/or fungus will be a suitable microbial host for expression of the present nucleic acid fragments.

Preferred microbial hosts, however, are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)).

Historically, various strains of Y. lipolytica have been used for the manufacture and production of: isocitrate lyase; lipases; polyhydroxyalkanoates; citric acid; erythritol; 2-oxoglutaric acid; γ-decalactone; γ-dodecalatone; and pyruvic acid. Specific teachings applicable for engineering ARA, EPA and DHA production in *Y. lipolytica* are provided in U.S. Patent Application No. 11/264784 (WO 2006/055322) now U.S. Patent 7,588,931, U.S. Patent Application No. 11/265761 (WO 2006/052870) and U.S. Patent Application No. 11/264737(WO 2006/052871) now U.S. Patent 7,550,286, respectively.

Other preferred microbial hosts include oleaginous bacteria, algae and other fungi; and, within this broad group of microbial hosts, of particular interest are microorganisms that synthesize omega-3/omega-6 fatty acids (or those that can be genetically engineered for this purpose [e.g., other yeast such as *Saccharomyces cerevisiae*]). Thus, for example, transformation of *Mortierella alpina* (which is commercially used for production of ARA) with any of the present delta-5 desaturase genes under the control of inducible or regulated promoters could yield a transformant organism capable of synthesizing increased quantities of DGLA. The method of transformation of *M. alpina* is described by Mackenzie et al. (*Appl. Environ. Microbiol.*, 66:4655 (2000)). Similarly, methods for transformation of Thraustochytriales microorganisms are disclosed in U.S. Pat. No. 7,001,772.

Based on the teachings described above, in one embodiment this invention is drawn to a method of producing either ARA or EPA, respectively, comprising:
(a) providing an oleaginous yeast comprising:
 (i) a first recombinant DNA construct comprising an isolated polynucleotide encoding a delta-5 desaturase polypeptide, operably linked to at least one regulatory sequence; and,
 (ii) a source of desaturase substrate consisting of either DGLA or ETA, respectively; and,
(b) growing the yeast of step (a) in the presence of a suitable fermentable carbon source wherein the gene encoding the delta-5 desaturase polypeptide is expressed and DGLA is converted to ARA or ETA is converted to EPA, respectively; and,
(c) optionally recovering the ARA or EPA, respectively, of step (b).

Substrate feeding may be required.

Of course, since naturally produced PUFAs in oleaginous yeast are limited to 18:2 fatty acids (i.e., LA), and less commonly, 18:3 fatty acids (i.e., ALA), in more preferred embodiments of the present invention the oleaginous yeast will be genetically engineered to express multiple enzymes necessary for long-chain PUFA biosynthesis (thereby enabling production of e.g., ARA, EPA, DPA and DHA), in addition to the delta-5 desaturases described herein.

Specifically, in one embodiment this invention concerns an oleaginous yeast comprising:
(a) a first recombinant DNA construct comprising an isolated polynucleotide encoding a delta-5 desaturase polypeptide, operably linked to at least one regulatory sequence; and,
(b) at least one additional recombinant DNA construct comprising an isolated polynucleotide, operably linked to at least one regulatory sequence, encoding a polypeptide selected from the group consisting of: a delta-4 desaturase, a delta-5 desaturase, delta-6 desaturase, a delta-9 desaturase, a delta-12 desaturase, a delta-15 desaturase, a delta-17 desaturase, a delta-9 elongase, a $C_{14/16}$ elongase, a $C_{16/18}$ elongase, a $C_{18/20}$ elongase and a $C_{20/22}$ elongase.

In particularly preferred embodiments, the at least one additional recombinant DNA construct encodes a polypeptide having delta-9 elongase activity, e.g., the delta-9 elongase isolated or derived from *Isochrysis galbana* (GenBank Accession No. AF390174; IgD9e or IgD9eS) or the delta-9 elongase isolated or derived from *Euglena gracilis*.

Metabolic Engineering of Omega-3 and/or Omega-6 Fatty Acid Biosynthesis in Microbes Methods for manipulating biochemical pathways are well known to those skilled in the art; and, it is expected that numerous manipulations will be possible to maximize omega-3 and/or omega-6 fatty acid biosynthesis in oleaginous yeasts, and particularly, in *Yarrowia lipolytica*. This manipulation may require metabolic engineering directly within the PUFA biosynthetic pathway or additional coordinated manipulation of various other metabolic pathways.

In the case of manipulations within the PUFA biosynthetic pathway, it may be desirable to increase the production of LA to enable increased production of omega-6 and/or omega-3 fatty acids. Introducing and/or amplifying genes encoding delta-9 and/or delta-12 desaturases may accomplish this. To maximize production of omega-6 unsaturated fatty acids, it is well known to one skilled in the art that production is favored in a host microorganism that is substantially free of ALA; thus, preferably, the host is selected or obtained by removing or inhibiting delta-15 or omega-3 type desaturase activity that permits conversion of LA to ALA. Alternatively, it may be desirable to maximize production of omega-3 fatty acids (and minimize synthesis of omega-6 fatty acids). In this example, one could utilize a host microorganism wherein the delta-12 desaturase activity that permits conversion of oleic acid to LA is removed or inhibited; subsequently, appropriate expression cassettes would be introduced into the host, along with appropriate substrates (e.g., ALA) for conversion to omega-3 fatty acid derivatives of ALA (e.g., STA, ETrA, ETA, EPA, DPA, DHA).

In alternate embodiments, biochemical pathways competing with the omega-3 and/or omega-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in PCT Publication Nos. WO 2006/055322, WO 2006/052870 and WO 2006/052871, respectively, as are desirable manipulations in the TAG biosynthetic pathway and the TAG degradation pathway (and associated techniques thereof).

Within the context of the present invention, it may be useful to modulate the expression of the fatty acid biosynthetic pathway by any one of the strategies described above. For example, the present invention provides methods whereby genes encoding key enzymes in the delta-9 elongase/delta-8 desaturase biosynthetic pathway are introduced into oleaginous yeasts for the production of omega-3 and/or omega-6 fatty acids. It will be particularly useful to express the present the delta-5 desaturase genes in oleaginous yeasts that do not naturally possess omega-3 and/or omega-6 fatty acid biosynthetic pathways and coordinate the expression of these genes, to maximize production of preferred PUFA products using various means for metabolic engineering of the host organism.

Microbial Fermentation Processes for PUFA Production

The transformed host cell is grown under conditions that optimize expression of chimeric desaturase genes and produce the greatest and the most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. *Yarrowia lipolytica* are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in PCT Publication No. WO 2004/101757. Although it is contemplated that the source of carbon utilized in the present invention may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in PCT Publication No. WO 2004/101757, as are various suitable fermentation process designs (i.e., batch, fed-batch and continuous) and considerations during growth.

Purification and Processing of PUFA Oils

PUFAs may be found in the host microorganisms and plants as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology*, 12(5/6): 463-491 (1992)). A brief review of downstream processing is also available by A. Singh and O. Ward (*Adv. Appl. Microbiol.*, 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of PCT Publication No. WO 2004/101757 for additional details. Methods of isolating seed oils are well known in the art: (Young et al., Processing of Fats and Oils, In *The Lipid Handbook*, Gunstone et al., eds., Chapter 5 pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in Table 3.

TABLE 3

Generalized Steps for Soybean Oil and Byproduct Production

| Process Step | Process | Impurities Removed and/or By-Products Obtained |
|---|---|---|
| #1 | soybean seed | |
| #2 | oil extraction | meal |
| #3 | degumming | lecithin |
| #4 | alkali or physical refining | gums, free fatty acids, pigments |
| #5 | water washing | soap |
| #6 | bleaching | color, soap, metal |
| #7 | (hydrogenation) | |
| #8 | (winterization) | stearine |
| #9 | deodorization | free fatty acids, tocopherols, sterols, volatiles |
| #10 | oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995). Soybean oil is liquid at room temperature because it is relatively low in saturated fatty acids when compared with oils such as coconut, palm, palm kernel and cocoa butter.

Plant and microbial oils containing PUFAs that have been refined and/or purified can be hydrogenated, to thereby result in fats with various melting properties and textures. Many processed fats (including spreads, confectionary fats, hard butters, margarines, baking shortenings, etc.) require varying degrees of solidity at room temperature and can only be produced through alteration of the source oil's physical properties. This is most commonly achieved through catalytic hydrogenation.

Hydrogenation is a chemical reaction in which hydrogen is added to the unsaturated fatty acid double bonds with the aid of a catalyst such as nickel. For example, high oleic soybean oil contains unsaturated oleic, LA and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have become somewhat controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

PUFA-Containing Oils for Use in Foodstuffs

The market place currently supports a large variety of food and feed products, incorporating omega-3 and/or omega-6 fatty acids (particularly ARA, EPA and DHA). It is contemplated that the plant/seed oils, altered seeds and microbial oils of the invention comprising PUFAs will function in food and feed products to impart the health benefits of current formulations. Compared to other vegetable oils, the oils of the invention are believed to function similarly to other oils in food applications from a physical standpoint (for example, partially hydrogenated oils such as soybean oil are widely used as ingredients for soft spreads, margarine and shortenings for baking and frying).

Plant/seed oils, altered seeds and microbial oils containing omega-3 and/or omega-6 fatty acids as described herein will be suitable for use in a variety of food and feed products including, but not limited to: food analogs, meat products, cereal products, baked foods, snack foods and dairy products. Additionally, the present plant/seed oils, altered seeds and microbial oils may be used in formulations to impart health benefit in medical foods including medical nutritionals, dietary supplements, infant formula as well as pharmaceutical products. One of skill in the art of food processing and food formulation will understand how the amount and composition of the plant and microbial oils may be added to the food or feed product. Such an amount will be referred to herein as an "effective" amount and will depend on the food or feed product, the diet that the product is intended to supplement or the medical condition that the medical food or medical nutritional is intended to correct or treat.

Food analogs can be made using processes well known to those skilled in the art. There can be mentioned meat analogs, cheese analogs, milk analogs and the like. Meat analogs made from soybeans contain soy protein or tofu and other ingredients mixed together to simulate various kinds of meats. These meat alternatives are sold as frozen, canned or dried foods. Usually, they can be used the same way as the foods they replace. Meat alternatives made from soybeans are excellent sources of protein, iron and B vitamins. Examples of meat analogs include, but are not limited to: ham analogs, sausage analogs, bacon analogs, and the like.

Food analogs can be classified as imitation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to, imitation milks and nondairy frozen desserts (e.g., those made from soybeans and/or soy protein products).

Meat products encompass a broad variety of products. In the United States "meat" includes "red meats" produced from cattle, hogs and sheep. In addition to the red meats there are poultry items which include chickens, turkeys, geese, guineas, ducks and the fish and shellfish. There is a wide assortment of seasoned and processed meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to: whole grain, crushed grain, grits, flour, bran, germ, breakfast cereals, extruded foods, pastas, and the like.

A baked goods product comprises any of the cereal food products mentioned above and has been baked or processed in a manner comparable to baking (i.e., to dry or harden by subjecting to heat). Examples of a baked good product include, but are not limited to: bread, cakes, doughnuts, bars, pastas, bread crumbs, baked snacks, mini-biscuits, mini-crackers, mini-cookies, and mini-pretzels. As was mentioned above, oils of the invention can be used as an ingredient.

A snack food product comprises any of the above or below described food products.

A fried food product comprises any of the above or below described food products that has been fried.

A health food product is any food product that imparts a health benefit. Many oilseed-derived food products may be considered as health foods.

A beverage can be in a liquid or in a dry powdered form.

For example, there can be mentioned non-carbonated drinks such as fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. "Infant formula" is defined herein as an enteral nutritional product which can be substituted for human breast milk in feeding infants and typically is composed of a desired percentage of fat mixed with desired percentages of carbohydrates and proteins in an aquous solution (e.g., see U.S. Pat. No. 4,670,285). Based on the worldwide composition studies, as well as levels specified by expert groups, average human breast milk typically contains about 0.20% to 0.40% of total fatty acids (assuming about 50% of calories from fat); and, generally the ratio of DHA to ARA would range from about 1:1 to 1:2 (see, e.g., formulations of Enfamil LIPIL™ (Mead Johnson & Company) and Similac Advance™ (Ross Products Division, Abbott Laboratories)). Infant formulas have a special role to play in the diets of infants because they are often the only source of nutrients for infants; and, although breast-feeding is still the best nourishment for infants, infant formula is a close enough second that babies not only survive but thrive.

A dairy product is a product derived from milk. A milk analog or nondairy product is derived from a source other than milk, for example, soymilk as was discussed above. These products include, but are not limited to: whole milk, skim milk, fermented milk products such as yoghurt or sour milk, cream, butter, condensed milk, dehydrated milk, coffee whitener, coffee creamer, ice cream, cheese, etc.

Additional food products into which the PUFA-containing oils of the invention could be included are, for example, chewing gums, confections and frostings, gelatins and puddings, hard and soft candies, jams and jellies, white granulated sugar, sugar substitutes, sweet sauces, toppings and syrups, and dry-blended powder mixes.

PUFA-Containing Oils for Use in Health Food Products and Pharmaceuticals

A health food product is any food product that imparts a health benefit and include functional foods, medical foods, medical nutritionals and dietary supplements. Additionally, the plant/seed oils, altered seeds and microbial oils of the invention may be used in standard pharmaceutical compositions (e.g., the long-chain PUFA containing oils could readily be incorporated into the any of the above mentioned food products, to thereby produce a functional or medical food). More concentrated formulations comprising PUFAs include capsules, powders, tablets softgels, gelcaps, liquid concentrations and emulsions which can be used as a dietary supplement in humans or animals other than humans.

PUFA-Containing Oils for Use in Animal Feeds

Animal feeds are generically defined herein as products intended for use as feed or for mixing in feed for animals other than humans. The plant/seed oils, altered seeds and microbial oils of the invention can be used as an ingredient in various animal feeds.

More specifically, although not limited therein, it is expected that the oils of the invention can be used within pet food products, ruminant and poultry food products and aquacultural food products. Pet food products are those products intended to be fed to a pet (e.g., dog, cat, bird, reptile, rodent). These products can include the cereal and health food products above, as well as meat and meat byproducts, soy protein products, grass and hay products (e.g., alfalfa, timothy, oat or brome grass, vegetables). Ruminant and poultry food products are those wherein the product is intended to be fed to an animal (e.g., turkeys, chickens, cattle, swine). As with the pet foods above, these products can include cereal and health food products, soy protein products, meat and meat byproducts, and grass and hay products as listed above. Aquacultural food products (or "aquafeeds") are those products intended to be used in aquafarming, i.e., which concerns the propagation, cultivation or farming of aquatic organisms and/or animals in fresh or marine waters.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T., *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* (XL1-Blue) competent cells were purchased from the Stratagene Company (San Diego, Calif.). *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "seq" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "pmole" mean micromole(s), "g" means gram(s), "µg" means microgram(s), "ng" means nanogram(s), "U" means unit(s), "bp" means base pair(s) and "kB" means kilobase(s).

Transformation and Cultivation of *Yarrowia lipolytica*

*Yarrowia lipolytica* strain ATCC #20362 was purchased from the American Type Culture Collection (Rockville, Md.). *Y. lipolytica* strains were usually grown at 28° C. on YPD agar (1% yeast extract, 2% bactopeptone, 2% glucose, 2% agar).

Transformation of *Y. lipolytica* was performed according to the method of Chen, D. C. et al. (*Appl. Microbiol. Biotechnol.*, 48(2):232-235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 µg sheared salmon sperm DNA. Then, approximately 500 ng of linearized plasmid DNA was incubated in 100 µl of resuspended cells, and maintained at 39° C. for 1 hr with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters were prepared by transesterification of the lipid extract with sodium methoxide (Roughan, G., and Nishida I., *Arch Biochem Biophys.*, 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Example 1

*Euglena gracilis* Growth Conditions, Lipid Profile and mRNA Isolation

*Euglena gracilis* was obtained from Dr. Richard Triemer's lab at Michigan State University (East Lansing, Mich.). From 10 mL of actively growing culture, a 1 mL aliquot was transferred into 250 mL of *Euglena gracilis* (Eg) Medium in a 500 mL glass bottle. Eg medium was made by combining 1 g of sodium acetate, 1 g of beef extract (Catalog #U126-01, Difco Laboratories, Detroit, Mich.), 2 g of Bacto® tryptone (Catalog #0123-17-3, Difco Laboratories) and 2 g of Bacto® yeast extract (Catalog #0127-17-9, Difco Laboratories) in 970 mL of water. After filter sterilizing, 30 mL of soil-water supernatant (Catalog #15-3790, Carolina Biological Supply Co., Burlington, N.C.) was aseptically added to give the final Eg medium. *Euglena gracilis* cultures were grown at 23° C. with a 16 h light, 8 h dark cycle for 2 weeks with no agitation.

Figure 2:
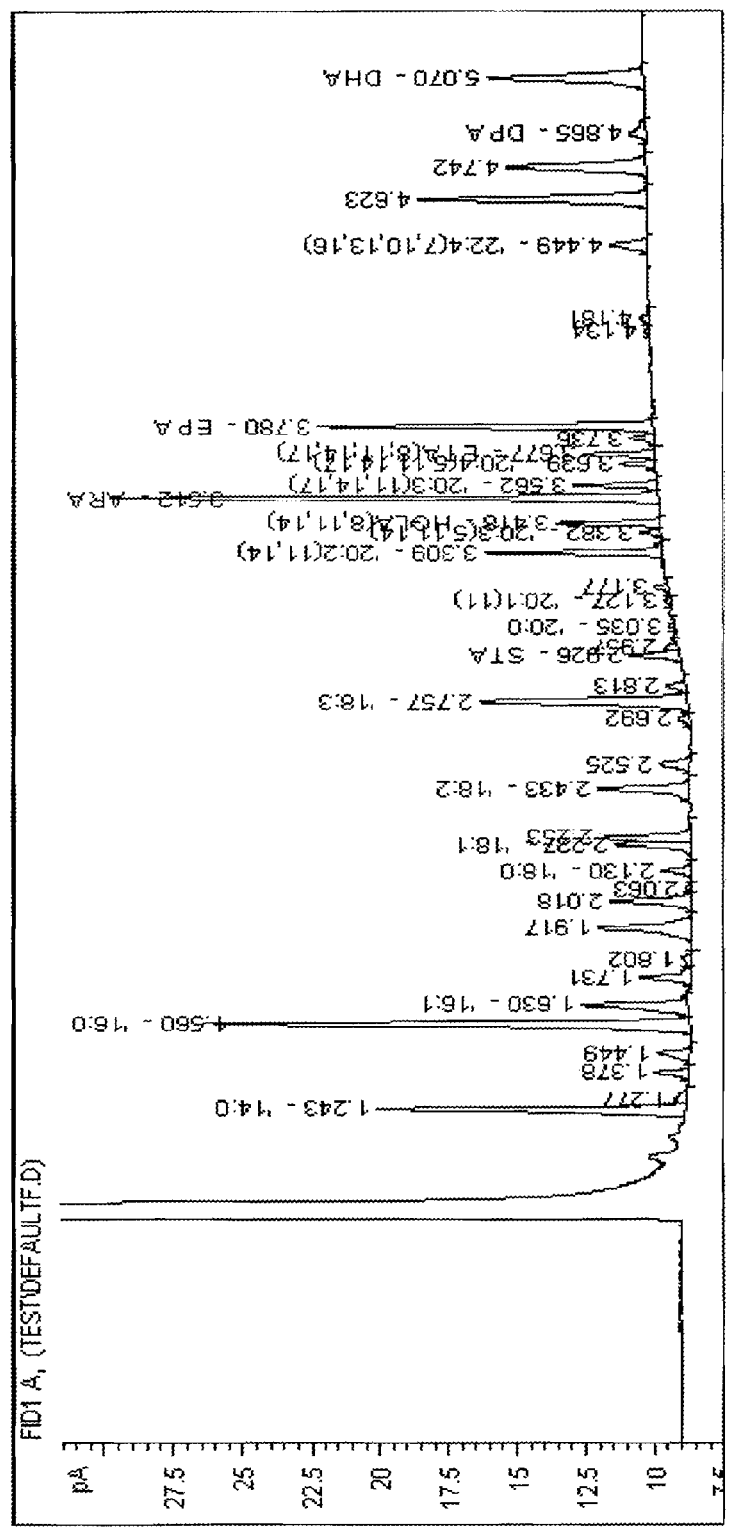
FIG. 2 shows a chromatogram of the lipid profile of an *Euglena gracilis* cell extract as described in Example 1.

After 2 weeks, 10 mL of culture was removed for lipid analysis and centrifuged at 1,800×g for 5 min. The pellet was washed once with water and re-centrifuged. The resulting pellet was dried for 5 min under vacuum, resuspended in 100 µL of trimethylsulfonium hydroxide (TMSH) and incubated at room temperature for 15 min with shaking. After this, 0.5 mL of hexane was added and the vials were incubated for 15 min at room temperature with shaking. Fatty acid methyl esters (5 µL injected from hexane layer) were separated and quantified using a Hewlett-Packard 6890 Gas Chromatograph fitted with an Omegawax 320 fused silica capillary column (Catalog #24152, Supelco Inc., Bellefonte, Pa.). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Catalog #U-99-A, Nu-Chek Prep, Inc., Elysian, Minn.) and the resulting chromatogram is shown in FIG. 2.

The remaining 2 week culture (240 mL) was pelleted by centrifugation at 1,800×g for 10 min, washed once with water and re-centrifuged. Total RNA was extracted from the resulting pellet using the RNA STAT-60™ reagent (TEL-TEST, Inc., Friendswood, Tex.) and following the manufacturer's protocol provided (use 5 mL of reagent, dissolved RNA in 0.5 mL of water). In this way, 1 mg of total RNA (2 mg/mL) was obtained from the pellet. The mRNA was isolated from 1 mg of total RNA using the mRNA Purification Kit (Amersham Biosciences, Piscataway, N.J.) following the manufacturer's protocol provided. In this way, 85 µg of mRNA was obtained.

Example 2

*Euglena gracilis* cDNA Synthesis cDNA was synthesized directly from the *Euglena gracilis* mRNA as follows. Specifically, the mRNA was primered with adapter primer AP (SEQ ID NO:65) from Invitrogen's 3'-RACE kit (Carlsbad, Calif.), in the presence of the Smart IV oligonucleotide (SEQ ID NO:66) from the BD-Clontech Creator™ Smart™ cDNA library kit (Mississauga, ON, Canada). The reverse transcription was done with Superscript II reverse transcriptase from the 3'-RACE kit according to the protocol of the Creator™ Smart™ cDNA library kit.

The 1$^{st}$ strand cDNA synthesis mixture was used as template for PCR amplification, using AP as the 3' primer and CDSIII 5' primer (SEQ ID NO:36) as the 5' primer (supplied with the BD-Clontech Creator™ Smart™ cDNA library kit). Amplification was carried out with Clontech Advantage cDNA polymerase mix at 94° C. for 30 sec, followed by 20 cycles of 94° C. for 10 sec and 68° C. for 6 min. A final extension at 68° C. for 7 min was performed.

Example 3

Isolation of a Portion of the Coding Region of the *Euglena gracilis*

Delta-5 Desaturase Gene

The present Example describes the identification of a portion of the *Euglena gracilis* gene encoding delta-5 desaturase (designated herein as "EgD5" (SEQ ID NOs:1 and 2)), by use of primers derived from conserved regions of other known delta-5 and delta-8 desaturase sequences.

Various considerations were made when evaluating which desaturases might enable design of degenerate primers suitable to isolate the *Euglena gracilis* delta-5 desaturase. Specifically, the Applicants knew that only delta-5, delta-6 and delta-8 desaturase sequences comprise a conserved 'HPGG' motif at their N-terminus (wherein the 'HPGG' domain is part of the well-known cytochrome B5 domain); in contrast, delta-9 desaturases possess a 'HPGG' motif of the cytochrome B5 domain at their C-terminus, while both delta-17 and delta-12 desaturases lack the cytochrome B5 domain. It was assumed that a delta-9 elongase/delta-8 desaturase pathway operated in *Euglena gracilis*; thus, among the desaturases sharing the N-terminal conserved 'HPGG' motif, only delta-5 and delta-8 desaturases were expected within the organism. Finally, although only a few delta-8 desaturase sequences are known, numerous delta-5 desaturase are publicly available. The Applicants selected those delta-5 desaturase sequences that possessed lower homology to "traditional" delta-5 desaturase genes and that also shared high homology to one another.

Based on the above, the four delta-5 desaturases and two delta-8 desaturases shown below in Table 3 were aligned, using the method of Clustal W (slow, accurate, Gonnet option; Thompson et al., *Nucleic Acids Res.*, 22:4673-4680 (1994)) of the MegAlign™ program of DNASTAR software.

TABLE 3

Delta-5 And Delta-8 Desaturases Aligned To Identify Regions Of Conserved Amino Acids

| Desaturase | Organism | Reference | SEQ ID NO: |
|---|---|---|---|
| delta-5 | *Pythium irregulare* | GenBank Accession No. AAL13311 | 12 |
| delta-5 | *Phytophthora megasperma* | GenBank Accession No. CAD53323 | 13 |
| delta-5 | *Phaeodactylum tricornutum* | GenBank Accession No. AAL92562 | 14 |
| delta-5 | *Dictyostelium discoideum* | GenBank Accession No. XP_640331 | 15 |
| delta-8 | *Euglena gracilis* | PCT Publications No. WO 2006/012325 and No. WO 2006/012326 | 16 |
| delta-8 | *Pavlova lutheri* | Example 12 (infra) | 18 |

Figure 3:
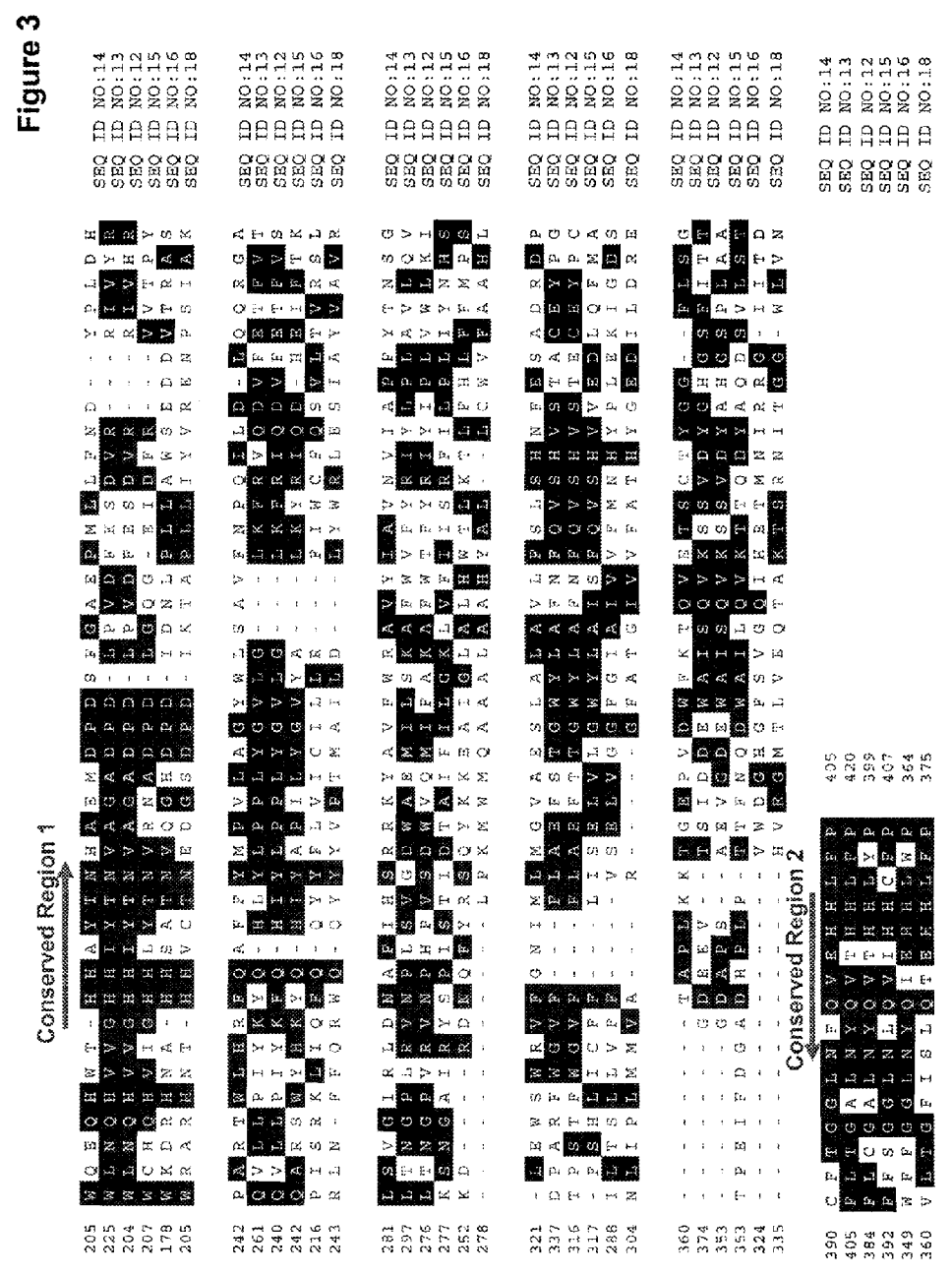

FIG. 3 shows a portion of the resulting alignment, containing several stretches of conserved amino acid sequence among the 6 different organisms. Based on this alignment, two sets of degenerate oligonucleotides were designed to amplify a portion of the coding region of the delta-5 desaturase gene from *Euglena gracilis*, corresponding to the regions of FIG. 3 that are labeled as "Conserved Region 1" and "Conserved Region 2". Specifically, the conserved amino acid sequence GHH(I/V)YTN (SEQ ID NO:19) was designed to correspond to Conserved Region 1, while the conserved amino acid sequence N(Y/F)Q(V/I)EHH (SEQ ID NO:20) was designed to correspond to Conserved Region 2. In order to reduce the degeneracy of the oligonucleotides, 4 sets of oligonucleotides (i.e., 5-1A, 5-1B, 5-1C and 5-1D) were designed to encode Conserved Region 1; and, 4 sets of oligonucleotides (i.e., 5-5AR, 5-5BR, 5-5CR and 5-5DR) were designed to encode the anti-sense strand of Conserved Region 2.

TABLE 4

Degenerate Oligonucleotides Used To Amplify The Delta-5 Desaturase Gene From *Euglena gracilis*

| Oligo-nucleotide Name | Sequence | SEQ ID NO |
|---|---|---|
| 5-1A | GGHCAYCAYRTBTAYACAAA | SEQ ID NO: 27 |
| 5-1B | GGHCAYCAYRTBTAYACCAA | SEQ ID NO: 28 |
| 5-1C | GGHCAYCAYRTBTAYACGAA | SEQ ID NO: 29 |
| 5-1D | GGHCAYCAYRTBTAYACTAA | SEQ ID NO: 30 |
| 5-5AR | TGRTGVACAAYYTGRWARTT | SEQ ID NO: 31 |
| 5-5BR | TGRTGVACTAYYTGRWARTT | SEQ ID NO: 32 |
| 5-5CR | TGRTGVACCAYYTGRWARTT | SEQ ID NO: 33 |
| 5-5DR | TGRTGVACGAYYTGRWARTT | SEQ ID NO: 34 |

[Note:
The nucleic acid degeneracy code used for SEQ ID NOs:27 to 34 was as follows: R = A/G; Y = C/T; W = A/T; B = G/T/C; V = G/A/C; and H = A/C/T.]

Based on the full-length sequences of the delta-5 sequences of Table 3, it was hypothesized that the *Euglena gracilis* delta-5 gene fragment amplified as described above would be about 600 bp in length (lacking about 210 amino acids at its N-terminal and 70 amino acids at its C-terminal).

A total of sixteen different PCR amplifications were conducted, as all combinations of the primers were tested (i.e., primer 5-1A was used with each of 5-5AR, 5-5BR, 5-5CR and 5-5DR, individually; similarly, primer 5-1B was used with each of 5-5AR, 5-5BR, 5-5CR and 5-5DR; etc.). The PCR amplifications were carried out in a 50 μl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 μg/mL BSA (final concentration), 200 μM each deoxyribonucleotide triphosphate, 10 pmole of each primer, 10 ng cDNA of *E. gracilis* and 1 μl of Taq DNA polymerase (Epicentre Technologies, Madison, Wis.). The thermocycler conditions were set for 35 cycles at 95° C. for 1 min, 56° C. for 30 sec and 72° C. for 1 min, followed by a final extension at 72° C. for 10 min.

The PCR products were purified using a Qiagen PCR purification kit (Valencia, Calif.). One fragment of the approximate expected size was then further purified following gel electrophoresis in 1% (w/v) agarose and then cloned into the pGEM-T-easy vector (Promega, Madison, Wis.). The ligated DNA was used to transform cells of *E. coli* DH10B and transformants were selected on LB (1% bacto-tryptone, 0.5% bacto-yeast extract and 1% NaCl) agar containing ampicillin (100 μg/mL). Analysis of the plasmid DNA from a group of 12 transformants confirmed the presence of the insert with the expected size (plasmids were designated as "pT-F10-1", "pT-F10-2", "pT-F10-3", etc. to "pT-F10-12").

Sequence analyses showed that pT-F10-1 contained a 590 bp fragment (SEQ ID NO:4), which encoded 196 amino acids (SEQ ID NO:5) (including amino acids that corresponded to Conserved Region 1 and 2). Identity of the Euglena sequence was determined by conducting BLAST (Basic Local Alignment Search Tool; Altschul, S. F., et al., *J. Mol. Biol.*, 215: 403-410 (1993)) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). The sequence was analyzed for similarity to all publicly available DNA sequences contained in the "nr" database using the BLASTN algorithm provided by the National Center for Biotechnology Information (NCBI). SEQ ID NO:4 was compared for similarity to all publicly available protein sequences contained in the "nr" database, using the BLASTX algorithm (Gish, W. and States, D. J., *Nature Genetics*, 3:266-272 (1993)) provided by the NCBI.

The results of the BLASTX comparison summarizing the sequence to which SEQ ID NO:4 has the most similarity are reported according to the % identity, % similarity and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance. Thus, the translated amino acid sequence of SEQ ID NO:4 (i.e., SEQ ID NO:5) had 38% identity and 53% similarity with the amino acid sequence of the delta-8-sphingolipid desaturase of *Thalassiosira pseudonana* (GenBank Accession No. AAX14502; SEQ ID NO:21), with an Expectation value of 5E-28; additionally, the partial fragment of SEQ ID NO:4 had 37% identity and 52% similarity with the delta-5 fatty acid desaturase of *Phaeodactylum tricornutum* (GenBank Accession No. AAL92562; SEQ ID NO:14), with an Expectation value of 7E-28.

Example 4

Isolation of the 5' Coding Region of the *Euglena gracilis* Delta-5 Desaturase Gene To isolate the N-terminal portion of the putative delta-5 desaturase identified in Example 3, a modified 5' RACE technique based on RACE protocols from two different companies (i.e., Invitrogen and BD-Clontech) was utilized.

Briefly, the double-stranded cDNA of *Euglena gracilis* (Example 2) was used as the template in a 5' RACE experiment, comprising two separate rounds of PCR amplification. In the first round of PCR amplification, the oligonucleotide primers consisted of a gene specific oligonucleotide (i.e., ODMW480; SEQ ID NO:35) and the generic oligonucleotide CDSIII 5' primer (SEQ ID NO:36) from the BD-Clontech Creator™ Smart™ cDNA library kit. The PCR amplifications were carried out in a 50 μl total volume, comprising: 25 μl of LA Taq™ pre-mix (TaKaRa Bio Inc., Otsu, Shiga, 520-2193, Japan), 10 pmole of each primer and 1 μl of Taq DNA polymerase (Epicentre Technologies, Madison, Wis.). The thermocycler conditions were set for 35 cycles at 95° C. for 1 min, 56° C. for 30 sec and 72° C. for 1 min, followed by a final extension at 72° C. for 10 min.

The second round of PCR amplification used 1 μl of the product from the first round PCR reaction as template. Primers consisted of a gene specific oligonucleotide (i.e., ODMW479; SEQ ID NO:37) and the generic oligonucleotide DNR CDS 5' (SEQ ID NO:38), supplied with BD-Clontech's Creator™ Smart™ cDNA library kit. Amplification was conducted as described above.

The products of the second round PCR reaction were electrophoresed in 1% (w/v) agarose. Products between 400 bp and 800 bp were then purified from the gel and cloned into the pGEM-T-easy vector (Promega, Madison, Wis.). The ligated DNA was used to transform *E. coli* DH10B and transformants were selected on LB agar containing ampicillin (100 µg/mL).

Analysis of the plasmid DNA from one transformant comprising the 5' region of the putative delta-5 desaturase gene confirmed the presence of the expected plasmid, designated pT-EgD5-5'C2. Sequence analyses showed that pT-EgD5-5'C2 contained a fragment of 797 bp (SEQ ID NO:6), which over-lapped with 238 bp from the 5' end of the 590 bp fragment of pT-F10-1 (Example 3, SEQ ID NO:4) and additionally provided 559 bp of 5' upstream sequence (SEQ ID NO:7) (FIG. 4). The sequence of pT-EgD5-5'C2 also corrected the sequence corresponding to Conserved Region 1, resulting from use of a degenerate oligonucleotide for initial PCR amplification of the 590 bp fragment in pT-F10-1 (Example 3). However, there was no translation initiation codon in the extended 797 bp fragment of SEQ ID NO:6.

A second round of the modified 5' RACE was carried out as described above, except that oligonucleotides YL791 (SEQ ID NO:39) and YL792 (SEQ ID NO:40) were used as gene-specific primers. Products between 200 bp and 400 bp were then purified from a gel and cloned into the pGEM-T-easy vector (Promega, Madison, Wis.). The ligated DNA was transformed into *E. coli* DH10B and transformants were selected on LB agar containing ampicillin (100 µg/mL).

Analysis of the plasmid DNA from one transformant comprising the 5' region of the putative delta-5 desaturase gene confirmed the presence of the expected plasmid, designated pT-EgD5-5'2$^{nd}$. Sequence analyses showed that pT-EgD5-5'2$^{nd}$ contained a fragment of 273 bp (SEQ ID NO:8), which over-lapped with 253 bp of the 5' end of the DNA fragment in pT-EgD5-5'C2 described above and additionally provided 20 bp of 5' upstream sequence (SEQ ID NO:9). Seventeen (17) bp of the 20 bp encoded the N-terminal portion of the putative delta-5 desaturase gene, including the translation initiation codon, thus providing the complete 5' sequence of the gene.

Example 5

Isolation of the 3' Coding Region of the *Euglena gracilis* Delta-5 Desaturase Gene To isolate the C-terminal portion of the putative delta-5 desaturase identified in Example 3, a 3' RACE technique was utilized. The methodology was described above in Example 4; however, the primers used on both the first and second round of PCR amplification were as shown below in Table 5.

TABLE 5

Oligonucleotide Primers Used For 3' RACE

| PCR Amplification | Gene Specific Oligonucleotide | Generic Oligonucleotide |
| --- | --- | --- |
| 1$^{st}$ Round | ODMW469 (SEQ ID NO: 41) | AUAP (SEQ ID NO: 42) |
| 2$^{nd}$ Round | YL470 (SEQ ID NO: 43) | AUAP (SEQ ID NO: 42) |

* Primer AUAP was supplied in Invitrogen's 3'-RACE kit (Carlsbad, CA).

Following isolation and purification of products (i.e., 400-800 bp), the fragments were cloned into the pGEM-T-easy vector (Promega) and transformed into *E. coli* DH10B, as in Example 4.

Analysis of the plasmid DNA from one transformant comprising the 3' region of the delta-5 desaturase gene confirmed the presence of the expected plasmid, designated pT-EgD5-3'. Sequence analyses showed that pT-EgD5-3' contained a fragment of 728 bp (SEQ ID NO:10), which over-lapped with 264 bp from the 3' end of the 590 bp fragment of pT-F10-1 (Example 3, SEQ ID NO:4) and provided 464 bp of additional 3' downstream sequence (SEQ ID NO:11). The first 184 bp of the 464 bp fragment included within pT-EgD5-3' encoded the C-terminal coding region (including the translation stop codon) of the putative delta-5 desaturase gene. The sequence of pT-EgD5-3' also corrected the sequence corresponding to Conserved Region 2, resulting from use of a degenerate oligonucleotide for initial PCR amplification of the 590 bp fragment in pT-F10-1 (Example 3).

After 2 rounds of 5' RACE and one round of 3' RACE, the DNA sequence of the entire putative *Euglena gracilis* delta-5 desaturase (EgD5) coding region was determined. As shown in FIG. 4, the EgD5 CDS was 1350 bp in length (SEQ ID NO:1) and encoded a polypeptide with 449 amino acids (SEQ ID NO:2), based on alignment of SEQ ID NOs:4, 6, 8 and 10. The results of BLASTP searches using the full length EgD5 gene as the query sequence showed that it shared 39% identity and 56% similarity with the delta-5 fatty acid desaturase of *Phaeodactylum tricornutum* (GenBank Accession No. AAL92562; SEQ ID NO:14), with an Expectation value of 1E-80. Additionally, the full length EgD5 gene shared 37% identity and 55% similarity with the delta-8-sphingolipid desaturase of *Thalassiosira pseudonana* (GenBank Accession No. AAX14502; SEQ ID NO:21), with an Expectation value of 3E-75.

Example 6

Generation of Construct pDMW367, Comprising EqD5

The present Example describes the generation of pDMW367, comprising a chimeric FBAIN::EgD5::Pex20-3' gene (FIG. 5C). This was designed to integrate the chimeric gene into the genome of *Yarrowia lipolytica* and then study the function of the *Euglena gracilis* delta-5 desaturase in *Yarrowia lipolytica*.

Based on the full length cDNA of EgD5 (SEQ ID NO:1), oligonucleotides YL794 and YL797 (SEQ ID NOs:44 and 45, respectively) were used as primers to amplify the first portion of EgD5 (FIG. 5A). Primer YL794 contained a NcoI site and primer YL797 contained a HindIII site. Then, primers YL796 and YL795 (SEQ ID NOs:46 and 47, respectively) were used as primers to amplify the second portion of EgD5. Primer YL796 contained a HindIII site, while primer YL797 contained a NotI site. The PCR reactions, using primer pairs YL794/YL797 or YL796/YL795, with *Euglena gracilis* cDNA (Example 2) as template, were individually carried out in a 50 µl total volume comprising: PCR buffer (containing 10 mM KCl, 10 mM (NH$_4$)$_2$SO$_4$, 20 mM Tris-HCl (pH 8.75), 2 mM MgSO$_4$, 0.1% Triton X-100), 100 µg/mL BSA (final concentration), 200 µM each deoxyribonucleotide triphosphate, 10 pmole of each primer and 1 µl of Pfu DNA polymerase (Stratagene, San Diego, Calif.). The thermocycler conditions were set for 35 cycles at 95° C. for 1 min, 56° C. for 30 sec and 72° C. for 1 min, followed by a final extension at 72° C. for 10 min.

The individual PCR products were purified using a Qiagen PCR purification kit. The PCR products from the reaction amplified with primers YL794/YL797 were digested with NcoI and HindIII, while the PCR products from the reaction amplified with primers YL796/YL795 were digested with HindIII and NotI. The NcoI/HindIII- and the HindIII/NotI-digested DNA fragments were purified following gel electrophoresis in 1% (w/v) agarose, and then directionally ligated with NcoI/NotI-digested pZUF17 (FIG. 5B; SEQ ID NO:22; comprising a synthetic delta-17 desaturase gene ["D17st"] derived from *Saprolegnia diclina* (U.S. Patent Publication No. 2003/0196217 A1), codon-optimized for expression in *Yarrowia lipolytica* (PCT Publication No. WO 2004/101757)). The product of this ligation was pDMW367 (FIG. 5C; SEQ ID NO:23), which thereby contained the following components:

TABLE 6

Components Of Plasmid pDMW367 (SEQ ID NO: 23)

| RE Sites And Nucleotides Within SEQ ID NO: 23 | Description Of Fragment And Chimeric Gene Components |
|---|---|
| EcoR I/BsiW I (7416-1671) | FBAIN::EgD5::Pex20, comprising:<br>FBAIN: *Yarrowia lipolytica* FBAIN promoter (PCT Publication No. WO 2005/049805; U.S. Pat. No. 7,202,356)<br>EgD5: *Euglena gracilis* delta-5 desaturase (SEQ ID NO: 1 described herein; labeled as "*Euglena* D5DS" in FIG.)<br>Pex20: Pex20 terminator sequence of *Yarrowia* Pex20 gene (GenBank Accession No. AF054613) |
| 2707-1827 | ColE1 plasmid origin of replication |
| 3637-2777 | ampicillin-resistance gene (Amp$^R$) for selection in *E. coli* |
| 4536-5840 | *Yarrowia* autonomous replication sequence (ARS18; GenBank Accession No. A17608) |
| 7373-5886 | *Yarrowia* Ura 3 gene (GenBank Accession No. AJ306421) |

The term "FBAIN promoter" or "FBAIN promoter region" refers to the 5' upstream untranslated region in front of the 'ATG' translation initiation codon of the *Yarrowia lipolytica* fructose-bisphosphate aldolase enzyme (E.C. 4.1.2.13) encoded by the fba1 gene and that is necessary for expression, plus a portion of 5' coding region that has an intron of the fba1 gene.

Example 7

Generation of *Yarrowia lipolytica* Strain M4 to Produce About 8% DGLA of Total Lipids The present Example describes the construction of strain M4, derived from *Yarrowia lipolytica* ATCC #20362, capable of producing 8% DGLA relative to the total lipids. This strain was engineered to express the delta-6 desaturase/delta-6 elongase pathway, via introduction of construct pKUNF12T6E (FIG. 6A; SEQ ID NO:24). This construct was generated to integrate four chimeric genes (comprising a delta-12 desaturase, a delta-6 desaturase and two $C_{18/20}$ elongases) into the Ura3 loci of wild type *Yarrowia* strain ATCC #20362, to thereby enable production of DGLA. Thus, pKUNF12T6E contained the following components:

TABLE 7

Description of Plasmid pKUNF12T6E (SEQ ID NO: 24)

| RE Sites And Nucleotides Within SEQ ID NO: 24 | Description Of Fragment And Chimeric Gene Components |
|---|---|
| AscI/BsiWI (9420-8629) | 784 bp 5' portion of *Yarrowia* Ura3 gene (GenBank Accession No. AJ306421) |
| SphI/PacI (12128-1) | 516 bp 3' portion of *Yarrowia* Ura3 gene (GenBank Accession No. AJ306421) |
| SwaI/BsiWI (6380-8629) | FBAIN::EL1S::Pex20, comprising:<br>FBAIN: *Yarrowia lipolytica* FBAIN promoter (PCT Publication No. WO 2005/049805; U.S. Pat. No. 7,202,356; labeled as "Fba1 + intron" in FIG.)<br>EL1S: codon-optimized elongase 1 gene (PCT Publication No. WO 2004/101753), derived from *Mortierella alpina* (GenBank Accession No. AX464731)<br>Pex20: Pex20 terminator sequence from *Yarrowia* Pex20 gene (GenBank Accession No. AF054613) |
| BglII/SwaI (4221-6380) | TEF::delta-6S::Lip1, comprising:<br>TEF: *Yarrowia lipolytica* TEF promoter (GenBank Accession No. AF054508)<br>delta-6S: codon-optimized delta-6 desaturase gene (PCT Publication No. WO 2004/101753), derived from *Mortierella alpina* (GenBank Accession No. AF465281)<br>Lip1: Lip1 terminator sequence from *Yarrowia* Lip1 gene (GenBank Accession No. Z50020) |
| PmeI/ClaI (4207-1459) | FBA::F.delta-12::Lip2, comprising:<br>FBA: *Yarrowia lipolytica* FBA promoter (PCT Publication No. WO 2005/049805; U.S. Pat. No. 7,202,356; labeled as "FBA1" in FIG.)<br>F.delta-12: *Fusarium moniliforme* delta-12 desaturase gene (PCT Publication No. WO 2005/047485)<br>Lip2: Lip2 terminator sequence from *Yarrowia* Lip2 gene (GenBank Accession No. AJ012632) |
| ClaI/PacI (1459-1) | TEF::EL2Syn::XPR2, comprising:<br>TEF: *Yarrowia lipolytica* TEF promoter (GenBank Accession No. AF054508)<br>EL2Syn: codon-optimized elongase gene (SEQ ID NO: 25), derived from *Thraustochytrium aureum* (U.S. Pat. No. 6,677,145)<br>XPR2: ~100 bp of the 3' region of the *Yarrowia* Xpr gene (GenBank Accession No. M17741) |

Plasmid pKUNF12T6E was digested with AscI/SphI, and then used for transformation of wild type *Y. lipolytica* ATCC #20362 according to the General Methods. The transformant cells were plated onto FOA selection media plates and maintained at 30° C. for 2 to 3 days. The FOA resistant colonies were picked and streaked onto MM and MMU selection plates. The colonies that could grow on MMU plates but not on MM plates were selected as Ura– strains. Single colonies of Ura– strains were then inoculated into liquid MMU at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKUNF12T6E, but not in the wild type *Yarrowia* control strain. Most of the selected 32 Ura– strains produced about 6% DGLA of total lipids. There were 2 strains (i.e., strains M4 and 13-8) that produced about 8% DGLA of total lipids.

Example 8

Functional Analysis of EgD5 Gene in *Yarrowia lipolytica* Strain M4

Plasmid pDMW367 (Example 6; comprising a chimeric FBAIN::EgD5::Pex20 gene was transformed into strain M4 (Example 7), as described in the General Methods. The transformants were selected on MM plates. After 2 days grown at 30° C., 3 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 5.6% DGLA and 2.8% ARA of total lipids produced in all three transformants, wherein the conversion efficiency of DGLA to ARA in these three strains was determined to be about 33% (average). The conversion efficiency was measured according to the following formula: ([product]/[substrate+product])*100, where 'product' includes the immediate product and all products in the pathway derived from it. Thus, this experimental data demonstrated that the cloned *Euglena gracilis* delta-5 desaturase, described herein as SEQ ID NOs:1 and 2, efficiently desaturated DGLA to ARA.

Example 9

Synthesis of a Codon-Optimized Delta-5 Desaturase Gene ("EgD5S") for Expression in *Yarrowia lipolytica*

The codon usage of the delta-5 desaturase gene of *Euglena gracilis* (SEQ ID NOs:1 and 2; EgD5) was optimized for expression in *Yarrowia lipolytica*, in a manner similar to that described in PCT Publication No. WO 2004/101753 and U.S. Pat. No. 7,125,672. Specifically, a codon-optimized delta-5 desaturase gene (designated "EgD5S", SEQ ID NO:3) was designed based on the coding sequence of the delta-5 desaturase gene of EgD5, according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, *Gene*, 265(1-2):11-23 (2001)). In addition to modification of the translation initiation site, 196 bp of the 1350 bp coding region were modified (14.5%; FIG. 7) and 189 codons were optimized (42%). The GC content was reduced from 55.5% within the wild type gene (i.e., EgD5) to 54.4% within the synthetic gene (i.e., EgD5S). A NcoI site and NotI sites were incorporated around the translation initiation codon and after the stop codon of EgD5S, respectively. None of the modifications in the codon-optimized gene changed the amino acid sequence of the encoded protein (SEQ ID NO:2). The designed EgD5S gene (SEQ ID NO:3) was synthesized by GenScript Corporation (Piscataway, N.J.) and cloned into pUC57 (GenBank Accession No. Y14837) to generate pEgD5S (FIG. 6B; SEQ ID NO:48).

Example 10

Generation of Construct pDMW369, Comprising EgD5S

The present Example describes the construction of plasmid pDMW369 comprising a chimeric FBAIN::EgD5S::Pex20 gene. Plasmid pDMW369 (FIG. 6C; SEQ ID NO:49) was constructed by replacing the Nco I/Not I fragment of pZUF17 (FIG. 5B; SEQ ID NO:22) with the Nco I/Not I EgD5S fragment from pEgD5S (FIG. 6B; SEQ ID NO:48). The product of this ligation was pDMW369, which thereby contained the following components:

TABLE 8

Components Of Plasmid pDMW369 (SEQ ID NO: 49)

| RE Sites And Nucleotides Within SEQ ID NO: 49 | Description Of Fragment And Chimeric Gene Components |
|---|---|
| EcoR I/BsiW I (6063-318) | FBAIN::EgD5S::Pex20, comprising: FBAIN: *Yarrowia lipolytica* FBAIN promoter (PCT Publication No. WO 2005/049805; U.S. Pat. No. 7,202,356; labeled as "FBA1 + Intron" in FIG.) EgD5S: codon-optimized delta-5 desaturase (SEQ ID NO: 3, described herein as EgD5S), derived from *Euglena gracilis* Pex20: Pex20 terminator sequence of *Yarrowia* Pex20 gene (GenBank Accession No. AF054613) |
| 1354-474 | ColE1 plasmid origin of replication |
| 2284-1424 | ampicillin-resistance gene (Amp$^R$) for selection in *E. coli* |
| 3183-4476 | *Yarrowia autonomous* replication sequence (ARS18; GenBank Accession No. A17608) |
| 6020-4533 | *Yarrowia* Ura 3 gene (GenBank Accession No. AJ306421) |

Example 11

Expression of the Codon-Optimized Delta-5 Desaturase ("EqD5S") in *Yarrowia lipolytica* Strain M4

Plasmid pDMW369 (Example 10; comprising a chimeric FBAIN::EgD5S::Pex20 gene) was transformed into strain M4 (Example 7), as described in the General Methods. The transformants were selected on MM plates. After 2 days growth at 30° C., 3 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 3.3% DGLA and 2.7% ARA of total lipids produced in all three transformants, wherein the conversion efficiency of DGLA to ARA in these three strains was determined to be about 45% (average; calculated as described in Example 8). Thus, this experimental data demonstrated that the synthetic *Euglena gracilis* delta-5 desaturase codon-optimized for expression in *Yarrowia lipolytica* (EgD5S, as set forth in SEQ ID NO:3) is about 36% more efficient desaturating DGLA to ARA than the wild type EgD5 gene (SEQ ID NO:1).

Example 12

Isolation of a *Pavlova lutheri* (CCMP459) Delta-8 Desaturase

The present example describes the isolation of the *Pavlova lutheri* (CCMP459) delta-8 desaturase utilized in Example 3 and in FIG. 3 (also described in U.S. patent application Ser. No. 11/737,772, filed Apr. 20, 2007). This required: synthesis of *Pavlova lutheri* (CCMP459) cDNA; library construction and sequencing; identification of delta-8 desaturase homologs; and, cloning of a full-length delta-8 desaturase from genomic DNA.

*Pavlova lutheri* (CCMP459) cDNA Synthesis, Library Construction and Sequencing

A cDNA library of *Pavlova lutheri* (CCMP459) was synthesized as described in PCT Publication No. WO 2004/071467 (published Aug. 26, 2004). Briefly, frozen pellets of Pav459 were obtained from the Provasoli-Guillard National Center for Culture of Marine Phytoplankton (CCMP, West Boothbay Harbor, Me.). These pellets were crushed in liquid nitrogen and total RNA was extracted from Pav459 by using the Qiagen RNeasy® Maxi Kit (Qiagen, Valencia, Calif.), per the manufacturer's instructions. From this total RNA, mRNA was isolated using oligo dT cellulose resin, which was then used for the construction of a cDNA library using the pSport1 vector (Invitrogen, Carlsbad, Calif.). The cDNA thus produced was directionally cloned (5' SalI/3' NotI) into pSport1 vector. The Pav459 library contained approximately $6.1 \times 10^5$ clones per mL, each with an average insert size of approximately 1200 bp. The *Pavlova lutheri* library was named eps1c.

For sequencing, clones first were recovered from archived glycerol cultures grown/frozen in 384-well freezing media plates, and inoculated with an automatic QPix® colony picker (Genetix) in 96-well deep-well plates containing LB+100 mg/mL ampicillin. After growing 20 hrs at 37° C., cells were pelleted by centrifugation and stored at −20° C. Plasmids then were isolated on an Eppendorf 5Prime robot, using a modified 96-well format alkaline lysis miniprep method (Eppendorf PerfectPrep®). Briefly, a filter and vacuum manifold was used to facilitate removal of cellular debris after acetate precipitation. Plasmid DNA was then bound on a second filter plate directly from the filtrate, washed, dried and eluted.

Plasmids were end-sequenced in 384-well plates, using vector-primed T7 primer (SEQ ID NO:50) and the ABI Big-Dye version 3 Prism sequencing kit. For the sequencing reaction, 100-200 ng of template and 6.4 pmol. of primer were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3700 automated sequencers.

Identification of Delta-8 Desaturase Enzyme Homologs from *Pavlova lutheri* cDNA Library eps1c cDNA clones encoding *Pavlova lutheri* delta-8 desaturase homologs (hereby called delta-8 desaturases) were identified by conducting BLAST searches for similarity to sequences contained in the BLAST "nr" database (as described in Example 3). The P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequence from clone eps1c.pk002.f22 revealed similarity of the protein encoded by the cDNA to the delta-6 desaturase from *Rhizopus stolonifer* (SEQ ID NO:51) (NCBI Accession No. AAX22052 (GI 60499699), locus AAX22052, CDS AY795076; Lu et al., unpublished). The sequence of a portion of the cDNA insert from clone eps1c.pk002.f22 is shown in SEQ ID NO:52 (5' end of cDNA insert). Subsequently, the full insert sequence (eps1c.pk002.f22:fis) was obtained and is shown in SEQ ID NO:53. Sequence for the deduced amino acid sequence (from nucleotide 1 of SEQ ID NO:53 to the first stop codon at nucleotide 864 of SEQ ID NO:53) is shown in SEQ ID NO:54. Full insert sequencing was carried out using a modified transposition protocol. Clones identified for full insert sequencing were recovered from archived glycerol stocks as single colonies, and plasmid DNA was isolated via alkaline lysis. Plasmid templates were transposed via the Template Generation System (TGS II) transposition kit (Finnzymes Oy, Espoo, Finland), following the manufacturer's protocol. The transposed DNA was transformed into EH10B electro-competent cells (Edge BioSystems, Gaithersburg, Md.) via electroporation. Multiple transformants were randomly selected from each transposition reaction, plasmid DNA was prepared, and templates were sequenced as above (ABI BigDye v3.1) outward from the transposition event site, utilizing unique primers SeqE (SEQ ID NO:55) and SeqW (SEQ ID NO:56).

Sequence data was collected (ABI Prism Collections software) and assembled using the Phrap sequence assembly program (P. Green, University of Washington, Seattle). Assemblies were viewed by the Consed sequence editor (D. Gordon, University of Washington, Seattle) for final editing.

The amino acid sequence set forth in SEQ ID NO:54 was evaluated by BLASTP, yielding a pLog value of 19.52 (E value of 3e-20) versus the delta-6 desaturase from *Mortierella alpina* (NCBI Accession No. BAC82361 (GI 34221934), locus BAC82361, CDS AB070557; Sakuradani and Shimizu, Biosci. Biotechnol. Biochem., 67:704-711 (2003)). Based on the results from the BLASTP comparison to the *Mortierella alpina* and other fatty acid desaturases, the *Pavlova lutheri* delta-8 desaturase was not full length and was lacking sequence at the 5' end.

Cloning A Full-Length Delta-8 Desaturase from *Pavlova lutheri* Genomic DNA

Genomic DNA was isolated from *Pavlova lutheri* (CCMP459) using the Qiagen DNeasy® Plant Maxi Prep Kit according to the manufacturer's protocol. Using 1 maxi column per 1 gm of frozen cell pellet, a total of 122 µg of genomic DNA was isolated from 4 gm of *Pavlova lutheri* culture. The final concentration of genomic DNA was 22.8 ng/µL. GenomeWalker libraries were synthesized using the Universal GenomeWalker™ kit (BD Biosciences Clonetech, Palo Alto, Calif.) following the manufacturer's protocol (Prot # PT3042-1, version PRO3300). Briefly, four restriction digests were set up as per the protocol using 300 ng of genomic DNA per reaction. After phenol clean up, pellets were dissolved in 4 µL of water and adapters were ligated as per the protocol.

For the primary PCR, the Advantage®-GC Genomic PCR kit (BD Biosciences Clonetech) was used following the manufacturer's protocol (Prot # PT3090-1, version PR1X433). For each restriction digest, 1 µL of library was combined with 22.8 µL of PCR grade water, 10 µL of 5×GC Genomic PCR Reaction Buffer, 2.2 µL of 25 mM Mg(CH$_3$CO$_2$)$_2$, 10 µL of GC-Melt (5 M), 1 µL of 50×dNTP mix (10 mM each), 1 µL of Advantage-GC Genomic Pol. Mix (50×), 1 µL of Universal GenomeWalker™ primer AP1 (10 µM, SEQ ID NO:57) and 1 µL of GSP PvDES (10 µM, SEQ ID NO:58). After denaturation at 95° C., the following reaction conditions were repeated 35 times: 94° C. for 30 sec, 68° C. for 6 min. After these reaction conditions, an additional extension at 68° C. was carried out for 6 min followed by cooling to 15° C. until removed.

The primary PCR reaction for each library was analyzed by agarose gel electrophoresis and DNA bands with molecular weights around 6 kB, 3.5 kB, 2.5 kB and 1.2 kB were observed. DNA bands for each library were purified using the Zymoclean™ Gel DNA Recovery Kit (Zymo Research, Orange, Calif.) following the manufacturer's protocol. The resulting DNA was cloned into the PGEM®-T Easy Vector (Promega) following the manufacturer's protocol and inserts were sequenced using the T7 (SEQ ID NO:50) and M13-28Rev (SEQ ID NO:59) primers as described above. Additional sequence was then obtained using a gene-specific sequencing primer PavDES seq (SEQ ID NO:60) that was derived from the newly acquired sequence data. The full 5' end sequence obtained by genome walking is shown in SEQ ID NO:61. The sequence of the overlapping regions of the genomic sequence (SEQ ID NO:61) and the fully sequenced EST eps1c.pk002.f22:fis (SEQ ID NO:53) were aligned using Sequencher™ (Version 4.2, Gene Codes Corporation, Ann Arbor, Mich.) using the Large Gap assembly algorithm. Interestingly, the comparison showed that the EST that was originally sequenced (SEQ ID NO:53) was lacking 459 bp when compared to the genomic sequence (SEQ ID NO:61). This missing sequence in the EST appeared to be a deletion rather than an intron as no clear intron splice sites were identified in the genomic DNA at the 5' end of the gene. The genomic sequence for the 5' end (SEQ ID NO:61) was combined with the 3' end of the EST sequence (SEQ ID NO:53) to yield SEQ ID NO:62. Using Editseq™ 6.1 sequence analysis software (DNASTAR Inc., Madison, Wis.), an ORF was identified (SEQ ID NO:17). The amino acid sequence coded for by SEQ ID NO:17 is shown in SEQ ID NO:18.

The amino acid sequence set forth in SEQ ID NO:18 was evaluated by BLASTP, yielding a pLog value of 35.10 (E value of 8e-36) versus the delta-6 desaturase from *Rhizopus stolonifer* (SEQ ID NO:63) (NCBI Accession No. ABB96724 (GI 83027409), locus ABB96724, CDS DQ291156; Zhang et al., unpublished). Furthermore, the *Pavlova lutheri* delta-8 desaturase is 78.0% identical to the *Pavlova salina* delta-8 desaturase sequence (SEQ ID NO:64) disclosed in PCT Publication No. WO 2005/103253 (published Apr. 22, 2005) using the Jotun Hein method. Sequence percent identity calculations performed by the Jotun Hein method (Hein, J. J., *Meth. Enz.*, 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2). The *Pavlova lutheri* delta-8 desaturase is 76.4% identical to the *Pavlova salina* delta-8 desaturase sequence using the Clustal V method. Sequence percent identity calculations performed by the Clustal V method (Higgins, D. G. and Sharp, P. M., *Comput. Appl. Biosci.*, 5:151-153 (1989); Higgins et al., *Comput. Appl. Biosci.*, 8:189-191 (1992)) were done using the MegAlign™ v6.1 program of the LASERGENE bioinformatics computing suite (DNASTAR Inc.) with the default parameters for pairwise alignment (KTUPLE=1, GAP PENALTY=3, WINDOW=5, DIAGONALS SAVED=5 and GAP LENGTH PENALTY=10). BLAST scores and probabilities indicate that the fragment of SEQ ID NO:17 encodes an entire *Pavlova lutheri* delta-8 desaturase.

FIGS. 8A and 8B show a Clustal V alignment (with default parameters) of SEQ ID NO:18 (the amino acid sequence of the *Pavlova lutheri* delta-8 desaturase), SEQ ID NO:64 (the amino acid sequence of *Pavlova salina* delta-8 desaturase sequence, supra), SEQ ID NO:16 (the amino acid sequence of *Euglena gracilis* delta-8 desaturase sequence disclosed as SEQ ID NO:2 in PCT Publication No. WO 2006/012325; published Feb. 2, 2006), SEQ ID NO:63 (the amino acid sequence for the *Rhizopus stolonifer* delta-6 fatty acid desaturase (NCBI Accession No. ABB96724, supra)) and SEQ ID NO:51 (the amino acid sequence for the *Rhizopus stolonifer* delta-6 fatty acid desaturase (NCBI Accession No. AAX22052, supra)). The results of the Clustal V alignment show that SEQ ID NO:18 is 76.4%, 22.6%, 22.2% and 22.2% identical to SEQ ID NO:64, SEQ ID NO:16, SEQ ID NO:63 and SEQ ID NO:51, respectively.

Example 13

Transformation of Somatic Soybean Embryo Cultures

Culture Conditions:

Soybean embryogenic suspension cultures (cv. Jack) are maintained in 35 mL liquid medium SB196 (infra) on a rotary shaker, 150 rpm, 26° C. with cool white fluorescent lights on 16:8 hr day/night photoperiod at light intensity of 60-85 $\mu E/m^2/s$. Cultures are subcultured every 7 days to 2 weeks by inoculating approximately 35 mg of tissue into 35 mL of fresh liquid SB196 (the preferred subculture interval is every 7 days).

Soybean embryogenic suspension cultures are transformed with soybean expression plasmids by the method of particle gun bombardment (Klein et al., *Nature*, 327:70 (1987)) using a DuPont Biolistic PDS1000/HE instrument (helium retrofit) for all transformations.

Soybean Embryogenic Suspension Culture Initiation:

Soybean cultures are initiated twice each month with 5-7 days between each initiation. Pods with immature seeds from available soybean plants 45-55 days after planting are picked, removed from their shells and placed into a sterilized magenta box. The soybean seeds are sterilized by shaking them for 15 min in a 5% Clorox solution with 1 drop of ivory soap (i.e., 95 mL of autoclaved distilled water plus 5 mL Clorox and 1 drop of soap, mixed well). Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment:

Either an intact plasmid or a DNA plasmid fragment containing the delta-5 desaturase genes of interest and the selectable marker gene are used for bombardment. Fragments from soybean expression plasmids comprising the delta-5 desaturase of the present invention are obtained by gel isolation of digested plasmids. The resulting DNA fragments are separated by gel electrophoresis on 1% SeaPlaque GTG agarose (BioWhitaker Molecular Applications) and the DNA fragments containing gene cassettes are cut from the agarose gel. DNA is purified from the agarose using the GELase digesting enzyme following the manufacturer's protocol.

A 50 μL aliquot of sterile distilled water containing 3 mg of gold particles is added to 5 μL of a 1 μg/μL DNA solution (either intact plasmid or DNA fragment prepared as described above), 50 μL 2.5 M $CaCl_2$ and 20 μL of 0.1 M spermidine. The mixture is shaken 3 min on level 3 of a vortex shaker and spun for 10 sec in a bench microfuge. After a wash with 400 μL of 100% ethanol, the pellet is suspended by sonication in 40 μL of 100% ethanol. DNA suspension (5 μL) is dispensed to each flying disk of the Biolistic PDS1000/HE instrument disk. Each 5 μL aliquot contains approximately 0.375 mg gold particles per bombardment (i.e., per disk).

Tissue Preparation and Bombardment with DNA:

Approximately 150-200 mg of 7 day old embryonic suspension cultures is placed in an empty, sterile 60×15 mm petri dish and the dish is covered with plastic mesh. Tissue is bombarded 1 or 2 shots per plate with membrane rupture pressure set at 1100 PSI and the chamber is evacuated to a vacuum of 27-28 inches of mercury. Tissue is placed approximately 3.5 inches from the retaining/stopping screen.

Selection of Transformed Embryos:

Transformed embryos ate selected using hygromycin as the selectable marker. Specifically, following bombardment, the tissue is placed into fresh SB196 media and cultured as described above. Six days post-bombardment, the SB196 is exchanged with fresh SB196 containing 30 mg/L hygromycin. The selection media is refreshed weekly. Four to six weeks post-selection, green, transformed tissue is observed growing from untransformed, necrotic embryogenic clusters. Isolated, green tissue is removed and inoculated into multi-well plates to generate new, clonally propagated, transformed embryogenic suspension cultures.

Embryo Maturation:

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 µE/m²s. After this time embryo clusters are removed to a solid agar media, SB166, for 1-2 weeks. Clusters are then subcultured to medium SB103 for 3 weeks. During this period, individual embryos are removed from the clusters and screened for alterations in their fatty acid compositions as described supra.

Media Recipes:

| SB 196 - FN Lite Liquid Proliferation Medium (per liter) | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

| FN Lite Stock Solutions | | | |
|---|---|---|---|
| Stock Number | | 1000 mL | 500 mL |
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 Solid Medium (Per Liter)

1 package MS salts (Gibco/BRL—Cat. No. 11117-066)
1 mL B5 vitamins 1000× stock
31.5 g sucrose
2 mL 2,4-D (20 mg/L final concentration)
pH 5.7
8 g TC agar SB 166 Solid Medium (Per Liter)

1 package MS salts (Gibco/BRL—Cat. No. 11117-066)
1 mL B5 vitamins 1000× stock
60 g maltose
750 mg $MgCl_2$ hexahydrate
5 g activated charcoal
pH 5.7
2 g gelrite SB 103 Solid Medium (Per Liter)

1 package MS salts (Gibco/BRL—Cat. No. 11117-066)
1 mL B5 vitamins 1000× stock
60 g maltose
750 mg $MgCl_2$ hexahydrate
pH 5.7
2 g gelrite SB 71-4 Solid Medium (Per Liter)

1 bottle Gamborg's B5 salts with sucrose (Gibco/BRL—Cat. No. 21153-036)
pH 5.7
5 g TC agar 2,4-D Stock Obtain premade from Phytotech Cat. No. D 295—concentration 1 mg/mL B5 Vitamins Stock (Per 100 mL)

Store aliquots at −20° C.
  10 g myo-inositol
  100 mg nicotinic acid
  100 mg pyridoxine HCl
  1 g thiamine
If the solution does not dissolve quickly enough, apply a low level of heat via the hot stir plate.

Example 14

Functional Analysis of Delta-5 Desaturase (SEQ ID NOs:1 and 2) in Somatic Soybean Embryos Mature somatic soybean embryos are a good model for zygotic embryos. While in the globular embryo state in liquid culture, somatic soybean embryos contain very low amounts of triacylglycerol (TAG) or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, TAG becomes the most abundant lipid class. As well, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is thus a good and rapid model system for analyzing the phenotypic effects of modifying the expression of genes in the fatty acid biosynthesis pathway (see PCT Publication No. WO 2002/00904, Example 3). Most importantly, the model system is also predictive of the fatty acid composition of seeds from plants derived from transgenic embryos.

Transgenic somatic soybean embryos containing the delta-5 desaturase of the present invention are analyzed in the following way. Fatty acid methyl esters are prepared from single, matured, somatic soy embryos by transesterification. Individual embryos are placed in a vial containing 50 µL of trimethylsulfonium hydroxide (TMSH) and 0.5 mL of hexane and incubated for 30 min at room temperature while shaking. Fatty acid methyl esters (5 µL injected from hexane layer) are separated and quantified using a Hewlett-Packard 6890 Gas Chromatograph fitted with an Omegawax 320 fused silica capillary column (Catalog #24152, Supelco Inc.). The oven temperature are programmed to hold at 220° C. for 2.6 min, increase to 240° C. at 20° C./min and then hold for an additional 2.4 min. Carrier gas is supplied by a Whatman hydrogen generator. Retention times are compared to those for methyl esters of standards commercially available (Nu-Chek Prep, Inc.). Routinely, 5-10 embryos per event are analyzed by GC, using the methodology described above.

Example 15

Co-Expressing Other Promoter/Gene/Terminator Cassette Combinations in Somatic Soybean Embryos In addition to the genes, promoters, terminators and gene cassettes described herein, one skilled in the art can appreciate that other promoter/gene/terminator cassette combinations can be synthesized in a way similar to, but not limited to, that described herein. For instance, PCT Publications No. WO 2004/071467 and No. WO 2004/071178 describe the isolation of a number of promoter and transcription terminator sequences for use in embryo-specific expression in soybean. Furthermore, PCT Publications No. WO 2004/071467, No. WO 2005/047479 and No. WO 2006/012325 describe the synthesis of multiple promoter/gene/terminator cassette combinations by ligating individual promoters, genes and transcription terminators together in unique combinations. Generally, a NotI site flanked by the suitable promoter (e.g., those listed in, but not limited to, Table 9) and a transcription terminator (e.g., those listed in, but not limited to, Table 10) is used to clone the desired gene. NotI sites can be added to a gene of interest such as those listed in, but not limited to, Table 11 using PCR amplification with oligonucleotides designed to introduce NotI sites at the 5' and 3' ends of the gene. The resulting PCR product is then digested with NotI and cloned into a suitable promoter/NotI/terminator cassette.

In addition, PCT Publications No. WO 2004/071467, No. WO 2005/047479 and No. WO 2006/012325 describe the further linking together of individual gene cassettes in unique combinations, along with suitable selectable marker cassettes, in order to obtain the desired phenotypic expression. Although this is done mainly using different restriction enzymes sites, one skilled in the art can appreciate that a number of techniques can be utilized to achieve the desired promoter/gene/transcription terminator combination. In so doing, any combination of embryo-specific promoter/gene/ transcription terminator cassettes can be achieved. One skilled in the art can also appreciate that these cassettes can be located on individual DNA fragments or on multiple fragments where co-expression of genes is the outcome of co-transformation of multiple DNA fragments.

TABLE 9

Seed-specific Promoters

| Promoter | Organism | Promoter Reference |
| --- | --- | --- |
| β-conglycinin α'-subunit | Soybean | Beachy et al., EMBO J., 4: 3047-3053 (1985) |
| kunitz trypsin inhibitor | Soybean | Jofuku et al., Plant Cell, 1: 1079-1093 (1989) |
| Annexin | Soybean | PCT Publication No. WO 2004/071467 |
| glycinin Gy1 | Soybean | PCT Publication No. WO 2004/071467 |
| albumin 2S | Soybean | U.S. Pat. No. 6,177,613 |
| legumin A1 | Pea | Rerie et al., Mol. Gen. Genet., 225: 148-157 (1991) |
| β-conglycinin β-subunit | Soybean | PCT Publication No. WO 2004/071467 |
| BD30 (also called P34) | Soybean | PCT Publication No. WO 2004/071467 |
| legumin A2 | Pea | Rerie et al., Mol. Gen. Genet., 225: 148-157 (1991) |

TABLE 10

Transcription Terminators

| Transcription Terminator | Organism | Reference |
| --- | --- | --- |
| phaseolin 3' | bean | PCT Publication No. WO 2004/071467 |
| kunitz trypsin inhibitor 3' | soybean | PCT Publication No. WO 2004/071467 |
| BD30 (also called P34) 3' | soybean | PCT Publication No. WO 2004/071467 |
| legumin A2 3' | pea | PCT Publication No. WO 2004/071467 |
| albumin 2S 3' | soybean | PCT Publication No. WO 2004/071467 |

TABLE 11

PUFA Biosynthetic Pathway Genes

| Gene | Organism | Reference |
| --- | --- | --- |
| delta-6 desaturase | Saprolegnia diclina | PCT Publication No. WO 2002/081668 |
| delta-6 desaturase | Mortierella alpina | U.S. Pat. No. 5,968,809 |
| elongase | Mortierella alpina | PCT Publication No. WO 2000/12720; U.S. Pat. No. 6,403,349 |
| delta-5 desaturase | Mortierella alpina | U.S. Pat. No. 6,075,183 |
| delta-5 desaturase | Saprolegnia diclina | PCT Publication No. WO 2002/081668 |
| delta-15 desaturase | Fusarium moniliforme | PCT Publication No. WO 2005/047479 |
| delta-17 desaturase | Saprolegnia diclina | PCT Publication No. WO 2002/081668 |
| elongase | Thraustochytrium aureum | PCT Publication No. WO 2002/08401; U.S. Pat. No. 6,677,145 |
| elongase | Pavlova sp. | Pereira et al., Biochem. J., 384:357-366 (2004) |
| delta-4 desaturase | Schizochytrium aggregatum | PCT Publication No. WO 2002/090493 |
| delta-9 elongase | Isochrysis galbana | PCT Publication No. WO 2002/077213 |
| delta-9 elongase | Euglena gracilis | U.S. Patent Application No. 11/601563 |
| delta-8 desaturase | Euglena gracilis | PCT Publication No. WO 2000/34439; U.S. Pat. No. 6,825,017; PCT Publication |

TABLE 11-continued

PUFA Biosynthetic Pathway Genes

| Gene | Organism | Reference |
|---|---|---|
| | | No. WO 2004/057001; PCT Publication No. WO 2006/012325 |
| delta-8 desaturase | *Acanthamoeba castellanii* | Sayanova et al., FEBS Lett., 580: 1946-1952 (2006) |
| delta-8 desaturase | *Pavlova salina* | PCT Publication No. WO 2005/103253 |
| delta-8 desaturase | *Pavlova lutheri* | U.S. Patent Application No. 11/737,772 |

Example 16

Chlorsulfuron Selection (ALS) and Plant Regeneration Chlorsulfuron (ALS) Selection:

Following bombardment, the plant tissue is divided between 2 flasks with fresh SB196 media and cultured as described in Example 13. Six to seven days post-bombardment, the SB196 is exchanged with fresh SB196 containing selection agent of 100 ng/mL chlorsulfuron. The selection media is refreshed weekly. Four to six weeks post selection, green, transformed tissue is observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants:

In order to obtain whole plants from embryogenic suspension cultures, the tissue must be regenerated. Embyros are matured as described in Example 13. After subculturing on medium SB103 for 3 weeks, individual embryos are removed from the clusters and screened for alterations in their fatty acid compositions as described in Example 14. It should be noted that any detectable phenotype, resulting from the expression of the genes of interest, can be screened at this stage. This would include, but not be limited to: alterations in fatty acid profile, protein profile and content, carbohydrate content, growth rate, viability, or the ability to develop normally into a soybean plant.

Matured individual embryos are desiccated by placing them into an empty, small petri dish (35×10 mm) for approximately 4 to 7 days. The plates are sealed with fiber tape (creating a small humidity chamber). Desiccated embryos are planted into SB71-4 medium where they are left to germinate under the same culture conditions described above. Germinated plantlets are removed from germination medium and rinsed thoroughly with water and then are planted in Redi-Earth in a 24-cell pack tray, covered with a clear plastic dome. After 2 weeks the dome is removed and plants hardened off for a further week. If plantlets look hardy, they are transplanted to 10" pots of Redi-Earth with up to 3 plantlets per pot. After 10 to 16 weeks, mature seeds are harvested, chipped and analyzed for fatty acids as described in Example 14.

Media recipes can be found in Example 13 and chlorsulfuron stock is 1 mg/mL in 0.01 N ammonium hydroxide.

Example 17

Comparing the Substrate Specificity of the *Mortierella alpina* Delta-5 Desaturase (MaD5) with the *Euglena gracilis* Delta-5 Desaturase (EgD5) in *Yarrowia lipolytica*

The present Example describes comparison of the substrate specificity of a *Mortierella alpina* delta-5 desaturase (MaD5; SEQ ID NOs:67 and 68), which is described in U.S. Pat. No. 6,075,183 and PCT Publications No. WO 2004/071467 and No. WO 2005/047479) to that of EgD5 (SEQ ID NO:2) in *Yarrowia lipolytica*.

This work included the following steps: (1) construction of *Yarrowia* expression vector pY98 comprising MaD5; (2) transformation of pY98 and pDMW367 into *Yarrowia* strain Y2224; and, 3.) comparison of lipid profiles within transformant organisms comprising pY98 or pDMW367 after feeding fatty acid substrates.

Construction of *Yarrowia* Expression Vector pY98, Comprising MaD5

Plasmid pY5-22 (SEQ ID NO:69) is a shuttle plasmid that can replicate both in *E. coli* and *Yarrowia lipolytica*, containing the following: a *Yarrowia* autonomous replication sequence (ARS18; GenBank Accession No. M91600); a ColE1 plasmid origin of replication; an ampicillin-resistance gene (AmpR) for selection in *E. coli*; a *Yarrowia* URA3 gene (GenBank Accession No. AJ306421) for selection in *Yarrowia*; and, a chimeric TEF::NcoI/NotI::XPR cassette, wherein "XPR" was ~100 bp of the 3' region of the *Yarrowia* Xpr gene (GenBank Accession No. M17741). Although the construction of plasmid pY5-22 is not described herein in detail, it was derived from pY5 (previously described in PCT Publication No. WO 2004/101757).

Plasmid pY5-22GPD (SEQ ID NO:70) was created from pY5-22 (SEQ ID NO:69), by replacing the TEF promoter with the *Yarrowia lipolytica* GPD promoter (SEQ ID NO:71) using techniques well known to one skilled in the art. The *Yarrowia* "GPD promoter" refers to the 5' upstream untranslated region in front of the 'ATG' translation initiation codon of a protein encoded by the *Yarrowia lipolytica* glyceraldehyde-3-phosphate dehydrogenase (GPD) gene and that is necessary for expression (PCT Publication No. WO 2005/003310). More specifically, the *Yarrowia lipolytica* GPD promoter was amplified from plasmid pYZDE2-S (SEQ ID NO:72; which was previously described in U.S. patent application Ser. No. 11/737,772 the contents of which are hereby incorporated by reference)) using oligonucleotides GPDsense (SEQ ID NO:73) and GPDantisense (SEQ ID NO:74). The resulting DNA fragment was digested with SalI/NotI and cloned into the SalI/NotI fragment of pY5-22 (SEQ ID NO:69), thus replacing the TEF promoter and NcoI/NotI site with the GPD promoter and a unique NotI site, and thereby producing pY5-22GPD (SEQ ID NO:70).

The *Mortierella alpina* delta-5 desaturase gene (SEQ ID NO:67) was released from pKR136 (SEQ ID NO:75; which was previously described in PCT Publication No. WO 2004/071467 (the contents of which are hereby incorporated by reference)) by digestion with NotI and cloned into the NotI site of pY5-22GPD to produce pY98 (SEQ ID NO:76; FIG. 9).

Transformation of pY98 (Comprising MaD5) and pDMW367 (Comprising EgD5) into *Yarrowia* Strain Y2224 and Comparison of Lipid Profiles Strain Y2224 was isolated in the following manner: *Yarrowia lipolytica* ATCC #20362 cells from a YPD agar plate (1% yeast extract, 2% bactopeptone, 2% glucose, 2% agar) were streaked onto a MM plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto MM plates containing 200 mg/mL 5-FOA and MM plates lacking uracil and uridine to confirm uracil Ura3 auxotrophy.

Strain Y2224 was transformed with pY98 (SEQ ID NO:76, FIG. 9) and pDMW367 (SEQ ID NO:23; FIG. 5C; Example 6) as described in the General Methods.

Single colonies of transformant *Yarrowia lipolytica* containing pY98 (SEQ ID NO:76) or pDMW367 (SEQ ID NO:23) were grown in 3 mL MM lacking uracil supplemented with 0.2% tergitol at 30° C. for 1 day. After this, 0.1 mL was transferred to 3 mL of the same medium supplemented with either EDA, ETrA, DGLA, ETA or no fatty acid. These were incubated for 16 h at 30° C., 250 rpm and then pellets were obtained by centrifugation. Cells were washed once with water, pelleted by centrifugation and air dried. Pellets were transesterified (Roughan, G. and Nishida, I., *Arch. Biochem. Biophys.*, 276(1):38-46 (1990)) with 500 µL of 1% sodium methoxide for 30 min at 50° C. after which 500 µL of 1 M NaCl and 100 µL of heptane were added. After thorough mixing and centrifugation, fatty acid methyl esters (FAMEs) were analyzed by GC.

FAMEs (5 µL injected from hexane layer) were separated and quantified using a Hewlett-Packard 6890 Gas Chromatograph fitted with an Omegawax 320 fused silica capillary column (Catalog No. 24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.).

The fatty acid profiles for *Yarrowia lipolytica* expressing pY98 (SEQ ID NO:76) or pDMW367 (SEQ ID NO:23) and fed various substrates are shown in FIG. 10A. In FIG. 10A shading indicates the substrates fed and products produced; fatty acids are identified as 16:0 (palmitate), 16:1, 18:0 (stearic acid), 18:1 (oleic acid), LA, GLA, ALA, STA, EDA, SCI (sciadonic acid or cis-5,11,14-eicosatrienoic acid; 20:3 omega-6), DGLA, ARA, ETrA, JUP (juniperonic acid or cis-5,11,14,17-eicosatrienoic acid; 20:4 omega-3), ETA and EPA. Fatty acid compositions were expressed as the weight percent (wt. %) of total fatty acids.

Percent delta-5 desaturation ("% delta-5 desat") of EgD5 and MaD5 for each substrate is shown in FIG. 10B and was calculated by dividing the wt. % for product (either SCI, JUP, ARA or EPA) by the sum of the wt. % for the substrate and product (either EDA and SCI, ETrA and JUP, DGLA and ARA, or ETA and EPA, respectively) and multiplying by 100 to express as a %, depending on which substrate was fed.

The activities of EgD5 and MaD5 are compared using the ratio of the percent delta-5 desaturation ("Ratio Desat Eg/Ma") in FIG. 10B and are calculated by dividing the percent delta-5 desaturation for EgD5 on a particular substrate by the percent delta-5 desaturation for MaD5 on the same substrate.

The substrate specificity of EgD5 and MaD5 for the correct omega-6 fatty acid substrate (i.e., DGLA) versus the by-product fatty acid (i.e., SCI) or the correct omega-3 fatty acid substrate (i.e., ETA) versus the by-product fatty acid (i.e., JUP) is also shown in FIG. 10B. Specifically, the substrate specificity ("Ratio Prod/By-Prod") for omega-6 substrates was calculated by dividing the percent delta-5 desaturation (% delta-5 desat) for DGLA by the percent delta-5 desaturation (% delta-5 desat) for EDA and is shown on the same lines as the results for DGLA. The substrate specificity ("Ratio Prod/By-Prod") for omega-3 substrates was calculated by dividing the percent delta-5 desaturation (% delta-5 desat) for ETA by the percent delta-5 desaturation (% delta-5 desat) for ETrA and is shown on the same lines as the results for ETA. Furthermore, the ratio of substrate specificity ("Ratio Prod/By-Prod Eg/Ma") for omega-6 substrates was determined by dividing the substrate specificity for EgD5 on the omega-6 substrates (i.e., DGLA/EDA) by that for MaD5. The ratio of substrate specificity ("Ratio Prod/By-Prod Eg/Ma") for omega-3 substrates was calculated by dividing the substrate specificity for EgD5 on the omega-3 substrates (i.e., ETA/ETrA) by that for MaD5.

The preference of EgD5 and MaD5 for omega-6 or omega-3 substrates is compared using the ratio of the percent delta-5 desaturation ("Ratio n-6/n-3") in FIG. 10B and is calculated by dividing the percent delta-5 desaturation for EgD5 and MaD5 on a particular omega-6 substrate (either DGLA or EDA) by the percent delta-5 desaturation on the corresponding omega-3 substrate (either ETA or ETrA, respectively).

From the results in FIG. 10B, it is clear that EgD5 is approximately 2.6- to 2.9-fold more active in *Yarrowia* than MaD5 when DGLA, EDA and ETA are used as substrates. The exception is the activity for ETrA which is approximately the same for both enzymes. The substrate specificity of EgD5 and MaD5 for the correct omega-6 substrate (i.e., DGLA versus EDA) is approximately the same in *Yarrowia* but there is an approximate 2.5-fold preference of EgD5 for ETA (versus ETrA) over MaD5. The high activity and preferred substrate specificity for ETA over ETrA of EgD5 may be useful in the production of long-chain PUFAs. EgD5 also has a preference for omega-6 substrates (i.e., EDA and DGLA) over the omega-3 substrates (i.e., ETrA and ETA), respectively.

Example 18

Construction of Soybean Expression Vector pKR916 for Co-Expression of the *Mortierella alpina* Delta-5 Desaturase (MaD5) with a Delta-9 Elongase Derived from *Euglena gracilis* (EqD9e) and a Delta-8 Desaturase Derived from *Euglena gracilis* (EgD8)

The present Example describes construction of a soybean vector for co-expression of MaD5 (SEQ ID NO:67, Example 17) with EgD9e (SEQ ID NO:77; which is described in U.S. application Ser. No. 11/601,563 (filed Nov. 16, 2006; ) and EgD8 (SEQ ID NO:78; described as Eg5 in PCT Publication No. WO 2006/012325).

*Euglena gracilis* Delta-9 Elongase (EqD9e):

A clone from the Euglena cDNA library (eeg1c), called eeg1c.pk001.n5f, containing the *Euglena gracilis* delta-9 elongase (EgD9e; SEQ ID NO:77) was used as template to amplify EgD9e with oligonucleotide primers oEugEL1-1 (SEQ ID NO:79) and oEugEL1-2 (SEQ ID NO:80) using the VentR® DNA Polymerase (Catalog No. M0254S, New England Biolabs Inc., Beverly, Mass.) following the manufacturer's protocol. The resulting DNA fragment was cloned into the pCR-Blunt® cloning vector using the Zero Blunt® PCR Cloning Kit (Invitrogen Corporation), following the manufacturer's protocol, to produce pKR906 (SEQ ID NO:81).

A starting plasmid pKR72 (ATCC Accession No. PTA-6019; SEQ ID NO:82, 7085 bp sequence), a derivative of pKS123 which was previously described in PCT Publication No. WO 02/008269 (the contents of which are hereby incorporated by reference), contains the hygromycin B phosphotransferase gene (HPT) (Gritz, L. and Davies, J., Gene, 25:179-188 (1983)), flanked by the T7 promoter and transcription terminator (i.e., a T7prom/HPT/T7term cassette), and a bacterial origin of replication (ori) for selection and replication in bacteria (e.g., *E. coli*). In addition, pKR72 also contains HPT, flanked by the 35S promoter (Odell et al., *Nature*, 313:810-812 (1985)) and NOS 3' transcription terminator (Depicker et al., *J. Mol. Appl. Genet.*, 1:561-570 (1982)) (i.e., a 35S/HPT/NOS3' cassette) for selection in plants such as soybean. pKR72 also contains a NotI restriction site, flanked by the promoter for the α' subunit of β-conglycinin (Beachy et al., *EMBO J.*, 4:3047-3053 (1985)) and the 3' transcription termination region of the phaseolin gene (Doyle et al., *J. Biol. Chem.*, 261:9228-9238 (1986)), thus allowing for strong tissue-specific expression in the seeds of soybean of genes cloned into the NotI site.

The AscI fragment from plasmid pKS102 (SEQ ID NO:83), previously described in PCT Publication No. WO 02/00905 (the contents of which are hereby incorporated by reference), containing a T7prom/hpt/T7term cassette and bacterial ori, was combined with the AscI fragment of plasmid pKR72 (SEQ ID NO:82), containing a βcon/NotI/Phas cassette to produce pKR197 (SEQ ID NO:84), previously described in PCT Publication No. WO 04/071467 (the contents of which are hereby incorporated by reference).

The gene for the *Euglena gracilis* delta-9 elongase was released from pKR906 (SEQ ID NO:81) by digestion with NotI and cloned into the NotI site of pKR197 (SEQ ID NO:84) to produce intermediate cloning vector pKR911 (SEQ ID NO:85).

*Euglena gracilis* Delta-8 Desaturase (EqD8):

Plasmid pKR680 (SEQ ID NO:86), which was previously described in PCT Publication No. WO 2006/012325 (the contents of which are hereby incorporated by reference), contains the *Euglena gracilis* delta-8 desaturase (EgD8; SEQ ID NO:78; described as Eg5 in WO 2006/012325) flanked by the Kunitz soybean Trypsin Inhibitor (KTi) promoter (Jofuku et al., *Plant Cell*, 1:1079-1093 (1989)) and the KTi 3' termination region, the isolation of which is described in U.S. Pat. No. 6,372,965, followed by the soy albumin transcription terminator, which was previously described in PCT Publication No. WO 2004/071467 (i.e., a Kti/NotI/Kti3'Salb3' cassette).

Plasmid pKR680 (SEQ ID NO:86) was digested with BsiWI and the fragment containing EgD8 was cloned into the BsiWI site of pKR911 (SEQ ID NO:85) to produce pKR913 (SEQ ID NO:87).

*Mortierella alpina* Delta-5 Desaturase (MaD5):

Plasmid pKR767 (SEQ ID NO:88), which was previously described in PCT Publication No. WO 2006/012325 (the contents of which are hereby incorporated by reference), contains the *Mortierella alpina* delta-5 desaturase (MaD5; SEQ ID NO:67) flanked by the promoter for the soybean glycinin Gy1 gene and the pea legumin A2 3' transcription termination region (i.e., a Gy1/MaD5/legA2 cassette; the construction of which is described in WO 2006/012325).

The Gy1/Mad5/legA2 cassette was released from pKR767 (SEQ ID NO:88) by digestion with SbfI and the resulting fragment was cloned into the SbfI site of pKR913 (SEQ ID NO:87) to produce pKR916 (SEQ ID NO:89). A schematic depiction of pKR916 is shown in FIG. 11A. In this way, the *Euglena gracilis* delta-9 elongase (labeled "eug el1" in FIG. 11A) was co-expressed with the *Euglena gracilis* delta-8 desaturase (labeled "eug d8-sq5" in FIG. 11A) and the *Mortierella alpina* delta-5 desaturase (labeled "DELTA 5 DESATURASE M ALPINA" in FIG. 11A) behind strong, seed specific promoters.

Example 19

Construction of Soybean Expression Vector pKR1037 for Co-Expression of the *Euglena gracilis* Delta-5 Desaturase (EqD5) with a Delta-9 Elongase Derived from *Euglena gracilis* (EgD9e) and a Delta-8 Desaturase Derived from *Euglena gracilis* (EgD8)

The present Example describes construction of a soybean vector for co-expression of EgD5 (SEQ ID NO:1, Example 5) with EgD9e (SEQ ID NO:77, Example 18) and EgD8 (SEQ ID NO:78, Example 18).

Starting plasmid pKR974 (SEQ ID NO:90) is identical to pKR767 (SEQ ID NO:88, Example 18) except the NotI fragment containing MaD5 was replaced with a NotI fragment containing the *Saprolegnia diclina* delta-5 desaturase (SdD5; SEQ ID NO:94, which is described in PCT Publication No. WO 2004/071467). In addition, a MfeI site in the legA2 terminator of pKR767 (SEQ ID NO:88) was removed by digestion with MfeI, filling the MfeI site and religating (i.e., CAATTG converted to CAATTAATTG) and therefore, the legA2 terminator of pKR974 (SEQ ID NO:90) is 770 bp versus 766 bp for pKR767 (SEQ ID NO:88).

In order to clone EgD5 into a soybean expression vector, a NotI restriction site needed to be introduced at the 5' end of the gene. One skilled in the art will realized that there are many ways to introduce restriction sites into genes such as, but not limited to PCR or by subcloning into vectors containing the appropriate sites. In this case, in order to introduce a NotI site at the 5' end of EgD5 (SEQ ID NO:1), pDMW367 (SEQ ID NO:23) was digested with MfeI and then partially digested with NcoI. The NcoI/MfeI fragment containing a full length EgD5 (SEQ ID NO:1) was cloned into the NcoI/MfeI site of an intermediate cloning vector having a NotI site directly upstream of the NcoI site (i.e., GCGGCCGCAAAC-CATGG). The resulting plasmid was then digested with NotI and the fragment containing EgD5 (SEQ ID NO:1) was cloned into the NotI site of pKR974 (SEQ ID NO:90) to produce pKR1032 (SEQ ID NO:91).

The Gy1/EgD5/legA2 cassette was released from pKR1032 (SEQ ID NO:91) by digestion with SbfI and the resulting fragment was cloned into the SbfI site of pKR913 (SEQ ID NO:87) to produce pKR1037 (SEQ ID NO:92). A schematic depiction of pKR1037 (SEQ ID NO:92) is shown in FIG. 11B. In this way, the *Euglena gracilis* delta-9 elongase (labeled "eug el1" in FIG. 11B) could be co-expressed with the *Euglena gracilis* delta-8 desaturase (labeled "eug d8-sq5" in FIG. 11B) and the *Euglena gracilis* delta-5 desaturase (labeled "eug d5 DS" in FIG. 11B) behind strong, seed specific promoters.

Example 20

Co-Expression of the *Euglena gracilis* Delta-9 Elongase, the *Euglena gracilis* Delta-8 Desaturase and the *Saprolegnia diclina* Delta-17 Desaturase with Either the *Mortierella alpina* Delta-5 Desaturase (pKR916 & pKR328) or the *Euglena gracilis* Delta-5 Desaturase (pKR1037 & pKR328) in Soybean Somatic Embryos The present Example describes the transformation and expression in soybean somatic embryos of pKR916 (SEQ ID NO:89, Example 18; containing EgD9e, EgD8 and MaD5)

with pKR328 (SEQ ID NO:93, FIG. 11C, previously described in PCT Publication No. WO 04/071467), containing the *Saprolegnia diclina* delta-17 desaturase (SdD17) and the hygromycin phosphotransferase gene for selection on hygromycin. The present Example further describes the transformation and expression in soybean somatic embryos of pKR1037 (SEQ ID NO:92, Example 19; containing EgD9e, EgD8 and EgD5) with pKR328 (SEQ ID NO:93, FIG. 11C).

Soybean embryogenic suspension culture (cv. Jack) was transformed with the AscI fragment containing the expression cassette of pKR916 (SEQ ID NO:89) and intact plasmid pKR328 (SEQ ID NO:93), or with the AscI fragment containing the expression cassette of pK1037 (SEQ ID NO:92) and intact plasmid pKR328 (SEQ ID NO:93), as described in Example 13.

Embryos were matured in soybean histodifferentiation and maturation liquid medium (SHaM liquid media; Schmidt et al., *Cell Biology and Morphogenesis*, 24:393 (2005)) using a modified procedure. Briefly, after 4 weeks of selection in SB196 as described in Example 13, embryo clusters were removed to 35 mL of SB228 (SHaM liquid media) in a 250 mL Erlenmeyer flask. Tissue was maintained in SHaM liquid media on a rotary shaker at 130 rpm and 26° C. with cool white fluorescent lights on a 16:8 hr day/night photoperiod at a light intensity of 60-85 µE/m$^2$/s for 2 weeks as embryos matured. Embryos grown for 2 weeks in SHaM liquid media were equivalent in size and fatty acid content to embryos cultured on SB166/SB103 for 5-8 weeks as described in Example 13.

Media Recipes:

| SB 228-Soybean Histodifferentiation & Maturation (SHaM) (per liter) | |
|---|---|
| DDI H$_2$O | 600 mL |
| FN-Lite Macro Salts for SHaM 10X | 100 mL |
| MS Micro Salts 1000x | 1 mL |
| MS FeEDTA 100x | 10 mL |
| CaCl 100x | 6.82 mL |
| B5 Vitamins 1000x | 1 mL |
| L-Methionine | 0.149 g |
| Sucrose | 30 g |
| Sorbitol | 30 g |
| Adjust volume to 900 | mL |
| pH 5.8 | |
| Autoclave | |
| Add to cooled media (≤30° C.): | |
| *Glutamine (final concentration 30 mM) 4% | 110 mL |

*Note: Final volume will be 1010 mL after glutamine addition. Since glutamine degrades relatively rapidly, it may be preferable to add immediately prior to using media. Expiration 2 weeks after glutamine is added; base media can be kept longer without glutamine.

| FN-lite Macro for SHAM 10X- Stock #1 (per liter) | |
|---|---|
| (NH$_4$)$_2$SO$_4$ (ammonium sulfate) | 4.63 g |
| KNO$_3$ (potassium nitrate) | 28.3 g |
| MgSO$_4$*7H$_2$O (magnesium sulfate heptahydrate) | 3.7 g |
| KH$_2$PO$_4$ (potassium phosphate, monobasic) | 1.85 g |

Bring to volume
Autoclave

| MS Micro 1000X- Stock #2 (per 1 liter) | |
|---|---|
| H$_3$BO$_3$ (boric acid) | 6.2 g |
| MnSO$_4$*H$_2$O (manganese sulfate monohydrate) | 16.9 g |
| ZnSO$_4$*7H$_2$O (zinc sulfate heptahydrate) | 8.6 g |
| Na$_2$MoO$_4$*2H$_2$O (sodium molybdate dihydrate) | 0.25 g |

-continued

| MS Micro 1000X- Stock #2 (per 1 liter) | |
|---|---|
| CuSO$_4$*5H$_2$O (copper sulfate pentahydrate) | 0.025 g |
| CoCl$_2$*6H$_2$O (cobalt chloride hexahydrate) | 0.025 g |
| KI (potassium iodide) | 0.8300 g |

Bring to volume
Autoclave

| FeEDTA 100X- Stock #3 (per liter) | |
|---|---|
| Na$_2$EDTA* (sodium EDTA) | 3.73 g |
| FeSO$_4$*7H$_2$O (iron sulfate heptahydrate) | 2.78 g |

*EDTA must be completely dissolved before adding iron.
Bring to Volume
Solution is photosensitive. Bottle(s) should be wrapped in foil to omit light.
Autoclave

| Ca 100X- Stock #4 (per liter) | |
|---|---|
| CaCl$_2$*2H$_2$O (calcium chloride dihydrate) | 44 g |

Bring to Volume
Autoclave

| B5 Vitamin 1000X- Stock #5 (per liter) | |
|---|---|
| Thiamine*HCl | 10 g |
| Nicotinic Acid | 1 g |
| Pyridoxine*HCl | 1 g |
| Myo-Inositol | 100 g |

Bring to Volume
Store frozen

| 4% Glutamine- Stock #6 (per liter) | |
|---|---|
| DDI water heated to 30° C. | 900 mL |
| L-Glutamine | 40 g |
| Gradually add while stirring and applying low heat. | |
| Do not exceed 35° C. | |
| Bring to Volume | |
| Filter Sterilize | |
| Store frozen* | |

*Note: Warm thawed stock in 31° C. bath to fully dissolve crystals.

After maturation in SHaM liquid media, individual embryos were removed from the clusters, dried and screened for alterations in their fatty acid compositions as described supra.

A subset of soybean embryos (i.e., six embryos per event) transformed with either pKR916 (SEQ ID NO:89) and pKR328 (SEQ ID NO:93), or pKR1037 (SEQ ID NO:92) and pKR328 (SEQ ID NO:93), were harvested and picked into glass GC vials and fatty acid methyl esters were prepared by transesterification. For transesterification, 50 µL of trimethylsulfonium hydroxide (TMSH) and 0.5 mL of hexane were added to the embryos in glass vials and incubated for 30 min at room temperature while shaking. Fatty acid methyl esters (5 µL injected from hexane layer) were separated and quantified using a Hewlett-Packard 6890 Gas Chromatograph fitted with an Omegawax 320 fused silica capillary column (Catalog No. 24152, Supelco Inc.). The oven temperature was programmed to hold at 220° C. for 2.6 min, increase to 240° C. at 20° C./min and then hold for an additional 2.4 min.

Carrier gas was supplied by a Whatman hydrogen generator. Retention times were compared to those for methyl esters of standards commercially available (Nu-Chek Prep, Inc.).

In this way, 60 events transformed with pKR916 (SEQ ID NO:89) and pKR328 (SEQ ID NO:93) and 45 events transformed with pKR1037 (SEQ ID NO:92) and pKR328 (SEQ ID NO:93) were analyzed. The average fatty acid profiles for the ten events having the highest delta-5 desaturase activity for each transformation (pKR916 and pKR328, pKR1037 and pKR328) are shown in FIG. 12A and FIG. 12B, respectively.

In FIGS. 12A and 12B, fatty acids are identified as 16:0 (palmitate), 18:0 (stearic acid), 18:1 (oleic acid), LA, ALA, EDA, SCI, DGLA, ARA, ERA, JUP, ETA and EPA. Fatty acids listed as "others" include: 18:2 (5, 9), GLA, STA, 20:0, 20:1 (11), 20:2 (7, 11) or 20:2 (8, 11) and DPA. Each of these "other" fatty acids is present at a relative abundance of less than 3.0% of the total fatty acids. Fatty acid compositions for an individual embryo were expressed as the weight percent (wt. %) of total fatty acids and the average fatty acid composition is an average of six individual embryos for each event.

The activity of the delta-5 desaturase for the "correct" substrates (i.e., DGLA and ETA) is expressed as percent delta-5 desaturation ("Correct % delta-5 desat"), calculated according to the following formula: ([product]/[substrate+product])*100. More specifically, the percent delta-5 desaturation for the "correct" substrates was determined as: ([ARA+EPA]/[DGLA+ETA+ARA+EPA])*100.

The activity of the delta-5 desaturase for the "wrong" substrates (i.e., EDA and ERA) is also expressed as percent delta-5 desaturation ("Wrong % delta-5 desat"), calculated as: ([SCI+JUP]/[EDA+ERA+SCI+JUP])*100.

The substrate specificities of MaD5 and EgD5 for the "correct" substrates (i.e., DGLA and ETA) versus the "wrong" substrates (i.e., EDA and ERA) were compared and the comparison is shown in FIG. 13. In FIG. 13, the activity of the delta-5 desaturase for the "correct" substrates ("Correct % delta-5 desat") is plotted on the x-axis and the activity of the delta-5 desaturase for the "wrong" substrates ("Wrong % delta-5 desat") is plotted on the y-axis for MaD5 (data from FIG. 12A) and EgD5 (data from FIG. 12B).

FIG. 12B shows that the activity of EgD5 in soy embryos is very high with an average conversion (Correct % delta-5 desat) from 77% to 99% in the top ten events. The substrate specificity of EgD5 (FIG. 13) has a preference for the "correct" substrates over the "wrong" substrates when compared to MaD5. Given the high activity and substrate specificity, EgD5 may be useful for producing PUFAs such as, but not limited to, EPA and DHA in a host cell.

What is claimed is:

1. A polynucleotide operably linked to a heterologous nucleic acid sequence comprising:
   (a) a nucleotide sequence encoding a polypeptide having delta-5 desaturase activity, wherein the polypeptide has an amino acid sequence of at least 90% amino acid identity, based on the Clustal W method of alignment provided by the MegAlign™ v6.1 program of the DNASTAR LASERGENE bioinformatics computing suite (default parameters: GAP PENALTY=20, GAP LENGTH PENALTY=0.2, Delay Divergen Seqs(%) =30, DNA Transition Weight=0.5, Protein Weight Matrix=Gonnet Series, DNA Weight Matrix=IUB), when compared to an amino acid sequence as set forth in SEQ ID NO:2;
   (b) a nucleotide sequence encoding a polypeptide having delta-5 desaturase activity, wherein the nucleotide sequence has at least 90% sequence identity, based on the Basic Local Alignment Search Tool ("BLASTN") method of alignment provide by the National Center for Biotechnology Information (default parameters: short queries=automatically adjust parameters for short input sequences, expect threshold=10, and filter=low complexity regions), when compared to a nucleotide sequence as set forth in SEQ ID NO:1 or SEQ ID NO:3; or
   (c) a complement of the nucleotide sequence of (a) or (b), wherein the complement and the nucleotide sequence consist of the same number of nucleotides and are 100% complementary.

2. The polynucleotide of claim 1 wherein the nucleotide sequence comprises SEQ ID NO:1 or SEQ ID NO:3.

3. The polynucleotide of claim 1, wherein the amino acid sequence of the polypeptide of step (a) comprises
   (a) SEQ ID NO:2; or
   (b) an amino acid sequence that differs from the amino acid sequences in (a) by at least one conservative amino acid substitution.

4. A recombinant DNA construct comprising the polynucleotide of claim 1, 2, or 3 operably linked to at least one regulatory sequence.

5. A cell comprising in its genome the recombinant DNA construct of claim 4.

6. The cell of claim 5 wherein said cell is selected from the group consisting of plants and yeast.

7. A method for transforming a cell, comprising transforming a cell with the recombinant DNA construct of claim 4 and selecting those cell transformed with the recombinant DNA construct.

8. A method for producing a transformed plant comprising transforming a plant cell with the recombinant DNA construct of claim 4 and regenerating a plant from the transformed plant cell, wherein the transformed plant comprises the recombinant DNA construct.

9. The method of claim 8 wherein the plant is a soybean plant.

10. A transgenic seed comprising in its genome the recombinant DNA construct of claim 4.

11. A transgenic seed obtained from the transformed plant made by the method of claim 8, wherein the transgenic seed comprises the recombinant DNA construct.

12. A method for making long-chain polyunsaturated fatty acids in a plant cell comprising:
 (a) transforming a cell with the recombinant DNA construct of claim 4; and
 (b) selecting those transformed cells that make long-chain polyunsaturated fatty acids.

13. An oilseed plant comprising in its genome the recombinant DNA construct of claim 4.

14. The oilseed plant of claim 13, wherein the oilseed plant is selected from the group consisting of soybean, Brassica species, sunflower, maize, cotton, flax and safflower.

15. A transgenic progeny plant obtained from the plant made by the method of claim 8, wherein the progeny plant comprises the recombinant DNA construct.

16. A polynucleotide operably linked to a heterologous nucleic acid sequence which encodes a delta-5 desaturase as set forth in SEQ ID NO:2 wherein at least one codon is codon-optimized for expression in Yarrowia sp.

17. A method for producing an altered level of at least one polyunsaturated fatty acid in a seed of an oilseed plant comprising:
 (a) transforming an oilseed plant cell with the recombinant DNA construct of claim 4 and at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a C14/16 elongase, a C16/18 elongase, a C18/20 elongase and a C20/22 elongase;
 (b) regenerating a transgenic oilseed plant from the transformed cell of step (a); and
 (c) selecting a transgenic seed obtained from the transgenic oilseed plant of step (b) having an altered level of at least one polyunsaturated fatty acids when compared to the level in a seed obtained from a nontransformed oilseed plant.

18. The method of claim 17 wherein the oilseed plant is selected from the group consisting of soybean, Brassica species, sunflower, maize, cotton, flax, and safflower.

19. An oilseed plant comprising:
 (a) the recombinant DNA construct of claim 4; and
 (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a C14/16 elongase, a C16/18 elongase, a C18/20 elongase and a C20/22 elongase.

20. The oilseed plant of claim 19, wherein the oilseed plant is selected from the group consisting of soybean, Brassica species, sunflower, maize, cotton, flax and safflower.

21. A transgenic seed obtained from the oilseed plant of claim 19, wherein the transgenic seed comprises the recombinant DNA construct.

22. A transgenic seed obtained from the oilseed plant of claim 20, wherein the transgenic seed comprises the recombinant DNA construct.

\* \* \* \* \*